US008163503B2

(12) United States Patent
Kingsbury

(10) Patent No.: US 8,163,503 B2
(45) Date of Patent: Apr. 24, 2012

(54) METHODS OF IDENTIFYING COMPOUNDS THAT BIND TANGO509

(75) Inventor: Gillian Kingsbury, Roslindale, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/800,681

(22) Filed: May 20, 2010

(65) Prior Publication Data

US 2011/0065124 A1  Mar. 17, 2011

Related U.S. Application Data

(60) Continuation of application No. 11/983,233, filed on Nov. 8, 2007, now abandoned, which is a division of application No. 11/287,573, filed on Nov. 23, 2005, now Pat. No. 7,385,036, which is a continuation of application No. 09/796,858, filed on Mar. 1, 2001, now Pat. No. 7,041,474, which is a continuation-in-part of application No. 09/599,596, filed on Jun. 22, 2000, now abandoned, which is a division of application No. 09/223,546, filed on Dec. 30, 1998, now abandoned, and a continuation-in-part of application No. 09/471,179, filed on Dec. 23, 1999, now abandoned, which is a continuation-in-part of application No. 09/223,546, filed on Dec. 30, 1998, now abandoned, said application No. 09/796,858 is a continuation-in-part of application No. 09/474,072, filed on Dec. 29, 1999, now abandoned, which is a continuation-in-part of application No. 09/224,246, filed on Dec. 30, 1998, now abandoned, said application No. 09/796,858 is a continuation-in-part of application No. 09/474,071, filed on Dec. 29, 1999, now abandoned, which is a continuation-in-part of application No. 09/223,094, filed on Dec. 30, 1998, now abandoned, said application No. 09/796,858 is a continuation-in-part of application No. 09/597,993, filed on Jun. 19, 2000, now abandoned, which is a continuation-in-part of application No. 09/336,536, filed on Jun. 18, 1999, now Pat. No. 6,406,884, said application No. 09/796,858 is a continuation-in-part of application No. 09/572,002, filed on May 15, 2000, now abandoned, which is a continuation-in-part of application No. 09/312,359, filed on May 14, 1999, now abandoned, said application No. 09/796,858 is a continuation-in-part of application No. 09/606,565, filed on Jun. 29, 2000, now abandoned, which is a continuation-in-part of application No. 09/342,687, filed on Jun. 29, 1999, now abandoned, said application No. 09/796,858 is a continuation-in-part of application No. 09/630,334, filed on Jul. 31, 2000, now abandoned, which is a continuation-in-part of application No. 09/365,164, filed on Jul. 30, 1999, now abandoned, said application No. 09/796,858 is a continuation-in-part of application No. 09/665,666, filed on Sep. 20, 2000, now abandoned, which is a continuation-in-part of application No. 09/399,723, filed on Sep. 20, 1999, now abandoned.

(51) Int. Cl.
  *G01N 33/53* (2006.01)
  *G01N 33/567* (2006.01)
(52) U.S. Cl. .................... 435/7.1; 435/7.2; 435/7.21
(58) Field of Classification Search ................ None
  See application file for complete search history.

(56) References Cited

U.S. PATENT DOCUMENTS 6,630,575 B2  10/2003  Coyle et al.
7,101,550 B2   9/2006  Wood et al.

FOREIGN PATENT DOCUMENTS

| EP | 1130094 A2 | 9/2001 |
| WO | WO 91/03553 | 3/1991 |
| WO | WO 99/41284 | 8/1999 |
| WO | WO 99/42470 | 8/1999 |
| WO | WO 01/14556 A1 | 3/2001 |
| WO | WO 01/14557 A1 | 3/2001 |
| WO | WO 01/75067 A3 | 10/2001 |

OTHER PUBLICATIONS

Genbank Accession No. AA119099 (mouse Soares thymus 2NbMT cDNA) Nov. 19, 1996.
Genbank Accession No. AA121533 (human Soares pregnant uterus NbHPU cDNA) Nov. 15, 1996.
Genbank Accession No. AA127696 (human Soares pregnant uterus NbHPU cDNA) Nov. 15, 1996.
Genbank Accession No. AA292201 (human Soares ovary tumor NbHOT cDNA) Apr. 2, 1997.
Genbank Accession No. AA399416 (human Soares ovary tumor NbHOT cDNA) Apr. 2, 1997.
Genbank Accession No. AA823166 (mouse Soares mammary gland NbMMG cDNA) Feb. 17, 1998. Genbank Accession No. AA896104 (Stratagene mouse macrophage) Apr. 6, 1998.
Genbank Accession No. AF142780 (mouse butyrophilin-like protein mRNA) Sep. 30, 1999.
Genbank Accession No. AI608902 (human NCI CGAP HN5 cDNA) Apr. 15, 1999.
Genbank Accession No. AI690414 (human NCI CGAP Ut4 cDNA) May 27, 1999.
Genbank Accession No. AI733919 (human Soares ovary tumor NbHOT cDNA) Jun. 14, 1999.
Genbank Accession No. AI799320(human NCI CGAP Ut3 cDNA) Jul. 6, 1999.
Genbank Accession No. AI810376 (human NCI CGAP PR28 cDNA) Jul. 7, 1999.
Genbank Accession No. AI819376 (human Soares NSF F8 9W OT PA P S1 cDNA) Jul. 9, 1999.
Genbank Accession No. P24071 (human IgA Fc receptor precursor—CD89 antigen) Dec. 1990.

(Continued)

*Primary Examiner* — Prema Mertz
(74) *Attorney, Agent, or Firm* — Millennium Pharmaceuticals Inc.

(57) ABSTRACT

The invention provides isolated TANGO 239, TANGO 219, TANGO 232, TANGO 281, A236 (INTERCEPT 236), TANGO 300, TANGO 353, TANGO 393, TANGO 402, TANGO 351 and TANGO 509 nucleic acid molecules and polypeptide molecules. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening and therapeutic methods utilizing compositions of the invention are also provided.

5 Claims, 85 Drawing Sheets

OTHER PUBLICATIONS

Genbank Accession No. NM005191 (human CD80 antigen, mRNA) Oct. 1989.
Genbank Accession No. NM005182 (human CD80 antigen) Oct. 1989.
Genbank Accession No. S82919 (Human CD89=IgA Fc receptor Fc α RIa2 variant m RNA) Sep. 1996.
Genbank Accession No. U43677 (human FC α receptor, splice variant Fc αR a.3 mRNA, complete cds) Jun. 1996.
Genbank Accession No. W46488 (human Soares senescent fibroblasts NbHSF cDNA) May 22, 1996.
Genbank Accession No. W78915 (human Soares fetal liver spleen 1NFLS S1 cDNA) Jun. 24, 1996.
Genbank Accession No. W97814 (Soares mouse embryo NbME13.5 14.5 cDNA) Jul. 16, 1996.
Genbank Accession No. W97816 (Soares mouse embryo NbME 13.5 14.5 cDNA) Jul. 16, 1996.
Genbank Accession No. AQ395363 (human genomic clone 2546M17) 1997.
Pfam Accession No. PF00047 (Pfam database of immunoglobulin domains: http://pfam.wustl.edu) 1988.
Atschul, et al., "Gapped BLAST and PSI-BLAST: a New Generation of Protein Database Search Programs," *Nucl. Acids Res.* 25:3389-3402 (1997).
Atschul, et al., "Basic Local Alignment Search Tool," *J. Mol. Biol.* 215:403-410 (1990).
de Wit, et al., "Structure of the Gene for the Human Myeloid IgA Fc Receptor (CD89)," *J. Immunol.* 155:1203-1209 (1995).
Freeman, et al., "Cloning of B7-2: a CTLA-4 Counter-Recpetor that Costimulates Human T Cell Proliferation," *Science* 262:909-911 (1993).
Freeman, et al., "The Gene for B7, a Costimulatory Signal for T-Cell Activation, Maps to Chromosomal Region 3q13.3-3q21," *Blood* 79:489-494 (1992).
Jellis, et al., "Genomic Organization of the Gene Coding for the Costimulatory Human B-Lymphocyte Antigen B7-2 (CD86)," *Immunogenetics* 42:85-89 (1995).
Karlin and Atschul, "Applications and Statistics for Multiple High-Scoring Segments in Molecular Sequences," *Proc. Natl. Acad. Sci. USA* 90:5873-5877 (1993).
Karlin and Atchul, "Methods of Assessing the Statistical Significance of Molecular Sequence Features by Using General Scoring Schemes," *Proc. Natl. Acad. Sci. USA*, 87:2264-2268(1990).
Maliszewski, et al., "Expression Cloning of a Human Fc Receptor IgA," *J. Exp. Med.* 172:1665-1672 (1990).
Myers and Miller, "Optimal Alignments in Linear Space," CABIOS 4:11-17 (1988).
Party, et al., "Identification of a FC α Receptor (CD89) Isoforms Generated by Alternative Splicing that are Differentially Expressed Between Blood Monocytes and Alveolar Macrophages," *J. Immunol.* 156:4442-4448 (1996).
Pearson and Lipman, "Improved Tools for Biological Sequence Comparison," *Proc. Natl. Acad. Sci. USA* 85:2444-2448 (1998).

Pfeffercorn and Yeaman, "Association of IgA-Fc Receptors (Fc αR) with FcεRIγ2 Subunits in U937 Cells. Aggregation Induces the Tyrosine Phosphorylation of γ2," *J. Immunol.* 153:3228-3236 (1994).
Pleass, et al., "Alternative Splicing of the Human IgA Fc Receptor CD89 in Nuetrophils and Eosinophils," *Biochem J.* 318:771-777 (1996).
Reeves, et al., "The Co-Stimulatory Genes *Cd80* and *Cd86* are Linked on Mouse Chromosome 16 and Human Chromosome 3," *Mamm. Genome* 8:581-582 (1997).
Selvakumar, et al., "Genmoic Organization and Chromosomal Location of the Human Gene Encoding the B-Lymphocyte Activation Antigen B7," *Immunogenet.* 36:175-181 (1992).
Skolnick and Fetrow, "From Genes to Protein Structure and Function: Novel Applications of Computorial Approaches in the Genomic Era," *Trends in Biotechnology* 18:34-39 (2000_.
Torelli and Robotti, "ADVANCE and ADAM: Two Algorithms for the Analysis of Global Similarity Between Homologous Informational Sequences," *Comput Appl. Biosci.* 10:3-5 (1994).
Ausubel, et al., eds. 1989, *Current Prolotols in Molecular Biology*, John Wiley & Sons, pp. 2.10.1-2.10.16.
Sambrook, et al., 1989, *Molecular Cloning: A Laboratory Manual*, $2^{nd}$ ed., Cold Spring Harbor Laboratory Press, Cold Spring Harbor, NY, pp. 1.53-1.104 and 9.31-9.58.
Halvorsen, Y.-D.C., et al., "Adipose as an Endocrine Organ: The Characterization of Secreted Proteins from Human Cultured Adipocytes," *FASEB Journal* 13(4):A369 (1999).
Celis, J.E., et al., "Secreted Proteins From Normal and SV40 Transformed Human MRC-5 Fibroblasts: Toward Establishing a Database of Human Secreted Proteins," *Leukemia* 1(10):707-717 (1987).
Skolnick, et al., "Structural Genomics And Its Importance For Gene Function Analysis," *Nature Biotechnology* 18:283-287 (2000).
Reiger, et al., Glossary of Genetics and Cytogenetics, Fourth Edition, Springer-Verlag pp. 16-19, 1976.
Dong, et al., "$B_7$-$B_{15}$ a third member of the $B_7$ family, co-stimulates T-cell proliferation and interleukin-10 selection," *Nature Medicine* 5(12):1365-1369 (1999).
Sawamura, T., et al., "An Endothelial Receptor for Oxidized Low-density Lipoprotein," *Nature* 386(6620): 73-77 (1997).
Weis, W.I., et al., "The C-type Lectin Superfamily in the Immune System," *Immunol. Rev.* 163:19-34 (1998).
Ariizumi, K., et al., "Cloning of Novel C-type Lectins that are Expressed Selectively by Dendritic Cells," *J. Invest. Dermatol.* (*Abstract*) 106(4):814 (1996).
Vasta, G.R., et al., "C-type Lectins and Galectins Mediate Innate and Adaptive Immune Funtions: Their Roles in the Complement Activation Pathway," *Dev. Compar. Dermatol.* 23:401-420 (1999).
Gordon,J., "B-cell Signalling Via the C-type Lectins CD23 and CD72," *Immunol. Today* 15(9):411-417 (1994).
Mikayama et al., Proc. Acad. Sci. USA vol. 90, pp. 10056-10060, 1993.
Voet et al., Biochemistry. John Wiley & Sons, Inc., pp. 126-128 and 228-234, 1990.

```
GTCGACCCACGCGGTCCCGGGCTGGCCTTTCAAAGTGTGCAGTTGTCTCCTCCTGTCCAGCCCATCGTCGCCAGGAC    79

CAGCTGGGCCGGCGGGTCTGACCTGAGGCCTGCTGCCTCAGGCGCCGGGAGCGCTGGCGCTCTCCATTCGAGCACCTTCCAGCAT  158

ACCGGCTCGGCTCCGGGAGCCGGCTCTGCAAAGTTGGGCAGCTCAGAGCGCAAGCTTTGCCTCTCGACTTCTCCCTCCTTG   237

GGTCCCCAGCGCGCCCCCGCCTCCCACGATCCCTTTCACTAGGAGCAGCCAGTCCCAGCGGGGCTGGCAACTTGCACCCCTT    316
```

|   |   |   |   |   |   |   |   |   |   |   |   |   |   |   |   |   |   |   |   |   |   |   |   |   |   |
|---|---|---|---|---|---|---|---|---|---|---|---|---|---|---|---|---|---|---|---|---|---|---|---|---|---|

```
                                   M   L   L   R   G   V   L   L   A   L   Q   A   L    13
CCTAGTCATCCTCCCTGAAACGCGACC  ATG CTG TTA AGG GGC GTC CTC CTG GCG TTG CAA GCC CTG    382

Q   L   A   G   A   L   D   L   P   A   G   S   C   A   F   E   E   S   T   C    33
CAG CTC GCC GGT GCC CTC GAC CTC CCC GCT GGG TCC TGT GCC TTT GAA GAG AGC ACT TGC    442

G   F   D   S   V   L   A   S   L   P   W   I   L   N   E   E   G   H   Y   I    53
GGC TTT GAC TCC GTG TTG GCC TCT CTG CCG TGG ATT TTA AAT GAG GAA GGC CAT TAC ATT    502

Y   V   D   T   S   F   G   K   Q   G   E   K   A   V   L   L   S   P   D   L    73
TAT GTG GAT ACC TCC TTT GGC AAG CAG GGG GAG AAA GCT GTG CTG CTA AGT CCT GAC TTA    562

Q   A   E   E   W   S   C   L   R   L   V   Y   Q   I   T   T   S   S   E   S    93
CAG GCT GAG GAA TGG AGC TGC CTC CGT TTG GTC TAC CAG ATA ACC ACA TCT TCG GAG TCT    622

L   S   D   P   S   Q   L   N   L   Y   M   R   F   E   D   E   S   F   D   R    113
CTG TCA GAT CCC AGC CAG CTG AAC CTG TAC ATG AGA TTT GAA GAT GAA AGC TTT GAT CGC    682

L   L   W   S   D   S   S   W   L   I   A   S   L   D   L   Q    133
TTG CTT TGG TCA GCT AAG GAA CCT TCA GAC AGC TGG CTC ATA GCC AGC TTG GAT TTG CAA    742

N   S   K   K   F   K   I   L   L   I   E   G   V   L   G   Q   Q   N   T   A    153
AAC AGT TCC AAG AAA TTC AAG ATT TTA ATA GAA GGT GTA CTA GGA CAG CAG GGA AAC ACA GCC    802
```

FIG. 1A

```
S   I   A   L   F   E   I   K   M   T   G   Y   C   I   E   C   D   F   E      173
AGC ATC GCA CTA TTT GAA ATC AAG ATG ACA GGC TAC TGT ATT GAA TGT GAC TTT GAA     862

E   N   H   L   C   G   F   V   N   R   W   N   P   N   V   N   W   F   V   G  193
GAA AAT CAT CTC TGT GGC TTT GTG AAC CGC TGG AAT CCC AAT GTG AAC TGG TTT GTT GGA 922

G   G   S   I   R   N   V   H   S   I   L   P   Q   Q   D   H   T   F   K   S   E  213
GGA GGA AGT ATT CGG AAT GTC CAC TCC ATT CTC CCA CAG CAG GAT CAC ACC TTC AAG AGT GAA 982

L   G   H   Y   M   Y   Y   D   S   V   Y   V   K   H   F   Q   E   V   A   Q  233
CTG GGC CAC TAC ATG TAC TAT GAC TCA GTT TAT GTG AAG CAC TTC CAG GAG GTG GCA CAG 1042

L   I   S   P   L   T   T   A   P   M   A   G   C   L   S   F   Y   Y   Q   I  253
CTC ATC TCC CCG TTG ACC ACG CCC ATG GCT GGC TGC CTG TCA TTT TAT TAC CAG ATC 1102

Q   Q   G   N   D   N   V   F   S   L   Y   T   R   D   V   A   G   L   Y   E  273
CAG CAG GGG AAT GAC AAT GTC TTT TCC CTT TAC ACT CGG GAT GTG GCT GGC CTT TAC GAG 1162

E   I   W   K   A   D   R   P   G   N   A   A   W   N   L   A   E   V   E   F  293
GAA ATC TGG AAA GCA GAC AGG CCA GGG AAT GCT GCC TGG AAC CTT GCG GAG GTC GAG TTC 1222

N   A   P   Y   P   M   E   V   I   F   E   V   A   F   N   G   P   K   G   G  313
AAT GCT CCT TAC CCC ATG GAG GTT ATT TTT GAA GTT GCT TTC AAT GGT CCC AAG GGA GGT 1282

Y   V   A   L   D   D   I   S   F   S   P   P   V   H   C   Q   N   Q   T   E   L  333
TAT GTT GCC CTG GAT GAT ATT TCA TTC TCT CCT GTT CAC TGC CAG AAT CAG ACA GAA CTT 1342

L   F   S   A   V   E   A   S   C   N   F   E   Q   D   L   C   N   F   Y   Q  353
CTG TTC AGT GCC GTG GAA GCC AGC TGC AAT TTT GAG CAA GAT CTC TGC AAC TTT TAC CAA 1402

D   K   E   G   P   G   W   T   R   V   K   P   N   M   Y   R   A   G   373
GAT AAA GAA GGT CCA GGT TGG ACC CGA GTA AAA CCA AAC ATG TAT CGG GCT GGA 1462
```

FIG. 1B

```
 D   H   T   T   G   L   G   Y   Y   L   L   A   N   T   K   F   T   S   Q   P       393
GAC CAC ACT ACA GGG CTA GGG TAT TAC CTG CTA GCC AAC ACA AAG TTC ACA TCT CAG CCT      1522

G   Y   I   G   R   L   Y   G   P   S   L   P   G   N   L   Q   Y   C   L   R       413
GGC TAC ATT GGA AGG CTC TAT GGG CCC TCC CTA CCA GGA AAC TTG CAG TAT TGT CTG CGT      1582

F   H   Y   A   I   Y   G   F   L   K   M   S   D   T   L   A   V   Y   I   F       433
TTT CAT TAT GCC ATC TAT GGA TTT TTA AAA ATG AGT GAC ACC CTA GCA GTT TAC ATC TTT      1642

E   E   N   H   V   Q   E   K   I   W   S   V   L   E   S   P   R   G   V           453
GAA GAG AAC CAT GTG CAA GAG AAG ATC TGG TCT GTG TTG GAG TCC CCA AGG GGT GTT          1702

W   M   Q   A   E   I   T   F   K   K   P   M   P   T   K   V   V   F   M   S       473
TGG ATG CAA GCT GAA ATC ACC TTT AAG AAG CCC ATG CCT ACC AAG GTG GTT TTC ATG AGC      1762

L   C   K   S   F   W   D   C   G   L   V   A   L   D   D   I   T   I   Q   L       493
CTA TGC AAA AGT TTC TGG GAC TGT GGG CTT GTA GCC CTG GAT GAC ATT ACA ATA CAA TTG      1822

G   S   C   S   S   E   K   L   P   P   H   L   E   S   V   L   S   S   K           513
GGA AGC TGC TCA TCT TCA GAG AAA CTT CCA CCT CAC CTG GAG AGT GTA CTT TCG AGC AAG      1882

M   N   V   H   L   L   R   R   K   E   T   G   A   A   G   T   G   G   E           533
ATG AAT GTA CAT CTC CTC AGG AGA AAA GAA ACC GGC ACA GCT GGC ACA GGA GGA GGG GAG      1942

K   L   P   L   P   T   Q   D   Q   R   E   I   T   L   L   G   *                   550
AAA CTC CCA CTT CCT ACA CAG GAC CAA AGG GAG ATC ACA CTA CTG GGG TAG                  1993

GCTACTACATGTACGTACATTGAGGCCTCCCATATGTGTATGGACAAAAGCACGCCTCTTGTCCAGGCCTCTGCGAGGAGT   2072

CTCTGGAAAACACTGCTTGACCTTTTCTACCACATGTATGGAGGGGCACTGGCCTGCTGAGTGTTTATCTGAAAAAG      2151

GAAGAAGACAGTGAAGAGTCCCTCTTATGGAGGAGAGAGGTGAACAGAGCATTTCCTGGCTACGAGCACTGATTGAAT     2230
```

FIG.1C

| | |
|---|---|
| ACAGCTGTGAGAGGCAACACCAGATAATTTTTGAAGCCATTCGAGGAGTATCAATAAGAAGTGATATTGCCATTGATGA | 2309 |
| TGTTAAATTTCAGGCAGGACCCTGTGGAGAATGGAAGATACAACTCAACAATCATCAGGATATTCTGAGGACTTAAAT | 2388 |
| GAAATTGAGTATTAAGAAATGATCTGCATTGGATTTACTAGACGAAAACCATACCTCTCTCAATCAAAATGAAAACAA | 2467 |
| AGCAAATGAATACTGGACAGTCTTAACAATTTATAAGTTATAAAAATGACTTTAGAGCACCCTCCTTCATTACTTTGC | 2546 |
| AAAAACATACTGACTCAGGGCTCTTTTTTCTTTTGCATCTGACAACTGTTACTAGAAATACAGGCTACTGGTTTTGC | 2625 |
| ATAGATCATTCATCTTAATTTTGGTACCAGTAAAAATACAAATGTACTATATTGTAGTCATTTTAAAGTACACAAAGG | 2704 |
| GCACAATCAAAATGAGATGCACTCATTTAAATCTGCATTCAGTGAATGTATTGGGAGAAAAATAGGTCTTGCAGGTTTC | 2783 |
| CTTTGAATTTTAAGTATCATAAATATTTTTAAGTAAATAATACGGGGTGTCAGTAATATCTGCAGAATGAATGCAGT | 2862 |
| CTTTCATGCTAATGAGTAGTCTGGAAAAATAAAGTCTTATTTCTATGTTTATTCATAGAAATGGAGTATTAATTTT | 2941 |
| TAATATTTCACCATATGTGATAACAAAGGATCTTTCATGAATGTCCAAGGGTAAGTCAGTATTAATTAATGCTGTATT | 3020 |
| ACAAGGCAATGCTACCTTCTTTATTCCCCCTTTGAACTACCTTTGAAGTCACTATGAGCACTGGATAGAAATTTAACT | 3099 |
| TTTTTTGTAAAGCAAGCTTAAAATGTTTAAATGTTTATGTATACATACCCAGCAACTTTATAAAGTGTTAAACAATTTTACTGA | 3178 |
| TTTTTATAATAAATATTTGGTAAGATTTTGAATAATATGAATTCAGGCAGATATACTAAACTGCTTTATTTACTTGT | 3257 |
| TTAGAAAATTGTATATATATGTTTGTGTATCCTAACAGCTGCTATGAAATTATAAAAATAAATAATT | 3336 |
| AAATCAAAAAAAAAAAAAAAAAAAAAAAAAAAAAAAAAAAAAAAAAAAAAAAAAAAAAAAAAAAAGGGGGGG | 3413 |

FIG. 1D

Alignment of TANGO 239 and the MAM Consensus Sequence

```
         MAM       *->dgCdFedgnqKTvCgyiQdlsDDaeWerlnsstppPSTGPtqDHtlv
                     ++C Fe+      +Cg+      +  +s+p          +
         T239.pro 24 GSCAFEES----TCGF----------DSVLASLP--------WIL 46

MAM       gqCKdsGffmlvntSegaeGerArLlspvLkPkrdqhCldFwYym..sGK
                     ++    G +++v+tS g Ge+A Llsp L    + Cl  Y  ++s+
         T239.pro 47 NE---EGHYIYVDTSFGKQGEKAVLLSPDLQ-AEEWSCLRLVYQIttSSE 92

MAM       snvgplsinvrvdvnegkvpllntIwtvsGnpgrnWkrAeVtLnTfetke
                   s ++p  +n++ + +     ++ ++w      p ++W++A + L+   k+
         T239.pro 93 SLSDPSQLNLYMRFEDE--SFDRLLWSAK-EPSDSWLIASLDLQ-NSSKK 138

MAM       yqViFeGtkgDPGgssGgIAiDDIkltetpSPSqCpa<-*
                   ++    eG+ g  g     IA+ +Ik  t +    C
         T239.pro 139 FKILIEGVLG--QGNTASIALFEIKMTTGY+---CIE 169

MAX: domain 2 of 3
         MAM       *->dgCdFedgnqKTvCgyiQdlsDDaeWerlnsstppPSTGPtqDHtlv
                      CdFe+     Cg+     +  +W ++ +s       ++qDHt+
         T239.pro 170 --CDFEENH---LCGFVNRWNPNVNWFVGGGSIRNVHSILPQDHTFK 211

MAM       ggCKdsGffmlvntS.egaeGerArLlspvLkPkrdqhCldFwYymsGks
                     ++    G +m+v++   + e A L sp      + + Cl+F+Y
         T239.pro 212 SE---LGHYMYVDSVyVKHFQEVAQLISPLTT-APMAGCLSFYYQIQQ-G 256

MAM       nvgplsinvrvdvnegkvpllntIwtvsGnpgrnWkrAeVtLnTfetkey
                   n + +s+++r dv+    +l  Iw      W++AeV  n  +
         T239.pro 257 NDNVFSLYTR-DVA----GLYEEIWKADRPGNAAWNLAEVEFN--APYPM 299

MAM       qViFeGtkgDPGgssGgIAiDDIkltetpSPSqCpa<-*
                   ViFe+  +. G    G+ A+DDI+   +      C
         T239.pro 300 EVIFEVAFN--GPKGGYVALDDISFSPVH----CQN 329

MAX: domain 3 of 3
         MAM       -->dgCdFedgnqKTvCgyiQdlsDDaeWerlnsstppPSTGPtqDHtlv
                     +C+Fe        C++ Qd       W r+   +    DHt
         T239.pro 340 ASCNFEQD----LCNFYQD-KEGPGWTRVKVKPN---MYRAGDHTT- 377

MAM       gqCKdsGffmlvntS.egaeGerArLlspvLkPkrdqhCldFwYymsG.k
                    + G++ l nt  + +G   rL   p L    + q Cl F+Y   +G
         T239.pro 378 ---GLGYYLLANTKfTSQPGYIGRLYGPSLP-GNLQYCLRFHYAIYGfL 422

MAM       snvgplsinvrvdvnegkvpllntIwtvsGnpgrnWkrAeVtLnTfetke
                   + +++l +++ ++         + +Iw v   p + W  Ae+t     +
         T239.pro 423 KMSDTLAVYIFEENH----VVQEKIWSVLESPRGVWMQAEITFK--KPHP 466

MAM       yqViFeGt.kgDPGgssGgIAiDDIkltetpSPSqCpa<-*
                   +V+F   k+        G  A+DDI++  +       C
         T239.pro 467 TKVVFHSLcKS--FWDCGLVALDDITIQLGS----CSS 498
```

FIG.3

```
GTCGACCCACGCGTCCCGGGCTGGCCTTTCAAAGTGTGCAGTTGTCTCCTCCCTGTCCAGCCCCATCGTCGCCCAGGAC      79

CAGCTGGGCCGCGGTCTGACCTGAGGCTGCTGCTCAGCGCCGGGGCGCTGGCGCTCTCCATTCGAGCACCTTCCAGCAT     158

ACCGCTCGGCTCCGGGAGCCGCTCTGCAAAGTTGGGCAGCTCAGAGCGCAAGCTTTGCCTCTCGACTTCTCCCTCCTTG     237

GGTCCCCGGCGCCCCCGCCTCCCACGATCCCTTTCACTAGGAGCAGCCAGTCCCAGCGGGCTGGCAACTTGCACCCCTT     316

M   L   L   R   G   V   L   L   A   L   Q   A   L      13
CCTAGTCATCCTCCCTGAAACGCGACC         ATG CTG TTA AGG GGC GTC CTC CTG GCG TTG CAA GCC CTG    382

Q   L   A   G   A   L   D   L   P   A   G   S   C   A   F   E   E   S   T   C        33
CAG CTC GCC GGT GCC CTC GAC CTG CCC GCT GGG TCC TGT GCC TTT GAA GAG AGC ACT TGC      442

G   F   D   S   V   L   A   S   L   P   W   I   L   N   E   E   G   H   Y   I        53
GGC TTT GAC TCC GTG TTG GCC TCT CTG CCG TGG ATT TTA AAT GAG GAA GGC CAT TAC ATT      502

Y   V   D   T   S   F   G   K   Q   G   E   K   A   V   L   L   S   P   D   L        73
TAT GTG GAT ACC TCC TTT GGC AAG CAG GGG GAG AAA GCT GTG CTG CTA AGT CCT GAC TTA      562

Q   A   E   E   W   S   C   L   R   L   V   Y   Q   I   T   T   S   S   E   S        93
CAG GCT GAG GAA TGG AGC TGC CTC CGT TTG GTC TAC CAG ATA ACC ACA TCT TCG GAG TCT      622

L   S   D   P   S   Q   L   N   L   Y   M   R   F   E   D   E   S   F   D   R       113
CTG TCA GAT CCC AGC CAG CTG AAC CTC TAC ATG AGA TTT GAA GAT GAA AGC TTT GAT CGC      682

L   L   W   S   A   K   E   P   S   D   S   W   L   I   A   S   L   D   L   Q       133
TTG CTT TGG TCA GCT AAG GAA CCT TCA GAC AGC TGG CTC ATA GCC AGC TTG GAT TTG CAA      742

N   S   S   K   K   F   K   I   L   I   E   G   V   L   G   Q   G   N   T   A       153
AAC AGT TCC AAG AAA TTC AAG ATT TTA ATA GAA GGT GTA CTA GGA CAG GGA AAC ACA GCC      802

S   I   A   L   F   E   I   K   M   T   T   G   Y   C   I   E   C   D   F   E       173
AGC ATC GCA CTA TTT GAA ATC AAG ATG ACA ACC GGC TAC TGT ATT GAA TGT GAC TTT GAA      862

E   N   H   L   C   G   F   V   N   R   W   N   P   N   V   N   W   F   V   G       193
GAA AAT CAT CTC TGT GGC TTT GTG AAC CGC TGG AAT CCC AAT GTG AAC TGG TTT GTT GGA      922

G   G   S   I   R   N   V   H   S   I   L   P   Q   D   H   T   F   K   S   E       213
GGA GGA AGT ATT CGG AAT GTC CAC TCC ATT CTC CCA CAG GAT CAC ACC TTC AAG AGT GAA      982

L   G   H   Y   M   Y   V   D   S   V   Y   V   K   H   F   Q   E   V   A   Q       233
CTG GGC CAC TAC ATG TAC GTG GAC TCA GTT TAT GTG AAG CAC TTC CAG GAG GTG GCA CAG     1042

L   I   S   P   L   T   T   A   P   M   A   G   C   L   S   F   Y   Y   Q   I       253
CTC ATC TCC CCG TTG ACC ACG GCC CCC ATG GCT GGC TGC CTG TCA TTT TAT TAC CAG ATC     1102

Q   Q   G   N   D   N   V   F   S   L   Y   T   R   D   V   A   G   L   Y   E       273
CAG CAG GGG AAT GAC AAT GTC TTT TCC CTT TAC ACT CGG GAT GTG GCT GGC CTT TAC GAG     1162
```

FIG.4A

```
    E   I   W   K   A   D   R   P   G   N   A   A   W   N   L   A   E   V   E   F    293
   GAA ATC TGG AAA GCA GAC AGG CCA GGG AAT GCT GCC TGG AAC CTT GCG GAG GTC GAG TTC   1222

N   A   P   Y   P   M   E   V   I   F   E   V   A   F   N   G   P   K   G   G    313
   AAT GCT CCT TAC CCC ATG GAG GTT ATT TTT GAA GTT GCT TTC AAT GGT CCC AAG GGA GGT   1282

Y   V   A   L   D   D   I   S   F   S   P   V   H   C   Q   N   Q   T   E   L    333
   TAT GTT GCC CTG GAT GAT ATT TCA TTC TCT CCT GTT CAC TGC CAG AAT CAG ACA GAA CTT   1342

L   F   S   A   V   E   A   S   C   N   F   E   Q   D   L   C   N   F   Y   Q    353
   CTG TTC AGT GCC GTG GAA GCC AGC TGC AAT TTT GAG CAA GAT CTC TGC AAC TTT TAC CAA   1402

D   K   E   G   P   G   W   T   R   V   K   V   K   P   N   M   Y   R   A   G    373
   GAT AAA GAA GGT CCA GGT TGG ACC CGA GTG AAA GTA AAA CCA AAC ATG TAT CGG GCT GGA   1462

D   H   T   T   G   L   G   Y   Y   L   L   A   N   T   K   F   T   S   Q   P    393
   GAC CAC ACT ACA GGC TTA GGG TAT TAC CTG CTA GCC AAC ACA AAG TTC ACA TCT CAG CCT   1522

G   Y   I   G   R   L   Y   G   P   S   L   P   G   N   L   Q   Y   C   L   R    413
   GGC TAC ATT GGA AGG CTC TAT GGG CCC TCC CTA CCA GGA AAC TTG CAG TAT TGT CTG CGT   1582

F   H   Y   A   I   Y   G   F   L   K   M   S   D   T   L   A   V   Y   I   F    433
   TTT CAT TAT GCC ATC TAT GGA TTT TTA AAA ATG AGT GAC ACC CTA GCA GTT TAC ATC TTT   1642

E   E   N   H   V   V   Q   E   K   I   W   S   V   L   E   S   P   R   G   V    453
   GAA GAG AAC CAT GTG GTT CAA GAG AAG ATC TGG TCT GTG TTG GAG TCC CCA AGG GGT GTT   1702

W   M   Q   A   E   I   T   F   K   K   P   M   P   T   K   V   V   F   M   S    473
   TGG ATG CAA GCT GAA ATC ACC TTT AAG AAG CCC ATG CCT ACC AAG GTG GTT TTC ATG AGC   1762

L   C   K   S   F   W   D   C   G   L   V   A   L   D   D   I   T   I   Q   L    493
   CTA TGC AAA AGT TTC TGG GAC TGT GGG CTT GTA GCC CTG GAT GAC ATT ACA ATA CAA TTG   1822

G   S   C   S   S   S   E   K   L   P   P   S   P   G   E   C   T   F   E   Q    513
   GGA AGC TGC TCA TCT TCA GAG AAA CTT CCA CCC TCA CCT GGA GAG TGT ACT TTC GAG CAA   1882

D   E   C   T   F   T   Q   E   K   R   N   R   S   S   W   H   R   R   R   G    533
   GAT GAA TGT ACA TTT ACT CAG GAG AAA AGA AAC CGG AGC AGC TGG CAC AGG AGG AGG GGA   1942

E   T   P   T   S   Y   T   G   P   K   G   D   H   T   T   G   V   G   Y   Y    553
   GAA ACT CCC ACT TCC TAC ACA GGA CCA AAG GGA GAT CAC ACT ACT GGG GTA GGC TAC TAC   2002

M   Y   I   E   A   S   H   M   V   Y   G   Q   K   A   R   L   L   S   R   P    573
   ATG TAC ATT GAG GCC TCC CAT ATG GTG TAT GGA CAA AAA GCA CGC CTC TTG TCC AGG CCT   2062

L   R   G   V   S   G   K   H   C   L   T   F   F   Y   H   M   Y   G   G   G    593
   CTG CGA GGA GTC TCT GGA AAA CAC TGC TTG ACC TTT TTC TAC CAC ATG TAT GGA GGG GGC   2122

T   G   L   L   S   V   Y   L   K   K   E   E   D   S   E   E   S   L   L   W    613
   ACT GGC CTG CTG AGT GTT TAT CTG AAA AAG GAA GAA GAC AGT GAA GAG TCC CTC TTA TGG   2182
```

FIG.4B

|   |   |   |   |   |   |   |   |   |   |   |   |   |   |   |   |   |   |   |   |   |
|---|---|---|---|---|---|---|---|---|---|---|---|---|---|---|---|---|---|---|---|---|
| R | R | R | G | E | Q | S | I | S | W | L | R | A | L | I | E | Y | S | C | E | 633 |
| AGG | AGA | AGA | GGT | GAA | CAG | AGC | ATT | TCC | TGG | CTA | CGA | GCA | CTG | ATT | GAA | TAC | AGC | TGT | GAG | 2242 |
| R | Q | H | Q | I | I | F | E | A | I | R | G | V | S | I | R | S | D | I | A | 653 |
| AGG | CAA | CAC | CAG | ATA | ATT | TTT | GAA | GCC | ATT | CGA | GGA | GTA | TCA | ATA | AGA | AGT | GAT | ATT | GCC | 2302 |
| I | D | D | V | K | F | Q | A | G | P | C | G | E | M | E | D | T | T | Q | Q | 673 |
| ATT | GAT | GAT | GTT | AAA | TTT | CAG | GCA | GGA | CCC | TGT | GGA | GAA | ATG | GAA | GAT | ACA | ACT | CAA | CAA | 2362 |
| S | S | G | Y | S | E | D | L | N | E | I | E | Y | * |   |   |   |   |   |   | 687 |
| TCA | TCA | GGA | TAT | TCT | GAG | GAC | TTA | AAT | GAA | ATT | GAG | TAT | TAA |   |   |   |   |   |   | 2404 |

```
GAAATGATCTGCATTGGATTTACTAGACGAAAACCATACCTCTCTTCAATCAAAATGAAAACAAAGCAAATGAATACTG    2483

GACAGTCTTAACAATTTTATAAGTTATAAAATGACTTTAGAGCACCCTCCTTCATTACTTTTGCAAAAACATACTGACT    2562

CAGGGCTCTTTTTTTTCTTTTTGCATATGACAACTGTTACTAGAAATACAGGCTACTGGTTTTGCATAGATCATTCATCT   2641

TAATTTTGGTACCAGTTAAAAATACAAATGTACTATATTGTAGTCATTTTAAAGTACACAAAGGGCACAATCAAAATGA    2720

GATGCACTCATTTAAATCTGCATTCAGTGAATGTATTGGGAGAAAAATAGGTCTTGCAGGTTTCCTTTTGAATTTTAAG    2799

TATCATAAATATTTTTTAAGTAAATAATACGGGGTGTCAGTAATATCTGCAGAATGAATGCAGTCTTTCATGCTAATGA    2878

GTTAGTCTGGAAAAATAAAGTCTTATTTTCTATGTTTTATTCATAGAAATGGAGTATTAATTTTTAATATTTTCACCAT    2957

ATGTGATAACAAAGGATCTTTCATGAATGTCCAAGGGTAAGTCAGTATTAATTAATGCTGTATTACAAGGCAATGCTAC    3036

CTTCTTTATTCCCCCTTTGAACTACCTTTGAAGTCACTATGAGCACATGGATAGAAATTTAACTTTTTTTTGTAAAGCA    3115

AGCTTAAAATGTTTATGTATACATACCCAGCAACTTTTATAAATGTGTTAAACAATTTTACTGATTTTTATAATAAATA    3194

TTTTGGTAAGATTTTGAATAATATGAATTCAGGCAGATATACTAAACTGCTTTTATTTACTTGTTTAGAAAATTGTATA   3273

TATATGTTTGTGTATCCTAACAGCTGCTATGAAATTATAAAATTACCTAATAAAAATAATTTGAAAATCAAAAAAAAAA    3352

AAAAAAAAAAAAAAAAAAAAAAAAAAAAAAAAAAAAAAAAAAAAAAAAAGGGGGG                           3413
```

FIG.4C

```
GTCGACCCACGCGTCCGCCGGGCTACGAGTGGCCGGACGCTACAGCCTTGCGCAGCGCGCTCTGCTCCTCAGACTCTTC        79

GAATTTGAGCAGCCTGTGGCATCCCCCAGCAGGTCCCCCAGCTCCTTGCCTAGCACCCTCCCTTCCCTAGGAGCAGCGG       158

M   L   L   E   G   V   L         7
GCCACAGTGAGCCAGCAGCCCTCGCGGGTCCTCCTGCCTGAAGTTCAACT ATG CTA CTA GAA GGG GTC CTG        229

L   V   V   Q   A   L   Q   L   A   N   A   L   D   L   P   A   G   S   C   A        27
CTG GTA GTG CAA GCC TTG CAG CTT GCC AAT GCC CTA GAC CTG CCC GCT GGC TCC TGC GCC        289

F   E   E   D   T   C   G   F   D   S   V   F   A   F   L   P   W   I   L   N        47
TTT GAA GAA GAC ACG TGT GGC TTT GAC TCC GTG TTT GCG TTT CTG CCT TGG ATA CTA AAT        349

E   E   G   K   G   T   S   *                                                         55
GAG GAA GGT AAG GGG ACT TCG TAG                                                         373

AAAGATGCTCGAGGTGAACTTTCTTCACGTCTTGTTCCTCCCAACCCCCCGGAAGTAAAGATATCTTGGAGTTACTTCC        452

CTTTGGGAGGAAAAGTGTGTGAGTCATGAAACCTCCTTCCAACTCTCCTGCAGCAAAGAGTGGCCAGGGAAACCACGGG        531

AAAGGGGGCGGAGGGGAACAGCTGTGTACCTGGCTCTGAGCATGCGCTCCTACCCCCAGCACACCCTATTGAAAGGGAC       610

AAAGGGGATTCTGCTAATGATTGTTGCCCCTAGCCGTGTGCCCCCTGCAGGCTGATAGCCTTGCTAGTCTCAGTGGCTA       689

CTTGCCCGAGCTGAGATTGTCAAACGGACTAGCTCACAGGAAGCTTTGCAGAAATTTTCCACACGGTTGTGAGCGTCCT       768

CTGTGCTAAGCTCTCCCACTTTGGTCCACCCACAGCAGTTTTACCTGTGATTCATCCTTTCCCATTGTATCTAATTCAG       847

CACTGGACAAAAGAGTTAACTCCACCACGGAGTCCCTGAAGCCACTGGGCTAGGGCCAATTGATCAGTCACATTACTCT       926

GCACCGCTGGGGTTCCGGTGACAACGTTTAAGTGAAAAGGAGTCTGTGATGTGTTTTCTTACCCTTCATTGTTACAGTA      1005

AAAAAAAAAAAAAAAGGGCGGCCGC                                                             1029
```

FIG.5

```
AGGACAGTCTGCTTGTGGGCTCTGAAAGCTGGGGTGGGGCCAGAGCCTNAGCGNTTAATTTATTCABGHCHHCGYRDAC    79

M   V   S   F   R   K   I   F   I   L   Q   L   V    13
DCGTKKBTCCNACTTAAGGCAACAGC   ATG GTT TCT TTC AGG AAA ATC TTC ATC TTA CAA CTT GTA   144

G   L   V   L   T   Y   D   F   T   N   C   D   F   E   K   I   K   A   A   Y    33
GGG CTG GTG TTA ACT TAC GAC TTC ACT AAC TGT GAC TTT GAG AAG ATT AAA GCA GCC TAT   204

L   S   T   I   S   K   D   L   I   T   Y   M   S   G   T   K   S   T   E   F    53
CTC AGT ACT ATT TCT AAA GAC CTG ATT ACA TAT ATG AGT GGG ACC AAA AGT ACC GAG TTC   264

N   N   T   V   S   C   S   N   R   P   H   C   L   T   E   I   Q   S   L   T    73
AAC AAC ACC GTC TCT TGT AGC AAT CGG CCA CAT TGC CTT ACT GAA ATC CAG AGC CTA ACC   324

F   N   P   T   A   G   C   A   S   L   A   K   E   M   F   A   M   K   T   K    93
TTC AAT CCC ACC GCC GGC TGC GCG TCG CTC GCC AAA GAA ATG TTC GCC ATG AAA ACT AAG   384

A   A   L   A   I   W   C   P   G   Y   S   E   T   Q   I   N   A   T   Q   A   113
GCT GCC TTA GCT ATC TGG TGC CCA GGC TAT TCG GAA ACT CAG ATA AAT GCT ACT CAG GCA   444

M   K   K   R   R   K   R   K   V   T   T   N   K   C   L   E   Q   V   S   Q   133
ATG AAG AAG AGG AGA AAA AGG AAA GTC ACA ACC AAT AAA TGT CTG GAA CAA GTG TCA CAA   504

L   Q   G   L   W   R   R   F   N   R   P   L   L   K   Q   Q   *               150
TTA CAA GGA TTG TGG CGT CGC TTC AAT CGA CCT TTA CTG AAA CAA CAG TAA               555

ACCATCTTTATTATGGTCATATTTCACAGCACCAAAATAAATCATCTTTATTAAGTAGATGAAACATTAACTCTAACTG    634

TGACAAAGAAGACCACAAATAGTTATCTTTTAATTACAGAAGAGTTTCTTAACTTACTTTTGTAAGTTTTTATTGTGTA    713

AGTTTATAATGCAGGGGAAGTACTACTCCTCAAATGTTGAGGGAAGCTTCCATAACATTGATGACTGGCTTCATGGCAG    792

NAATTCTCGGCTGTAGTTGCATAAGCATTGCTCAAGAGGAAAATCCAAAAGTGCAGCAGGAGAACTCTTTTCCCTGAAA    871

AAGGAAAAATATTGAACTCAATGATAGCACCTAAACTTACATTTTAAAAGACAGACATTCCTTCTACATGTAATGACACT    950

TCTTGTGTTAAACTAAAAATTTACAAGAGAAGAAAGTGAAAGCAAATGGGGTTTCACAAATAGTTGTAAATATAGTGAA   1029

GCAATTTGAAATAATTTTTCAAGCAAAGTATTGTGAAAGTATTCTAAGCCAAGTTTTAAATATTATCTAACAGACAAGAG   1108

TGGTATATACAAGTAGATCCTGAGAAGTACCTTTGTTACAGCTACTATAAATATACATATAAATTATAGAATCTACTTT   1187

AATTTATTTTGTGAACACTTTTGAAAATGTACATGTTCCTTTGTAATTGACACTATATATTTCTTAATAAAATAATTCT   1266

```
         L   I   P   D   T   F   L   V   S   F   P   P   I   P   I   P   F   P   V    19
       T CTG ATA CCA GAC ACC TTC CTG GTG TCT TTC CCT CCT ATC CCC ATC CCC TTC CCT GTC    58

P   F   I   Q   F   L   I   S   G   G   F   N   L   L   S   L   S   N   C   A  39
       CCT TTC ATT CAA TTT TTA ATA TCT GGC GGT TTT AAT CTT CTC TCT CTC TCG AAC TGT GCC 118

A   C   E   Q   P   A   C   L   L   K   I   E   Y   Y   T   L   N   P   I   P  59
       GCT TGT GAG CAG CCA GCT TGT CTC CTG AAA ATC GAG TAT TAT ACT CTC AAT CCT ATC CCT 178

G   C   P   S   L   P   D   K   T   F   A   R   R   T   R   E   A   L   N   D  79
       GGC TGC CCT TCA CTC CCC GAC AAA ACA TTT GCC CGG AGA ACA AGA GAA GCC CTC AAT GAC 238

H   C   P   G   Y   P   E   T   E   R   N   D   G   T   Q   E   M   A   Q   E  99
       CAC TGC CCA GGC TAC CCT GAA ACT GAG AGA AAT GAC GGT ACT CAG GAA ATG GCA CAA GAA 298

V   Q   N   I   C   L   N   Q   T   S   Q   I   L   R   L   W   Y   S   F   M 119
       GTC CAA AAC ATC TGT CTG AAT CAA ACC TCA CAA ATT CTA AGA TTG TGG TAT TCC TTC ATG 358

Q   S   P   E   *                                                              124
       CAA TCT CCA GAA TAA                                                              373
       AATTAGCTTTCAGCTTCTGCTATG                                                         397
```

FIG.8

```
GTCGACCCACGCGTCCGCTTGGGGATCCCTCAGCTTAACACCCACAGACATCGGCTGGTGGATTCCCGCTGCATCAAGG      79
                               M   L   G   S   P   C   L   L   W   L   L   A   V   T   F    15
        CCTACCCACTGTCTCC ATG CTG GGC TCT CCC TGC CTT CTG TGG CTC CTG GCC GTG ACC TTC      140
 L   V   P   R   A   Q   P   L   A   P   Q   D   F   E   E   E   E   D   E    35
TTG GTT CCC AGA GCT CAG CCC TTG GCC CCT CAA GAC TTT GAA GAA GAG GAA GAA GAT GAG           200
 T   E   T   A   W   P   P   L   P   A   V   P   C   D   Y   D   H   C   R   H    55
ACT GAG ACG GCG TGG CCG CCT TTG CCG GCT GTC CCC TGC GAC TAC GAC CAC TGC CGA CAC           260
 L   Q   V   P   C   K   E   L   Q   R   A   G   P   A   A   C   L   C   P   G    75
CTG CAG GTG CCC TGT AAG GAG CTA CAG AGG GCC GGG CCG GCG GCC TGC CTG TGC CCA GG            320
 L   S   S   P   A   Q   P   P   D   P   P   R   M   G   E   V   S   I   V   A    95
CTC TCT AGC CCT GCC CAG CCG CCC GAC CCG CCG CGC ATG GGA GAA GTG AGC ATT GTG GCC           380
 E   E   G   R   A   V   V   H   W   C   A   P   F   S   P   V   L   H   Y   W   115
GAA GAG GGC CGC GCA GTG GTC CAC TGG TGT GCC CCC TTC TCC CCG GTC CTC CAC TAC TGG           440
 L   L   L   W   D   G   S   E   A   Q   K   G   P   S   L   N   A   T   V       135
CTG CTG CTT TGG GAC GGC AGC GAG GCT GCG CAG AAG GGG CCC TCG CTG AAC GCT ACG GTC           500
 R   R   A   E   L   K   G   L   K   P   G   G   V   Y   V   V   C   V   V   A   155
CGC AGA GCC GAA CTG AAG GGG CTG AAG CCA GGG GGC GTT TAT GTC GTT TGC GTG GTG GCC           560
 A   N   E   A   G   A   S   R   V   P   E   A   G   R   E   G   L   E   G   A   175
GCT AAC GAG GCT GGG GCA AGC CGC GTG CCT GAG GCT GGA AGA GAG GGC CTC GAG GGG GCC           620
 D   I   P   A   F   G   P   C   S   R   F   A   V   P   P   N   P   R   T   L   195
GAC ATC CCT GCC TTC GGG CCT TGC AGC CGC TTT GCA GTG CCG CCC AAC CCC CGC ACT CTG           680
 V   H   A   A   V   G   V   G   T   A   L   A   L   L   S   C   A   A   L   V   215
GTC CAC GCC GCC GTC GGG GTG GGC ACG GCC CTG GCC CTG CTG AGC TGT GCC GCC CTG GTG           740
 W   H   F   C   L   R   D   R   W   G   C   P   R   R   A   V   A   R   A   A   235
TGG CAC TTC TGC CTA CGC GAT CGC TGG GGC TGC CCG CGC CGA GCC GTC GCC CGA GCA GCA           800
 G   A   L   *                                                                    238
GGG GCG CTC TGA                                                                   812
AAGGGGCCTGGGGGCATCTCGGGCACAGCCAGCCCCACCTGCGGCGTTCAGCCCGGCTCCTGGAAAGAGGGGAACCCGC   891
TGCCTCCAGGGAGGGTTGGACGGTGAGCTGGGAGCCAGCCCCAGGCTCTAGAGCCACAGCAGAGTCATGGTTCTCTGGG   970
CTGAGCGCTTGTTTAGGTCCGGAACTTGGTGCTGTTTCCTGGCTGAGGTCTGGGAAAGAATAGAAAGGGGCCCCCAATT  1049
TTTCTTTTTTAACGGTCAGATAGTAAATAATGTAACCTTTGCGGTTTAAGAGGATAAAATGGAGAATATTATGTGGGTA  1128
TTTATATGACCTTTGTAACCATTTATAAAGGAAAAACCACACGACATAGTAATGCGAACCTAGAGTAGCAGCTACTCCG  1207
GAAGCTGAAATGGGAGGATCTCTTGAGCCCAGGAGTTTGAGTCCAGTCCAGCCAGGGCAACACAGCCAGACGCCCTTGT  1286
GTTTTGTTTTGTTTTGTTTTTTGAGAAGAAGTCTCCCTCTGTTACACAGGGTGGATTGCAATGACACGATATATGTCGG  1365
TTCACTGCAACCTCCACCTCCTAGGTTCAAGTGATTCTCCCGTATCAGCATCCTAAGTAGTTGGGGTTACAGGTGCCCA  1444
CGACCATGCCCGGCTAATTATTGTGTTTTTTTAGTAGAGATGGGTTTTCACCATGTTGGTCAGCCTGGTCTCAAACTCC  1523
TGACCTCAGGTACTCCACCCACCTTGGCCTCCCAAAGTGCTGGGATTACAGGCGTGAGCCACGGTGCCCAGGCAGACCC  1602
CCTTCTTTAAAGATGTAAAATCATTCTTAGTCCGTGGGCCTTACAAATCAGGTCACTGGCCCATTGCTTGTAGTTAGTT  1681
GATCCATATCATGCACCCTCAAAACGGCTCTGTCAATGAGTGTCTTCAGTGGGATTCTGAGAATAAATTTATATTCTTG  1760
CTAGGTAGAACAAAACAAAAATGACAGTAATATCAAGGAATTTCTCATCCCTTTTTTTCCCTCCATTTGTATTTATTGC  1839
ATATCCACTGTAAAAACATTAAAGGATCTTTAAAAGAAAAAAAAAAAAAAAAAAAAAAAAAAAAAAAAAAAAAAAAAAA  1918
AAAAAAAAGGGGCGGCCGC                                                               1937
```

FIG. 9

```
                1                                                              50
Macaque    MLGSPCLLWL  LAV.TFLVPR  AQPIapqdfe  eeeedeteta  wpplpavpcd
Rabbit     MLGSPCFLWL  LIM.TFLVPR  AQFIasqdse  eegdd..qps  lppsravycd
Mouse      MLGSLSLLWL  AAMTTSLVSq  pqiltledyq  egeeddvtva  tpsl.avrcd
   cons    MLGSpclLWL  lam.TfLVpr  aQ.la.qd.e  eeeed....a  .ppl.av.cd 51                                                             100
Macaque    ydhcrhlqvp  ckelqragpa  aclcpglssp  aqppdpprmg  evsivaeegr
Rabbit     ydrcrhlqvp  cqelqkaepv  pclcpglssp  dqqpeqprlg  evhvvaexgr
Mouse      ydrcrhlqvs  cqelqkvgpv  aclcpglsre  dqqpepprlg  rsanng~~~
   cons    ydrcrhlqvp  cqelqkagpv  aclcpglssp  dqqpepprlg  ev..vae.gr 101                                       139
Macaque    avvhwcapfs  pvlhywlllw  dgkrglrrrg  pr~~~~~
Rabbit     alvhwcapss  pvlqywlllw  e.xngdpwkg  tnlnahgpq
Mouse      ~~~~~~~~~~  ~~~~~~~~~~  ~~~~~~~~~~  ~~~~~~~~
   cons    a.vhwcap.s  pvl.ywlllw  ....g....g  ..~~~~~
```

FIG. 11

```
  V   D   P   R   V   R   E   A   A   Q   K   G   P   P   L   N   A   T   V   R      20
GTC GAC CCA CGC GTC CGC GAG GCT GCG CAG AAG GGG CCC CCG CTG AAC GCT ACG GTC CGC      60
  R   A   E   L   K   G   L   K   P   G   G   I   Y   V   V   C   V   V   A   A      40
AGA GCC GAA CTG AAG GGG CTG AAG CCA GGG GGC ATT TAT GTC GTT TGC GTA GTG GCC GCT     120
  N   E   A   G   A   S   R   V   P   Q   A   G   G   E   G   L   E   G   A   D      60
AAC GAG GCC GGG GCA AGC CGC GTG CCC CAG GCT GGA GGA GAG GGC CTC GAG GGG GCC GAC     180
  I   P   A   F   G   P   C   S   R   L   A   V   P   P   N   P   R   T   L   V      80
ATC CCT GCC TTC GGG CCT TGC AGC CGC CTT GCG GTG CCG CCC AAC CCC CGC ACT CTG GTC     240
  H   A   A   V   G   V   G   T   A   L   A   L   L   S   C   A   A   L   V   W     100
CAC GCG GCC GTC GGG GTG GGC ACG GCC CTG GCC CTG CTA AGC TGT GCC GCC CTG GTG TGG     300
  H   F   C   L   R   D   R   W   G   C   P   R   R   A   A   A   R   A   A   G     120
CAC TTC TGC CTG CGC GAT CGC TGG GGC TGC CCG CGC CGA GCC GCC GCC CGA GCC GCA GGG     360
  A   L   *                                                                          122
GCG CTC TGA                                                                          369
AAGGGGCCTGGGGGCATCTCGGGCACAGACAGCCCCACCTGGGGCGCTCAGCCTGGCCCCCGGGAAAGAGGAAAACCCG     448
CTGCCTCCAGGGAGGGCTGGACGGCGAGCTGGGAGCCAGCCCCAGGCTCCAGGGCCACGGCGGAGTCATGGTTCTCAGG     527
ACTGAGCGCTTGTTTAGGTCCGGTACTTGGCGCTTTGTTTCCTGGCTGAGGTCTGGGAAGGAATAGAAAGGGGCCCCCA     606
ATTTTTTTTTAAGCGGCCAGATAATAAATAATGTAACCTTTGCGGTTTAAGAGGATAAAATGGAGGATATTATTATGTG     685
GGTATTTATATGACCTTTGTAACCATTTAAAAATGTAAAAACGACCTGACTTAGTAATGCGAACCTATAGTAGCAGCTA     764
CTCCAGAGGCTGAAATGGGAGGATCTCTTGAGCCCAGGAGTTGGAGTCCAGTCCAGCCAGGGCAACACAGCCAGACGCC     843
CTTGTTTTTTATTTTGTTTTGTTTTGGTTTTTTGTTTTTTGAGGAGTTTCCCTCTGTCACACAAGCTGGAGGGCAATGG     922
CGCCATCTCAGCTCACTGCAACGTCCACCTCCTGGGTTCAGGCGATTCTCCTGCCTCAGCATCCTAATTGGTGGGTACC    1001
TGTGGTCCCAGCTACTCCGGAGGCTGAGGCAGGAGAATGGCGTGGGCCCGGGAGGCGGATCTTGCAGTGAGCGGAGATT    1080
GCGCCACTGCACTCCAGCCTGGGTGACAGAGCAAGACTCCCTCTCAAAAGAAAAAGAAAAAAGATGTAAAAACCATTCT    1159
TAGTTTGTGGGCCTTACAAATCAGGCCACTGGCCCATTGCTTGTAGTTAGTTGATCCATGTCATGCACCCTAAAAATGG    1238
CTCTGTCACTGTGAGTGGCTTCAGTAGGATTTTGAGAATAAGTTTATATTCTTGCTAGGTAAAACAAAACAAAAACGAC    1317
AGTAATACCAAGGAATCTCCCCCCCCTTTTACCCTCCATTTGTGTTTATTGCATATCCACTATAACAACATTAAAGGAC    1396
CTTTAAAAGGAAAAAAAAAAAAAAAAAAAAAAAAAAAAAAAAAAAAAAAAAAAAGGGGCGGCCGC                  1459
```

FIG. 12

```
                                        10          20          30          40
Human                            GTCGACCCACGCGTCCGCGAGGCTGCGCAGAAGGGGCCCC
                                .X: : :::::::::::::::::::::::::::::::::::
Macaque  CGGTCCTCCACTACTGGCTGCTGCTTTGGGACGGCAGCGAGGCTGCGCAGAAGGGGCCCT
             430         440         450         460         470         480

50          60          70          80          90          100
Human     CGCTGAACGCTACGGTCCGCAGAGCCGAACTGAAGGGGCTGAAGCCAGGGGGCATTTATG
          ::::::::::::::::::::::::::::::::::::::::::::::::::::.:::::
Macaque   CGCTGAACGCTACGGTCCGCAGAGCCGAACTGAAGGGGCTGAAGCCAGGGGGCGTTTATG
             490         500         510         520         530         540

110         120         130         140         150         160
Human     TCGTTTGCGTAGTGGCCGCTAACGAGGCCGGGGCAAGCCGCGTGCCCCAGGCTGGAGGAG
          :::::::::.:::::::::::::::::: :::::::::::::::: :::::::::.:::
Macaque   TCGTTTGCGTGGTGGCCGCTAACGAGGCTGGGGCAAGCCGCGTGCCTGAGGCTGGAAGAG
             550         560         570         580         590         600

170         180         190         200         210         220
Human     AGGGCCTCGAGGGGGCCGACATCCCTGCCTTCGGGCCTTGCAGCCGCCTTGCGGTGCCGC
          :::::::::::::::::::::::::::::::::::::::::::::::.:::::.:::::
Macaque   AGGGCCTCGAGGGGGCCGACATCCCTGCCTTCGGGCCTTGCAGCCGCTTTGCAGTGCCGC
             610         620         630         640         650         660

230         240         250         260         270         280
Human     CCAACCCCCGCACTCTGGTCCACGCGGCCGTCGGGGTGGGCACGGCCCTGGCCCTGCTAA
          ::::::::::::::::::::::::::::.:::::::::::::::::::::::::::::.
Macaque   CCAACCCCCGCACTCTGGTCCACGCCGCCGTCGGGGTGGGCACGGCCCTGGCCCTGCTGA
             670         680         690         700         710         720

290         300         310         320         330         340
Human     GCTGTGCCGCCCTGGTGTGGCACTTCTGCCTGCGCGATCGCTGGGGCTGCCCGCGCCGAG
          ::::::::::::::::::::::::::::::::::.:::::::::::::::::::::::
Macaque   GCTGTGCCGCCCTGGTGTGGCACTTCTGCCTACGCGATCGCTGGGGCTGCCCGCGCCGAG
             730         740         750         760         770         780

350         360         370         380         390         400
Human     CCGCCGCCCGAGCCGCAGGGGCGCTCTGAAAGGGGCCTGGGGGCATCTCGGGCACAGACA
          ::: :::::::::::.::::::::::::::::::::::::::::::::::::::::.::
Macaque   CCGTCGCCCGAGCAGCAGGGGCGCTCTGAAAGGGGCCTGGGGGCATCTCGGGCACAGCCA
             790         800         810         820         830         840
```

FIG.13A

```
         410       420       430       440       450       460
Human    GCCCCACCTGGGGCGCTCAGCCTGGCCCCCGGGAAAGAGGAAAACCCGCTGCCTCCAGGG
         ::::::::::  ::::  ::::::: ::: ::  :::::::::,:::::::::::::::
Macaque  GCCCCACCTGCGGCGTTCAGCCCGGCTCC-TGGAAAGAGGGGAACCCGCTGCCTCCAGGG
         850       860       870       880       890       900

470       480       490       500       510       520
Human    AGGGCTGGACGGCGAGCTGGGAGCCAGCCCCAGGCTCCAGGGCCACGGCGGAGTCATGGT
         :::: :::::::: :::::::::::::::::::::::: ::::: ::: ::::::::::
Macaque  AGGGTTGGACGGTGAGCTGGGAGCCAGCCCCAGGCTCTAGAGCCACAGCAGAGTCATGGT
         910       920       930       940       950       960

530       540       550       560       570       580
Human    TCTCAGGACTGAGCGCTTGTTTAGGTCCGGTACTTGGCGCTTTGTTTCCTGGCTGAGGTC
         ::::: :: ::::::::::::::::::::: ::::: :::  :::::::::::::::::
Macaque  TCTCTGGGCTGAGCGCTTGTTTAGGTCCGGAACTTGGTGCT--GTTTCCTGGCTGAGGTC
         970       980       990       1000      1010      1020

590       600       610       620       630
Human    TGGGAAGGAATAGAAAGGGGCCCCCAATTTTT--TTTTAAGCGGCCAGATAATAAATAAT
         :::::: ::::::::::::::::::::::::::   ::::  ::::::: :::::::::
Macaque  TGGGAAAGAATAGAAAGGGGCCCCCAATTTTTTCTTTTTTAACGGTCAGATAGTAAATAAT
         1030      1040      1050      1060      1070      1080

640       650       660       670       680       690
Human    GTAACCTTTGCGGTTTAAGAGGATAAAATGGAGGATATTATTATGTGGGTATTTATATGA
         ::::::::::::::::::::::::::::::::::: ::::: ::  ::::::::::::::
Macaque  GTAACCTTTGCGGTTTAAGAGGATAAAATGGAGAATATTAT--GTGGGTATTTATATGA
         1090      1100      1110      1120      1130

700       710       720       730       740       750
Human    CCTTTGTAACCATTTAAAAATGTAAAAACGACCTGACTTAGTAATGCGAACCTATAGTAG
         :::::::::::::::: :::: ::::::: ::::: ::::::::::::::::: :::::
Macaque  CCTTTGTAACCATTTATAAA-GGAAAAACCACACGACATAGTAATGCGAACCTAGAGTAG
         1140      1150      1160      1170      1180      1190

760       770       780       790       800       810
Human    CAGCTACTCCAGAGGCTGAAATGGGAGGATCTCTTGAGCCCAGGAGTTGGAGTCCAGTCC
         :::::::::: :: ::::::::::::::::::::::::::::::::::: ::::::::::
Macaque  CAGCTACTCCGGAAGCTGAAATGGGAGGATCTCTTGAGCCCAGGAGTTTGAGTCCAGTCC
         1200      1210      1220      1230      1240      1250

820       830       840       850       860       870
Human    AGCCAGGGCAACACAGCCAGACGCCCTTGTTTTTTTATTTTGTTTTGTTTTGGTTTTTTGT
         :::::::::::::::::::::::::::::::: :::::::::::::::::::
Macaque  AGCCAGGGCAACACAGCCAGACGCCCTTGTGTTTTGTTTTGTTTTGTTTT------
         1260      1270      1280      1290      1300
```

FIG.13B

```
         880       890       900       910       920       930
Human    TTTTTGAGGAGTTTCCCTCTGTCACACAAGCTGGAGGGCAATGGCGCCATCT---CAGC
         ::  .:::::: :::::::::: :::::: :::: :::::::::::: ::   ..:
Macaque  TTGAGAAGAAGTCTCCCTCTGTTACACAGGGTGGATTGCAATGACACGATATATGTCGGT
         1310      1320      1330      1340      1350      1360

940       950       960       970       980       990
Human    TCACTGCAACGTCCACCTCCTGGGTTCAGGCGATTCTCCTGCCTCAGCATCCTAATTGGT
         :::::::::: :::::::::::: :::::: ::::::::  : :::::::::: : :::
Macaque  TCACTGCAACCTCCACCTCCTAGGTTCAAGTGATTCTCCCGTATCAGCATCCTAAGTAGT
         1370      1380      1390      1400      1410      1420

1000      1010      1020      1030      1040
Human    --GGGTACCTGTGGTCC-CAGC--TACTCCGG---AGGCTGAGGCAGGAGAATGGCG-T
          :::.  :::  ::  :::  .: : ::::    .  :::  .  ..:.: ::
Macaque  TGGGGTTACAGGTGCCCACGACCATGC-CCGGCTAATTATTGTGTTTTTTTAGTAGAGAT
         1430      1440      1450      1460      1470      1480

1050      1060      1070      1080
Human    GGG---C-CCGGGAGG------CGGATCT-------TGCAGTGAGCGGAGATTGCGCC-AC
         :::    .   :: .:      : :.:         :  : .:.  ..   : :..:
Macaque  GGGTTTTCACCATGTTGGTCAGCCTGGTCTCAAACTCCTGACCTCAGGTACTCCACCCAC
         1490      1500      1510      1520      1530      1540

1090      1100      1110      1120      1130
Human    -TGCACTCC--------AGCCTGGGTGACAGA-GCAAGACTC-------CCTCTCAAAAGAAAA
         ::  ::::       ...   ::::  ::::.  .  ::: :::       ::.:
Macaque  TTGGCCTCCCAAAGTGCTGGGATTACAGGCGTGAGCCACGGTGCCCAGGCAGACCCCCT
         1550      1560      1570      1580      1590      1600

1140      1150      1160      1170      1180      1190
Human    AGAAAAAAGATGTAAAAACCATTCTTAGTTTGTGGGCCTTACAAATCAGGCCACTGGCCC
         .  .::::.::::::::  ::::::::  : ::::::::::::::::: :::::::::
Macaque  TCTTTAAAGATGTAAAATC-ATTCTTAGTCCGTGGGCCTTACAAATCAGGTCACTGGCCC
         1610      1620      1630      1640      1650      1660

1200      1210      1220      1230      1240      1250
Human    ATTGCTTGTAGTTAGTTGATCCATGTCATGCACCCTAAAAATGGCTCTGTCACTGTGAGT
         :::::::::::::::::::::::: :::::::::::  ::  :::::::::  :::::
Macaque  ATTGCTTGTAGTTAGTTGATCCATATCATGCACCCTCAAAACGGCTCTGTCA--ATGAGT
         1670      1680      1690      1700      1710      1720

1260      1270      1280      1290      1300      1310
Human    GGCTTCAGTAGGATTTTGAGAATAAGTTTATATTCTTGCTAGGTAAAACAAAACAAAAAC
         : :::::::.:::: :::::::::: ::::::::::::::::: :::.:::::::::: 
Macaque  GTCTTCAGTGGGATTCTGAGAATAAATTTATATTCTTGCTAGGTAGAACAAAACAAAAAT
         1730      1740      1750      1760      1770      1780
```

FIG. 13C

```
              1320      1330      1340      1350      1360      1370
Human    GACAGTAATACCAAGGAATCTCCCCCCCCTTTTA---CCCTCCATTTGTGTTTATTGCATA
         ::::::::::  :::::::::  ::  :    :::::::::.  ::::::::::::.::::::::::
Macaque  GACAGTAATATCAAGGAATTTCTCATCCCTTTTTTTCCCTCCATTTGTATTTATTGCATA
              1790      1800      1810      1820      1830      1840

1380      1390      1400      1410      1420      1430
Human    TCCACTATAACAACATTAAAGGACCTTTAAAAGGAAAAAAAAAAAAAAAAAAAAAAAAAA
         :::::::.::: ::::::::::::: ::::::::::.::::::::::::::v::::::::::
Macaque  TCCACTGTAAAAACATTAAAGGATCTTTAAAAGAAAAAAAAAAAAAAAAAAAAAAAAAAA
              1850      1860      1870      1880      1890      1900

1440      1450
Human    AAAAAAAAAAAAAAAA--------GGGGCGGCCGC
         :::::::::::::::::^       :::::::::::
Macaque  AAAAAAAAAAAAAAAAAAAAAAAAAGGGGCGGCCGC
              1910      1920      1930
```

FIG.13D

```
                                              10        20        30
Human                                EAAQKGPPLNATVRRAELKGLKPGGIYVVC
                                     X:::::::::::::::::::::::::::::
Macaque  IVAEEGRAVVHWCAPFSPVLHYWLLLWDGSEAAQKGPSLNATVRRAELKGLKPGGVYVVC
         100       110       120       130       140       150

40        50        60        70        80        90
Human    VVAANEAGASRVPQAGGEGLEGADIPAFGPCSRLAVPPNPRTLVHAAVGVGTALALLSCA
         ::::::::::::::: ::  ::::::::::::::: :::::::::::::::::::::::
Macaque  VVAANEAGASRVPEAGREGLEGADIPAFGPCSRFAVPPNPRTLVHAAVGVGTALALLSCA
         160       170       180       190       200       210

100       110
Human    ALVWHFCLRDRWGCPRRAAARAAGAL
         :::::::::::::::::: :::::::
Macaque  ALVWHFCLRDRWGCPRRAVARAAGAL
         220       230
```

FIG.14

```
GTCGACCCACGCGTCCGGCACAGCCTGAGATCTTGGGGATCCCTCAGCCTAACACCCACAGACGTCAGCTGGTGGATTC  79
                                          M   L   G   S   P   C   L   L   W   L   L   A    12
CCGCTGCATCAAGGCCTACCCACTGTCTCC ATG CTG GGC TCT CCC TGC CTT CTG TGG CTC CTG GCC  145

V   T   F   L   V   P   R   A   Q   P   L   A   P   Q   D   F   E   E   E   E    32
GTG ACC TTC TTG GTT CCC AGA GCT CAG CCC TTG GCC CCT CAA GAC TTT GAA GAA GAG GAG  205

A   D   E   T   E   T   A   W   P   P   L   P   A   V   P   C   D   Y   D   H    52
GCA GAT GAG ACT GAG ACG GCG TGG CCG CCT TTG CCG GCT GTC CCC TGC GAC TAC GAC CAC  265

C   R   H   L   Q   V   P   C   K   E   L   Q   R   V   G   P   A   A   C   L    72
TGC CGA CAC CTG CAG GTG CCC TGC AAG GAG CTA CAG AGG GTC GGG CCG GCG GCC TGC CTG  325

C   P   G   L   S   S   P   A   Q   P   P   D   P   P   R   M   G   E   V   R    92
TGC CCA GGA CTC TCC AGC CCC GCC CAG CCG CCC GAC CCG CCG CGC ATG GGA GAA GTG CGC  385

I   A   A   E   E   G   R   A   V   V   H   W   C   A   P   F   S   P   V   L   112
ATT GCG GCC GAA GAG GGC CGC GCA GTG GTC CAC TGG TGT GCC CCC TTC TCC CCG GTC CTC  445

H   Y   W   L   L   L   W   D   G   S   E   A   A   Q   K   G   P   P   L   N   132
CAC TAC TGG CTG CTG CTT TGG GAC GGC AGC GAG GCT GCG CAG AAG GGG CCC CCG CTG AAC  505

A   T   V   R   R   A   E   L   K   G   L   K   P   G   G   I   Y   V   V   C   152
GCT ACG GTC CGC AGA GCC GAA CTG AAG GGG CTG AAG CCA GGG GGC ATT TAT GTC GTT TGC  565

V   V   A   A   N   E   A   G   A   S   R   V   P   Q   A   G   G   E   G   L   172
GTA GTG GCC GCT AAC GAG GCC GGG GCA AGC CGC GTG CCC CAG GCT GGA GGA GAG GGC CTC  625

E   G   A   D   I   P   A   F   G   P   C   S   R   L   A   V   P   P   N   P   192
GAG GGG GCC GAC ATC CCT GCC TTC GGG CCT TGC AGC CGC CTT GCG GTG CCG CCC AAC CCC  685

R   T   L   V   H   A   A   V   G   V   G   T   A   L   A   L   L   S   C   A   212
CGC ACT CTG GTC CAC GCG GCC GTC GGG GTG GGC ACG GCC CTG GCC CTG CTA AGC TGT GCC  745

A   L   V   W   H   F   C   L   R   D   R   W   G   C   P   R   R   A   A   A   232
GCC CTG GTG TGG CAC TTC TGC CTG CGC GAT CGC TGG GGC TGC CCG CGC CGA GCC GCC GCC  805

R   A   A   G   A   L   *                                                       239
CGA GCC GCA GGG GCG CTC TGA                                                       826
AAGGGGCCTGGGGGCATCTCGGGCACAGACAGCCCCACCTGGGGCGCTCAGCCTGGCCCCCGGGAAAGAGGAAAACCCG  905
CTGCCTCCAGGGAGGGCTGGACGGCGAGCTGGGAGCCAGCCCCAGGCTCCAGGGCCACGGCGGAGTCATGGTTCTCAGG  984
ACTGAGCGCTTGTTTAGGTCCGGTACTTGGCGCTTTGTTTCCTGGCTGAGGTCTGGGAAGGAATAGAAAGGGGCCCCCA 1063
ATTTTTTTTTAAGCGGCCAGATAATAAATAATGTAACCTTTGCGGTTTAAAAAAAAAAAAAAAAAAGGGCGGCCGC    1136
```

FIG.15

```
CGTCCGGGCCTCTCCGCCTGATAGCCACGGATATCTGGGGGCAAACCCTCACTGTGACGAGGCCTACCCACTGACTCC  78

M   L   G   S   L   S   L   L   W   L   A   A   M   T   T   S   L   V   S   Q    20
ATG TTG GGC TCT CTT TCC CTT CTG TGG CTG GCA GCC ATG ACC ACC TCC TTG GTT TCC CAA  138

P   Q   I   L   T   L   E   D   Y   Q   E   G   E   E   D   D   V   T   V   A    40
CCT CAG ATC TTG ACC CTG GAA GAC TAC CAG GAA GGG GAA GAG GAT GAT GTG ACA GTA GCT  198

T   P   S   L   A   V   R   C   D   Y   D   R   C   R   H   L   Q   V   S   C    60
ACA CCT TCC TTA GCT GTC CGT TGC GAC TAT GAC CGT TGC CGC CAC CTG CAG GTG TCC TGC  258

Q   E   L   Q   K   V   G   P   V   A   C   L   C   P   G   L   S   R   E   D    80
CAG GAG CTG CAG AAG GTT GGG CCA GTA GCC TGC CTG TGC CCA GGG CTC TCC AGG GAA GAT  318

Q   Q   P   E   P   P   R   L   G   E   V   Q   I   M   A   E   E   G   Y   A   100
CAA CAG CCA GAG CCT CCT CGC CTG GGA GAA GTG CAA ATA ATG GCT GAA GAA GGC TAC GCA  378

V   V   H   W   C   A   P   F   S   P   V   S   H   Y   W   L   L   L   W   E   120
GTG GTT CAC TGG TGT GCT CCC TTC TCT CCA GTC AGC CAC TAC TGG CTT CTG CTT TGG GAA  438

S   N   G   A   P   Q   K   S   A   P   L   N   A   T   V   R   R   A   E   L   140
AGC AAC GGG GCT CCA CAG AAG AGT GCC CCT CTC AAT GCT ACA GTT CGA AGA GCA GAG CTG  498

K   G   L   K   P   G   V   A   Y   V   L   C   V   V   A   A   N   D   A   G   160
AAG GGA CTA AAG CCT GGG GTT GCT TAT GTC CTT TGC GTG GTG GCT GCT AAT GAC GCA GGT  558

E   S   N   V   P   G   A   E   V   E   G   P   E   N   W   T   G   P   S   F   180
GAG AGC AAT GTT CCT GGG GCA GAA GTC GAG GGT CCT GAG AAC TGG ACT GGC CCT TCC TTT  618

G   P   C   R   K   F   I   M   P   P   K   P   V   T   L   V   Y   A   A   V   200
GGG CCC TGT CGC AAG TTT ATC ATG CCG CCT AAG CCT GTT ACC CTG GTC TAT GCA GCC GTG  678

G   V   G   T   A   L   A   L   L   S   C   A   A   L   V   W   H   F   C   L   220
GGA GTG GGC ACA GCC TTA GCT CTG CTG AGC TGT GCA GCC CTG GTT TGG CAT TTC TGC CTT  738

R   E   R   W   G   C   P   R   R   Q   G   M   A   Q   A   S   E   A   L   *   240
CGT GAG CGA TGG GGT TGC CCC CGA CGT CAA GGT ATG GCC CAA GCG TCA GAA GCT CTC TGA  798

CAGGAGTCCCCTCGACTACAAACAACTCATCTGGAGAGCCCAACCCACTCCCAGGAGGAGTGTGGGGCTTGTTGCCACC   877

TGGCAACCAGAGGCACAGCCAAGCCAGAGCGGAAGCCCAGGCAATTAGCCTCAGCACTGAGGGCTTGGTTAGTCCCTAA   956

CTGGTCACTATGTTCCTTCCCTGTTGGGGGTTAGAAAAAGTAGCAATTATTCCTTGGAGGTCTGATGAAAATGATTTAA  1035
```

FIG.16A

```
GCTTTATGGGTTTGAAGGGGTAAAATTACAGACATTATACATGAACTTATATATAGCCAGTTAAAATGGAGCTATTTAA    1114
AGGCCTGGCATGGTGGTTTACAATTTTGGTCTCCAGCGCCCTGGAGGCAGAGGCAGGCGGATCTGAGTTTCCGGGGCAG    1193
CCTGATCTACATAGAAAGATTCCAGGCCAACCCAGATAATATAGTGAGACCCTGTCTCAAAAAGAGTAAAACAGAAGCA    1272
AAACAAACAAAAGGTGGGGCGGGATAGAGAGATTGTTCAGCAGTTAAGAATACTGGCTATTTTTCCAGAGGACAGAATT    1351
TTATTCCTAGCATCCACATGGCAGCTCACAACCATCTGTAATTCCATTTCCAGGAGATCCAGTGTCTAATTCTGACCTC    1430
TGCCAGCATCAGGCACATACATACGCACACATACATACATACATACATACATACACACACACACACACACACACACACA    1509
CACAGAGAGAGACAAAACACTCATACACATAAAATAAAAATTAATTTGAAGTGTAGCTGTTTAAAAATGTAAACTGTTC    1588
ATAGCTCATAGGTCTCTCACAGCAAGCAGCAGACTACATTTGGCCTGTTGGCTGATTTGCCAACACCTATCATTCTCAA    1667
AGGGACTTTGTGACTGTCGGTGGCTTCCCTGCATATTTTGAGAATAAGCTGAGTTTTGCCAACACCTGTTATTCTGAAA    1746
AGGACTCTGCGACTGTGGGTGGCTTCCACGCATGTTTTGAGAATAAGCAGGGTAGATGTGGAGACTGGAGCTCTGTCTT    1825
TCTGCTACTTGTTGTTTCCTTCCTAAGGATGATCCTGCTCAGACTCCACCTGGGGCTATGGAAGCTGGGGATTAAAAAT    1904
CAGCATGGGCTGGAGGAGACAGGGCCCAAGCTTCTGGCTACATAAGTTAGTGGTCTTGTTTGTTTTGGGGGTTTTTGTT    1983
TGTTTGTTTTTTCAAGACAGGGTTTCTCTGTGTAGCTCTGGCTGTCCTGGAACTCACTTTGTAGACCAGGCTGGCCTCG    2062
AACTCAGAAATCCGCCTGCCTCTGCCTCCCAAGTGCTGGGATTAAAGGCATGCGCCACCACCGCCCAGCAGTGGTTTTA    2141
TTTGTAACTAACAGTTTATACCAATGACTCCCCACAACTTTGTGTAATTGTTTTTCCACTGTATTAACATTAAAGGGAA    2220
T                                                                                2221
```

FIG.16B

```
                                                                          M   R   L       3
GTCGACCCACGCGTCCGGCGGAGGTTGTGGCTGCACCGTGGTCCTGGGCTTGGTCCTGGGCTTG ATG CGT CTG      73
 F   V   R   P   S   V   R   P   A   M   A   A   P   A   P   S   P   W   T   L    23
TTT GTC CGT CCG TCC GTC CGT CCC GCC ATG GCT GCG CCG GCG CCC TCT CCG TGG ACC CTT   133
 S   L   L   L   L   L   L   L   P   S   P   G   A   H   G   E   L   C   R   P    43
TCG CTG CTG CTG TTG TTG CTA CTG CCG TCT CCG GGT GCC CAT GGC GAG CTG TGC AGG CCC   193
 F   G   E   D   N   S   I   P   E   S   C   P   D   F   C   C   G   S   C   S    63
TTC GGT GAA GAC AAT TCG ATC CCA GAG TCC TGT CCT GAC TTC TGT TGT GGC TCC TGT TCC   253
 S   Q   Y   C   C   S   D   V   L   K   K   I   Q   W   N   E   E   M   C   P    83
AGC CAA TAC TGC TGC TCT GAC GTG CTG AAG AAA ATC CAG TGG AAT GAG GAA ATG TGC CCT   313
 E   P   E   S   S   R   F   S   A   H   P   E   T   P   E   Q   L   G   S   A   103
GAG CCA GAG TCC AGC AGA TTT TCC GCC CAC CCG GAG ACA CCA GAA CAG CTG GGT TCA GCG   373
 L   K   Y   Q   S   S   L   D   S   D   N   M   P   G   F   G   A   T   V   A   123
CTG AAG TAT CAG TCC AGT CTT GAC AGT GAC AAC ATG CCA GGG TTC GGA GCG ACC GTG GCC   433
 I   G   L   T   V   F   V   V   F   I   A   T   I   I   V   C   F   T   C   S   143
ATC GGC CTG ACC GTC TTC GTG GTG TTT ATC GCT ACC ATC ATT GTG TGC TTT ACC TGC TCC   493
 C   C   C   L   Y   K   M   C   C   R   P   R   P   V   V   S   N   T   T   T   163
TGC TGC TGT CTA TAT AAG ATG TGC TGC CGC CCA CGA CCT GTC GTG TCC AAC ACC ACA ACT   553
 T   T   V   V   H   T   A   Y   P   Q   P   Q   P   V   A   P   S   Y   P   G   183
ACT ACC GTG GTT CAC ACC GCT TAC CCT CAG CCT CAA CCT GTG GCC CCC AGC TAT CCT GGA   613
 P   T   Y   Q   G   Y   H   P   M   P   P   Q   P   G   M   P   A   A   P   Y   203
CCA ACA TAC CAG GGC TAC CAT CCC ATG CCC CCC CAG CCA GGA ATG CCA GCA GCA CCC TAC   673
 P   T   Q   Y   P   P   P   Y   L   A   Q   P   T   G   P   P   A   Y   H   E   223
CCA ACG CAG TAC CCT CCA CCC TAC CTG GCC CAG CCC ACA GGG CCA CCA GCC TAT CAT GAG   733
 T   L   A   G   A   S   Q   P   P   Y   N   P   A   Y   M   D   P   P   K   A   243
ACG TTG GCT GGA GCC AGC CAG CCT CCA TAC AAC CCG GCC TAC ATG GAT CCC CCA AAG GCA   793
 V   P   *   246
GTT CCC TGA   802
GCCTGCCCCCAGCCTCTTTGGCTAACATTTGATTATGTCATGTGTGTGTGAGTGCTATGCAGAGTTCTTTACTGCTGTC   881
TGTGGTGCGTGTGCCTTGTCTAGACATGTGGCTTCCTCTGCTGATGACCAGGTAGGCACAAATCTTACCAGTGCTGGTT   960
GGGACCAATCTGTTTTCTTCCTCACTTGAAATTGTAATTTCTGAAATTTCAAGTAAATTAAAAACAATAGGGTAGGAGG  1039
TATTTCCCGCTTCACCCCAAGGTGACCAGCCATAGCCTGCCACACATAGGAGAGCAAGCTTTTTGTGGGTCCATGTCCT  1118
GCTTTGGGGAGTAGCCAGCTAGCTGCTGCTATGGGTTTATTCCCAGGGCTTGGCTGCATTTAGCTGGACAGAGAACAAG  1197
GGGCCTCAGTGGCAGTGGGTCAGTGACTGATGTCAGAGCACACTAGGCAGAGAGCCCCGTCCGTCTCCATCAGCTGTCT  1276
GTCTGGACGGTCCCACTGTCTTTCCTGGGACTATGTAGAGGGCCACATGTATTCACTATTCAGGCTCCAGTGGCTTCCA  1355
GGCCAGGGGCCTCTGTCTACTACACACTCTGGTTTCTCCCTACAGTGTCTTTTTACGATTAGCCAAACATATTGCCTGT  1434
TTTTTGTATCCAGATGTGTGATAATTGGTGAGGTTGAAATCCTTGGTTCCTGGAGAACAGGAAACCTGACCTCTGACAG  1513
```

FIG.17A

```
TCCGTTTCCCTTGACACCAGCTTCATAGCCTACCTGACTCCTGTACTACAGTCCAGTTTGTTCCAGTAGCAGGGACACC  1592
AGGGCCAGGGGTTATCTGGACCAAGGGTGGGGGTGGAGAGCCTGGATGGTAGCTCTGGACCAGATGTGAATGCCTCCAT  1671
ATTCCCTGTTGGTTCCTGTTTCACTGGCTGTTTTAGTTTTGTGTTAATTGGTGTTTCTGAGCATTCAAACTCCGCACCC  1750
TCGTTTATAATAAATGAATATTTGGAAAAAAAAAAAAAAAAAAAAAAAAAA                              1812
```

FIG. 17B

>hT281
MRLFVRPSVRPAMAAPAPSPWTLSLLLLLLLPSPGAHGELCRPFGEDNSIPESCPDFCCG
SCSSQYCCSDVLKKIQWNEEMCPEPESSRFSAHPETPEQLGSALKYQSSLDSDNMPGFGA
TVAIGLTVFVVFIATIIVCFTCSCCCLYKMCCRPRPVVSNTTTTTVVHTAYPQPQPVAPS
YPGPTYQGYHPMPPQPGMPAAPYPTQYPPPYLAQPTGPPAYHETLAGASQPPYNPAYMDP
PKAVP

```
Alignments of top-scoring domains:
PSBH: domain 1 of 1, from 97 to 146: score 5.5, E = 8.5
                 *->ktalgelLkPlnseyGKvaPgWGttplmgvfmalfavFLliileiYn
                    +lg+ Lk    s     +Pg+G t+ +g  +++f+vF+  i+  +
      hT281   97    PEQLGSALKYQSSLDSDNMPGFGATVAIG--LTVFVVFIATIIVCFT  141 ssvll<-*
                  s
      hT281  142  CSCCC      146

```
      GTCGACCCACGCGTCCGCGCGGAGGTTGCGGCGGCACCGTGGTCTTGGGCTTGGTCCGTCTGTTCGTCCGTCCGTTGGT  79
                     M   A   A   P   A   P   S   L   W   T   L   L   L   L   L   L   L      17
CTGTCCCGCC ATG GCT GCG CCG GCG CCC TCT CTG TGG ACC CTA TTG CTG CTG CTG TTG CTG          140

L   P   P   P   P   G   A   H   G   E   L   C   R   P   F   G   E   D   N   S      37
  CTG CCG CCG CCT CCG GGT GCC CAT GGT GAG CTG TGC AGG CCC TTT GGT GAA GAC AAT TCG       200

I   P   V   F   C   P   D   F   C   C   G   S   C   S   N   Q   Y   C   C   S      57
  ATC CCA GTG TTC TGT CCT GAT TTC TGT TGT GGT TCC TGT TCC AAC CAA TAC TGC TGC TCG       260

D   V   L   R   K   I   Q   W   N   E   E   M   C   P   E   P   E   S   S   R      77
  GAC GTG CTG AGG AAA ATC CAG TGG AAT GAG GAA ATG TGT CCT GAG CCA GAG TCC AGC AGA       320

F   S   T   P   A   E   E   T   P   E   H   L   G   S   A   L   K   F   R   S      97
  TTT TCC ACC CCC GCG GAG GAG ACA CCC GAA CAT CTG GGT TCA GCG CTG AAA TTT CGA TCC       380

S   F   D   S   D   P   M   S   G   F   G   A   T   V   A   I   G   V   T   I     117
  AGT TTT GAC AGT GAC CCT ATG TCA GGG TTC GGA GCG ACC GTC GCC ATT GGC GTG ACC ATC       440

F   V   V   F   I   A   T   I   I   I   C   F   T   C   S   C   C   C   L   Y     137
  TTT GTG GTG TTT ATT GCC ACT ATC ATC ATC TGC TTC ACC TGC TCC TGC TGC TGT CTG TAT       500

K   M   C   C   P   Q   R   P   V   V   T   N   T   T   T   T   T   V   V   H     157
  AAG ATG TGC TGC CCC CAA CGC CCT GTC GTG ACC AAC ACC ACA ACT ACT ACC GTG GTT CAT       560

A   P   Y   P   Q   P   Q   P   Q   P   V   A   P   S   Y   P   G   P   T   Y     177
  GCC CCT TAC CCT CAG CCT CAA CCT CAA CCT GTG GCC CCC AGC TAT CCT GGA CCA ACA TAC       620

Q   G   Y   H   P   M   P   P   P   A   R   N   A   S   S   T   L   P   N   A     197
  CAG GGC TAC CAT CCC ATG CCC CCC CCA GCC AGG AAT GCC AGC AGC ACC CTA CCC AAC GCA       680

V   P   T   T   L   P   G   P   A   H   R   A   A   T   L   P   *                 214
  GTA CCC ACC ACC CTA CCT GGC CCA GCC CAC AGG GCC GCC ACC CTA CCA TGA                   731

.GTCCTTGGCTGGAGCCAGCCAGCCTCCATACAACCCGACCTACATGGATTCCCTAAAGACAATTCCCTGAACCTGCCCC          810

CAGCCTCTTTGGCTGCCATTTATGTCGTGTGTGAGTGAGTGATACGCAGAGTTCTTTACTGCTGTCTGTGGTGTGTGTG           889

CCTTGTCTAGACATGTGGCTTCCTCTGCTGTTGACCAGGTAGGCGCAAGTCTTACCAGTGTGGGTCGGGACCAACCTGT           968

TTTCTTCCTCACTTGAAATTGTACTTTCTGAAATTTCAAGCAAATTAAAAACAATAAGGTAGGAGGTATTTCCCACGTC          1047

ACCCCAAGGTGACCAGCCATGGCCTGTCATACTTAGGAGAGCAAGCTTTTTGCGGGTACAGAGCAGGCTTTGGGGGGTA          1126

ACCAGCTAGCTGCTGCTAGGCCTTTATTCCCAGGGTTTGGCTGCATTGGCAGTGAGGCAGGTGGCTGGGGGTGACACCA          1205

GGTGACAAGGGGACTCAGTGGCAGGGGGTCACACCAGGCAGAACACCATACACTCTCCATCAGCTGTCTGTCTGGATGT          1284

CACTGTCCTTCCCGGGGCTGTATAGAGGGCCACATGTGTTCACTATTCAGGCTCCACTGGGGGAATTTTCCTACCTTTG          1363

CTGGCTTGGCTCCTGCTCCCAGGCCAGGGACCTCGGTCTGTCTACTACACACTCTGGTTTCTCCCTGCACTGTCTTTTT         1442
```

FIG.20A

```
CTGTTAGCCAAACATTTTGCCTGTTTTCTGTCTCCAGATGTGTGATAATTGGTGTGAGGTTGAAATCCCTGGTTCCTG    1521

AGGACAGACAACCTGACCTCCGACTGTCAGTTTCCCTTGACACCATCTTCATAGAAATACCTGACTCCTGTACCACAG    1600

CCAGTTTGTCCCAGTAGCAGGGACACCAAGGCCAATGGGTTATCTGGACCAAAGGTGGGGTGGAGGGCCTAGATGGTA    1679

CTCCGGCCCAGATGTGAATACCTCCATATTCCCTGTTGGTTCCTGTTTCACTGGCTGTTTTAGCTTTGTGTTGATTGG    1758

GTTTCTGAGCATTCAGACTCCGCACCCTCATTTCTAATAAATGCAACATTGGAAAAAAAAAAAAAAAAAAAAAAAAAA    1837

AAAAAAAAAAGGGCGGCCGC                                                            1858
```

FIG.20B

>mT281
MAAPAPSLWTLLLLLLLLLPPPPGAHGELCRPFGEDNSIPVFCPDFCCGSCSNQYCCSDVL
RKIQWNEEMCPEPESSRFSTPAEETPEHLGSALKFRSSFDSDPMSGFGATVAIGVTIFVV
FIATIIICFTCSCCCLYKMCCPQRPVVTNTTTTTVVHAPYPQPQPQPVAPSYPGPTYQGY
HPMPPPARNASSTLPNAVPTTLPGPAHRAATLP

```
ALIGN calculates a global alignment of two sequences
 version 2.0uPlease cite: Myers and Miller, CABIOS (1989)
> hT281 a.a                                    245 aa vs.
> mT281 a.a                                    213 aa
scoring matrix: pam120.mat, gap penalties: -12/4
66.5% identity:          Global alignment score: 739

10        20        30        40        50        60        70
inputs  MRLFVRPSVRPAMAAPAPSPWTLSLLLLLLLLPSPGAHGELCRPFGEDNSIPESCPDFCCGSCSSQYCCSD
        :       :::::: ::: ::::::  :.:::::::::::::::::::  :::::::::::::: :::::
        M-----------AAPAPSLWTLLLLLLLLLPPPPGAHGELCRPFGEDNSIPVFCPDFCCGSCSNQYCCSD
                              10        20        30        40        50

80        90        100       110       120       130
inputs  VLKKIQWNEEMCPEPESSRFSAHPE-TPEQLGSALKYQSSLDSDNMPGFGATVAIGLTVFVVFIATIIVC
        ::.:::::::::::::::::::. .: :::.::::::.: ..:::.::::::::::.::::::::::::
        VLRKIQWNEEMCPEPESSRFSTPAEETPEHLGSALKFRSSFDSDPMSGFGATVAIGVTIFVVFIATIIIC
         60        70        80        90        100       110       120

140       150       160       170       180       190       200
inputs  FTCSCCCLYKMCCRPRPVVSNTTTTTTVVHTAYPQPQP--VAPSYPGPTYQGYHPMPPQPGMPAAPYPTQY
        :::::::::::::: .::::.:::::::::: :::::::  :::::::::::::::::::
        FTCSCCCLYKMCCPQRPVVTNTTTTTTVVHAPYPQPQPQPVAPSYPGPTYQGYHPMPP--------PARN
         130       140       150       160       170       180

210       220       230       240
inputs  PPPYLAQPTGPPAYHETLAGASQPPYNPAYMDPPKAVP
        ....  : ... :.  :::: ..            ..:
        ASSTL--PNAVPT---TLPGPAHRA---------ATLP
         190       200         210
```

FIG.22

```
CGCTTACTCCTTTGCCTTCGCAAACAGGGAAAAGTGTTCCACGAAGCGGTAGCGCCTTTCCGCCTCGCGTTTTCCTCCC    79
TGACCCTGGTCCCGGCTCCCGTCCGGGCGCCAGCTGGTGGGGCGAGCGCCGGGAGCCCATCTGCCCCCAGGGGCACGGG   158
GCGCGGGGCCGGCTCCCGCCCGGCACATGGCTGCAGCCACCTCGCGCGCACCCCGAGGCGCCGCGCCCAGCTCGCCCGA   237
GGTCCGTCGGAGGCGCCCGGCCGCCCCGGAGCCAAGCAGCAACTGAGCGGGGAAGCGCCCGCGTCCGGGGATCGGG     313
 M   S   L   L   L   L   L   L   L   V   S   Y   Y   V   G   T   L   G   T   H    20
ATG TCC CTC CTC CTT CTC CTC TTG CTA GTT TCC TAC TAT GTT GGA ACC TTG GGG ACT CAC   373
 T   E   I   K   R   V   A   E   E   K   V   T   L   P   C   H   H   Q   L   G    40
ACT GAG ATC AAG AGA GTG GCA GAG GAA AAG GTC ACT TTG CCC TGC CAC CAT CAA CTG GGG   433
 L   P   E   K   D   T   L   D   I   E   W   L   L   T   D   N   E   G   N   Q    60
CTT CCA GAA AAA GAC ACT CTG GAT ATT GAA TGG CTG CTC ACC GAT AAT GAA GGG AAC CAA   493
 K   V   V   I   T   Y   S   S   R   H   V   Y   N   N   L   T   E   E   Q   K    80
AAA GTG GTG ATC ACT TAC TCC AGT CGT CAT GTC TAC AAT AAC TTG ACT GAG GAA CAG AAG   553
 G   R   V   A   F   A   S   N   F   L   A   G   D   A   S   L   Q   I   E   P   100
GGC CGA GTG GCC TTT GCT TCC AAT TTC CTG GCA GGA GAT GCC TCC TTG CAG ATT GAA CCT   613
 L   K   P   S   D   E   G   R   Y   T   C   K   V   K   N   S   G   R   Y   V   120
CTG AAG CCC AGT GAT GAG GGC CGG TAC ACC TGT AAG GTT AAG AAT TCA GGG CGC TAC GTG   673
 W   S   H   V   I   L   K   V   L   V   R   P   S   K   P   K   C   E   L   E   140
TGG AGC CAT GTC ATC TTA AAA GTC TTA GTG AGA CCA TCC AAG CCC AAG TGT GAG TTG GAA   733
 G   E   L   T   E   G   S   D   L   T   L   Q   C   E   S   S   S   G   T   E   160
GGA GAG CTG ACA GAA GGA AGT GAC CTG ACT TTG CAG TGT GAG TCA TCC TCT GGC ACA GAG   793
 P   I   V   Y   Y   W   Q   R   I   R   E   K   E   G   E   D   E   R   L   P   180
CCC ATT GTG TAT TAC TGG CAG CGA ATC CGA GAG AAA GAG GGA GAG GAT GAA CGT CTG CCT   853
 P   K   S   R   I   D   Y   N   H   P   G   R   V   L   L   Q   N   L   T   M   200
CCC AAA TCT AGG ATT GAC TAC AAC CAC CCT GGA CGA GTT CTG CTG CAG AAT CTT ACC ATG   913
 S   Y   S   G   L   Y   Q   C   T   A   G   N   E   A   G   K   E   S   C   V   220
TCC TAC TCT GGA CTG TAC CAG TGC ACA GCA GGC AAC GAA GCT GGG AAG GAA AGC TGT GTG   973
 V   R   V   T   V   Q   Y   V   Q   S   I   G   M   V   A   G   A   V   T   G   240
GTG CGA GTA ACT GTA CAG TAT GTA CAA AGC ATC GGC ATG GTT GCA GGA GCA GTG ACA GGC  1033
 I   V   A   G   A   L   L   I   F   L   L   V   W   L   L   I   R   R   K   D   260
ATA GTG GCT GGA GCC CTG CTG ATT TTC CTC TTG GTG TGG CTG CTA ATC CGA AGG AAA GAC  1093
 K   E   R   Y   E   E   E   E   R   P   N   E   I   R   E   D   A   E   A   P   280
AAA GAA AGA TAT GAG GAA GAA GAG AGA CCT AAT GAA ATT CGA GAA GAT GCT GAA GCT CCA  1153
 K   A   R   L   V   K   P   S   S   S   S   G   S   R   S   S   R   S   G   300
AAA GCC CGT CTT GTG AAA CCC AGC TCC TCT TCC TCA GGC TCT CGG AGC TCA CGC TCT GGT  1213
 S   S   S   T   R   S   T   A   N   S   A   S   R   S   Q   R   T   L   S   T   320
TCT TCC TCC ACT CGC TCC ACA GCA AAT AGT GCC TCA CGC AGC CAG CGG ACA CTG TCA ACT  1273
```

FIG.23A

```
D   A   A   P   Q   P   G   L   A   T   Q   A   Y   S   L   V   G   P   E   V    340
GAC GCA GCA CCC CAG CCA GGG CTG GCC ACC CAG GCA TAC AGC CTA GTG GGG CCA GAG GTG  1333

R   G   S   E   P   K   K   V   H   H   A   N   L   T   K   A   E   T   T   P    360
AGA GGT TCT GAA CCA AAG AAA GTC CAC CAT GCT AAT CTG ACC AAA GCA GAA ACC ACA CCC  1393

S   M   I   P   S   Q   S   R   A   F   Q   T   V   *                            374
AGC ATG ATC CCC AGC CAG AGC AGA GCC TTC CAA ACG GTC TGA                          1435

ATTACAATGGACTTGACTCCCACGCTTTCCTAGGAGTCAGGGTCTTTGGACTCTTCTCGTCATTGGAGCTCAAGTCACC  1514

AGCCACACAACCAGATGAGAGGTCATCTAAGTAGCAGTGAGCATTGCACGGAACAGATTCAGATGAGCATTTTCCTTAT  1593

ACAATACCAAACAAGCAAAAGGATGTAAGCTGATTCATCTGTAAAAAGGCATCTTATTGTGCCTTTAGACCAGAGTAAG  1672

GGAAAGCAGGAGTCCAAATCTATTTGTTGACCAGGACCTGTGGTGAAGAAAGGTTGGGGAAAGGTGAGGTGAATATACC  1751

TAAAACTTTTAATGTGGGATATTTTGTATCAGTGCTTTGATTCACAATTTTCAAGAGGAAATGGGATGCTGTTTGTAAA  1830

TTTTCTATGCATTTCTGCAAACTTATTGGATTATTAGTTATTCAGACAGTCAAGCAGAACCCNCAGCCTTATTACNCCT  1909

GTCTACACCATGTACTGAGCTAACCACTTTTAAGAAACT                                          1948
```

FIG.23B

```
CONSENSUS      *->GesvtLtCsvs..gfgppgvsvtWyfkngk.lgpsllgysysrlesg
                  e+vtL+C      +    +  ++ W+   + +  +++++++++sr++  +
           28  EEKVTLPCHHQlgLPEKDTLDIEWL-LTDNeGNQKVVITYSSRHVYN    73
A236
               ekanlsegrfsis......sltLtissvekeDsGtYtCvv<-*
                ++gr+ + ++    -  ++L+i +++++D+G YtC  v
           74  NLTEEQKGRVAFAsnflagDASLQIEPLKPSDEGRYTCKV    113

CONSENSUS      *->GesvtLtCsvsgfgppgvsvtWyf.kngk.lgpsllgysysrlesge
                  G+++tL+C++s +g+ ++ ++W + ++   ++         rl ++
          146  GSDLTLQCESS-SGTEPIVYYWQRiREKEgED--------ERLPPK-  182
A236
               kanlsegrfsis.sltLtissvekeDsGtYtCvv<-*
                 r  +++  +++++++++++ sG Y C++
          183  ------SRIDYNhPGRVLLQNLTMSYSGLYQCTA    210
```

FIG. 25

```
gtcgacccac gcgtccggtt ccacgaagcg gtagctcctt gccgcctcgc cttctcctcc   60
ctaaccctgg gcccggcccc cgtcccggcg cgagctggtg gagccagggc tagaagccct  120
cggtgccccc ggagcgcagc gcgcagggga cccgggcgcg gggccagcgc cgcacatgg   180
ctgcagcccc ccgcgcgcac cccgaggcgc cgcgccctgc tcacagaagg tccgtcggct  240
gggctcggtc gccctgcagc caggctgcgc tgagccggga agtgcccgtg tccggagatc  300
ggg atg tcc ctc ttc ttc ctc tgg cta gta tcc tat tat gtt gga acg   348
    Met Ser Leu Phe Phe Leu Trp Leu Val Ser Tyr Tyr Val Gly Thr
    1               5                   10                  15
```

```
ctg gga act cac act gag atc aag aga gtg gca gag gaa aag gtt acc   396
Leu Gly Thr His Thr Glu Ile Lys Arg Val Ala Glu Glu Lys Val Thr
                20                  25                  30
```

```
ttg ccc tgt cac cat caa ctg ggg ctt ccc gag aaa gac acc ctg gac   444
Leu Pro Cys His His Gln Leu Gly Leu Pro Glu Lys Asp Thr Leu Asp
            35                  40                  45
```

```
att gaa tgg ctg ctc acc gat aat gaa ggg aac caa aaa gtg gtt att   492
Ile Glu Trp Leu Leu Thr Asp Asn Glu Gly Asn Gln Lys Val Val Ile
        50                  55                  60
```

```
acg tat tcc agc cgt cat gtc tac aat aac ttg acc gag gag cag aag   540
Thr Tyr Ser Ser Arg His Val Tyr Asn Asn Leu Thr Glu Glu Gln Lys
    65                  70                  75
```

```
ggc cga gtg gcc ttc gct tcc aac ttc ctg gca gga gat gct tcc ctg   588
Gly Arg Val Ala Phe Ala Ser Asn Phe Leu Ala Gly Asp Ala Ser Leu
80                  85                  90                  95
```

```
cag att gag cct ctg aaa ccc agt gat gaa ggc aga tac acc tgc aag   636
Gln Ile Glu Pro Leu Lys Pro Ser Asp Glu Gly Arg Tyr Thr Cys Lys
                100                 105                 110
```

```
gtg aag aat tca gga cgc tat gtc tgg agc cat gtc atc ttg aaa gtg   684
Val Lys Asn Ser Gly Arg Tyr Val Trp Ser His Val Ile Leu Lys Val
            115                 120                 125
```

```
cta gtg aga cca tcc aag ccc aag tgt gag ctg gaa gga gag ccg acc   732
Leu Val Arg Pro Ser Lys Pro Lys Cys Glu Leu Glu Gly Glu Pro Thr
        130                 135                 140
```

```
gaa gga agt gac ctg acg ctg cag tgt gag tct gcc tct gga act aag   780
Glu Gly Ser Asp Leu Thr Leu Gln Cys Glu Ser Ala Ser Gly Thr Lys
    145                 150                 155
```

```
ccc att gtg tat tat tgg cag cga atc cgg gag aag gag gga gaa gat   828
Pro Ile Val Tyr Tyr Trp Gln Arg Ile Arg Glu Lys Glu Gly Glu Asp
160                 165                 170                 175
```

FIG.26A

```
gaa cac ctg cca ccc aaa tcc aga att gat tac aac aac cct ggc cga    876
Glu His Leu Pro Pro Lys Ser Arg Ile Asp Tyr Asn Asn Pro Gly Arg
            180                 185                 190 gtg ctg ctg cag aat ctc acc atg gcc tcc tct ggg ctt tac cag tgc    924
Val Leu Leu Gln Asn Leu Thr Met Ala Ser Ser Gly Leu Tyr Gln Cys
            195                 200                 205 aca gca ggc aac gag gct gga aag gag agc tgt gtg gta cgg gtg act    972
Thr Ala Gly Asn Glu Ala Gly Lys Glu Ser Cys Val Val Arg Val Thr
            210                 215                 220 gta cag tat gtg cag agc att ggc atg gtg gca gga gca gtg aca ggc   1020
Val Gln Tyr Val Gln Ser Ile Gly Met Val Ala Gly Ala Val Thr Gly
            225                 230                 235 ata gtg gca gga gcc ctg ctc att ttc ctc ctg ata tgg ctg cta ata   1068
Ile Val Ala Gly Ala Leu Leu Ile Phe Leu Leu Ile Trp Leu Leu Ile
240                 245                 250                 255 cga agg aaa agc aaa gac aga tac gag gaa gaa gac aga cct aat gaa   1116
Arg Arg Lys Ser Lys Asp Arg Tyr Glu Glu Glu Asp Arg Pro Asn Glu
            260                 265                 270 atc cga gaa gac gcc gaa gcg ccc cga gcc cgc ctt gtg aag cct agc   1164
Ile Arg Glu Asp Ala Glu Ala Pro Arg Ala Arg Leu Val Lys Pro Ser
            275                 280                 285 tcc tct tcc tca ggc tcc cgg agc tca cgc tct ggc tcc tcc tcc acc   1212
Ser Ser Ser Ser Gly Ser Arg Ser Ser Arg Ser Gly Ser Ser Ser Thr
            290                 295                 300 cgc tcc acc ggg aac agt gcc tcc aga agc cag cgg acg ctg tcg agt   1260
Arg Ser Thr Gly Asn Ser Ala Ser Arg Ser Gln Arg Thr Leu Ser Ser
            305                 310                 315 gaa gca gcg ccg cag cag ccc ggg cta gcc ccg cag gca tac agc ctc   1308
Glu Ala Ala Pro Gln Gln Pro Gly Leu Ala Pro Gln Ala Tyr Ser Leu
320                 325                 330                 335 ata gga ccg gaa gtg aga ggt tct gaa cca aag aaa gtc cac cat acg   1356
Ile Gly Pro Glu Val Arg Gly Ser Glu Pro Lys Lys Val His His Thr
            340                 345                 350 acc ctg acc aaa gca gaa acc aca ctc agc aca acg ccc agc cag agc   1404
Thr Leu Thr Lys Ala Glu Thr Thr Leu Ser Thr Thr Pro Ser Gln Ser
            355                 360                 365
```

FIG.26B

```
aaa gcc ttc caa act gtc tga ct tagagtggac ttgacttgcg cttgccccaa  1457
Lys Ala Phe Gln Thr Val  *
        370 agtcaggatc ttagcctagt cactggagct cgtccaccag ccacgcaagc ccctcagcca 1517
gatacgatct cacttaagta gctgcagaaa tggcacggac cagttctgat gagtaccctc 1577
cttatatagg ataccaaaca aacacaagga cggaggctga ccatctatct ctaaaggcac 1637
ctcactgtgc cttcagacag agtggagggg aggaggggcc caagcttatt tggtgaaaat 1697
aaagggaaag gtgaggctgc acacacctga acatcttac ctaggatgtt gcaagtcacc 1757
acagtcaaga agaagcggga atctcgtaga tcaattttct attcatttct gcaaatttat 1817
tggattagtg tgattattca gatagtcaaa acagaagccc acgccttata atatacctat 1877
ctgcaacatg tactgggaga actgcgttta agaaattcac attaaaaaaa aaaaaaaaa  1937
aagggcggcc gc                                                     1949
```

FIG.26C

```
  1 ATGTCCCTCTTC....TTCCTCTGGCTAGTATCCTATTATGTTGGAACGCT  47
    ||||||||| ||    |||||| |||||| ||||| ||||||||||| |
  1 ATGTCCCTCCTCCTTCTCCTCTTGCTAGTTTCCTACTATGTTGGAACCTT  50

48 GGGAACTCACACTGAGATCAAGAGAGTGGCAGAGGAAAAGGTTACCTTGC  97
    ||| |||||||||||||||||||||||||||||||||||||| || ||||
 51 GGGGACTCACACTGAGATCAAGAGAGTGGCAGAGGAAAAGGTCACTTTGC 100

98 CCTGTCACCATCAACTGGGGCTTCCCGAGAAAGACACCCTGGACATTGAA 147
    |||| |||||||||||||||||||| || |||||||| ||||| ||||||
101 CCTGCCACCATCAACTGGGGCTTCCAGAAAAAGACACTCTGGATATTGAA 150

148 TGGCTGCTCACCGATAATGAAGGGAACCAAAAAGTGGTTATTACGTATTC 197
    |||||||||||||||||||||||||||||||||||||| || || || ||
151 TGGCTGCTCACCGATAATGAAGGGAACCAAAAAGTGGTGATCACTTACTC 200

198 CAGCCGTCATGTCTACAATAACTTGACCGAGGAGCAGAAGGGCCGAGTGG 247
    ||| |||||||||||||||||||||| ||||| |||||||||||||||||
201 CAGTCGTCATGTCTACAATAACTTGACTGAGGAACAGAAGGGCCGAGTGG 250

248 CCTTCGCTTCCAACTTCCTGGCAGGAGATGCTTCCCTGCAGATTGAGCCT 297
    |||| |||||||| |||||||||||||||||| |||||||||||| |||
251 CCTTTGCTTCCAATTTCCTGGCAGGAGATGCCTCCTTGCAGATTGAACCT 300

298 CTGAAACCCAGTGATGAAGGCAGATACACCTGCAAGGTGAAGAATTCAGG 347
    ||||| |||||||||||| || ||||||||| ||||| ||||||||||||
301 CTGAAGCCCAGTGATGAGGGCCGGTACACCTGTAAGGTTAAGAATTCAGG 350

348 ACGCTATGTCTGGAGCCATGTCATCTTGAAAGTGCTAGTGAGACCATCCA 397
    | ||||| || ||||||||||||||||| ||||| |||||||||||||||
351 GCGCTACGTGTGGAGCCATGTCATCTTAAAAGTCTTAGTGAGACCATCCA 400

398 AGCCCAAGTGTGAGCTGGAAGGAGAGCCGACCGAAGGAAGTGACCTGACG 447
    ||||||||||||||| |||||||||||| ||| |||||||||||||||| 
401 AGCCCAAGTGTGAGTTGGAAGGAGAGCTGACAGAAGGAAGTGACCTGACT 450
```

FIG.27A

```
448  CTGCAGTGTGAGTCTGCCTCTGGAACTAAGCCCATTGTGTATTATTGGCA  497
     |||||||||||| ||||||| ||  |||||||||||||||||| |||||
451  TTGCAGTGTGAGTCATCCTCTGGCACAGAGCCCATTGTGTATTACTGGCA  500

498  GCGAATCCGGGAGAAGGAGGGAGAAGATGAACACCTGCCACCCAAATCCA  547
     ||||||||| |||||  ||||||||| |||||||  |||||  ||||||| |
501  GCGAATCCGAGAGAAAGAGGGAGAGGATGAACGTCTGCCTCCCAAATCTA  550

548  GAATTGATTACAACAACCCTGGCCGAGTGCTGCTGCAGAATCTCACCATG  597
     | |||| |||||| |||||| ||||| ||||||||||||||| ||||||
551  GGATTGACTACAACCACCCTGGACGAGTTCTGCTGCAGAATCTTACCATG  600

598  GCCTCCTCTGGGCTTTACCAGTGCACAGCAGGCAACGAGGCTGGAAAGGA  647
     ||| |||||| || ||||||||||||||||||||||||| ||||||||||
601  TCCTACTCTGGACTGTACCAGTGCACAGCAGGCAACGAAGCTGGGAAGGA  650

648  GAGCTGTGTGGTACGGGTGACTGTACAGTATGTGCAGAGCATTGGCATGG  697
     ||||||||||| || || ||||||||||||||||| |||||| ||||||||
651  AAGCTGTGTGGTGCGAGTAACTGTACAGTATGTACAAAGCATCGGCATGG  700

698  TGGCAGGAGCAGTGACAGGCATAGTGGCAGGAGCCCTGCTCATTTTCCTC  747
     | ||||||||||||||||||||||||||| ||||||||||| ||||||||
701  TTGCAGGAGCAGTGACAGGCATAGTGGCTGGAGCCCTGCTGATTTTCCTC  750

748  CTGATATGGCTGCTAATACGAAGGAAAAGCAAAGACAGATACGAGGAAGA  797
     || | |||||||||||| ||||||||| ||||| ||||| ||||||||||
751  TTGGTGTGGCTGCTAATCCGAAGGAAAGACAAAGAAAGATATGAGGAAGA  800

798  AGACAGACCTAATGAAATCCGAGAAGACGCCGAAGCGCCCCGAGCCCGCC  847
     ||| ||||||||||||||| |||||||| || |||||  ||  |||||| |
801  AGAGAGACCTAATGAAATTCGAGAAGATGCTGAAGCTCCAAAAGCCCGTC  850

848  TTGTGAAGCCTAGCTCCTCTTCCTCAGGCTCCCGGAGCTCACGCTCTGGC  897
     ||||||| || |||||||||||||||||||| ||||||||||||||||||
851  TTGTGAAACCCAGCTCCTCTTCCTCAGGCTCTCGGAGCTCACGCTCTGGT  900
```

FIG.27B

```
898  TCCTCCTCCACCCGCTCCACCGGGAACAGTGCCTCCAGAAGCCAGCGGAC  947
     || |||||||| |||||||| | || ||||||||  | |||||||||||
901  TCTTCCTCCACTCGCTCCACAGCAAATAGTGCCTCACGCAGCCAGCGGAC  950

948  GCTGTCGAGTGAAGCAGCGCCGCAGCAGCCCGGGCTAGCCCCGCAGGCAT  997
     ||||| | ||| |||||| ||    ||||| ||||| ||| | |||||||
951  ACTGTCAACTGACGCAGCACC...CCAGCCAGGGCTGGCCACCCAGGCAT  997

998  ACAGCCTCATAGGACCGGAAGTGAGAGGTTCTGAACCAAAGAAAGTCCAC  1047
     |||||||  | || || || |||||||||||||||||||||||||||||
998  ACAGCCTAGTGGGGCCAGAGGTGAGAGGTTCTGAACCAAAGAAAGTCCAC  1047

1048 CATACGACCCTGACCAAAGCAGAAACCACACTCAGCACAACGCCCAGCCA  1097
     ||| ||  ||||||||||||||||||||||| ||||| |  ||||||||
1048 CATGCTAATCTGACCAAAGCAGAAACCACACCCAGCATGATCCCCAGCCA  1097

1098 GAGCAAAGCCTTCCAAACTGTC  1119
     ||||| |||||||||||||| |||
1098 GAGCAGAGCCTTCCAAACGGTC  1119
```

FIG. 27C

```
1    .MSLFFLWLVSYYVGTLGTHTEIKRVAEEKVTLPCHHQLGLPEKDTLDIE    49
      |  |||||||||||||||||||||||||||||||||||||||||||||||
1    MSLLLLLLLVSYYVGTLGTHTEIKRVAEEKVTLPCHHQLGLPEKDTLDIE    50

50   WLLTDNEGNQKVVITYSSRHVYNNLTEEQKGRVAFASNFLAGDASLQIEP    99
     |||||||||||||||||||||||||||||||||||||||||||||||||
51   WLLTDNEGNQKVVITYSSRHVYNNLTEEQKGRVAFASNFLAGDASLQIEP    100

100  LKPSDEGRYTCKVKNSGRYVWSHVILKVLVRPSKPKCELEGEPTEGSDLT    149
     ||||||||||||||||||||||||||||||||||||||||||  |||||||
101  LKPSDEGRYTCKVKNSGRYVWSHVILKVLVRPSKPKCELEGELTEGSDLT    150

150  LQCESASGTKPIVYYWQRIREKEGEDEHLPPKSRIDYNNPGRVLLQNLTM    199
     ||||| ||| |||||||||||||||||| |||||||||.|||||||||||
151  LQCESSSGTEPIVYYWQRIREKEGEDERLPPKSRIDYNHPGRVLLQNLTM    200

200  ASSGLYQCTAGNEAGKESCVVRVTVQYVQSIGMVAGAVTGIVAGALLIFL    249
      |||||||||||||||||||||||||||||||||||||||||||||||||
201  SYSGLYQCTAGNEAGKESCVVRVTVQYVQSIGMVAGAVTGIVAGALLIFL    250

250  LIWLLIRRKSKDRYEEEDRPNEIREDAEAPRARLVKPSSSSSGSRSSRSG    299
     |:|||||||:||||||||:||||||||||||:|||||||||||||||||
251  LVWLLIRRKDKERYEEEERPNEIREDAEAPKARLVKPSSSSSGSRSSRSG    300

300  SSSTRSTGNSASRSQRTLSSEAAPQQPGLAPQAYSLIGPEVRGSEPKKVH    349
     |||||||  ||||||||||.:||| |||||||:|||||||||||||||
301  SSSTRSTANSASRSQRTLSTDAAP.QPGLATQAYSLVGPEVRGSEPKKVH    349

350  HTTLTKAETTLSTTPSQSKAFQTV  373
     |  ||||||| |  ||||:|||||
350  HANLTKAETTPSMIPSQSRAFQTV  373
```

FIG.28

```
                                    M   A   S   L   G   L   L   L   L   L   L   L       12
CCAAGAATTCGGCACGAGGAGAGGCCGGCC ATG GCC AGC CTG GGG CTG CTG CTC CTG CTC TTA CTG          66

T   A   L   P   P   L   W   S   S   L   P   G   L   D   T   A   E   S   K            32
ACA GCA CTG CCA CCG CTG TGG TCC TCC TCA CTG CCT GGG CTG GAC ACT GCT GAA AGT AAA        126

A   T   I   A   D   L   I   L   S   A   I   E   R   A   T   V   F   L   E   Q        52
GCC ACC ATT GCA GAC CTG ATC CTG TCT GCG CTG GAG AGA GCC ACC GTC TTC CTA GAA CAG        186

R   L   P   E   I   N   L   D   G   M   V   G   V   R   V   L   E   E   Q   P        72
AGG CTG CCT GAA ATC AAC CTG GAT GGC ATG GTG GGG GTC CGA GTG CTG GAA GAG CAG CTA        246

K   S   V   R   E   K   W   A   Q   E   P   L   L   Q   P   L   S   L   R   V        92
AAA AGT GTC CGG GAG AAG TGG GCC CAG GAG CCC CTG CTG CAA CCG CTG AGC CTG CGC GTG        306

G   M   L   G   E   K   L   E   A   A   I   Q   R   S   L   H   Y   I   K   L       112
GGG ATG CTG GGG GAG AAG CTG GAG GCT GCC ATC CAG AGA TCC CTC CAC TAC ATC AAG CTG        366

S   D   P   K   Y   L   R   E   F   Q   L   T   L   Q   P   G   F   W   K   L       132
AGT GAT CCC AAG TAC CTA AGA GAG TTC CAG CTG ACC CTC CAG CCC GGG TTT TGG AAG CTC        426

P   H   A   W   I   H   T   D   A   S   L   V   Y   P   T   F   G   F   Q   D       152
CCA CAT GCC TGG ATC CAC ACT GAT GCC TCC TTG GTG TAC CCC ACG TTC GGG CCC CAG GAC        486

S   F   S   E   E   R   S   D   V   C   L   V   Q   L   L   G   T   G   T   D       172
TCA TTC TCA GAG GAG AGA AGT GAC GTG TGC CTG GTG CAG CTG CTG GGA ACC GGG ACG GAC        546

S   S   E   P   C   G   L   S   D   L   C   R   S   L   M   T   K   P   G   C       192
AGC AGC GAG CCC TGC GGC CTC TCA GAC CTC TGC AGG AGC CTC ATG ACC AAG CCC GGC TGC        606

S   G   Y   C   L   S   H   Q   L   L   F   F   L   W   A   R   M   R   G   C       212
TCA GGC TAC TGC CTG TCC CAC CAA CTG CTC TTC TTC CTC TGG GCC AGA ATG AGG GGG CGC        666

T   Q   G   P   L   Q   Q   S   Q   D   Y   I   N   L   F   C   A   N   M   M       232
ACA CAG GGA CCA CTC CAA CAG AGC CAG GAC TAT ATC AAC CTC TTC TGC GCC AAC ATG ATG        726

D   L   N   R   R   A   E   A   I   G   Y   A   Y   P   T   R   D   E   F   M       252
GAC TTG AAC CGC AGA GCT GAG GCC ATC GGA TAC GCC TAC CCT ACC CGG GAC ATC TTC ATG        786

E   N   I   M   F   C   G   M   G   G   F   S   D   F   Y   K   L   R   W   L       272
GAA AAC ATC ATG TTC TGT GGA ATG GGC GGC TTC TCC GAC TTC TAC AAG CTC CGG TGG CTG        846

E   A   I   L   S   W   Q   K   Q   Q   E   G   C   F   G   E   P   D   A   E       292
GAG GCC ATT CTC AGC TGG CAG AAA CAG CAG GAA GGA TGC TTC GGG GAG CCT GAT GCT GAA        906

D   E   E   L   S   K   A   I   Q   Y   Q   Q   H   F   S   R   R   V   K   R       312
GAT GAA GAA TTA TCT AAA GCT ATT CAA TAT CAG CAG CAT TTT TCG AGG AGA GTG AAG ACG        966

R   E   K   Q   F   P   D   G   C   S   S   H   N   T   A   T   A   V   A   A       332
CGA GAA AAA CAA TTT CCA GAT GGC TGC TCC TCC CAC AAC ACA GCC ACA GCA GTG GCA GCC       1026

L   G   G   F   L   Y   I   L   A   E   Y   F   P   A   N   R   E   P   H   P       352
CTG GGT GGC TTC CTA TAC ATC CTG GCA GAA TAC CCC CCA GCA AAC AGA GAG CCA CAC CCA       1086
```

FIG.30A

```
    S   T   P   P   P   P   S   S   R   *
362
TCC ACA CCG CCA CCA CCA AGC AGC CGC TGA                                         1116

GACGGACGGTTCCATGCCAGCTGCCTGGAGGAGGAACAGACCCCTTTAGTCCTCATCCCTTAGATCCTGGAGGGCACGG 1195

ATCACATCCTGGGAAGAAGGCATCTGGAGGATAAGCAAAGCCACCCCGACACCCAATCTTGGAAGCCCTGAGTAGGCAG 1274

GGCCAGGGTAGGTGGGGCCGGGAGGGACCCAGGTGTGAACGGATGAATAAAGTTCAA                       1332
```

FIG.30B

```
gtcgacccac gcgtccgcat ccaccagcag aaatcctgtc atg gcg aga ctc ggg
                                             Met Ala Arg Leu Gly
                                               1               5 ctg ctt ctc ctc ctg ctg ctg gcc ctg cca cca cac ttc tcc tca gtg
103
Leu Leu Leu Leu Leu Leu Leu Ala Leu Pro Pro His Phe Ser Ser Val
                 10              15              20 tca tgg cca gac act gca cag ggc acc atg gca aac ttg atc ctg act
151
Ser Trp Pro Asp Thr Ala Gln Gly Thr Met Ala Asn Leu Ile Leu Thr
             25              30              35 gca tta gaa aaa gcc acc ttg ttc ttg gag gac agg ctg ccc aca atc
199
Ala Leu Glu Lys Ala Thr Leu Phe Leu Glu Asp Arg Leu Pro Thr Ile
         40              45              50 aac ctg gat ggt gtg gtg ggc ttc caa gtg ctg gaa gtg caa ctc cga
247
Asn Leu Asp Gly Val Val Gly Phe Gln Val Leu Glu Val Gln Leu Arg
         55              60              65 gga gtt cag gaa aaa tgg gct cac aag ccc ttg ctg cag cct ctc agc
295
Gly Val Gln Glu Lys Trp Ala His Lys Pro Leu Leu Gln Pro Leu Ser
 70              75              80              85 atg cgc gct gga cag atg gcc aac aca ctg tct gct ctc ctc caa aaa
343
Met Arg Ala Gly Gln Met Ala Asn Thr Leu Ser Ala Leu Leu Gln Lys
             90              95             100 tcc atc ttc tac ctc aag cag agt gac ccc acg tac cta aga gag ttc
391
Ser Ile Phe Tyr Leu Lys Gln Ser Asp Pro Thr Tyr Leu Arg Glu Phe
            105             110             115 cag cca agc att cag cct ggg ttt tgg aag ttg ccc aat gac tgg aca
439
Gln Pro Ser Ile Gln Pro Gly Phe Trp Lys Leu Pro Asn Asp Trp Thr
        120             125             130 cgc acc aat gcc tcc cta gtc tac ccc tgg ctg gaa ccc ctg gac tct
487
Arg Thr Asn Ala Ser Leu Val Tyr Pro Trp Leu Glu Pro Leu Asp Ser
        135             140             145 ttc tca gag gaa agc agc gat gtg tgc ctg gtg caa cta cta gga aca
535
Phe Ser Glu Glu Ser Ser Asp Val Cys Leu Val Gln Leu Leu Gly Thr
150             155             160             165
```

FIG.32A

```
     ggg aca gac agc agc cag cct tgc agg ctc tcc aac ttc tgc aga acc
583
     Gly Thr Asp Ser Ser Gln Pro Cys Arg Leu Ser Asn Phe Sys Arg Thr
                 170                 175                 180 ctt atg acc aag gcc ggc tgc tca ggc tac agc ctc tcc cat cag ctg
631
     Leu Met Thr Lys Ala Gly Cys Ser Gly Tyr Ser Leu Ser His Gln Leu
                 185                 190                 195 ctc ttc ttc ctc tgg gcc aga atg caa ggg tgc acg gag gga ctg tcc
679
     Leu Phe Phe Leu Trp Ala Arg Met Gln Gly Cys Thr Glu Gly Leu Phe
                 200                 205                 210 ctc cag agc caa cac tac atg gac atc ttc tgt gcc aat atg atg gaa
727
     Leu Gln Ser Gln His Tyr Met Asp Ile Phe Cys Ala Asn Met Met Glu
                 215                 220                 225 ctg aac cac aga gct gag gcc gtt gga tac gct tac ccc acc caa gac
775
     Leu Asn His Arg Ala Glu Ala Val Gly Tyr Ala Tyr Pro Thr Gln Asp
     230             235                 243                 245 ctc ttc atg gaa aac att atg ttc tgt ggt atg gct ggc ttc tct gac
823
     Leu Phe Met Glu Asn Ile Met Phe Cys Gly Mat Ala Gly Phe Ser Asp
                 250                 255                 260 ttc tac aag ctg cgc tgg ctg gag gcc att ctc agc tgg cag aac ccc
871
     Phe Tyr Lys Leu Arg Trp Leu Glu Ala Ile Leu Ser Trp Gln Asn Pro
                 265                 270                 275 cag gtg gga tgc ttc ggg agg cct gac aca aag ggt gaa cct tct gaa
919
     Gln Val Gly Cys Phe Gly Arg Pro Asp Thr Lys Gly Glu Pro Ser Glu
                 280                 285                 290 gtt cca cat cag cag ggc att ctg aga aga gtg cga agg cgg gaa aaa
967
     Val Pro His Gln Gln Gly Ile Leu Arg Arg Val Arg Arg Arg Glu Lys
                 295                 300                 305 ctg ttc gca gat ggc tgt tcg tgc cac aac aca gcc aca gca gtc gca
1015
     Leu Phe Ala Asp Gly Cys Ser Cys His Asn Thr Ala Thr Ala Val Ala
     310             315                 320                 325 gcc ctg ggt ggc ttt ctc tac atc ctg gca gaa tac cac cca gac aat
1063
     Ala Leu Gly Gly Phe Leu Tyr Ile Leu Ala Glu Tyr His Pro Asp Asn
                 330                 335                 340
```

FIG.32B

```
gga gat gca cat cca gaa tac tac cca aac cat gga gat cca tac tca
1111
Gly Asp Ala His Pro Glu Tyr Tyr Pro Asn His Gly Asp Pro Tyr Ser
                345             350             355 tcc tca cag tca cca gca agc aac tac caa gat ggt gct gcc ggc cct
1159
Ser Ser Gln Ser Pro Ala Ser Asn Tyr Gln Asp Gly Ala Ala Gly Pro
        360             365             370 gac gtc cag agg act ggc agg ccc ctt agt gtt tct taagtcctga
1205
Asp Val Gln Arg Thr Gly Arg Pro Leu Ser Val Ser
        375             380             385 gtcagaggtc acaggctgag gaggcaattg aggaaagtga ccagctatat ccccatcgcc
1265
acttctgggt gtttaaaagt cttgggagag cagggccagg gaaagcaggg ttggagagtg
1325 ggtggccca gatgtcagca gaatacataa agcacagtca attggagctg aaaaaaaaaa
1385
aaaaagggcg gccgc
1400
```

FIG.32C

```
Gap of: FrGcgManager_686_DBFOL.To2    check: 4995    from: 1 to: 1083 hT300 ORF (analysis only) - Import - complete to: FrGcgManager_686_EBF03Uvti    check: 4265    from: 1 to: 1155 mT300 ORF (analysis only) - Import - complete

Gap Weight:    12        Average Match:    10.000
      Length Weight:     4        Average Mismatch:  0.000

Quality:  8110              Length:    1174
               Ratio: 7.488                Gaps:       7
   Percent Similarity: 77.726    Percent Identity: 77.726

HUMAN  1 ATGGCCAGCCTGGGGCTGCTGCTCCTGCTCTTACTGACAGCACTGCCACC  50
         ||||| || || ||||||||| ||||| ||  | |||   || ||||||||
MOUSE  1 ATGGCGAGACTCGGGCTGCTTCTCCTCCTGCTGCTG...GCCCTGCCACC  47

51 GCTGTGGTCCTCCTCACTGCCTGGGCTGGACACTGCTGAAAGTAAAGCCA 100
         |       | ||||||| || |    ||| |||||||  | ||    | ||
      48 AC...ACTTCTCCTCAGTGTCATGGCCAGACACTGC...ACAG....GGCA  88

101 CCATTGCAGACCTGATCCTGTCTGCGCTGGAGAGAGCCACCGTCTTCCTA 150
         |||| ||| || ||||||||||| ||| | ||| | ||||||| | ||| |
      89 CCATGGCAAACTTGATCCTGACTGCATTAGAAAAAGCCACCTTGTTTCTTG 138

151 GAACAGAGGCTGCCTGAAATCAACCTGGATGGCATGGTGGGGGTCCGAGT 200
         ||  | |||||||||   ||||||||||||||| |||||||| ||| |||
     139 GAGGACAGGCTGCCCACAATCAACCTGGATGGTGTGGTGGGCTTCCAAGT 188

201 GCTGGAAGAGCAGCTAAAAAGTGTCCGGGAGAAGTGGGCCCAGGAGCCCC 250
         |||||||| ||| ||   | | || | ||| || |||||| ||  |||||
     189 GCTGGAAGTGCAACTCCGAGGAGTTCAGGAAAAATGGGCTCACAAGCCCT 238

251 TGCTGCAACCGCTGAGCCTGCGCGTGGGGATGCTGGGGGAGAAGCTGGAG 300
         |||||||| || || ||  ||| |||||| || | |||  |  | |||
     239 TGCTGCAGCCTCTCAGCATGCGCGCTGGACAGATGGCCAACACACTGTCT 288

301 GCTGCCATCCAGAGATCCCTCCACTACCTCAAGCTGAGTGATCCCAAGTA 350
         ||| | ||||| | |||| || ||||||||||||| |||||| |||| |||
     289 GCTCTCCTCCAAAAATCCATCTTCTACCTCAAGCAGAGTGACCCCACGTA 338
```

FIG.34A

```
351 CCTAAGAGAGTTCCAGCTGACCCTCCAGCCCGGGTTTTGGAAGCTCCCAC 400
    |||||||||||||||||| | | | |||||| |||||||||||| | ||
339 CCTAAGAGAGTTCCAGCCAAGCATTCAGCCTGGGTTTTGGAAGTTGCCCA 388

401 ATGCCTGGATCCACACTGATGCCTCCTTGGTGTACCCCACGTTCGGGCCC 450
    ||| ||||| | ||| ||||||||| | || |||||| | | |||
389 ATGACTGGACACGCACCAATGCCTCCCTAGTCTACCCCTGGCTGGAACCC 438

451 CAGGACTCATTCTCAGAGGAGAGAAGTGACGTGTGCCTGGTGCAGCTGCT 500
    | |||||| |||||||||| || || || |||||||||||| || ||
439 CTGGACTCTTTCTCAGAGGAAAGCAGCGATGTGTGCCTGGTGCAACTACT 488

501 GGGAACCGGGACGGACAGCAGCGAGCCCTGCGGCCTCTCAGACCTCTGCA 550
    ||||| ||||| |||||||||| |||| ||| | |||||| || ||||||
489 AGGAACAGGGACAGACAGCAGCCAGCCTTGCAGGCTCTCCAACTTCTGCA 538

551 GGAGCCTCATGACCAAGCCCGGCTGCTCAGGCTACTGCCTGTCCCACCAA 600
    | | ||| ||||||||| |||||||||||||||||| |||| ||||| ||
539 GAACCCTTATGACCAAGGCCGGCTGCTCAGGCTACAGCCTCTCCCATCAG 588

601 CTGCTCTTCTTCCTCTGGGCCAGAATGAGGGGGTGCACACAGGGACCACT 650
    |||||||||||||||||||||||||||| ||||||| || |
589 CTGCTCTTCTTCCTCTGGGCCAGAATGCAAGGGTGCACGGAGGGACTGTT 638

651 CCAACAGAGCCAGGACTATATCAACCTCTTCTGCGCCAACATGATGGACT 700
    || |||||||| |||| || || |||||||| ||||| ||||||||
639 CCTCCAGAGCCAACACTACATGGACATCTTCTGTGCCAATATGATGGAAC 688

701 TGAACCGCAGAGCTGAGGCCATCGGATACGCCTACCCTACCCGGGACATC 750
    |||||| |||||||||||||||| | |||||||| |||| |||| ||| ||
689 TGAACCACAGAGCTGAGGCCGTTGGATACGCTTACCCCACCCAAGACCTC 738

751 TTCATGGAAAACATCATGTTCTGTGGAATGGGCGGCTTCTCCGACTTCTA 800
    |||||||||||||| |||||||||| ||||| |||||||| ||||||||
739 TTCATGGAAAACATTATGTTCTGTGGTATGGCTGGCTTCTCTGACTTCTA 788

801 CAAGCTCCGGTGGCTGGAGGCCATTCTCAGCTGGCAGAAACAGCAGGAAG 850
    |||||| || |||||||||||||||||||||||||||| | |||| |
769 CAAGCTGCGCTGGCTGGAGGCCATTCTCAGCTGGCAGAACCCCCAGGTGG 838

851 GATGCTTCGGGGAGCCTGATGCTGAAGATGAAGAATTATCTAAAGCTATT 900
    |||||||||| |||||| | ||| ||| ||| ||
839 GATGCTTCGGGAGGCCTGACAC...AAAGGGTGAACCTTCTGAAG...TT 882
```

FIG.34B

```
 901 CAATATCAGCAGCATTTTTCGAGGAGAGTGAAGAGGCGAGAAAAACAATT  950
     | | ||||||||   ||  ||| |||||||   ||||| |||'|||  ||
 883 CCACATCAGCAGGGCATTCTGAGAAGAGTGCGAAGGCGGGAAAAACTGTT  932

951 TCCAGATGGCTGCTCCTCCCACAACACAGCCACAGCAGTGGCAGCCCTGG 1000
     ||||||||||  || | |||||||||||||||||||||| |||||||||
 933 CGCAGATGGCTGTTCGTGCCACAACACAGCCACAGCAGTCGCAGCCCTGG  982

1001 GTGGCTTCCTATACATCCTGGCAGAATACCCCCCAGCAAACAGAGAGCCA 1050
     ||||||  ||  ||||||||||||||||||||| |||||  ||||  ||
 983 GTGGCTTTCTCTACATCCTGGCAGAATACCACCCAGACAATGGAGATGCA 1032

1051 CACCCATCCACACCGCCACCACCAAGCAGCCGC.................  1083
     || |||   | || ||    |||| || |  |
1033 CATCCA GAATACTACCCAAACCATGGAGATCCATACTCATCCTCACAGT 1081
```

FIG.34C

```
Gap of: FrGcgManager_687_IBFG1iaq_  check: 8297  from: 1 to: 361 hT300 prot (analysis only) - Import - complete to: FrGcgManager_687_JBFmT7mm  check: 9127  from: 1 to: 385 mT300 prot (analysis only) - Import - complete

Gap Weight:      12     Average Match:     2.778
      Length Weight:       4     Average Mismatch:  2.248

Quality:    1237            Length:      391
               Ratio:   3.427              Gaps:        4
   Percent Similarity: 74.930    Percent Identity:   69.577
```

```
HUMAN     1 MASLGLLLLLLLLTALPPLWSSSLPGLDTAESKATIADLILSALERATVFL  50
            || |||||||||| ||||  .  ||.    |||:    |.|.|||.|||:|| ||
MOUSE     1 MARLGLLLLLLLL.ALPPHF.SSVSWPDTAQ...GTMANLILTALEKATLFL  46

51 EQRLPRINLDGMVGVTVLEEQLKSVREKWAQEPLLQPLSRVGMLGEKLE  100
            | |||  ||||||.||  .|||  ||:  |.||||  .||||||||:|  | :    |
         47 EDRLPTINLDGVVGFQVLEVQLRGVQEKWAHKPLLQPLSMRAGQMANTLS   96

101 AAIQRSLHYLKLSDPKYLREFQLTLQPGFWKLPHAWIHTDASLVYPTFGP  150
            | :|:|| ||| |||  ||||||    .:|||||||. |   |.|||||| |
         97 ALLQKSIFYLKQSDPTYLREFQPSIQPGFWKLPNDWTRTNASLVYPWLEP  146

151 QDSFSEERSDVCLVQLLGTGTDSSEPCGLSDLCRSLMTKPGCSGYCLSHQ  200
            |||||| ||||||||||||||||||||:|| ||. ||.|||| ||||| ||||
        147 LDSFSEESSDVCLVQLLGTGTDSSQPCRLSNFCRTLMTKAGCSGYSLSHQ  196

201 LLFFLWARMRGCTQGPLQQSQDYINLFCANMMDLNRRAEAIGYAYPTRDI  250
            |||||||||| |||:|    |||  |...:||||||:||  ||||:|||||||.|:
        197 LLFFLWARMQGCTEGLFLQSQHYMDIFCANMMELNHRAEAVGYAYPTQDL  246

251 FMENIMFCGMGGFSDFYKLRWLEAILSWQKQQEGCFGEPDAEDEELSKAI  300
            ||||||||||||  |||||||||||||||||||| |  |||| || . |       :
        247 FMENIMFCGMAGFSDFYKLRWLEAILSWQNPQVGCFGRPDTKGE...PSEV  294

301 QYQQHFSRRVKRREKQFPDGCSSHNTATAVAALGGFLYILAEYPPANREP  350
            :||    |||:|||| |  ||||  |||||||||||||||||||||||  |  |  |  .:
        295 PHQQGILRRVRRREKLFADGCSCHNTATAVAALGGFLYILAEYHPDNGDA  344

351 HPSTPPPPSSR................361
            ||  |
        345 HPEYYPNHGDPYSSSQSPASNYQDGAAGPDVQRTGRPLSVS 385
```

FIG.35

```
Input file T353; Output File T353.pat
Sequence length 1239

M      1
CTCACAGGAGGAGTTGGCGGGGAGCCTTGGGCCCCTCTGGCCTCAGCCGGATTTCCCAGCCAAACGCAGAGAGAG ATG   78

P   W   T   I   L   L   F   A   A   G   S   L   A   I   P   A   P   S   I   R    21
CCC TGG ACC ATC TTG CTC TTT GCA GCT GGC TCC TTG GCG ATC CCA GCA CCA TCC ATC CGG   138

L   V   P   P   Y   P   S   S   Q   E   D   P   I   H   I   A   C   M   A   P    41
CTG GTG CCC CCG TAC CCA AGC AGC CAA GAG GAC CCC ATC CAC ATC GCA TGC ATG GCC CCT   198

G   N   F   P   G   A   N   F   T   L   Y   R   G   G   Q   V   V   Q   L   L    61
GGG AAC TTC CCG GGG GCG AAT TTC ACA CTG TAT CGA GGG GGG CAG GTG GTC CAG CTC CTG   258

Q   A   P   T   D   Q   R   G   V   T   F   N   L   S   G   G   S   S   K   A    81
CAG GCC CCC ACG GAC CAG CGC GGG GTG ACA TTT AAC CTG AGC GGC GGC AGC AGC AAG GCT   318

P   G   G   P   F   H   C   Q   Y   G   V   L   G   E   L   N   Q   S   Q   L   101
CCA GGG GGA CCC TTC CAC TGC CAG TAT GGA GTG TTA GGT GAG CTC AAC CAG TCC CAG CTG   378

S   D   L   S   E   P   V   N   V   S   F   P   V   P   T   W   I   L   V   L   121
TCA GAC CTC AGC GAG CCC GTG AAC GTC TCC TTC CCA GTG CCC ACT TGG ATC TTG GTG CTC   438

S   L   S   L   A   G   A   L   F   L   L   A   G   L   V   A   V   A   L   V   141
TCC CTG AGC CTG GCT GGT GCC CTC TTC CTC CTT GCT GGG CTG GTG GCT GTT GCC CTG GTG   498

V   R   K   V   K   L   R   N   L   Q   K   K   R   D   R   E   S   C   W   A   161
GTC AGA AAA GTT AAA CTC AGA AAT TTA CAG AAG AAA AGA GAT CGA GAA TCC TGC TGG GCC   558

Q   I   N   F   D   S   T   D   M   S   F   D   N   S   L   F   T   V   S   A   181
CAG ATT AAC TTC GAC AGC ACA GAC ATG TCC TTC GAT AAC TCC CTG TTT ACC GTC TCC GCG   618

K   T   M   P   E   E   D   P   A   T   L   D   D   H   S   G   T   T   A   T   201
AAA ACG ATG CCA GAA GAA GAC CCG GCC ACC TTG GAT GAT CAC TCA GGC ACC ACT GCC ACC   678

P   S   N   S   R   T   R   K   R   P   T   S   T   S   S   S   P   E   T   P   221
CCC AGC AAC TCC AGG ACC CGG AAG AGG CCC ACT TCC ACG TCC TCC TCG CCT GAG ACC CCC   738

E   F   S   T   F   R   A   C   Q   *                                           231
GAA TTC AGC ACT TTC CGG GCC TGC CAG TGA                                           768

GGCTGAGGACTGGGGGACCCCTCTGTCTCCAGGCATTCGGGGGCCTGAGGTCCCTCCAGCTACTTCTGGGGGGGCTCTG    847

TCAGCCACTTTCTCAGGGAATTGGACAGAGGAAAGGAAGGGGAACCCTGGCCTTGGGATTTTCATCACAGAGGAGTGGG    926

AGAGGGGACACAGGCATGGGCCTGGCACTATACAGACAACAGGAAGTTCCCCTCTCGACCTTCGGCTCCTCAGGACCAC   1005

CAGAGAAGGAGATGTCAGGACCCCTTCTTGTCCCCCAGCTGGGCCATAAGACGTCCCAGGTCTCTGCACACCCGTGGAA   1084

TTCCTCCCTTCCCCAGTGGGTTTTTGAGCATAGGGTGCCCTTGGGTGTGTTGTGTGTCTGCCTGCTGGCTTGCTTAAGT   1163

TATTAATTATAACACGGGTCAAGGTGTTAAAAAAAAAAAAAAAAAAAAAAAAAAAAAAAAAAAAAAAAAAAAAAAAAAA   1239
```

FIG.36

```
Input file Ht393; Output File hT393 pat
Sequence length 1778
                                              M   K   R   A   S   A   G   G   S   R    10
CGACTTTCAGTCCCCGACGCGCCCCGCCCAACCCCTACG ATG AAG AGG GCG TCC GCT GGA GGG AGC CGG   69

L   L   A   W   V   L   W   L   Q   A   W   Q   V   A   A   P   C   P   G   A    30
CTG CTG GCA TGG GTG CTG TGG CTG CAG GCC TGG CAG GTG GCA GCC CCA TGC CCA GGT GCC  129

C   V   C   Y   N   E   P   K   V   T   T   S   C   P   Q   Q   G   L   Q   A    50
TGC GTA TGC TAC AAT GAG CCC AAG GTG ACG ACA AGC TGC CCC CAG CAG GGC CTG CAG GCT  189

V   P   V   G   I   P   A   A   S   Q   R   I   F   L   H   G   N   R   I   S    70
GTG CCC GTG GGC ATC CCT GCT GCC AGC CAG CGC ATC TTC CTG CAC GGC AAC CGC ATC TCG  309

H   V   P   A   A   S   F   R   A   C   R   N   L   T   I   L   W   L   H   S    90
CAT GTG CCA GCT GCC AGC TTC CGT GCC TGC CGC AAC CTC ACC ATC CTG TGG CTG CAC TCG  309

N   V   L   A   R   I   D   A   A   A   F   T   G   L   A   L   L   E   Q   L   110
AAT GTG CTG GCC CGA ATT GAT GCG GCT GCC TTC ACT GGC CTG GCC CTC CTG GAG CAG CTG  369

D   L   S   D   N   A   Q   L   R   S   V   D   P   A   T   F   H   G   L   G   130
GAC CTC AGC GAT AAT GCA CAG CTC CGG TCT GTG GAC CCT GCC ACA TTC CAC GGC CTG GGC  429

R   V   H   T   L   H   L   D   R   C   G   L   Q   E   L   G   P   G   L   F   150
CGC GTA CAC ACG CTG CAC CTG GAC CGC TGC GGC CTG CAG GAG CTG GGC CCG GGG CTG TTC  489

R   G   L   A   A   L   Q   Y   L   Y   L   Q   D   N   A   L   Q   A   L   P   170
CGC GGC CTG GCT GCC CTG CAG TAC CTC TAC CTG CAG GAC AAC GCG CTG CAG GCA CTG CCT  549

D   D   T   F   R   D   L   G   N   L   T   H   L   F   L   H   G   N   R   I   190
GAT GAC ACC TTC CGC GAC CTG GGC AAC CTC ACA CAC CTC TTC CTG CAC GGC AAC CGC ATC  609

S   S   V   P   E   R   A   F   R   G   L   H   S   L   D   R   L   L   L   H   210
TCC AGC GTG CCC GAG CGC GCC TTC CGT GGG CTG CAC AGC CTC GAC CGT CTC CTA CTG CAC  669

Q   N   R   V   A   H   V   H   P   H   A   F   R   D   L   G   R   L   M   T   230
CAG AAC CGC GTG GCC CAT GTG CAC CCG CAT GCC TTC CGT GAC CTT GGC CGC CTC ATG ACA  729

L   Y   L   F   A   N   N   L   S   A   L   P   T   E   A   L   A   P   L   R   250
CTC TAT CTG TTT GCC AAC AAT CTA TCA GCG CTG CCC ACT GAG GCC CTG GCC CCC CTG CGT  789

A   L   Q   Y   L   R   L   N   D   N   P   W   V   C   D   C   R   A   R   P   270
GCC CTG CAG TAC CTG AGG CTC AAC GAC AAC CCC TGG GTG TGT GAC TGC CGG GCA CGC CCA  849

L   W   A   W   L   Q   K   F   R   G   S   S   S   E   V   P   C   S   L   P   290
CTC TGG GCC TGG CTG CAG AAG TTC CGC GGC TCC TCC TCC GAG GTG CCC TGC AGC CTC CCG  909

Q   R   L   A   G   R   D   L   K   R   L   A   A   N   D   L   Q   G   C   A   310
CAA CGC CTG GCT GGC CGT GAC CTC AAA CGC CTA GCT GCC AAT GAC CTG CAG GGC TGC GCT  969

V   A   T   G   P   Y   H   P   I   W   T   G   R   A   T   D   E   E   P   L   330
GTG GCC ACC GGC CCT TAC CAT CCC ATC TGG ACC GGC AGG GCC ACC GAT GAG GAG CCG CTG 1029

G   L   P   K   C   C   Q   P   D   A   A   D   K   A   S   V   L   E   P   G   350
GGG CTT CCC AAG TGC TGC CAG CCA GAT GCC GCT GAC AAG GCC TCA GTA CTG GAG CCT GGA 1089
```

FIG.38A

```
  R   P   A   S   A   G   N   A   L   K   G   R   V   P   P   G   D   S   P   P   370
 AGA CCA GCT TCG GCA GGC AAT GCG CTG AAG GGA CGC GTG CCG CCC GGT GAC AGC CCG CCG 1149

G   N   G   S   G   P   R   H   I   N   D   S   P   F   G   T   L   P   G   S   390
 GGC AAC GGC TCT GGC CCA CGG CAC ATC AAT GAC TCA CCC TTT GGG ACT CTG CCT GGC TCT 1209

A   E   P   P   L   T   A   V   R   P   E   G   S   E   P   P   G   F   P   T   410
 GCT GAG CCC CCG CTC ACT GCA GTG CGG CCC GAG GGC TCC GAG CCA CCA GGG TTC CCC ACC 1269

S   G   P   R   R   R   P   G   C   S   R   K   N   R   T   R   S   H   C   R   430
 TCG GGC CCT CGC CGG AGG CCA GGC TGT TCA CGC AAG AAC CGC ACC CGC AGC CAC TGC CGT 1329

L   G   Q   A   G   S   G   G   G   T   G   D   S   E   G   S   G   A   L       450
 CTG GGC CAG GCA GGC AGC GGG GGT GGC GGG ACT GGT GAC TCA GAA GGC TCA GGT GCC CTA 1389

P   S   L   T   C   S   L   T   P   L   G   L   A   L   V   L   W   T   V   L   470
 CCC AGC CTC ACC TGC AGC CTC ACC CCC CTG GGC CTG GCG CTG GTG CTG TGG ACA GTG CTT 1449

G   P   C   *                                                                   474
 GGG CCC TGC TGA                                                                  1461
```

CCCCCAGCGGACACAAGAGCGTGCTCAGCAGCCAGGTGTGTGTACATACGGGGTCTCTCTCCACGCCGCCAAGCCAGCC 1540

GGGCGGCCGACCCCGTGGGGCAGGCCAGGCCAGGTCCTCCCTGATGGACGCCTGCCGCCCGCCACCCCCATCTCCACCCC 1619

ATCATGTTTACAGGGTTCGGCGGCAGCGTTTGTTCCAGAACGCCGCCTCCCACCCAGATCGCGGTATATAGAGATATGC 1698

ATTTTATTTTACTTGTGGAAAAATATCGGACGACGTGGAATAAAGAGCTCTTTTCTTAAAAAAAAAAAAAAAAAAAAAA 1777

Input file mT393; Output File mT393 pat
Sequence length 1946

```
CGCGCTGCGAGCGCCCCGCCAGTCCGCGCCGCCGCCCTCACCCTGTGCGCCCGCAGCCGCGAGCCCAGCCCGGCCCGG    79

TAGAGCGGAGCGCCGGAGCCTCGTCCCGCGGCCGGGCCGGGACCGGGCCGGAGCAGCGGCGCCTGGATGCGGACCCGGC   158

M   K   R     3
CGCGCGCAGACGGGCGCCCGCCCCGAAGCCGCTTCCAGTGCCCGACGCGCCCCGCTCGACCCCGAAG ATG AAG AGG   234

A   S   S   G   G   S   R   L   L   A   W   V   L   W   L   Q   A   W   R   V    23
GCG TCC TCC GGA GGA AGC AGG CTG CTG GCA TGG GTG TTA TGG CTA CAG GCC TGG AGG GTA   294

A   T   P   C   P   G   A   C   V   C   Y   N   E   P   K   V   T   T   S   C    43
GCA ACA CCA TGC CCT GGT GCT TGT GTG TGC TAC AAT GAG CCC AAG GTA ACA ACA AGC TGC   354

P   Q   Q   G   L   Q   A   V   P   T   G   I   P   A   S   S   Q   R   I   F    63
CCC CAG CAG GGT CTG CAG GCT GTG CCC ACT GGC ATC CCA GCC TCT AGC CAG CGA ATC TTC   414

L   H   G   N   R   I   S   H   V   P   A   A   S   F   Q   S   C   R   N   L    83
CTG CAT GGC AAC CGA ATC TCT CAC GTG CCA GCT GCG AGC TTC CAG TCA TGC CGA AAT CTC   474

T   I   L   W   L   H   S   N   A   L   A   R   I   D   A   A   A   F   T   G   103
ACT ATC CTG TGG CTG CAC TCT AAT GCG CTG GCT CGG ATC GAT GCT GCT GCC TTC ACT GGT   534

L   T   L   L   E   Q   L   D   L   S   D   N   A   Q   L   H   V   V   D   P   123
CTG ACC CTC CTG GAG CAA CTA GAT CTT AGT GAT AAT GCA CAG CTT CAT GTC GTG GAC CCT   594

T   T   F   H   G   L   G   H   L   H   T   L   H   L   D   R   C   G   L   R   143
ACC ACG TTC CAC GGC CTG GGC CAC CTG CAC ACA CTG CAC CTA GAC CGA TGT GGC CTG CGG   654

E   L   G   P   G   L   F   R   G   L   A   A   L   Q   Y   L   Y   L   Q   D   163
GAG CTG GGT CCC GGC CTA TTC CGT GGA CTA GCA GCT CTG CAG TAC CTC TAC CTA CAA GAC   714

N   N   L   Q   A   L   P   D   N   T   F   R   D   L   G   N   L   T   H   L   183
AAC AAT CTG CAG GCA CTC CCT GAC AAC ACC TTT CGA GAC CTG GGC AAC CTC ACG CAT CTC   774

F   L   H   G   N   R   I   P   S   V   P   E   H   A   F   R   G   L   H   S   203
TTT CTG CAT GGC AAC CGT ATC CCC AGT GTG CCT GAG CAC GCT TTC CGT GGC CTG CAC AGT   834

L   D   R   L   L   L   H   Q   N   H   V   A   R   V   H   P   H   A   F   R   223
CTT GAC CGC CTC CTC TTG CAC CAG AAC CAT GTG GCT CGT GTG CAC CCA CAT GCC TTC CGG   894

D   L   G   R   L   M   T   L   Y   L   F   A   N   N   L   S   M   L   P   A   243
GAC CTT GGC CGC CTC ATG ACC CTC TAC CTG TTT GCC AAC AAC CTC TCC ATG CTG CCT GCA   954

E   V   L   M   P   L   R   S   L   Q   Y   L   R   L   N   D   N   P   W   V   263
GAG GTC CTA ATG CCC CTG AGG TCT CTG CAG TAC CTG CGA CTC AAT GAC AAC CCC TGG GTG  1014

C   D   C   R   A   R   P   L   W   A   W   L   Q   K   F   R   G   S   S   S   283
TGT GAC TGC CGG GCA CGT CCA CTC TGG GCC TGG CTG CAG AAG TTC CGA GGT TCC TCA TCA  1074

E   V   P   C   N   L   P   Q   R   L   A   D   R   D   L   K   R   L   A   A   303
GAG GTG CCC TGC AAC CTG CCC CAA CGC CTG GCA GAC CGT GAT CTT AAG CGC CTC GCT GCC  1134

S   D   L   E   G   C   A   V   A   S   G   P   F   R   P   I   Q   T   S   Q   323
AGT GAC CTA GAG GGC TGT GCT GTG GCT TCA GGA CCC TTC CGT CCC ATC CAG ACC AGT CAG  1194
```

FIG.40A

```
L   T   D   E   E   L   L   S   L   P   K   C   C   Q   P   D   A   A   D   K    343
CTC ACT GAT GAG GAG CTG CTG AGC CTC CCC AAG TGC TGC CAG CCA GAT GCT GCA GAC AAA  1254

A   S   V   L   E   P   G   R   P   A   S   A   G   N   A   L   K   G   R   V    363
GCC TCA GTA CTG GAA CCC GGG AGG CCA GCT TCT GCC GGA AAC GCC CTC AAG GGA CGT GTG  1314

P   P   G   D   T   P   P   G   N   G   S   G   P   R   H   I   N   D   S   P    383
CCT CCC GGT GAC ACT CCA CCA GGC AAT GGC TCA GGC CCT CGG CAC ATC AAT GAC TCT CCA  1374

F   G   T   L   P   S   S   A   E   P   P   L   T   A   L   R   P   G   G   S    403
TTT GGA ACT TTG CCC AGC TCT GCA GAG CCC CCA CTG ACT GCC CTG CGG CCT GGG GGT TCC  1434

E   P   P   G   L   P   T   T   G   P   R   R   R   P   G   C   S   R   K   N    423
GAG CCA CCA GGA CTT CCC ACC ACT GGT CCC CGC AGG AGG CCA GGT TGT TCC CGG AAG AAT  1494

R   T   R   S   H   C   R   L   G   Q   A   G   S   G   A   S   G   T   G   D    443
CGC ACC CGC AGC CAC TGC CGT CTG GGC CAG GCG GGA AGT GGG GCC AGT GGA ACA GGG GAC  1554

A   E   G   S   G   A   L   P   A   L   A   C   S   L   A   P   L   G   L   A    463
GCA GAG GGT TCA GGG GCT CTG CCT GCT CTG GCC TGC AGC CTT GCT CCT CTG GGC CTT GCA  1614

L   V   L   W   T   V   L   G   P   C   *                                        474
CTG GTA CTT TGG ACA GTG CTT GGG CCC TGC TGA                                      1647

CCAGCCACCAGCCACCAGGTGTGTGTACATATGGGGTCTCCCTCCACGCCGCCAGCCAGAGCCAGGGACAGGCTCTGAG  1726

GGGCAGGCCAGGCCCTCCCTGACAGATGCCTCCCCACCAGCCCACCCCCATCTCCACCCCATCATGTTTACAGGGTTCC  1805

GGGGGTGGCGTTTGTTCCAGAACGCCACCTCCCACCCGGATCGCGGTATATAGAGATATGAATTTTATTTTTACTTGTGT  1884

AAAATATCGGATGACGTGGAATAAAGAGCTCTTTTCTTAAAAAAAAAAAAAAAAAAAAAAAA                  1946
```

FIG.40B

```
ALIGN calculates a global alignment of two sequences
 version 2.0uPlease cite: Myers and Miller, CABIOS (1989)
> m T393 ORF                                   1419 aa vs.
> h T393 ORF                                   1419 aa
scoring matrix: pam120.mat, gap penalties: -12/-4
82.8% indentity;        Global alignment score: 6628

10        20        30        40        50        60        70
inputs ATGAAGAGGGCGTCCTCCGGAGGAAGCAGGCTGCTGGCATGGGTGTTATGGCTACAGGCCTGGAGGGTAG
       ::::::::::::::: : :::::::: ::::::::::::::::::: :::::::::::::::: :::::
       ATGAAGAGGGCGTCCGCTGGAGGGAGCCGGCTGCTGGCATGGGTGCTGTGGCTGCAGGCCTGGCAGGTGG
             10        20        30        40        50        60        70

80        90       100       110       120       130       140
inputs CAACACCATGCCCTGGTGCTTGTGTGTGCTACAATGAGCCCAAGGTAACAACAAGCTGCCCCCAGCAGGG
       :::.: :::::::::::::.::::::: :: :::::::::::::::::.:::::::::::::::::::::
       CAGCCCCATGCCCAGGTGCCTGCGTATGCTACAATGAGCCCAAGGTGACGACAAGCTGCCCCCAGCAGGG
             80        90       100       110       120       130       140

150       160       170       180       190       200       210
inputs TCTGCAGGCTGTGCCCACTGGCATCCCAGCCTCTAGCCAGCGAATCTTCCTGCATGGCAACCGAATCTCT
       :::::::::::::::::.  :::::::::::: :  :::::::::::::::::.:::::::::::.:::
       CCTGCAGGCTGTGCCCGTGGGCATCCCTGCTGCCAGCCAGCGCATCTTCCTGCACGGCAACCGCATCTCG
            150       160       170       180       190       200       210

220       230       240       250       260       270       280
inputs CACGTGCCAGCTGCGAGCTTCCAGTCATGCCGAAATCTCACTATCCTGTGGCTGCACTCTAATGCGCTGG
       ::  :::::::::::: :::::.  :  :::::  ::::::: :::::::::::::::: :::.:::::
       CATGTGCCAGCTGCCAGCTTCCGTGCCTGCCGCAACCTCACCATCCTGTGGCTGCACTCGAATGTGCTGG
            220       230       240       250       260       270       280

290       300       310       320       330       340       350
inputs CTCGGATCGATGCTGCTGCCTTCACTGGTCTGACCCTCCTGGAGCAACTAGATCTTAGTGATAATGCACA
       :  ::.:: :::::  ::::::::::::: :::.:::::::::::::.::.:: ::.:: ::::::::::
       CCCGAATTGATGCGGCTGCCTTCACTGGCCTGGCCCTCCTGGAGCAGCTGGACCTCAGCGATAATGCACA
            290       300       310       320       330       340       350

360       370       380       390       400       410
inputs GCTTCATGTC-GTGGACCCTACCACGTTCCACGGCCTGGGCCACCTGCACACACTGCACCTAGACCGATG
       ::: :. ::: :::::::::.:::: :::::::::::::::.: ::::::.::::::::::::.::: ::
       GCTCCG-GTCTGTGGACCCTGCCACATTCCACGGCCTGGGCCGCGTACACACGCTGCACCTGGACCGCTG
             360       370       380       390       400       410

420       430       440       450       460       470       480
inputs TGGCCTGCGGGAGCTGGGTCCCGGCCTATTCCGTGGACTAGCAGCTCTGCAGTACCTCTACCTACAAGAC
      ::::::::.:::::::::::::.:: :::.:: : ::::: ::. ::::::::::::::::::: ::.::
      CGGCCTGCAGGAGCTGGGCCCGGGGCTGTTCCGCGGCCTGGCTGCCCTGCAGTACCTCTACCTGCAGGAC
      420       430       440       450       460       470       480
```

FIG.42A

```
        490       500       510       520       530       540       550
inputs AACAATCTGCAGGCACTCCCTGACAACACCTTTCGAGACCTGGGCAACCTCACGCATCTCTTTCTGCATG
       :::.  :::::::::::: :::::  ::::::::: :: :::::::::::::::.:: ::::: ::::: :
       AACGCGCTGCAGGCACTGCCTGATGACACCTTCCGCGACCTGGGCAACCTCACACACCTCTTCCTGCACG
        490       500       510       520       530       540       550

560       570       580       590       600       610       620
inputs GCAACCGTATCCCCAGTGTGCCTGAGCACGCTTTCCGTGGCCTGCACAGTCTTGACCGCCTCCTCTTGCA
       ::::::::  :::  :::::: :::::: ::::  :::::::::  ::::::::: :: ::::: :::: ::::
       GCAACCGCATCTCCAGCGTGCCCGAGCGCGCCTTCCGTGGGCTGCACAGCCTCGACCGTCTCCTACTGCA
        560       570       580       590       600       610       620

630       640       650       660       670       680       690
inputs CCAGAACCATGTGGCTCGTGTGCACCCACATGCCTTCCGGGACCTTGGCCGCCTCATGACCCTCTACCTG
       ::::::::::. :::::  :.:::::::::::::::: :::::::::: :::::::::::::: ::::: :::
       CCAGAACCGCGTGGCCCATGTGCACCCGCATGCCTTCCGTGACCTTGGCCGCCTCATGACACTCTATCTG
        630       640       650       660       670       680       690

700       710       720       730       740       750       760
inputs TTTGCCAACAACCTCTCCATGCTGCCTGCAGAGGTCCTAATGCCCCTGAGGTCTCTGCAGTACCTGCGAC
       ::::::::::::  : ::::: :: ::::: ::::  ::::::  :::::: :  : ::::::::::: ::
       TTTGCCAACAATCTATCAGCGCTGCCCACTGAGGCCCTGGCCCCCCTGCGTGCCCTGCAGTACCTGAGGC
        700       710       720       730       740       750       760

770       780       790       800       810       820       830
inputs TCAATGACAACCCCTGGGTGTGTGACTGCCGGGCACGTCCACTCTGGGCCTGGCTGCAGAAGTTCCGAGG
       ::::  ::::::::::::::::::::::::::::::: : ::::::::::::::::::::::::::::: ::
       TCAACGACAACCCCTGGGTGTGTGACTGCCGGGCACGCCCACTCTGGGCCTGGCTGCAGAAGTTCCGCGG
        770       780       790       800       810       820       830

840       850       860       870       880       890       900
inputs TTCCTCATCAGAGGTGCCCTGCAACCTGCCCCAACGCCTGGCAGACCGTGATCTTAAGCGCCTCGCTGCC
       :::: ::  :: :::::::::::::: ::::: :::::::::::::: :::::::::: :::::::::: :::
       CTCCTCCTCCGAGGTGCCCTGCAGCCTCCCGCAACGCCTGGCTGGCCGTGACCTCAAACGCCTAGCTGCC
        840       850       860       870       880       890       900

910       920       930       940       950       960       970
inputs AGTGACCTAGAGGGCTGTGCTGTGGCTTCAGGACCCTTCCGTCCCATCCAGACCAGTCAGCTCACTGATG
       ::::::::  ::::::: :: ::::::  :: :: :::::::  ::::::::  : ::: ::::
       AATGACCTGCAGGGCTGCGCTGTGGCCACCGGCCCCTTACCATCCCATCTGGACCGGCAGGGCCACCGATG
        910       920       930       940       950       960       970

980       990      1000      1010      1020      1030      1040
inputs AGGAGCTGCTGAGCCTCCCCAAGTGCTGCCAGCCAGATGCTGCAGACAAAGCCTCAGTACTGGAACCCGG
       ::::::  :::::.  :::::::::::::::::::::::: ::::: ::: :::::::::::::: :: ::
       AGGAGCCGCTGGGGCTTCCCAAGTGCTGCCAGCCAGATGCCGCTGACAAGGCCTCAGTACTGGAGCCTGG
        980       990      1000      1010      1020      1030      1040

1050      1060      1070      1080      1090      1100      1110
inputs GAGGCCAGCTTCTGCCGGAAACGCCCTCAAGGGACGTGTGCCTCCCGGTGACACTCCACCAGGCAATGGC
       ::: :::::::::  :: :::::: :: :::::::::::::: ::::::::::: :::::  ::::: :::
       AAGACCAGCTTCGGCAGGCAATGCGCTGAAGGGACGCGTGCCGCCCGGTGACAGCCCGCCGGGCAACGGC
        1050      1060      1070      1080      1090      1100      1110
```

FIG.42B

```
        1120      1130      1140      1150      1160      1170      1180
inputs TCAGGCCCTCGGCACATCAATGACTCTCCATTTGGAACTTTGCCCAGCTCTGCAGAGCCCCCACTGACTG
       ::::::::.::::::::::::::::::::.:: ::::::.::: :::: .:::::::::.:::::::.: ::::
       TCTGGCCCACGGCACATCAATGACTCACCCTTTGGGACTCTGCCTGGCTCTGCTGAGCCCCCGCTCACTG
        1120      1130      1140      1150      1160      1170      1180

1190      1200      1210      1220      1230      1240      1250
inputs CCCTGCGGCCTGGGGGTTCCGAGCCACCAGGACTTCCCACCACTGGTCCCCGCAGGAGGCCAGGTTGTTC
       : :::::::: :.:::: :::::::::::::::::. : :::::::.: :: ::: ::::::::::: :::::
       CAGTGCGGCCCGAGGGCTCCGAGCCACCAGGGTTCCCCACCTCGGGCCCTCGCCGGAGGCCAGGCTGTTC
        1190      1200      1210      1220      1230      1240      1250

1260      1270      1280      1290      1300      1310      1320
inputs CCGGAAGAATCGCACCCGCAGCCACTGCCGTCTGGGCCAGGCGGGAAGTGGGGCCAGTGGAACAGGGGAC
       :: ::::::  :::::::::::::::::::::::::::::::::.:: :: ::::  .: ::.::.:: :::
       ACGCAAGAACCGCACCCGCAGCCACTGCCGTCTGGGCCAGGCAGGCAGCGGGGGTGGCGGGACTGGTGAC
        1260      1270      1280      1290      1300      1310      1320

1330      1340      1350      1360      1370      1380      1390
inputs GCAGAGGGTTCAGGGGCTCTGCC-TGCTCTGGCCTGCAGCCTTGCTCCTCTGGGCCTTGCACTGGTACTT
       ::::::.:: :::::  :: ::.::  :: :::::::::::  :: :: ::::::: ::::::::::::
       TCAGAAGGCTCAGGTGCCCTACCCAGC-CTCACCTGCAGCCTCACCCCCCTGGGCCTGGCGCTGGTGCTG
        1330      1340      1350      1360      1370      1380      1390

1400      1410
inputs TGGACAGTGCTTGGGCCCTGC
       :::::::::::::::::::::
       TGGACAGTGCTTGGGCCCTGC
        1400      1410
```

FIG. 42C

```
ALIGN calculates a global alignment of two sequences
 version 2.0uPlease cite: Myers and Miller, CABIOS (1989)
> hT393 a.a.                                  473 aa vs.
> mT393 a.a.                                  473 aa
scoring matrix: pam120.mat, gap penalties: -12/-4
89.2% identitiy;        Global alignment score: 2279

10        20        30        40        50        60        70
inputs  MKRASAGGSRLLAWVLWLQAWQVAAPCPGACVCYNEPKVTTSCPQQGLQAVPVGIPAASQRIFLHGNRIS
        :::::.::::::::::::::::.::.:::::::::::::::::::::::::::.:::::.:::::::::
        MKRASSGGSRLLAWVLWLQAWRVATPCPGACVCYNEPKVTTSCPQQGLQAVPTGIPASSQRIFLHGNRIS
                10        20        30        40        50        60        70

80        90       100       110       120       130       140
inputs  HVPAASFRACRNLTILWLHSNVLARIDAAAFTGLALLEQLDLSDNAQLRSVDPATFHGLGRVHTLHLDRC
        ::::::::.:::::::::::::::.:::::::::::.:::::::::::::::.:::.::::.:::::::
        HVPAASFQSCRNLTILWLHSNALARIDAAAFTGLTLLEQLDLSDNAQLHVVDPTTFHGLGHLHTLHLDRC
                80        90       100       110       120       130       140

150       160       170       180       190       200       210
inputs  GLQELGPGLFRGLAALQYLYLQDNALQALPDDTFRDLGNLTHLFLHGNRISSVPERAFRGLHSLDRLLLH
        ::.:::::::::::::::::::::::::::::::::::::::::::::::::::::::::::::::::::
        GLRELGPGLFRGLAALQYLYLQDNNLQALPDNTFRDLGNLTHLFLHGNRIPSVPEHAFRGLHSLDRLLLH
               150       160       170       180       190       200       210

220       230       240       250       260       270       280
inputs  QNRVAHVHPHAFRDLGRLMTLYLFANNLSALPTEALAPLRALQYLRLNDNPWVCDCRARPLWAWLQKFRG
        ::.:.::::::::::::::::::::::::.::.:.:::::.:::::::::::::::::::::::::::::
        QNHVARVHPHAFRDLGRLMTLYLFANNLSMLPAEVLMPLRSLQYLRLNDNPWVCDCRARPLWAWLQKFRG
               220       230       240       250       260       270       280

290       300       310       320       330       340       350
inputs  SSSEVPCSLPQRLAGRDLKRLAANDLQGCAVATGPYHPIWTGRATDEEPLGLPKCCQPDAADKASVLEPG
        ::::::::.::::::.::::::::.::::::.:::..::    :.. ::::.::::::::::::::::::
        SSSEVPCNLPQRLADRDLKRLAASDLEGCAVASGPFRPIQTSQLTDEELLSLPKCCQPDAADKASVLEPG
               290       300       310       320       330       340       350

360       370       380       390       400       410       420
inputs  RPASAGNALKGRVPPGDSPPGNGSGPRHINDSPFGTLPGSAEPPLTAVRPEGSEPPGFPTSGPRRRPGCS
        :::::::::::::::::::.:::::::::::::::::::.::::::::::.::::::::.:::::::::
        RPASAGNALKGRVPPGDTPPGNGSGPRHINDSPFGTLPSSAEPPLTALRPGGSEPPGLPTTGPRRRPGCS
               360       370       380       390       400       410       420

430       440       450       460       470
inputs  RKNRTRSHCRLGQAGSGGGGTGDSEGSGALPSLTCSLTPLGLALVLWTVLGPC
        ::::::::::::::::::.:::::.:::::: :.:::.:::::::::::::::
        RKNRTRSHCRLGQAGSGASGTGDAEGSGALPALACSLAPLGLALVLWTVLGPC
               430       440       450       460       470
```

FIG.43

```
Input file T402; Output File.pat
Sequence length 1348

GCCAAAGAGACATATCCAAGGTTGAGATTAGTTTCCATTTTCTTTGTACTATTTTCTGGATAATAAGACATTAGACATT    79

M   E   N   E   D   G   Y   M   T   L   S   F   K   N   R   C   K   S     18
TGAAGAG ATG GAG AAT GAA GAT GGG TAT ATG ACG CTG AGT TTC AAG AAT CGT TGT AAA TCG   140

K   Q   K   S   K   D   F   S   L   Y   P   Q   Y   Y   C   L   L   L   I   F     38
AAG CAG AAA TCT AAA GAT TTC TCC CTA TAT CCA CAA TAT TAT TGT CTT CTG CTC ATA TTT   200

G   C   I   V   I   L   I   F   I   M   T   G   I   D   L   K   F   W   H   K     58
GGA TGC ATT GTG ATC CTT ATA TTC ATT ATG ACA GGG ATT GAC CTG AAG TTC TGG CAT AAA   260

K   M   D   F   S   Q   N   V   N   I   S   S   L   S   G   H   N   Y   L   C     78
AAA ATG GAT TTC TCC CAG AAT GTA AAC ATC AGC AGT CTA TCA GGA CAC AAT TAC TTG TGC   320

P   N   D   W   L   L   N   E   G   K   C   Y   W   F   S   T   S   F   K   T     98
CCA AAT GAC TGG CTG TTG AAC GAA GGG AAA TGT TAC TGG TTT TCA ACT TCT TTT AAA ACG   380

W   K   E   S   Q   R   D   C   T   Q   L   Q   A   H   L   L   V   I   Q   N    118
TGG AAA GAG AGT CAA CGT GAT TGT ACA CAG CTA CAG GCA CAT TTA CTG GTG ATT CAA AAT   440

L   D   E   L   E   F   I   Q   N   S   L   K   P   G   H   F   G   W   I   G    138
TTG GAT GAG CTG GAG TTC ATA CAG AAC AGT TTA AAA CCT GGA CAT TTT GGT TGG ATT GGA   500

L   Y   V   T   F   Q   G   N   L   W   M   W   I   D   E   H   F   L   V   P    158
CTA TAT GTT ACA TTC CAA GGG AAC CTA TGG ATG TGG ATA GAT GAA CAC TTT TTA GTT CCA   560

E   L   F   S   V   I   G   P   T   D   D   R   S   C   A   V   I   T   G   N    178
GAA TTG TTT TCA GTG ATT GGA CCA ACT GAT GAC AGG AGC TGT GCC GTT ATC ACA GGA AAC   620

W   V   Y   S   E   D   C   S   S   T   F   K   G   I   C   Q   R   D   A   I    198
TGG GTG TAT TCT GAA GAC TGT AGC TCC ACA TTT AAG GGC ATT TGC CAG AGA GAT GCG ATC   680

L   T   H   N   G   T   S   G   V   *                                             208
TTG ACG CAC AAT GGA ACC AGT GGT GTG TAA                                            710

ATGTACAACCAAATATAGAAATACTTTGCATGTTAAAGCAGAGCTAGATTTTAAAGACTTAAGATTTTTAGATAAAGTT   789

TCTAACAGAAAGTTTCTGCTAACAGACATCATCTAAATAGGAGAAAAGTATTTTATCCTGAATTGACTATAAAGACAAC   868

TTCTGAACAGAACTTTTACTCTATACTTGGATTTCTGGTTTGTCTTTTCCATGGCATTGACAAGAAAAGCTAAATAAAA   947

AATTAGTAATTATTTTAATAGTTATTTAATAGTTTGATTTTTTTGCATTTAAAATAGCATAGAATAAAACAACTTTAAA 1026

GGAATGTTATTTAGCTATATGTGCTATGTGGTAGATTGGAAGGAAAGAAGCAGTATATGTACAAATATAATATTTGAAG 1105

CATGGAATTCTGAATTTTTCATCTGTGTATTATAGCCTGAAGTGTTTGGTGGGGAGTGGGTAATGAGAAATTACCTACT 1184

GGGTATAATGTACAATATTTAGGTGATGGATAAACTAAAAGCTCAGACTTCTCCACTTTGTGATATATCCATGTAACAA 1263

AATTATGCTTGTACCCTTTAAATGTATTCAAATAAAATAAAATAAAGTCATGTGGCCAAATATTCAAAACAAAAAAAAA 1342

AAAAAA                                                                           1348
```

FIG.44

ALIGN calculates a global alignmnent of two sequences
 version 2.0uPlease cite: Myers and Miller, CABIOS (1989)
> AB010710 a.a.                                        273 aa vs.
> T402 a.a.                                            207 aa
scoring matrix: pam120.mat, gap penalties: -12/-4
25.1% identity;         Global alignment score: -92

```
              10        20        30        40        50        60
inputs MTFDD-LKIQTVKDQPDEKSNGKKAKGLQFLYSPWWCLAAATLGVLCLGLVVTIMVLGMQLSQVSDLLTQ
       :    .:    .. .:..    :      .:.:..  :::..  ::     ..: :. ... ::. :..:
       MENEDGYMTLSFKNRCKSK---QKSKDFS-LYPQYYCLLL-IFG--CIVILIFIMT-GIDL----------
              10        20        30          40        50

70        80        90       100       110       120       130
inputs EQANLTHQKKKLEGQISARQQAEEASQESENELKEMIETLARKLNEKSKEQMELHHQNLNLQETLKRVAN
            .. :.:.           ::. .              : .:.                :. :
       ---KFWHKKMDF------------SQNVN------ISSLSG-------------HNYL----------
              60                    70

140       150       160       170       180       190       200
inputs CSAPCPQDWIWHGENCYLFSSGSFNWEKSQEKCLSLDAKLLKINSTADLDFIQQAISYSSFPFWMGLSRR
           :::.. . .:: ::..  .: :: : :.: :: :..  ...:::..   . :    ::::
       ----CPNDWLLNEGKCYWFSTSFKTWKESQRDCTQLQAHLLVIQNLDELEFIQNSLKPGHFG-WIGLYVT
              80        90       100       110       120       130       140

210       220       230       240       250       260       270
inputs NPSYPWLWEDGSPLMPHLFRVRGAVSQTYPSGTCAYIQRGAVYAENCILAAFSICQKKANL-----RAQ
           .. :.:    :: :: :: :.....      .::. ..:::.:  .  .:::.:  :   .
       FQGNLWMWIDEHFLVPELFSVIGPTDDR----SCAVITGNWVYSEDCSSTFKGICQRDAILTHNGTSGV
              150       160       170         180       190       200
```

FIG.46

```
ALIGN calculates a global alignment of two sequences
 version 2.0uPlease cite: Myers and Miller, CABIOS (1989)
> LOX-1 ORF                                          819 aa vs.
> T402 ORF                                           621 aa
scoring matrix: pam120.mat, gap penalties: -12/-4
42.0% identity;         Global alignment score: 462

10        20        30        40        50        60        70
inputs ATGACTTTTGATGACCTAAAGATCCAGACTGTGAAGGACCAGCCTGATGAGAAGTCAAATGGAAAAAAAG
       :::.  ..::: ..     .:::    .:  ::  :: .. .. ::.: :::..
       ATGGAGAATGAAGA---TGGGTATATGACGCTGAGTTTCAAGAATCGTTGTAAATCGAA---GCAGAAAT
              10        20        30        40        50        60

80        90       100       110       120       130       140
inputs CTAAAGGTCTTCAGTTTCTTTACTCTCCATGGTGGTGCCTGGCTGCTGCGACTCTAGGGGTCCTTTGCCT
       :::::::. :::   :   ::..: :: ::. ::. :. :: ::::: . :  .::: :..:::  :
       CTAAAGAT-TTC--TCCCTATATCCACAATATTATTGTCTT-CTGCT-CA--TATTTGGATGCATTG--T 150       160       170       180       190       200       210
inputs GGGATTAGTAGTGACCATTATGGTGCTGGGCATGCAATTATCCCAGGTGTCTGACCTCCTAACACAAGAG
       .  :.  ::.:  :::::::::  :.:::   ::::..  ::. .:::::::..: :. ::: .. :.
       GATCCTTATATT---CATTATGA--CAGGG------ATTGACCTGAAGTTCTGGCAT--AAAAAAATGGA
              130       140         150          160       170       180

220       230       240       250       260       270       280
inputs CAAGCAAACCTAACTCACCAGAAAAAGAAACTGGAGGGACAGATCTCAGCCCGGCAACAAGCAGAAGAAG
                   ::.:::  ::::::::.  ::::    .:::. :::  ::: .. :.  ::::::.:::
       ----------TTTCTC-CCAGAATGT-AAAC------ATCAG----CAGTCTATCAGGACACAATTACTT
                       190       200              210       220       230

290       300       310       320       330       340
inputs CTTCACAGGAGTCAGA-AAACGAACTCAAGGAAATGATAGAAACCCTTGCTCGGAAGCTGAATGAGAAAT
       : :.::  ... ...   .::::  :  :.:::::::::.:.  :   :  :: ...:: .. ..:::
       GTGCCCAAATGACTGGCTGTTGAACGAAGGGAAATGTTA----CTGGTTTTC---AACTTCTTTTAAAA-
              240       250       260       270       280       290

350       360       370       380       390       400       410
inputs CCAAAGAGCAAATGGAACTTCACCACCAGAATCTGAATCTCCAAGAAACACTGAAGAGAGTAGCAAATTG
       .:.::.   .:::.::::  :    :   :: .. :  ::  ::..::  ::     ...::: :::::
       -CGTGGA--AAGAGAGTCAACGTGATTGTACACAG---CTACAGG---CAC------ATTTACTGGTGA
              300       310       320       330                 340

420       430       440       450       460       470       480
inputs TTCAGCTCCTTGTCCGCAAGACTGGATCTGGCATGGAGAAAACTGTTACCTATTTTCCTCGGGCTCATTT
       :::. . :::   .:   ..:::::   :.  ::: :::..   ::::   ......:: :::. ::::
       TTCAAAAT-TTG---GATGAGCTGGAGTT--CATACAGA--ACAGTTT----AAAACCT-GGAC--ATTT
              350       360       370         380           390        400

490       500       510       520       530       540       550
inputs AACTGGGAAAAGAGCCAAGAGAAGTGCTTGTCTTTGGATGCCAAGTTGCTGAAAATTAATAGCACAGCTG
       : :.::    ::::  :::. ::.:.   ::.  :    :::  .. :::::  : : .:: :::: ::
       TGGTTGGATTGGA-CTATATGT--TACAT-TCCAAGGGAACCTA-TGGATGTGGATAGAT-GAACA-CTT
              410       420       430       440       450       460
```

FIG.47A

```
        560       570       580       590       600       610       620
inputs ATCTGGACTTCATCCAGCAAGCAATTTCCTATTCCAGTTTTCCATTCTGGATGGGGCTGTCTCGGAGGAA
        .:    .::::    .::.    :.    :    .:::   :::.    .:.    :    :::
       TTTAG------TTCCAG--AATTGTTTTCAGTG--ATTGGACCAA-CTGAT---GACAGGAGCTGTG---
                  470          480          490        500          510
        630       640       650       660       670       680       690
inputs CCCCAGCTACCCATGGCTCTGGGAGGACGGTTCTCCTTTGATGCCCCACTTATTTAGAGTCCGAGGCGCT
        .:.   .:.    ::.::::.::    ::::                        .::.    .:::
       --CCGTTATCACAGGAAACTGGGTGTA---TTCT---------------------GAAGACTGTAGC---
         520       530        540                                550
        700       710       720       730       740       750       760
inputs GTCTCCCAGACATACCCTTCAGGTACCTGTGCATATATACAACGAGGAGCTGTTTATGCGGAAAACTGCA
           .::    .:.:     ::.::::    :    .:    ::.::::::    .:        ::.::
       ---TCC---ACAT----TTAAGG-GCATTTGC------CAGAGAGATGCGATCTTGACG-----CA-CA
          560       570          580           590              600
        770       780       790       800       810
inputs TTTTAGCTGCCTTCAGTATATGTCAGAAGAAGGCAAACCTAAGAGCACAG
        .:  .:::     :::::.   .::::                    :
       ATGGAAC------CAGTG-GTGT------------------------G
        610          620
```

FIG.47B

```
                                                                                              79
GGGGGGCGCAGGACCCTCGCAACTTCTTCGCAGGACTCCAGCCTGGCCGCCGGCGCCCGCAGCCGTCCGAGAGCCCTGC

M   P   A   A    4
GCCCGCGCCTCCCCTTGCGCACCGTGGCAGCGCCCGGCGGGCGGTCCTGCCAGCCCCGACGGG ATG CCC GCA GCC  154

M   L   P   Y   A   C   V   L   V   L   L   G   A   H   T   A   P   A   A   G    24
ATG CTC CCC TAC GCT TGC GTC CTG GTG CTT TTG GGA GCC CAC ACT GCA CCG GCG GCT GGG  214

E   A   G   G   S   C   L   R   W   E   P   H   C   Q   Q   P   L   P   D   R    44
GAG GCC GGG GGC AGC TGC CTG CGC TGG GAA CCC CAC TGC CAG CAG CCC TTG CCA GAT AGA  274

V   P   S   T   A   I   L   P   P   R   L   N   G   P   W   I   S   T   G   R    64
GTG CCC AGC ACT GCG ATC CTG CCT CCA CGC CTT AAT GGA CCT TGG ATC TCC ACA GGC CGG  334

L   F   R   A   H   Q   F   Y   Y   E   D   P   F   C   G   E   P   A   H   S    84
CTC TTT CGA GCC CAC CAG TTC TAC TAC GAG GAC CCC TTC TGC GGG GAA CCT GCC CAC TCG  394

L   L   V   K   G   K   V   R   L   R   R   A   S   W   V   T   R   G   A   T   104
CTG CTC GTC AAG GGC AAA GTC CGC CTG CGC CGG GCC TCC TGG GTC ACC CGG GGA GCC ACC  454

E   A   D   Y   H   L   H   K   V   G   I   V   F   H   S   R   R   A   L   V   124
GAG GCC GAC TAC CAC CTG CAC AAG GTG GGC ATC GTC TTC CAC AGC CGC CGG GCC CTG GTC  514

D   V   T   G   R   L   N   Q   T   R   A   G   R   D   C   A   R   R   L   P   144
GAC GTC ACC GGG CGC CTC AAC CAG ACC CGC GCC GGC CGG GAC TGC GCG CGG CGG CTG CCT  574

P   A   R   A   W   L   P   G   A   L   Y   E   L   R   S   A   R   A   Q   G   164
CCG GCC CGG GCC TGG CTG CCT GGG GCG CTG TAC GAG CTG CGG AGC GCC CGG GCT CAG GGG  634

D   C   L   E   A   L   G   L   T   M   H   E   L   S   L   V   R   V   Q   R   184
GAC TGC CTG GAG GCG CTG GGC CTC ACC ATG CAC GAG CTC AGC CTG GTC CGC GTG CAG CGC  694

R   L   Q   P   Q   P   R   A   S   P   R   L   V   E   E   L   Y   L   G   D   204
CGC CTG CAG CCG CAG CCC CGG GCG TCG CCC CGG CTG GTG GAG GAG CTG TAC CTG GGG GAC  754

I   H   T   D   P   A   E   R   R   H   Y   R   P   T   G   Y   Q   R   P   L   224
ATC CAC ACC GAC CCG GCG GAG AGG CGG CAC TAC CGG CCC ACG GGC TAC CAG CGC CCG CTG  814

Q   S   A   L   H   H   V   Q   P   C   P   A   C   G   L   I   A   R   S   D   244
CAG AGC GCA CTG CAC CAC GTG CAG CCG TGC CCA GCC TGT GGC CTC ATT GCC CGC TCC GAT  874

V   H   H   P   P   V   L   P   P   P   L   A   L   P   L   H   L   G   G   W   264
GTG CAC CAC CCG CCC GTG CTG CCG CCC CCT CTG GCC CTG CCC CTG CAC CTG GGC GGC TGG  934

W   V   S   S   G   C   E   V   R   P   A   V   L   F   L   T   R   L   F   T   284
TGG GTC AGC TCG GGG TGC GAG GTG CGC CCA GCA GTC CTG TTC CTC ACC CGG CTC TTC ACT  994

F   H   G   H   S   R   S   W   E   G   Y   Y   H   H   F   S   D   P   A   C   304
TTC CAC GGG CAC AGC CGC TCC TGG GAA GGG TAT TAC CAC CAC TTC TCA GAC CCA GCC TGC 1054

R   Q   P   T   F   T   V   Y   A   A   G   R   Y   T   R   G   T   P   S   T   324
CGG CAG CCC ACC TTC ACC GTG TAT GCC GCC GGC CGC TAC ACC AGG GGC ACG CCA TCC ACC 1114

R   V   R   G   G   T   E   L   V   F   E   V   T   R   A   H   V   T   P   M   344
AGG GTC CGC GGC GGC ACC GAG CTG GTG TTT GAG GTC ACA CGG GCC CAT GTG ACC CCC ATG 1174
```

FIG.48A

```
  D   Q   V   T   T   A   M   L   N   F   S   E   P   S   S   C   G   G   A   G    364
GAC CAG GTC ACC ACG GCC ATG CTC AAC TTC TCT GAG CCA AGC AGC TGT GGG GGT GCG GGG   1234

A   W   S   M   G   T   E   R   D   V   T   A   T   N   G   C   L   P   L   G    384
GCC TGG TCC ATG GGC ACT GAG CGG GAT GTC ACA GCC ACC AAC GGC TGC CTA CCG CTG GGC   1294

I   R   L   P   H   V   E   Y   E   L   F   K   M   E   Q   D   P   L   G   Q    404
ATC CGG CTC CCG CAT GTG GAG TAC GAG CTT TTC AAG ATG GAA CAA GAC CCC CTC GGG CAA   1354

S   L   L   F   I   G   Q   R   P   T   D   G   S   S   P   D   T   P   E   K    424
AGC CTG CTC TTC ATC GGA CAA AGG CCC ACC GAT GGC TCA AGT CCC GAT ACC CCA GAG AAA   1414

R   P   T   S   Y   Q   A   P   L   V   L   C   H   G   E   A   P   D   F   S    444
CGT CCC ACC TCC TAC CAA GCA CCC CTG GTG CTC TGT CAT GGG GAG GCC CCC GAC TTC TCC   1474

R   P   P   Q   H   R   P   S   L   Q   K   H   P   S   T   G   G   L   H   I    464
AGG CCA CCG CAG CAC AGG CCA TCG CTG CAG AAG CAC CCC AGC ACA GGG GGT CTT CAC ATA   1534

A   P   F   P   L   L   P   L   V   L   G   L   A   F   L   H   W   L   *         483
GCC CCC TTC CCA CTT CTG CCC CTA GTT CTA GGG CTG GCC TTC CTC CAC TGG CTA TGA       1591

CATTGGACTTGACATCAGGATGGCGGCTCTGGACACCCATTCAACCCTTCAGACTCCCTCCTGGCAGCTGTAGGGAAGG 1670
AACCATTCTCCTCTGCTCTGTCATGGATGGATGCACAGCCCCACTGCTTCCAAACTCTGCCTGTGTCCCATGTGGCTCA 1749
GGACATGAGCTTAACCCCTGCAAAGCCTATACCACATCCCACAGCCCGGGTCCCCAGTCAAGCACTTGGATGCGGCAGT 1828
GATGTTCATCGCTACGTGAGTTTCTAAAGATCACTCCCAATTTTTCTACTTTCCTCATCCTTGGCAGCTCGCCAACAGG 1907
TGCAGTCAGGGGGCCACACGGAACACCCCCATCCCATGTTCCCCCCAGTTCTTCCCATCCTGACCCTTGGGATTCCAAG 1986
ATGGGAGCAAGAGGAGATCCTGAGGCTCTGCCTAGGGACGAGGCCTACAGTTCTGCCATGTCTGTAGGTTGTTGTTTAA 2065
AGATTATTAATTCGAATTTAGCAATACGATCTCTAAGTGGTGCCATGAATTAAAGATGCCACTTCGGGCTTTCAGTGCT 2144
TCTCAGCTTTTGGGCAAAGGGCTTGTGTCTTCAGGGGCAGCTCAGCTTTCCTGAGTCCTGACTGCTGGCATTCGTCTGC 2223
ATTTGCCTGTGCTTCTGCGAGTCGGACCTCAAGCTGCCAACACTGCATGTGGATAAATCCAGTTTTCCCGGGCCAGCAT 2302
GCAAAATGAAGAGGACTCCATCTAAGCTGAGAAGCATGGCCTCCCCAGAGCAGCCTGCAGCCTCCAAGCCTTCCTGGCC 2381
CAGGCAAATGCCAGTGTGCACCAGGCTGGCTGCTGGGGGCAGGTCTTTGGAGGGGAGCAGCATTTCCAGCCTTCTGAAC 2460
ATAGTTAATAGTAATGACAGCCGTAACACTAACGCGCTCTGCAATTCGCCCTGCCCAGCCATCCTCGGTTGCCAAGATT 2539
GCCTGTGCCTGCCTGACAAAGGAAGAGAATCTCCGAATGTGTATCTTTGGGCCCACCCTAGGGAGAGGTCGGGGTCACC 2618
AGGCTACATGGCGACATCTAGGCAGCTCCGCCTTGCCCAGCCTCCTTGCCATAATCCTAATATATTGGTGTCCTCTGCT 2697
CAGAGGGGACTGTCATCATGGTGGGAACAGGCTGTGCCTCCCCAGGGACTCTGCCCATGTTCCCAGGGCCTCATCTGTA 2776
CACTGTGAAATTAACTGGCATCCTGGTGGGCCCAAGGGTTTTCAGGACTGGGGGCCAATGACTCACCCCCTCCTTCCTC 2855
CTCCTGATCCCTATCTCTAGCTCTTATCACAGATTTTGAACAATTGTCTGTGAGGTTAATGATGGTTTCAGAGGGAAGC 2934
```

FIG.48B

```
CCTTTTCCTCCCTGAGACTGTGTGGGGTTCAGTCAGCCTGCTGAAATTGCTTCCACTTATTACCCATCCTTCCTCTTAA 3013

AAAAAAAAAAAAGCCCACCAAGTTAGTATTCTCTGTAGCTCTCAGACAGCTACAAGTGTTCCTGGCATATTTACCAAAG 3092

TACAAGAAATCATTACATTATTTACGGTCTCAGACTACATCAGGGTTGGGGGAGCTCCTGGTGGGGATGGCAGTGGGTG 3171

TCGATGATATGTCCACGGCTGAGCAGGTCTTGTATCCGAAGCTTGAAGTAACCATGCCACCATTTATCATCAAATTTGA 3250

ACCTTTTAATAAAATTAAACAGCCTGAAAAAAAAAAAAAAAAAAAAAAAAAAAAAAAAAAAAAAAAAAAAAAAAAAAAA 3329

AAAAAAAAAAAAAAAA                                                                 3345
```

FIG.48C

```
                                                                M   R   I   F   A     5
GCTTCCCGAGGCTCCGCACCAGCCGCGCTTCTGTCCGCCTGCAGGGCATTCCAGAAAG ATG AGG ATA TTT GCT    73

V   F   I   F   M   T   Y   W   H   L   L   N   A   F   T   V   T   V   P   K    25
GTC TTT ATA TTC ATG ACC TAC TGG CAT TTG CTG AAC GCA TTT ACT GTC ACG GTT CCC AAG   133

D   L   Y   V   V   E   Y   G   S   N   M   T   I   E   C   K   F   P   V   E    45
GAC CTA TAT GTG GTA GAG TAT GGT AGC AAT ATG ACA ATT GAA TGC AAA TTC CCA GTA GAA   193

K   Q   L   D   L   A   A   L   I   V   Y   W   E   M   E   D   K   N   I   I    65
AAA CAA TTA GAC CTG GCT GCA CTA ATT GTC TAT TGG GAA ATG GAG GAT AAG AAC ATT ATT   253

Q   F   V   H   G   E   E   D   L   K   V   Q   H   S   S   Y   R   Q   R   A    85
CAA TTT GTG CAT GGA GAG GAA GAC CTG AAG GTT CAG CAT AGT AGC TAC AGA CAG AGG GCC   313

R   L   L   K   D   Q   L   S   L   G   N   A   A   L   Q   I   T   D   V   K   105
CGG CTG TTG AAG GAC CAG CTC TCC CTG GGA AAT GCT GCA CTT CAG ATC ACA GAT GTG AAA   373

L   Q   D   A   G   V   Y   R   C   M   I   S   Y   G   G   A   D   Y   K   R   125
TTG CAG GAT GCA GGG GTG TAC CGC TGC ATG ATC AGC TAT GGT GGT GCC GAC TAC AAG CGA   433

I   T   V   K   V   N   A   P   Y   N   K   I   N   Q   R   I   L   V   V   D   145
ATT ACT GTG AAA GTC AAT GCC CCA TAC AAC AAA ATC AAC CAA AGA ATT TTG GTT GTG GAT   493

P   V   T   S   E   H   E   L   T   C   Q   A   E   G   Y   P   K   A   E   V   165
CCA GTC ACC TCT GAA CAT GAA CTG ACA TGT CAG GCT GAG GGC TAC CCC AAG GCC GAA GTC   553

I   W   T   S   S   D   H   Q   V   L   S   G   K   T   T   T   T   N   S   K   185
ATC TGG ACA AGC AGT GAC CAT CAA GTC CTG AGT GGT AAG ACC ACC ACC ACC AAT TCC AAG   613

R   E   E   K   L   F   N   V   T   S   T   L   R   I   N   T   T   T   N   E   205
AGA GAG GAG AAG CTT TTC AAT GTG ACC AGC ACA CTG AGA ATC AAC ACA ACA ACT AAT GAG   673

I   F   Y   C   T   F   R   R   L   D   P   E   E   N   H   T   A   E   L   V   225
ATT TTC TAC TGC ACT TTT AGG AGA TTA GAT CCT GAG GAA AAC CAT ACA GCT GAA TTG GTC   733

I   P   E   L   P   L   A   H   P   P   N   E   R   T   H   L   V   I   L   G   245
ATC CCA GAA CTA CCT CTG GCA CAT CCT CCA AAT GAA AGG ACT CAC TTG GTA ATT CTG GGA   793

A   I   L   L   C   L   G   V   A   L   T   F   I   F   R   L   R   K   G   R   265
GCC ATC TTA TTA TGC CTT GGT GTA GCA CTG ACA TTC ATC TTC CGT TTA AGA AAA GGG AGA   853

M   M   D   V   K   K   C   G   I   Q   D   T   N   S   K   K   Q   S   D   T   285
ATG ATG GAT GTG AAA AAA TGT GGC ATC CAA GAT ACA AAC TCA AAG AAG CAA AGT GAT ACA   913

H   L   E   E   T   *                                                            291
CAT TTG GAG GAG ACG TAA                                                           931

TCCAGCATTGGAACTTCTGATCTTCAAGCAGGGATTCTCAACCTGTGGTTTAGGGGTTCATCGGGGCTGAGCGTGACAA  1010

GAGGAAGGAATGGGCCCGTGGGATGCAGGCAATGTGGGACTTAAAAGGCCCAAGCACTGAAAATGGAACCTGGCGAAAG  1089

CAGAGGAGGAGAATGAAGAAAGATGGAGTCAAACAGGGAGCCTGGAGGGAGACCTTGATACTTTCAAATGCCTGAGGGG  1168
```

FIG.50A

```
CTCATCGACGCCTGTGACAGGGAGAAAGGATACTTCTGAACAAGGAGCCTCCAAGCAAATCATCCATTGCTCATCCTAG    1247
GAAGACGGGTTGAGAATCCCTAATTTGAGGGTCAGTTCCTGCAGAAGTGCCCTTTGCCTCCACTCAATGCCTCAATTTG    1326
TTTTCTGCATGACTGAGAGTCTCAGTGTTGGAACGGGACAGTATTTATGTATGAGTTTTTCCTATTTATTTTGAGTCTG    1405
TGAGGTCTTCTTGTCATGTGAGTGTGGTTGTGAATGATTTCTTTTGAAGATATATTGTAGTAGATGTTACAATTTTGTC    1484
GCCAAACTAAACTTGCTGCTTAATGATTTGCTCACATCTAGTAAAACATGGAGTATTTGTAAGGTGCTTGGTCTCCTCT    1563
ATAACTACAAGTATACATTGGAAGCATAAAGATCAAACCGTTGGTTGCATAGGATGTCACCTTTATTTAACCCATTAAT    1642
ACTCTGGTTGACCTAATCTTATTCTCAGACCTCAAGTGTCTGTGCAGTATCTGTTCCATTTAAATATCAGCTTTACAAT    1721
TATGTGGTAGCCTACACACATAATCTCATTTCATCGCTGTAACCACCCTGTTGTGATAACCACTATTATTTTACCCATC    1800
GTACAGCTGAGGAAGCAAACAGATTAAGTAACTTGCCCAAACCAGTAAATAGCAGACCTCAGACTGCCACCCACTGTCC    1879
TTTTATAATACAATTTACAGCTATATTTTACTTTAAGCAATTCTTTTATTCAAAAACCATTTATTAAGTGCCCTTGCAA    1958
TATCAATCGCTGTGCCAGGCATTGAATCTACAGATGTGAGCAAGACAAAGTACCTGTCCTCAAGGAGCTCATAGTATAA    2037
TGAGGAGATTAACAAGAAAATGTATTATTACAATTTAGTCCAGTGTCATAGCATAAGGATGATGCGAGGGGAAAACCCG    2116
AGCAGTGTTGCCAAGAGGAGGAAATAGGCCAATGTGGTCTGGGACGGTTGGATATACTTAAACATCTTAATAATCAGAG    2195
TAATTTTCATTTACAAAGAGAGGTCGGTACTTAAAATAACCCTGAAAAATAACACTGGAATTCCTTTTCTAGCATTATA    2274
TTTATTCCTGATTTGCCTTTGCCATATAATCTAATGCTTGTTTATATAGTGTCTGGTATTGTTTAACAGTTCTGTCTTT    2353
TCTATTTAAATGCCACTAAATTTTAAATTCATACCTTTCCATGATTCAAAATTCAAAAGATCCCATGGGAGATGGTTGG    2432
AAAATCTCCACTTCATCCTCCAAGCCATTCAAGTTTCCTTTTCCAGAAGCAACTGCTACTGCCTTTCATTCATATGTTCT    2511
TCTAAAGATAGTCTACATTTGGAAATGTATGTTAAAAGCACGTATTTTTAAAATTTTTTTCCTAAATAGTAACACATTG    2590
TATGTCTGCTGTGTACTTTGCTATTTTTATTTATTTTAGTGTTTCTTATATAGCAGATGGAATGAATTTGAAGTTCCCA    2669
GGGCTGAGGATCCATGCCTTCTTTGTTTCTAAGTTATCTTTCCCATAGCTTTTCATTATCTTTCATATGATCCAGTATA    2748
TGTTAAATATGTCCTACATATACATTTAGACAACCACCATTTGTTAAGTATTTGCTCTAGGACAGAGTTTGGATTTGTT    2827
TATGTTTGCTCAAAAGGAGACCCATGGGCTCTCCAGGGTGCACTGAGTCAATCTAGTCCTAAAAAGCAATCTTATTATT    2906
AACTCTGTATGACAGAATCATGTCTGGAACTTTTGTTTTCTGCTTTCTGTCAAGTATAAACTTCACTTTGATGCTGTAC    2985
TTGCAAAATCACATTTTCTTTCTGGAAATTCCGGCAGTGTACCTTGACTGCTAGCTACCCTGTGCCAGAAAAGCCTCAT    3064
TCGTTGTGCTTGAACCCTTGAATGCCACCAGCTGTCATCACTACACAGCCCTCCTAAGAGGCTTCCTGGAGGTTTCGAG    3143
ATTCAGATGCCCTGGGAGATCCCAGAGTTTCCTTTCCCTCTTGGCCATATTCTGGTGTCAATGACAAGGAGTACCTTGG    3222
CTTTGCCACATGTCAAGGCTGAAGAAACAGTGTCTCCAACAGAGCTCCTTGTGTTATCTGTTTGTACATGTGCATTTGT    3301
ACAGTAATTGGTGTGACAGTGTTCTTTGTGTGAATTACAGGCAAGAATTGTGGCTGAGCAAGGCACATAGTCTACTCAG    3380
TCTATTCCTAAGTCCTAACTCCTCCTTGTGGTGTTGGATTTGTAAGGCACTTTATCCCTTTTGTCTCATGTTTCATCGT    3459
```

FIG.50B

```
AAATGGCATAGGCAGAGATGATACCTAATTCTGCATTTGATTGTCACTTTTTGTACCTGCATTAATTTAATAAAATATT    3538
CTTATTTATTTTGTTACTTGGTAAAAAAAAAAAAAAA                                            3575
```

FIG.50C

```
        10         20         30         40         50         60
inputs MRIFAVFIFMTY-WHLLNA-FTVTVPKDLYVVEYGSNMTIECKFPVEKQLDLAALIVYWEMEDKNIIQFV
       : ..  ..  ..    :  ..: :::::.::..:.:. ::......:: :     .:...    .. .: :
       MLLLLPILNLSLQLHPVAALFTVTAPKEVYTVDVGSSVSLECDFDRRECTELEGI--------RASLQKV
        10         20         30         40         50                60

70         80         90        100        110        120        130
inputs HGEEDLKVQHSSYRQRARLLKDQLSLGNAALQITDVKLQDAGVYRCMISYGGA-DYKRITVKVNAPYNKI
       :.:  ..     .::   ..:.::::::..  ..: :.:::.  :. ::.. :: ::: :.::.:.: .:
       --ENDTSLQ----SERATLLEEQLPLGKALFHIPSVQVRDSGQYRCLVICGAAWDYKYLTVKVKASYMRI
              70         80         90        100        110        120

140        150        160        170        180        190        200
inputs NQRILVVDPVTSEHELTCQAEGYPKAEVIWTSSDHQVLSGKTTTTNSKREEKLFNVTSTLRINTTTNEIF
       . :::  : .. : .:::::: ::: ::: :      :  .:  ....  . :  :..:::::.::..   . :
       DTRILEV-PGTGEVQLTCQARGYPLAEVSW-----QNVSVPANTSHIRTPEGLYQVTSVLRLKPQPSRNF
       130        140        150             160        170        180

210        220        230        240        250        260        270
inputs YCTFRRLDPEENHTAELVIPELPLAHPPNERT-HLVILGAILLCLGVALTFIFRLRKGRMMDVKKCGIQD
       : :.    .: :.    .:  :.  ::  ::      : :  :  .::::..             .:
       SCMFWNAHMKELTSA--IIDPLSRMEPKVPRTWPLHVF--IPAC-TIALIFL-------------AIVI
       200        210        220        230                            240

280        290
inputs TNSKKQSDTHLEET
       .. :.          .
       IQRKR--------I
```

FIG.52

```
                                                           M   R   I   F   A   G     6
CGTCCGCTTGCACGTCGCGGGCCAGTCTCCTCGCCTGCAGATAGTTCCCAAAAC ATG AGG ATA TTT GCT GGC    72

I   I   F   T   A   C   C   H   L   L   R   A   F   T   I   T   A   P   K   D    26
ATT ATA TTC ACA GCC TGC TGT CAC TTG CTA CGG GCG TTT ACT ATC ACG GCT CCA AAG GAC   132

L   Y   V   V   E   Y   G   S   N   V   T   M   E   C   R   F   P   V   E   R    46
TTG TAC GTG GTG GAG TAT GGC AGC AAC GTC ACG ATG GAG TGC AGA TTC CCT GTA GAA CGG   192

E   L   D   L   L   A   L   V   V   Y   W   K   E   D   E   Q   V   I   Q        66
GAG CTG GAC CTG CTT GCG TTA GTG GTG TAC TGG GAA AAG GAA GAT GAG CAA GTG ATT CAG   252

F   V   A   G   E   E   D   L   K   P   Q   H   S   N   F   R   G   R   A   S    86
TTT GTG GCA GGA GAG GAG GAC CTT AAG CCT CAG CAC AGC AAC TTC AGG GGG AGA GCC TCG   312

L   P   K   D   Q   L   L   K   G   N   A   A   L   Q   I   T   D   V   K   L   106
CTG CCA AAG GAC CAG CTT TTG AAG GGA AAT GCT GCC CTT CAG ATC ACA GAC GTC AAG CTG   372

Q   D   A   G   V   Y   C   C   I   I   S   Y   G   G   A   D   Y   K   R   I   126
CAG GAC GCA GGC GTT TAC TGC TGC ATA ATC AGC TAC GGT GGT GCG GAC TAC AAG CGA ATC   432

T   L   E   V   N   A   P   Y   R   K   I   N   Q   R   I   S   V   D   P   A   146
ACG CTG GAA GTC AAT GCC CCA TAC CGC AAA ATC AAC CAG AGA ATT TCC GTG GAT CCA GCC   492

T   S   E   H   E   L   I   C   Q   A   E   G   Y   P   E   A   E   V   I   W   166
ACT TCT GAG CAT GAA CTA ATA TGT CAG GCC GAG GGT TAT CCA GAA GCT GAG GTA ATC TGG   552

T   N   S   D   H   Q   P   V   S   G   K   R   S   V   T   T   S   R   T   E   186
ACA AAC AGT GAC CAC CAA CCC GTG AGT GGG AAG AGA AGT GTC ACC ACT TCC CGG ACA GAG   612

G   M   L   L   N   V   T   S   S   L   R   S   T   P   H   X   X   R   M   M   206
GGG ATG CTT CTC AAT GTG ACC AGC AGT CTG AGG TCA ACG CCA CAT GAN NAG CGA ATG ATG   672

F   L   L   Y   V   L   E   I   T   A   R   A   K   P   H   S   G   X   I   I   226
TTT CTA CTG TAC GTA TTG GAG ATC ACA GCC AGG GCA AAA CCA CAC AGC GGC GAN ATC ATC   732

P   E   L   P   A   T   H   P   P   Q   N   R   T   H   W   V   L   L   G   S   246
CCA GAA CTG CCT GCA ACA CAT CCT CCA CAG AAC AGG ACT CAC TGG GTG CTT CTG GGA TCC   792

I   L   L   F   L   I   V   V   S   T   V   L   L   F   L   R   K   Q   V   R   266
ATC CTG TTG TTC CTC ATT GTA GTG TCC ACG GTC CTC CTC TTC TTG AGA AAA CAA GTG AGA   852

M   L   D   V   E   K   C   G   V   E   D   T   S                                 279
ATG CTA GAT GTG GAG AAA TGT GGC GTT GAA GAT ACA AGC                                891
```

FIG.53

```
ALIGN calculates a global alignment of two sequences
 version 2.0uPlease cite: Myers and Miller, CABIOS (1989)
> mT509 a.a.                                            279 aa vs.
> AF142780 butyrophilin-like                            247 aa
scoring matrix: pam120.mat, gap penalties: -12/4
31.9% identity;          Global alignment score: 119

10         20         30         40         50         60
inputs  MRIFAGII-FTACCHLLRA-FTITAPKDLYVVEYGSNVTMECRFPVERELDLLALVVYWEKEDEQVIQFV
         : ..   ..      :  : ::.::.... ::.:.:::  :    : ..     :. ...    .: :
        MLLLLPILNLSLQLHPVAAL FTVTAPKEVYTVDVGSSVSLECDFDR-RECTELEGI----RAS---LQKV
                10         20         30         40         50         60

70         80         90        100        110        120        130
inputs  AGEEDLKPQHSNFRGRASLPKDQLLKGNAALQITDVKLQDAGVYCCIISYGGA-DYKRITLEVNAPYRKI
        ... .:....       ::.: ...:.:: ...:..........: :..  ...:::  .. .:..: ..
        ENDTSLQSE------RATLLEEQLPLGKALFHIPSVQVRDSGQYRCLVICGAAWDYKYLTVKVKASYMRI
                70         80         90        100        110        120

140        150        160        170        180        190        200
inputs  NQRISVDPATSEHELICQAEGYPEAEVIWTNSDHQPVSGKRSVTTSRTEGMLLNVTSSLRSTPHXXRMMF
         :    :.:.: .:.:::: :::  ::: :          :  ::    .:   :: :: :    .....:
        DTRILEVPGTGEVQLTCQARGYPLAEVSW-----QNVSVPANTSHIRTPEGLYQVTSVLRLKPQPSRNFS
                130        140        150             160        170        180        190

210        220        230        240        250        260        270
inputs  LLYVLEITARAKPHSGXIIPELPATHPPQNRTHWVLLGSILLFLIVVSTVLLFLRKQVRMLDVEKCGVED
         ..       . :     ....:. :.   :: ..       ..       . . ....          ..  ...
        CMF---WNAHMKELTSAIIDPLSRMEPKVPRT-WPLH----VFIPACTIALIFL----AIVIIQR----K
                 200        210        220             230        240 inputs  TS

METHODS OF IDENTIFYING COMPOUNDS THAT BIND TANGO509

CROSS REFERENCE TO RELATED APPLICATIONS

This application is a continuation of U.S. application Ser. No. 11/983,233, filed Nov. 8, 2007 now abandoned, which is a divisional of U.S. application Ser. No. 11/287,573, filed Nov. 23, 2005 now U.S. Pat. No. 7,385,036, which is a continuation of U.S. application Ser. No. 09/796,858, filed Mar. 1, 2001, now U.S. Pat. No. 7,041,474, which is:

1) a continuation-in-part of U.S. patent application Ser. No. 09/599,596, filed Jun. 22, 2000 (abandoned), which is a divisional of U.S. patent application Ser. No. 09/223,546, filed Dec. 30, 1998 (abandoned), and a continuation-in-part of U.S. patent application Ser. No. 09/471,179, filed Dec. 23, 1999 (abandoned), which is a continuation-in-part of U.S. patent application Ser. No. 09/223,546, filed Dec. 30, 1998 (abandoned);

2) a continuation-in-part of U.S. patent application Ser. No. 09/474,072, filed Dec. 29, 1999 (abandoned), which is a continuation-in-part of U.S. patent application Ser. No. 09/224,246, filed Dec. 30, 1998 (abandoned);

3) a continuation-in-part of U.S. patent application Ser. No. 09/474,071, filed Dec. 29, 1999 (abandoned), which is a continuation-in-part of U.S. patent application Ser. No. 09/223,094, filed Dec. 30, 1998 (abandoned);

4) a continuation-in-part of U.S. patent application Ser. No. 09/597,993, filed Jun. 19, 2000 (abandoned), which is a continuation-in-part of U.S. patent application Ser. No. 09/336,536, filed Jun. 18, 1999, now U.S. Pat. No. 6,406,884;

5) a continuation-in-part of U.S. patent application Ser. No. 09/572,002, filed May 15, 2000 (abandoned), which is a continuation-in-part of U.S. patent application Ser. No. 09/312,359, filed May 14, 1999 (abandoned);

6) a continuation-in-part of U.S. patent application Ser. No. 09/606,565, filed Jun. 29, 2000 (abandoned), which is a continuation-in-part of U.S. patent application Ser. No. 09/342,687, filed Jun. 29, 1999 (abandoned);

7) a continuation-in-part of U.S. patent application Ser. No. 09/630,334, filed Jul. 31, 2000 (abandoned), which is a continuation-in-part of U.S. patent application Ser. No. 09/365,164, filed Jul. 30, 1999 (abandoned); and 8) a continuation-in-part of U.S. patent application Ser. No. 09/665,666, filed Sep. 20, 2000 (abandoned), which is a continuation-in-part of U.S. patent application Ser. No. 09/399,723, filed Sep. 20, 1999 (abandoned).

The entire teachings of the above applications are incorporated by references.

BACKGROUND OF THE INVENTION

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted and transmembrane proteins and the genes which encode them.

Many secreted proteins are receptors which bind a ligand and transduce an intracellular signal, leading to a variety of cellular responses. The identification and characterization of such a receptor enables one to identify both the ligands which bind to the receptor and the intracellular molecules and signal transduction pathways associated with the receptor, permitting one to identify or design modulators of receptor activity, e.g., receptor agonists or antagonists and modulators of signal transduction.

SUMMARY OF THE INVENTION

The present invention is based, at least in part, on the discovery of cDNA molecules which encode the TANGO 239, TANGO 219, TANGO 232, TANGO 281, A236 (INTERCEPT 236), TANGO 300, TANGO 353, TANGO 393, TANGO 402, TANGO 351 and TANGO 509 proteins, all of which are either wholly secreted or transmembrane polypeptides.

The TANGO 353, A236 (INTERCEPT 236), TANGO 232 and TANGO 300 proteins are transmembrane proteins. In an additional embodiment, the nucleic acids encoding these proteins are alternatively spliced such that the resulting protein products are secreted proteins.

TANGO 239 proteins are secreted proteins with homology to proteins containing MAM domains.

TANGO 219 proteins have a signal peptide and the mRNA is weakly expressed in heart tissues.

The TANGO 281 proteins represent proteins downregulated in megakaryocytes that fail to express the gata-1 transcription factor (a factor critical for blood cell formation) and can, therefore, represent direct or indirect gata-1 targets.

The TANGO 393 protein are transmembrane proteins with homology to proteins containing Leucine-rich repeats (LRR) such as the Leucine-Rich α-2-Glycoprotein (LRG), SLIT-1, and Platelet Glycoprotein V (GPV) precursor.

The TANGO 402 proteins are homologous to the LOX-1 protein, which has been associated with low density lipoprotein metabolism and atherosclerosis.

The TANGO 351 proteins are transmembrane polypeptides involved in signaling, e.g., signaling in renal cells.

The TANGO 509 proteins are transmembrane polypeptides related to butyrophilin-like proteins and containing immunoglobulin domains.

The TANGO 239, TANGO 219, TANGO 232, TANGO 281, A236 (INTERCEPT 236), TANGO 300, TANGO 353, TANGO 393, TANGO 402, TANGO 351 and TANGO 509 proteins, fragments, derivatives, and variants thereof of the present invention are collectively referred to herein as "polypeptides of the invention" or "proteins of the invention." Nucleic acid molecules encoding the polypeptides or proteins of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable for use as primers or hybridization probes for the detection of nucleic acids encoding a polypeptide of the invention.

The invention includes fragments of any of the nucleic acids described herein wherein the fragment retains a biological or structural function by which the full-length nucleic acid is characterized (e.g., an activity, an encoded protein, or a binding capacity). The invention furthermore includes fragments of any of the nucleic acids described herein wherein the fragment has a nucleotide sequence sufficiently (e.g., 50%, 60%, 70%, 80%, 85%, 90%, 95%, 98%, or 99% or greater) identical to the nucleotide sequence of the corresponding full-length nucleic acid that it retains a biological or structural function by which the full-length nucleic acid is characterized (e.g., an activity, an encoded protein, or a binding capacity).

The invention includes fragments of any of the polypeptides described herein wherein the fragment retains a biological or structural function by which the full-length polypeptide is characterized (e.g., an activity or a binding capacity). The invention furthermore includes fragments of any of the polypeptides described herein wherein the fragment has an amino acid sequence sufficiently (e.g., 50%, 60%, 70%, 80%, 85%, 90%, 95%, 98%, or 99% or greater) identical to the amino acid sequence of the corresponding full-length polypeptide that it retains a biological or structural function by which the full-length polypeptide is characterized (e.g., an activity or a binding capacity).

The invention also features nucleic acid molecules which are at least 40% (or 50%, 60%, 70%, 80%, 90%, 95%, or 98%) identical to the nucleotide sequence of any of SEQ ID NOs: 1, 3, 5, 7, 9, 11, 13, 15, 17, 19, 21, 23, 25, 27, 29, 31, 33, 35, 37, 39, 41, and 43, the TANGO 239 nucleotide sequence of the cDNA insert of a clone deposited on Nov. 20, 1998 with the ATCC® as accession no. 98999, the TANGO 219 nucleotide sequences of cDNA insert of a clone deposited on Sep. 25, 1998 with the ATCC® as accession no. 98899, the macaque TANGO 232 nucleotide sequence of the cDNA insert of a clone deposited on Jan. 7, 1999 with the ATCC® as accession no. 207045, the human TANGO 232 nucleotide sequence of the cDNA insert of a clone deposited on Jan. 7, 1999 with the ATCC® as accession no. 207046, the human TANGO 281 nucleotide sequence of the cDNA insert of a clone deposited on Jan. 7, 1999 with the ATCC® as accession no. 207222, the mouse TANGO 281 nucleotide sequence of the cDNA insert of a clone deposited on Apr. 30, 1999 with the ATCC® as accession no. PTA-224, the human A236 (INTERCEPT 236) nucleotide sequence of the cDNA insert of a clone deposited on May 7, 1999 with the ATCC® as accession no. PTA-34, the TANGO 300 nucleotide sequence of the cDNA insert of a clone deposited on Jun. 30, 1999 with the ATCC® as accession no. PTA-293, the TANGO 353 nucleotide sequence of the cDNA insert of a clone deposited on Jun. 29, 1999 with the ATCC® as accession no. PTA-292, the TANGO 393 nucleotide sequence of the cDNA insert of a clone deposited on Jun. 29, 1999 with the ATCC® as accession no. PTA-295, the TANGO 402 nucleotide sequence of the cDNA insert of a clone deposited on Jun. 29, 1999 with the ATCC® as accession no. PTA-294, the TANGO 351 nucleotide sequences of cDNA inserts of clones deposited on Jul. 23, 1999 with the ATCC® as accession no. PTA-424, and the TANGO 509 nucleotide sequence of the cDNA insert of a clone deposited on Aug. 5, 1999 with the ATCC® as accession no. PTA-438.

These deposited nucleotide sequences are hereafter individually and collectively referred to as "the nucleotide sequence of any of the clones deposited as ATCC® Accession numbers 98999, 98899, 207045, 207046, 207222, PTA-34, PTA-224, PTA-293, PTA-292, PTA-295, PTA-294, PTA-424, and PTA-438."

The invention features nucleic acid molecules which include a fragment of at least 15 (25, 40, 60, 80, 100, 150, 200, 250, 300, 350, 400, 450, 500, 600, 700, 800, 900, 1000, 1200, 1400, 1600, 1800, 2000, 2200, 2400, 2600, 2800, 3000, 3500, 4000, 4500, 5000, or more) consecutive nucleotide residues of any of SEQ ID NOs:1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438, or a complement thereof.

The invention also features nucleic acid molecules which include a nucleotide sequence encoding a protein having an amino acid sequence that is at least 50% (or 60%, 70%, 80%, 90%, 95%, or 98%) identical to the amino acid sequence of any of SEQ ID NOs:2, 4, 6, 8, 10, 12, 14, 16, 18, 20, 22, 24, 26, 28, 30, 32, 34, 36, 38, 40, 42, 44, or the amino acid sequence encoded by the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438 or a complement thereof.

In certain embodiments, the nucleic acid molecules have the nucleotide sequence of any of SEQ ID NOs:1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438.

Also within the invention are nucleic acid molecules which encode a fragment of a polypeptide having the amino acid sequence of any of SEQ ID NOs:2, 4, 6, 8, 10, 12, 14, 16, 18, 20, 22, 24, 26, 28, 30, 32, 34, 36, 38, 40, 42, and 44, the fragment including at least 10 (12, 15, 20, 25, 30, 40, 50, 75, 100, 125, 150, 200, 250, 300, 400, 500, 750, 1000 or more) consecutive amino acid residues of any of SEQ ID NOs:2, 4, 6, 8, 10, 12, 14, 16, 18, 20, 22, 24, 26, 28, 30, 32, 34, 36, 38, 40, 42, and 44.

The invention includes nucleic acid molecules which encode a naturally occurring allelic variant of a polypeptide comprising the amino acid sequence of any of SEQ ID NOs:2, 4, 6, 8, 10, 12, 14, 16, 18, 20, 22, 24, 26, 28, 30, 32, 34, 36, 38, 40, 42, and 44, wherein the nucleic acid molecule hybridizes under stringent conditions to a nucleic acid molecule having a nucleic acid sequence of any of SEQ ID NOs:1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438, or a complement thereof.

Also within the invention are isolated polypeptides or proteins having an amino acid sequence that is at least about 50%, preferably 60%, 75%, 90%, 95%, or 98% identical to the amino acid sequence of any of SEQ ID NOs:2, 4, 6, 8, 10, 12, 14, 16, 18, 20, 22, 24, 26, 28, 30, 32, 34, 36, 38, 40, 42, and 44.

Also within the invention are isolated polypeptides or proteins which are encoded by a nucleic acid molecule having a nucleotide sequence that is at least about 40%, preferably 50%, 60%, 75%, 85%, or 95% identical the nucleic acid sequence encoding any of SEQ ID NOs:2, 4, 6, 8, 10, 12, 14, 16, 18, 20, 22, 24, 26, 28, 30, 32, 34, 36, 38, 40, 42, and 44, and isolated polypeptides or proteins which are encoded by a nucleic acid molecule consisting of the nucleotide sequence which hybridizes under stringent hybridization conditions to a nucleic acid molecule having the nucleotide sequence of any of SEQ ID NOs:1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438.

Also within the invention are polypeptides which are naturally occurring allelic variants of a polypeptide that includes the amino acid sequence of any of SEQ ID NOs:2, 4, 6, 8, 10, 12, 14, 16, 18, 20, 22, 24, 26, 28, 30, 32, 34, 36, 38, 40, 42, and 44, wherein the polypeptide is encoded by a nucleic acid molecule which hybridizes under stringent conditions to a nucleic acid molecule having the nucleotide sequence of any of SEQ ID NOs:1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-34, PTA-224, PTA-293, PTA-292, PTA-295, PTA-294, PTA-424, and PTA-438, or a complement thereof.

The invention also features nucleic acid molecules that hybridizes under stringent conditions to a nucleic acid molecule having the nucleotide sequence of any of SEQ ID NOs: 1, 3, 5, 7, 9, 11, 13, 15, 17, 19, 21, 23, 25, 27, 29, 31, 33, 35, 37, 39, 41, and 43, and the nucleotide sequence of any of the clones deposited as ATCC® Accession numbers 98999, 98899, 207045, 207046, 207222, PTA-34, PTA-224, PTA-293, PTA-292, PTA-295, PTA-294, PTA-424, and PTA-438, or a complement thereof. In some embodiments, the isolated nucleic acid molecules encode a cytoplasmic, transmembrane, extracellular, or other domain of a polypeptide of the invention. In other embodiments, the invention provides an isolated nucleic acid molecule which is antisense to the coding strand of a nucleic acid of the invention.

The invention features nucleic acid molecules of at least 550, 600, 650, 700, 750, 800, 850, 900, 950, 1000, 1100, 1200, 1300, 1400, 1500, 1600, 1700, 1800, 1900, 2000, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 or 3400 nucleotides of the nucleotide sequence of SEQ ID NO:1 or 3, the nucleotide sequence of the TANGO 239 cDNA clone of ATCC® Accession No. 98999, or a complement thereof. The invention also features nucleic acid molecules comprising at least 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2150, 2200 or 2225 nucleotides of nucleic acids 1 to 2227 of SEQ ID NO:1 or 3, or a complement thereof.

The invention features nucleic acid molecules which include a fragment of at least 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 or 1650 nucleotides of the nucleotide sequence of the open reading frame (ORF) of SEQ ID NO:1, or a complement thereof.

The invention features nucleic acid molecules which include a fragment of at least 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or 2050 nucleotides of the nucleotide sequence of the ORF of SEQ ID NO:3, or a complement thereof.

The invention features nucleic acid molecules of at least 25, 50, 100, 150, 200, 250, 300, 350, 400, 450, 500, 550, 600, 650, 700, 750, 800, 850, 900, 950, 1000 or 1028 nucleotides of the nucleotide sequence of SEQ ID NO:5 the nucleotide sequence of a mouse TANGO 239 cDNA, or a complement thereof.

The invention features nucleic acid molecules which include a fragment of at least 25, 50, 100, 150 or 160 nucleotides of the nucleotide sequence of the ORF of SEQ ID NO:5, or a complement thereof.

The invention features nucleic acid molecules of at least 280, 300, 350, 400, 450, 500, 550, 600, 650, 700, 750, 800, 850, 900, 950, 1000, 1050, 1100, 1150, 1200, or 1240 nucleotides of the nucleotide sequence of SEQ ID NO:7, the nucleotide sequence of a human TANGO 219 cDNA, the nucleotide sequence of the human TANGO 219 cDNA clone of ATCC® Accession No. 98899, or a complement thereof. The invention also features nucleic acid molecules comprising at least 25, 30, 35, 40, 45, 50, 55, 60, 65, 70, 75, 80, 85, 90, 95, or 100 nucleotides of nucleic acids 1 to 2227 of SEQ ID NO:7, or a complement thereof.

The invention features nucleic acid molecules which include a fragment of at least 25, 50, 75, 100, 125, 150, 175, 200, 225, 250, 275, 300, 325, 350, 375, 400, 425, or 440 nucleotides of the nucleotide sequence of the ORF of SEQ ID NO:7, or a complement thereof.

The invention features nucleic acid molecules of at least 300, 305, 310, 315, 320, 325, 330, 335, 340, 345, 350, 355, 360, 365, 370, 375, 380, 385, or 390 nucleotides of the nucleotide sequence of SEQ ID NO:9, the nucleotide sequence of a mouse TANGO 219 cDNA, or a complement thereof.

The invention features nucleic acid molecules which include a fragment of at least or 300, 305, 310, 315, 320, 325, 330, 335, 340, 345, 350, 355, 360 nucleotides of the nucleotide sequence of the ORF of SEQ ID NO:9, or a complement thereof.

The invention features nucleic acid molecules of at least 285, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1925, or 1930 nucleotides of the nucleotide sequence of SEQ ID NO:11, the nucleotide sequence of the macaque TANGO 232 cDNA clone of ATCC® Accession No. 207045 or a complement thereof. The invention also features nucleic acid molecules comprising at least 25, 50, 75, 100, 125, 150, 175, 200, 225, 250, 275, 300, 325, 350, 375, 400, 425, 450, 475, 500, 525, or 540 nucleotides of nucleic acids 505 to 1050 of SEQ ID NO:11, or a complement thereof.

The invention features nucleic acid molecules which include a fragment of at least 25, 50, 75, 100, 125, 150, 175, 200, 225, 250, 275, 300, 325, 350, 375, 400, 425, 450, 475, 500, 525, 550, 575, 600, 625, 675, 700, or 710 nucleotides of the nucleotide sequence of the ORF of SEQ ID NO:11, or a complement thereof.

The invention features nucleic acid molecules of at least 275, 300, 350, 400, 450, 500, 550, 600, 650, 700, 750, 800, 850, 900, 950, 1000, 1050, 1100, 1150, 1200, 1250, 1300, 1350, 1400, or 1450 nucleotides of the nucleotide sequence of SEQ ID NO:13, the nucleotide sequence of the human TANGO 232 form 1 cDNA clone of ATCC® Accession No. 207046, or a complement thereof. The invention also features nucleic acid molecules comprising at least 25, 50, 75, 100, 125, 150, 175, 200, 225, 250, 275, 300, 325, 350, 375, 400, or 410 nucleotides of nucleic acids 1 to 415 of SEQ ID NO:13, or a complement thereof.

The invention features nucleic acid molecules which include a fragment of at least 25, 50, 75, 100, 125, 150, 175, 200, 225, 250, 275, 300, 325, 350, or 360 nucleotides of the nucleotide sequence of the ORF of SEQ ID NO:13, or a complement thereof.

The invention features nucleic acid molecules of at least 320, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, or 1130 nucleotides of the nucleotide sequence of SEQ ID NO:15, the nucleotide sequence of a human TANGO 232 form 2 cDNA, or a complement thereof. The invention also features nucleic acid molecules comprising at least 15, 20, 25, 30, 35, 40, 45, 50, or 55 nucleotides of nucleic acids 40 to 100 of SEQ ID NO:15, or a complement thereof.

The invention features nucleic acid molecules which include a fragment of at least 320, 350, 375, 400, 425, 450, 475, 500, 525, 550, 575, 600, 625, 650, 675, 700, 710, or 714 nucleotides of the nucleotide sequence of the ORF of SEQ ID NO:15, or a complement thereof.

The invention features nucleic acid molecules of at least 325, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, or 2215 nucleotides of the nucleotide sequence of SEQ ID NO:17, the nucleotide sequence of a mouse TANGO 232 cDNA, or a complement thereof. The invention also features nucleic acid molecules comprising at least 25, 50, 75, 100, 125, 150, 175, 200, 225, 250, 275, 300, 325, 350, 360, or 370 nucleotides of nucleic acids 490 to 865 of SEQ ID NO:17, or a complement thereof.

The invention features nucleic acid molecules which include a fragment of at least 25, 50, 75, 100, 125, 150, 175, 200, 225, 250, 275, 300, 325, 350, 375, 400, 425, 450, 475, 500, 525, 550, 575, 600, 625, 675, 700, or 710 nucleotides of the nucleotide sequence of the ORF of SEQ ID NO:17, or a complement thereof.

The invention features nucleic acid molecules which include a fragment of at least 50, 100, 200, 300, 400, 500, 600, 700, 800, 900, 1000, 1100, 1200, 1300, 1400, 1500, 1600, 1700 or 1800 contiguous nucleotides of the nucleotide sequence of SEQ ID NO:19 the nucleotide sequence of an EpT281 cDNA of ATCC® Accession Number 207222, or a complement thereof.

The invention features nucleic acid molecules which include a fragment of at least 50, 100, 200, 300, 400, 500, 600, 700 or 750 contiguous nucleotides of the nucleotide sequence of the ORF of SEQ ID NO:19, or a complement thereof.

The invention features nucleic acid molecules which include a fragment of at least 550, 600, 700, 800, 900, 1000, 1100, 1200, 1300, 1400, 1500, 1600, 1700, 1800 or 1850 contiguous nucleotides of the nucleotide sequence of SEQ ID NO:21 the nucleotide sequence of an EpTm281 cDNA of ATCC® patent deposit Number PTA-224, or a complement thereof.

The invention features nucleic acid molecules which include a fragment of at least 50, 100, 200, 300, 400, 500, 600 or 700 contiguous nucleotides of the nucleotide sequence of the ORF of SEQ ID NO:21, or a complement thereof.

The invention also features nucleic acid molecules that hybridize under stringent conditions to a nucleic acid molecule having the nucleotide sequence of SEQ ID NOs:19, 21, an EpTm281 cDNA of ATCC® Accession Number 207222, or a complement thereof. In other embodiments, the nucleic acid molecules are at least 710, 750, 800, 900, 1000, 1100, 1200, 1300, 1400, 1500, 1600, 1700 or 1800 contiguous nucleotides in length and hybridize under stringent conditions to a nucleic acid molecule comprising the nucleotide sequence of SEQ ID NOs:19, 21, an EpT281 cDNA of ATCC® Accession Number 207222, or a complement thereof.

The invention also features nucleic acid molecules that hybridize under stringent conditions to a nucleic acid molecule having the nucleotide sequence of SEQ ID NOs:19, 21, an EpTm281 cDNA of ATCC® patent deposit Number PTA-224, or a complement thereof. In other embodiments, the nucleic acid molecules are at least 580, 600, 700, 800, 900, 1000, 1100, 1200, 1300, 1400, 1500, 1600, 1700, 1800 or 1850 contiguous nucleotides in length and hybridize under stringent conditions to a nucleic acid molecule comprising the nucleotide sequence of SEQ ID NOs:19, 21, an EpTm281 cDNA of ATCC® patent deposit Number PTA-224, or a complement thereof.

The invention features nucleic acid molecules comprising at least 25, 50, 100, 150, 200, 250, 300, 350, 400, 450, 500, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or 1948 nucleotides of the nucleotide sequence of SEQ ID NO:23, the nucleotide sequence of the human TANGO A236 cDNA of ATCC® PTA-34, or a complement thereof.

The invention features nucleic acid molecules comprising at least 25, 50, 100, 150, 200, 250, 300, 350, 400, 450, 500, 550, 600, 650, 700, 750, 800, 850, 900, 950, 1000, 1050, 1100, or 1118 nucleotides of the nucleotide sequence of the ORF of SEQ ID NO:23, or a complement thereof.

The invention features nucleic acid molecules comprising at least 25, 50, 100, 150, 200, 250, 300, 350, 400, 450, 500, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or 1945 nucleotides of the nucleotide sequence of the mouse A236 cDNA of SEQ ID NO:25, or a complement thereof.

The invention features nucleic acid molecules comprising at least 25, 50, 100, 150, 200, 250, 300, 350, 400, 450, 500, 550, 600, 650, 700, 750, 800, 850, 900, 950, 1000, 1050, 1100, or 1115 nucleotides of the nucleotide sequence of the ORF of SEQ ID NO:25, or a complement thereof.

The invention features nucleic acid molecules of at least 575, 600, 650, 700, 800, 900, 1000, 1100 or 1200 contiguous nucleotides of the nucleotide sequence of SEQ ID NO:31, the nucleotide sequence of an EpT353 cDNA of ATCC® Accession Number PTA-292, or a complement thereof. The invention also features nucleic acid molecules comprising at least 20, 50, 100, 150, 200, 250, 300, 350, 400, 450, 500, 550, 600 or 630 contiguous nucleotides of nucleic acids 1 to 634 of SEQ ID NO:31, or a complement thereof.

The invention features nucleic acid molecules which include a fragment of at least 150, 200, 250, 300, 350, 400, 450, 500, 550, 600, 650 or 690 contiguous nucleotides of the nucleotide sequence of SEQ ID NO:28, or a complement thereof. The invention also features nucleic acid molecules comprising at least 20, 50, 100, 150, 200, 250, 300, 350, 400, 450, 500, 550 or 560 contiguous nucleotides of nucleic acids 1 to 560 of the ORF of SEQ ID NO:31, or a complement thereof.

The invention features nucleic acid molecules of at least 500, 550, 600, 650, 700, 750, 800, 850, 900, 1000, 1100, 1200, 1300, 1400, 1500, 1600 or 1700 contiguous nucleotides of the nucleotide sequence of SEQ ID NO:33, the nucleotide sequence of a human EpT393 cDNA of ATCC® Accession Number PTA-295, or a complement thereof.

The invention features nucleic acid molecules which include a fragment of at least 20, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or 1400 contiguous nucleotides of the nucleotide sequence of the ORF of SEQ ID NO:33, or a complement thereof.

The invention features nucleic acid molecules which include a fragment of at least 20, 50, 100, 150, 200, 250, 300, 350, 400, 450, 500, 550, 600, 650, 700, 750, 800, 850, 900, 950, 1000, 1050, 1100, 1150, 1200 or 1250 contiguous nucleotides of nucleotides 1 to 1250 of SEQ ID NO:33, or a complement thereof.

The invention features nucleic acid molecules of at least 250, 300, 350, 400, 450, 500, 550, 600, 650, 700, 750, 800, 850, 900, 1000, 1100, 1200, 1300, 1400, 1500, 1600, 1700, 1800, or 1900 contiguous nucleotides of the nucleotide sequence of SEQ ID NO:35, the nucleotide sequence of a mouse EpT393 cDNA, or a complement thereof.

The invention features nucleic acid molecules which include a fragment of at least 20, 50, 100, 150, 200, 250, 300, 350, 400, 450, 500, 550, 600, 650, 700, 750, 800, 850, 900, 950 or 984 contiguous nucleotides nucleotides of nucleic acids 1 to 984 of SEQ ID NO:35, or a complement thereof. The invention also features nucleic acid molecules which include a fragment of at least 20, 50, 100, 150, 200, 250 or 292 contiguous nucleotides of the nucleic acids 1177 to 1469 of SEQ ID NO:35, or a complement thereof. The invention also features nucleic acid molecules which include a fragment of at least 20, 50, 100, 150, 200, 250 or 280 contiguous nucleotides of the nucleic acids 1666 to 1946 of SEQ ID NO:35, or a complement thereof.

The invention features nucleic acid molecules which include a fragment of at least 200, 250, 300, 350, 400, 450, 500, 550, 600, 650, 700, 750, 800, 850, 900, 950, 1000, 1050, 1100, 1150, 1200, 1250, 1300, 1350, or 1400 contiguous nucleotide of the nucleotide sequence of the ORF of SEQ ID NO:35, or a complement thereof.

The invention features nucleic acid molecules of at least 20, 50, 100, 150, 200, 250, 300, 350, 400, 450, 500, 550, 600, 650, 700, 750, 800, 850, 900, 1000, 1100, 1200 or 1300 contiguous nucleotides of the nucleotide sequence of SEQ ID NO:37, the nucleotide sequence of an EpT402 cDNA of ATCC® Accession Number PTA-294, or a complement thereof.

The invention features nucleic acid molecules which include a fragment of at least 20, 50, 100, 150, 200, 250, 300, 350, 400, 450, 500, 550, 600 or 620 contiguous nucleotides of the nucleotide sequence of the ORF of SEQ ID NO:37, or a complement thereof.

The invention features nucleic acid molecules of at least 460, 500, 550, 600, 650, 700, 750, 800, 850, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300 or 3340 contiguous nucleotides of the nucleotide sequence of SEQ ID NO:39, the nucleotide sequence of an EpT351 cDNA of ATCC® Accession Number PTA-424, or a complement thereof. The invention also features nucleic acid molecules comprising at least 25, 50, 100, 150, 200, 250, 300, 400, 450, 500, 550, 600, 650, 700, 750, 800, 850, 1000, 1100, 1200, 1300, 1400, 1500, 1600, 1700, 1800, 1900, 2000, 2050 or 2071 contiguous nucleotides of nucleic acids 1 to 2071 of SEQ ID NO:39, or a complement thereof.

The invention features nucleic acid molecules which include a fragment of at least 25, 50, 100, 150, 200, 250, 300, 400, 450, 500, 550, 600, 650, 700, 750, 800, 850, 900, 950, 1000, 1050, 1100, 1200, 1300, 1400 or 1440 contiguous nucleotides of the nucleotide sequence of the ORF of SEQ ID NO:39, or a complement thereof.

The invention features nucleic acid molecules of at least 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500 or 3575 contiguous nucleotides of the nucleotide sequence of SEQ ID NO:41, the nucleotide sequence of an human EpT5.09 cDNA of ATCC® Accession Number PTA-438, or a complement thereof. The invention also features nucleic acid molecules comprising at least 25, 50, 100, 150, 200, 250, 300, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1700, 1800, 1900, 2000, 2100, 2200, 2300, 2400, 2500, 2600, 2700, 2800, 2900 or 3000 contiguous nucleotides of nucleic acids 1 to 3023 of SEQ ID NO:41 or a complement thereof.

The invention features nucleic acid molecules which include a fragment of at least 25, 50, 100, 150, 200, 250, 300, 400, 450, 500, 550, 600, 650, 700, 750, 800, 850 or 860 contiguous nucleotides of the nucleotide sequence of the ORF of SEQ ID NO:41, or a complement thereof.

The invention features nucleic acid molecules of at least 265, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1700, 1800, 1900, 2000, 2100, 2200, 2300, 2400, 2500, 2600, 2700, 2800, 2900, 3100, 3200, 3300, 3400, 3500, 3600 or 3637 contiguous nucleotides of the nucleotide sequence of SEQ ID NO:43, the nucleotide sequence of a mouse EpT509 cDNA or a complement thereof. The invention also features nucleic acid molecules comprising at least 25, 50 or 100 contiguous nucleotides of nucleic acids 1 to 106 of SEQ ID NO:43, or a complement thereof.

The invention features nucleic acid molecules which include a fragment of at least 265, 300, 350, 400, 450, 500, 550, 600, 650, 700, 750, 800, 850 or 860 contiguous nucleotides of the nucleotide sequence of the ORF of SEQ ID NO:43, or a complement thereof. The invention features nucleic acid molecules which include a fragment of at least 25 or 50 contiguous nucleotides of nucleic acids 1 to 52 of the ORF of SEQ ID NO:43, or a complement thereof.

In preferred embodiments, the isolated nucleic acid molecules encode a cytoplasmic, transmembrane, or extracellular domain of a polypeptide of the invention.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector or engineered to contain and/or express a nucleic acid molecule of the invention. The invention also provides methods for producing a polypeptide of the invention by culturing, in a suitable medium, a host cell of the invention containing a recombinant expression vector encoding a polypeptide of the invention such that the polypeptide of the invention is produced.

Another aspect of this invention features isolated or recombinant proteins and polypeptides of the invention, or modulators thereof. Preferred proteins and polypeptides possess at least one biological activity possessed by the corresponding naturally-occurring human polypeptide. An activity, a biological activity, and a functional activity of a polypeptide of the invention refers to an activity exerted by a protein or polypeptide of the invention on a responsive cell as determined in vivo, or in vitro, according to standard techniques. Such activities can be a direct activity, such as an association with or an enzymatic activity on a second protein or an indirect activity, such as a cellular signaling activity mediated by interaction of the protein with a second protein. Thus, such activities include, e.g., (1) the ability to form protein-protein interactions with proteins in the signaling pathway of the naturally-occurring polypeptide; (2) the ability to bind a ligand of the naturally-occurring polypeptide; (3) the ability to bind to an intracellular target of the naturally-occurring polypeptide.

Further activities of polypeptides of the invention include the ability to modulate (this term, as used herein, includes, but is not limited to, "stabilize", promote, inhibit or disrupt, protein-protein interactions (e.g., homophilic and/or heterophilic)), protein-ligand interactions, e.g., in receptor-ligand recognition, development, differentiation, maturation, proliferation and/or activity of cells function, survival, morphology, proliferation and/or differentiation of cells of tissues in which it is expressed. Additional activities include but are not limited to: (1) the ability to modulate cell surface recognition; (2) the ability to transduce an extracellular signal (e.g., by interacting with a ligand and/or a cell-surface receptor); (3) the ability to modulate a signal transduction pathway; and (4) the ability to modulate intracellular signaling cascades (e.g., signal transduction cascades).

Other activities of polypeptides of the invention may include, e.g., (1) the ability to modulate cellular proliferation; (2) the ability to modulate cellular differentiation; (3) the ability to modulate chemotaxis and/or migration; and (4) the ability to modulate cell death.

For TANGO 219, biological activities include, the ability to modulate the normal function, migration, proliferation, and/or differentiation of cells in which it is expressed (see description of expression data below).

For TANGO 232, biological activities include, e.g., the ability to interact with a TANGO 232 receptor. Other activities include the ability to modulate function, survival, morphology, proliferation and/or differentiation of cells of tissues in which it is expressed (e.g., cells of adipose tissue). In adipose tissue, for example, TANGO 232 biological activities include the ability to modulate synthesis, storage, and release of lipids, and to modulate the conversion of stored chemical energy into heat.

For TANGO 281, biological activities include, e.g., (1) the ability to modulate the host immune response; (2) the ability to modulate the proliferation, differentiation and/or activity of hematopoeitic cells (e.g. megakaryocytes); (3) the ability to modulate the development, differentiation, maturation, proliferation and/or activity of pulmonary system cells; (4) the ability to modulate the development, differentiation, maturation, proliferation and/or activity intestinal cells such as M cells; (5) the ability to modulate the development, differentiation, maturation, proliferation and/or activity of stomach cells such as cells of the gastric epithelium; (6) the ability to modulate intracellular signaling cascades (e.g., signal transduction cascades); and (7) the ability to modulate platelet function (e.g., the promotion of platelet aggregation).

For A236, biological activities include, e.g., the ability to interact with a A236 receptor. Other activities include the ability to modulate function, survival, morphology, proliferation and/or differentiation of cells of tissues in which it is expressed. A236 biological activities can include the ability to modulate an inflammatory response and the ability to modulate viral entry.

For TANGO 300, biological activities include, e.g., the ability to interact with a TANGO 300 receptor. Other activities include the ability to modulate function, survival, morphology, proliferation and/or differentiation of cells of tissues in which it is expressed.

For TANGO 353 or modulators thereof, biological activities include, e.g., (1) the ability to modulate development, differentiation, proliferation and/or activity of immune cells, such as lymphocytes (e.g., T cells and B cells); (2) ability to modulate cell proliferation, e.g., abnormal cell proliferation; (3) the ability to modulate intracellular signaling cascades (e.g., signal transduction cascades); and (4) the ability to modulate intercellular signaling (e.g., in the immune system).

For TANGO 393 or modulators thereof, biological activities include, e.g., (1) the ability to modulate the proliferation, differentiation and/or activity of hypothalamus cells; (2) the ability to modulate intracellular signaling cascades (e.g., signal transduction cascades); (3) the ability to modulate intercellular signaling; and (4) ability to modulate cell-cell interactions and/or cell-extracellular matrix interactions.

For TANGO 402 or modulators thereof, biological activities include, e.g., (1) the ability to modulate development, differentiation, proliferation and/or activity of immune cells (e.g., leukocytes and macrophages), endothelial cells and smooth muscle cells; (2) the ability to modulate the host immune response; (3) the ability to modulate intracellular signaling cascades (e.g., signal transduction cascades); (4) the ability to modulate the development of organs, tissues and/or cells of the embryo and/or fetus; (5) the ability to modulate cell-cell interactions and/or cell-extracellular matrix interactions; (6) the ability to modulate atherosclerosis, e.g., the initiation and progression of atherosclerosis; (7) the ability to modulate low-density lipoproteins e.g., the ability to modulate levels, metabolism and/or cellular uptake of oxidized low-density lipoprotein (Ox-LDL), the ability to bind to Ox-LDL, and the ability to modulate Ox-LDL activity in cells; (8) the ability to modulate atherogenesis; and (9) the ability to modulate inflammatory functions e.g., by modulating leukocyte adhesion to extracellular matrix and/or endothelial cells; (10) the ability to bind proteins, e.g., lipoproteins, e.g., low-density lipoproteins, e.g., oxidatively modified low-density lipoproteins; (11) the ability to modulate internalization of proteins, e.g., lipoproteins, e.g., low-density lipoproteins, e.g., oxidatively modified low-density lipoproteins; (12) the ability to modulate degradation, e.g., proteolytic degradation, of proteins, e.g., lipoproteins, e.g., low-density lipoproteins, e.g., oxidatively modified low-density lipoproteins; (13) the ability to modulate, e.g., increase, uptake of proteins, e.g., lipoproteins, e.g., low-density lipoproteins, e.g., oxidatively modified low-density lipoproteins, by cells, e.g., macrophages and muscle cells, e.g., smooth muscle cells; (14) the ability to modulate, e.g., prevent, lipid deposition, e.g., in arteries, and thus modulate, e.g., prevent, intimal thickening; (15) the ability to modulate, e.g., induce or prevent, changes in cells, e.g., transformation of cells (e.g., macrophages and smooth muscle cells) into foam cells and functional alteration of cells (e.g., endothelial cells, e.g., intimal neovascular endothelial cells); (16) the ability to bind and phagocytose cells, e.g., aged and apoptotic cells; (17) the ability to remove debris, e.g., apoptotic cells, from blood vessel walls; (18) the ability to modulate homeostasis, e.g., vascular homeostasis, e.g., by modulating, e.g., preventing the impairment of, nitric oxide production; (19) the ability to modulate, e.g., inhibit, the expression of molecules, e.g., adhesion molecules (e.g., leukocyte adhesion molecules) and growth factors (e.g., smooth-muscle growth factors); (20) the ability to alter, e.g., increase, expression in response to stimuli, e.g., TNF, shear stress, and pathophysiological stimuli relevant to disorders (e.g., atherosclerosis and inflammation); (21) the ability to form, e.g., stabilize, promote, facilitate, inhibit, or disrupt, cell to cell and cell to blood product interaction, e.g., between leukocytes and platelets or leukocytes and vascular endothelial cells; and (22) the ability to recognize large molecules, e.g., carbohydrates.

For TANGO 351 or modulators thereof, biological activities include, e.g., (1) the ability to modulate the development, differentiation, morphology, migration or chemotaxis, proliferation and/or activity of kidney cells and the kidney; (2) the ability to modulate, protein-protein interactions (e.g., homophilic and/or heterophilic), and protein-ligand interactions, e.g., in receptor-ligand recognition; (3) ability to modulate cell-cell interactions and/or cell-extracellular matrix interactions; (4) the ability to modulate intracellular signaling cascades (e.g., signal transduction cascades); (5) the ability to modulate the development of organs, tissues and/or cells in an embryo and/or fetus.

For TANGO 509 or modulators thereof, biological activities include, e.g., (1) the ability to modulate the development, differentiation, morphology, migration or chemotaxis, proliferation and/or activity of mammary cells, e.g., mammary epithelial cells; (2) the ability to modulate the development and progression of cell proliferative disorders such as cancer (e.g. breast or breast-associated cancer); (3) the ability to modulate, protein-protein interactions (e.g., homophilic and/or heterophilic), and protein-ligand interactions, e.g., in receptor-ligand recognition; (4) ability to modulate cell-cell interactions and/or cell-extracellular matrix interactions; (5) the ability to modulate mammary processes (e.g., milk secretion or fat secretion in milk); (6) the ability to modulate intracellular signaling cascades (e.g., signal transduction cascades); (7) the ability to modulate intercellular signaling (e.g., hormonal signals to secrete milk); (8) the ability to modulate the development of embryonic organs, tissues and/or cells; (9) the ability to modulate the development, differentiation, morphology, migration or chemotaxis, proliferation and/or activity of immune cells (e.g., B-lymphocytes, T-lymphocytes and monocytes); (10) the ability to modulate hematopoietic processes (e.g., immune response); (11) the ability to modulate MHC class I recognition and binding; (12) the ability to modulate ligand-receptor interactions in proteins with immunoglobulin domains; (13) the ability to modulate immunoglobulin binding to antigens; (14) the ability to modulate lymphocyte selection such as modulation of B-cell receptor or T-cell receptor stimulation in developing lymphocytes, e.g., through modulation of interaction of antigens with the immunoglobulin domain(s) of the immune cell's antigen receptors; (15) the ability to modulate immunoglobulin production; and (16) the ability to modulate cell killing, such as, the ability to modulate production of cytokines or activation of cytotoxic T-cell killing.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have or encode a common structural domain and/or common functional activity. For example, amino acid or nucleotide sequences which contain or encode a common structural domain having about 60% identity, preferably about 65% identity, more preferably about 75%, 85%, 95%, 98% or more identity are defined herein as sufficiently identical.

In one embodiment, the isolated polypeptides of the invention include at least one or more of the following domains: a signal sequence, an extracellular domain, a transmembrane domain and an intracellular or cytoplasmic domain.

In another embodiment, the isolated polypeptide of the invention lacks both a transmembrane and cytoplasmic domain. In yet another embodiment, a polypeptide of the invention lacks both a transmembrane and a cytoplasmic domain and is soluble under physiological conditions. In yet another embodiment, a polypeptide of the invention is fused to either heterologous sequences, or is fused in two or more repeats of a domain, e.g., binding or enzymatic, and is soluble under physiological conditions.

The polypeptides of the present invention, or biologically active portions thereof, can be operably linked to a heterologous amino acid sequence to form fusion proteins. The invention further features antibody substances that specifically bind a polypeptide of the invention, such as monoclonal or polyclonal antibodies, antibody fragments, and single-chain antibodies. In addition, the polypeptides of the invention or biologically active portions thereof can be incorporated into pharmaceutical compositions, which optionally include pharmaceutically acceptable carriers. These antibody substances can be made, for example, by providing the polypeptide of the invention to an immuno-competent vertebrate and thereafter harvesting blood or serum from the vertebrate.

In another aspect, the present invention provides methods for detecting the presence, activity or expression of a polypeptide of the invention in a biological sample by contacting the biological sample with an agent capable of detecting an indicator of the presence, activity or expression such that the presence activity or expression of a polypeptide of the invention is detected in the biological sample.

In another aspect, the invention provides methods for modulating activity of a polypeptide of the invention comprising contacting a cell with an agent that modulates (e.g., inhibits or stimulates) the activity or expression of a polypeptide of the invention such that activity or expression in the cell is modulated. In one embodiment, the agent is an antibody that specifically binds to a polypeptide of the invention. In another embodiment, the agent is a fragment of a polypeptide of the invention or a nucleic acid molecule encoding such a polypeptide fragment.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a polypeptide (e.g., an antibody or a fragment of a polypeptide of the invention), a peptidomimetic, or other small molecule (e.g., a small organic molecule).

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIG. 1A-1D depicts the cDNA sequence of human TANGO 239, form 1 (SEQ ID NO:1) and predicted amino acid sequence of TANGO 239, form 1 (SEQ ID NO:2). The open reading frame extends from nucleotide 344 to 1990 of SEQ ID NO:1.

FIG. 3 depicts the alignment of amino acids 24 to 169, amino acids 170 to 329 and amino acids 340 to 498 of TANGO 239 (SEQ ID NO:2) and the MAM consensus sequence (SEQ ID NO:51). In these alignments, an uppercase letter between the two sequences indicates an exact match, and a (+) indicates a conservative amino acid substitution.

FIG. 4A-4C depicts the cDNA sequence of human TANGO 239, form 2 (clone Athxe3b8) (SEQ ID NO:3) and predicted amino acid sequence of human TANGO 239, form 2 (clone Athxe3b8) (SEQ ID NO:4). The open reading frame extends from nucleotide 344 to 2401 of SEQ ID NO:3.

FIG. 5 depicts the cDNA sequence of mouse TANGO 239 (SEQ ID NO:5) and predicted amino acid sequence of mouse TANGO 239 (SEQ ID NO:6). The open reading frame extends from nucleotide 209 to 370 of SEQ ID NO:5.

FIG. 6 depicts the cDNA sequence of human TANGO 219 (SEQ ID NO:7) and the predicted amino acid sequence of TANGO 219 (SEQ ID NO:8). The open reading frame extends from nucleotide 106 to nucleotide 552 of SEQ ID NO:7.

FIG. 8 depicts the cDNA sequence of mouse TANGO 219 (SEQ ID NO:9) and the predicted amino acid sequence of TANGO 219 (SEQ ID NO:10). The open reading frame comprises from nucleotide 2 to 370 nucleotide of SEQ ID NO:9.

FIG. 9 depicts the cDNA sequence (SEQ ID NO:11) and the predicted amino acid sequence (SEQ ID NO:12) of macaque TANGO 232. The open reading frame extends from nucleotide 96 to nucleotide 809 of SEQ ID NO:11.

FIG. 11 depicts an alignment of a portion of the macaque TANGO 232 amino acid sequence (amino acids 1-132 of SEQ ID NO:12) with a translation of a rabbit nucleotide sequence (GenBank Accession Number C83084; SEQ ID NO:45) and a mouse nucleotide sequence (clone jtmoa31f1; SEQ ID NO:18). This alignment defines a cysteine-rich domain that is conserved among these three species (cons (SEQ ID NO:52)). The arrows point to the conserved cysteine residues at positions 49, 54, 61, 72, and 74 of SEQ ID NO:12. An additional cysteine residue at position 106 is conserved in the macaque and rabbit sequences.

FIG. 12 depicts the cDNA sequence (SEQ ID NO:13) and the predicted amino acid sequence (SEQ ID NO:14) of human TANGO 232, form 1. The open reading frame comprises nucleotide 1 to nucleotide 366 of SEQ ID NO:13.

FIG. 13A-13D depicts an alignment of a portion of the cDNA sequence of macaque (nucleotides 424-1937 of SEQ ID NO:11) and human (SEQ ID NO:13) TANGO 232, form 1 and shows that there is 83.4% identity between the two sequences.

FIG. 14 depicts an alignment of a portion of the amino acid sequence of macaque (amino acids 93-238 of SEQ ID NO:12) and human (SEQ ID NO:14) TANGO 232 and shows that there is 94.9% identity between the two sequences.

FIG. 15 depicts the cDNA sequence of human TANGO 232 (SEQ ID NO:15) and predicted amino acid sequence of human TANGO 232 (SEQ ID NO:16). The open reading frame extends from nucleotide 110 to 823 of SEQ ID NO:15.

FIG. 16A-16B depicts the cDNA sequence of mouse TANGO 232 (SEQ ID NO:17) and predicted amino acid sequence of mouse TANGO 232 (SEQ ID NO:18). The open reading frame extends from nucleotide 79 to 795 of SEQ ID NO:17.

FIG. 17A-17B depict the cDNA sequence of human TANGO 281 (SEQ ID NO:19) and the predicted amino acid sequence of human TANGO 281 (SEQ ID NO:20). The open reading frame extends from nucleotide 65 to nucleotide 799 of SEQ ID NO:19.

FIG. 19 depicts an alignment of the amino acid sequence of photosystem II 10 kD phosphoprotein domain (SEQ ID NO:46; GenBank Accession Number PF00737) and the amino acid sequence 97 to 146 of human TANGO 281 (SEQ ID NO:20). This alignment was performed using the ALIGN alignment program with a PAM120 scoring matrix, a gap length penalty of 12, and a gap penalty of 4.

FIG. 20A-20B depict the cDNA sequence of mouse TANGO 281 (SEQ ID NO:21) and the predicted amino acid sequence of mouse TANGO 281 (SEQ ID NO:22). The open reading frame extends from nucleotide 90 to nucleotide 728 of SEQ ID NO:21.

FIG. 22 depicts an alignment of the amino acid sequence of human TANGO 281 (SEQ ID NO:20) and the amino acid sequence of mouse TANGO 281 (SEQ ID NO:22). The alignment demonstrates that the amino acid sequences of human and mouse TANGO 281 are 66.5% identical. This alignment was performed using the ALIGN program with a PAM120 scoring matrix, a gap length penalty of 12 and a gap penalty of 4.

FIG. 23A-23B depict the cDNA sequence (SEQ ID NO:23) and the predicted amino acid sequence (SEQ ID NO:24) of human A236. The open reading frame extends from nucleotide 314 to nucleotide 1432 of SEQ ID NO:23.

FIG. 25 depicts an alignment of the immunoglobulin domains, residues 28 to 113 and 146 to 210, of human A236 (SEQ ID NO:24) with a consensus immunoglobulin domain (SEQ ID NO:53).

FIG. 26A-26C depicts the cDNA sequence (SEQ ID NO:25) and the predicted amino acid sequence (SEQ ID NO:26) of mouse A236. The open reading frame extends from nucleotide to nucleotide 304 to 1422 of SEQ ID NO:25.

FIG. 27A-27C depict an alignment of the open reading frames of human A236 (SEQ ID NO:23; bottom sequence) and mouse A236 (SEQ ID NO:25; top sequence).

FIG. 28 depicts an alignment of the amino acid sequences of human A236 (SEQ ID NO:24; bottom sequence) and mouse A236 (SEQ ID NO:26; top sequence).

FIG. 30A-30B depicts the cDNA sequence (SEQ ID NO:27) and the predicted amino acid sequence (SEQ ID NO:28) of human TANGO 300. The open reading frame extends from nucleotide 31 to nucleotide 1113 of SEQ ID NO:27.

FIG. 32A-32C depicts the cDNA sequence (SEQ ID NO:29) and the predicted amino acid sequence (SEQ ID NO:30) of mouse TANGO 300. The open reading frame extends from nucleotide 41 to nucleotide 1195 of SEQ ID NO:29.

FIG. 34A-34C depicts an alignment of the nucleotide sequence of the open reading frame (ORF) of human TANGO 300 (SEQ ID NO:27) and the nucleotide sequence of the ORF of mouse TANGO 300 (SEQ ID NO:29). This alignment was created using BESTFIT (BLOSUM 62 scoring matrix; gap open penalty of 12; frame shift penalty of 5; gap extend penalty of 4). In this alignment, the sequences are 77.7% identical.

FIG. 35 depicts an alignment of the amino acid sequence of human TANGO 300 (SEQ ID NO:28) and the amino acid sequence of mouse TANGO 300 (SEQ ID NO:30). This alignment was created using BESTFIT (BLOSUM 62 scoring matrix; gap open penalty of 12; frame shift penalty of 5; gap extend penalty of 4). In this alignment, the sequences are 69.6% identical.

FIG. 36 depicts the cDNA sequence of human TANGO 353 (SEQ ID NO:31) and the predicted amino acid sequence of human TANGO 353 (SEQ ID NO:32). The open reading frame of human TANGO 353 extends from nucleotide 76 to nucleotide 765 of SEQ ID NO:31.

FIG. 38A-38B depicts the cDNA sequence of human TANGO 393 (SEQ ID NO:33) and the predicted amino acid sequence of human TANGO 393 (SEQ ID NO:34). The open reading frame extends from nucleotide 40 to nucleotide 1458 (SEQ ID NO:33).

FIG. 40A-40B depicts the cDNA sequence of mouse TANGO 393 (SEQ ID NO:35) and the predicted amino acid sequence of mouse TANGO 393 (SEQ ID NO:36). The open reading frame extends from nucleotide 226 to nucleotide 1644 (SEQ ID NO:35).

FIG. 42A-42C depicts an alignment of the open reading frames of human TANGO 393 (SEQ ID NO:33) and mouse TANGO 393 (SEQ ID NO:35) demonstrating an identity of 82.8%. The algorithm used to align the sequences was the ALIGN program which calculates a global alignment of two sequences. (Version 2.0u, Myers and Miller, 1989)

FIG. 43 depicts an alignment of the immature proteins of human TANGO 393 (SEQ ID NO:34) and mouse TANGO 393 (SEQ ID NO:36) demonstrating an identity of 89.2%. The algorithm used to align the sequences was the ALIGN program which calculates a global alignment of two sequences. (Version 2.0u, Myers and Miller, 1989)

FIG. 44 depicts the cDNA sequence of human TANGO 402 (SEQ ID NO:37) and the predicted amino acid sequence of human TANGO 402 (SEQ ID NO:38). The open reading frame of human TANGO 402 extends from nucleotide 87 to nucleotide 707 of SEQ ID NO:37.

FIG. 46 depicts an alignment of the amino acid sequence of human TANGO 402 (SEQ ID NO:38) and the amino acid sequence of human LOX-1 (SEQ ID NO:47; Accession Number AB010710). The alignment demonstrates that the amino acid sequences of human TANGO 402 and human LOX-1 are 25.1% identical. This alignment was performed using the ALIGN program with a PAM120 scoring matrix, a gap length penalty of 12 and a gap penalty of 4.

FIG. 47A-47B depicts an alignment of the nucleotide sequences of the open reading frames of human TANGO 402 (nucleotide 87 to nucleotide 707 of SEQ ID NO:37) and human LOX-1 (SEQ ID NO:54; Accession Number AB010710). The alignment of the open reading frame of human TANGO 402 and that of human LOX-1 demonstrates that those two coding regions are 42.0% identical. An alignment demonstrates that the nucleotide sequences of the cDNA of human TANGO 402 and human LOX-1 are 44.0% identical. The alignments were performed using the ALIGN program with a PAM120 scoring matrix, a gap length penalty of 12, and a gap penalty of 4. A (:) between nucleotides represents an exact match, a (.) between nucleotides represents a C to T or T to C change, or an A to G or G to A change.

FIG. 48A-48C depicts the cDNA sequence of human TANGO 351 (SEQ ID NO:39) and the predicted amino acid sequence of human TANGO 351 (SEQ ID NO:40). The open reading frame of human TANGO 351 extends from nucleotides 143 to 1588 of SEQ ID NO:39.

FIG. 50A-50C depicts the cDNA sequence of human TANGO 509 (SEQ ID NO:41) and the predicted amino acid sequence of human TANGO 509 (SEQ ID NO:42). The open reading frame of human TANGO 509 extends from nucleotides 59 to 928 of SEQ ID NO:41.

FIG. 52 depicts an alignment of the human TANGO 509 amino acid sequence (SEQ ID NO:42) with the butyrophilin-like protein amino acid sequence (SEQ ID NO:48; Accession Number AF142780). The alignment shows that there is a 33.0% overall amino acid sequence identity between human TANGO 509 and the butyrophilin-like protein. This alignment was performed using the ALIGN alignment program with a PAM120 scoring matrix, a gap length penalty of 12, and a gap penalty of 4.

FIG. 53 depicts the cDNA sequence of mouse TANGO 509 (SEQ ID NO:43) and the predicted amino acid sequence of mouse TANGO 509 (SEQ ID NO:44). The open reading frame of mouse TANGO 509 extends from nucleotide 49 to 918 of SEQ ID NO:43.

FIG. 55 depicts an alignment of the mouse TANGO 509 amino acid sequence (SEQ ID NO:44) with the butyrophilin-like protein amino acid sequence (SEQ ID NO:48; Accession Number AF142780). The alignment shows that there is a 31.9% overall amino acid sequence identity between mouse TANGO 509 and the butyrophilin-like protein. This alignment was performed using the ALIGN alignment program with a PAM120 scoring matrix, a gap length penalty of 12, and a gap penalty of 4.

DESCRIPTION OF THE PREFERRED EMBODIMENTS

Figure 2:
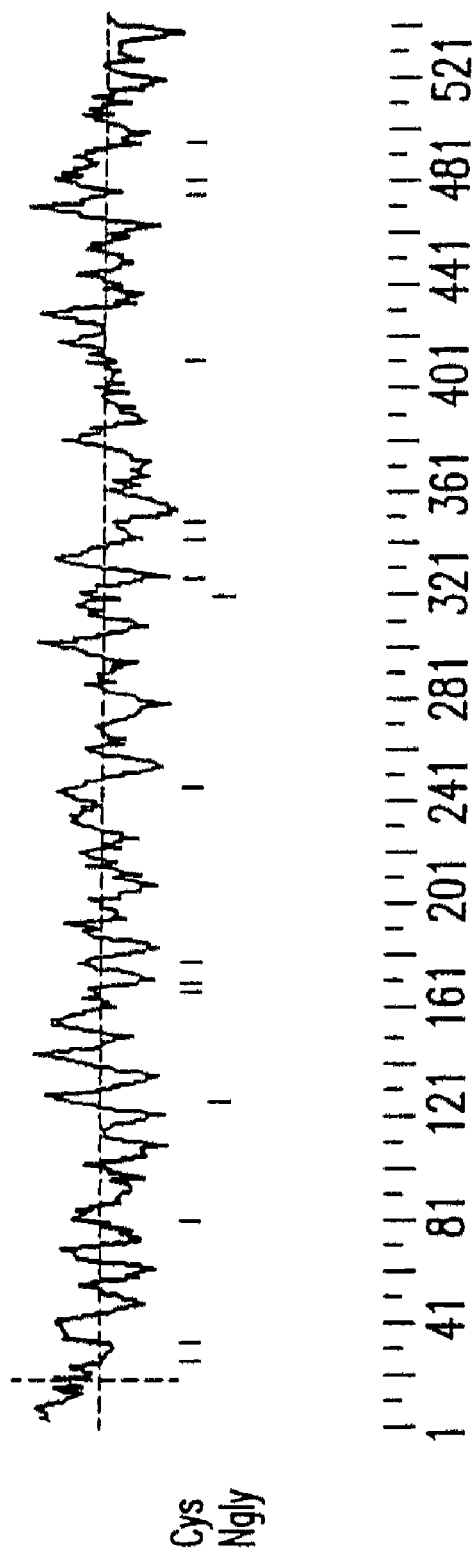
FIG. 2 depicts a hydropathy plot of a human TANGO 239 (SEQ ID NO:2). Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The TANGO 239, TANGO 219, TANGO 232, TANGO 281, A236 (INTERCEPT 236), TANGO 300, TANGO 353, TANGO 393, TANGO 402, TANGO 351 and TANGO 509 proteins and nucleic acid molecules comprise families of molecules having certain conserved structural and functional features among family members. Examples of conserved structural domains include signal sequence (or signal peptide or secretion signal), transmembrane domains, cytoplasmic domains and extracellular domains.

As used herein, the terms "family" or "families" are intended to mean two or more proteins or nucleic acid molecules having a common structural domain and having sufficient amino acid or nucleotide sequence identity as defined herein. Family members can be from either the same or different species. For example, a family can comprise two or more proteins of human origin, or can comprise one or more proteins of human origin and one or more of non-human origin. Members of the same family may also have common structural domains.

As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19-34 amino acid residues, and has at least about 60-80%, more preferably at least about 65-75%, and more preferably at least about 70% hydrophobic residues. A signal sequence serves to direct a protein containing such a sequence to a lipid bilayer. A signal sequence is usually cleaved during processing of the mature protein.

As used herein, a "transmembrane domain" refers to an amino acid sequence having at least about 25 to 40 amino acid residues in length and which contains hydrophobic amino acid residues such as alanine, leucine, isoleucine, phenylalanine, proline, tyrosine, tryptophan, or valine. In a preferred embodiment, a transmembrane domain contains at least about 25 to 40 amino acid residues, preferably about 25-30 amino acid residues, and has at least about 60-80% hydrophobic residues.

As used herein, a "cytoplasmic loop" includes an amino acid sequence located within a cell or within the cytoplasm of a cell and is typically associated with a transmembrane protein segment which extends through the cellular membrane to the extracellular region.

As used herein, an "extracellular domain" is a protein structural domain which is part of a transmembrane protein and resides outside the cell membrane, or is extracytoplasmic. A protein which has more than one transmembrane domain likewise has more than one extracellular domain. When located at the N-terminal domain the extracellular domain is referred to herein as an "N-terminal extracellular domain". As used herein, an "N-terminal extracellular domain" includes an amino acid sequence. The N-terminal extracellular domain can be at least 10 amino acids in length or more, about 25, about 50, about 100, about 150, about 250, about 300, about 350, about 400, about 450, about 500, about 550, about 600, about 650, about 700, or more than about 750 amino acids.

The N-terminal extracellular domain is located outside of a cell or is extracellular. The C-terminal amino acid residue of a "N-terminal extracellular domain" is adjacent to an N-terminal amino acid residue of a transmembrane domain in a naturally-occurring protein. Preferably, the N-terminal extracellular domain is capable of interacting (e.g., binding to) with an extracellular signal, for example, a ligand (e.g., a glycoprotein hormone) or a cell surface receptor (e.g., an integrin receptor). Most preferably, the N-terminal extracellular domain mediates a variety of biological processes, for example, protein-protein interactions, signal transduction and/or cell adhesion.

TANGO 239

In one aspect, the present invention is based on the discovery of cDNA molecules which encode a novel family of proteins referred to herein as TANGO 239 proteins. The TANGO 239 proteins and nucleic acid molecules comprise a family of molecules having certain conserved structural and functional features. For example, the present invention features TANGO 239 proteins having at least one, preferably two or three, MAM domain(s). The MAM domain is associated with various adhesive proteins and as such is likely to have adhesive function. Within MAM domains are conserved cysteine residues which play a role in the adhesion of a MAM domain to other proteins. As used herein, a MAM domain refers to an amino acid sequence of about 130 to about 170, preferably about 140 to 165, and more preferably about 145, 146 to 159 or 160 amino acids in length.

Conserved amino acid motifs, referred to herein as "consensus patterns" or "signature patterns", can be used to identify TANGO 239 family members having a MAM domain. For example, the following signature pattern can be used to identify TANGO 239 family members: G-x-[LIVMFY] (2)-x(3)-[STA]-x(10, 11)-[LV]-x(4,6)-[LIVMF]-x(6, 7)-C-[LIVM]-x(3)-[LIVMFY]-x(3, 4)-[GSC]. The signature patterns or consensus patterns described herein are described according to the following designations: all amino acids are indicated according to their universal single letter designation; "x" designates any amino acid; x(n) designates "n" number of amino acids, e.g., x (2) designates any two amino acids, e.g., x (6, 7) designates any six to seven amino acids; and, amino acids in brackets indicates any one of the amino acids within the brackets, e.g., [STA] indicates any of one of either S (serine), T (threonine) or A (alanine). TANGO 239 has such a signature pattern at about amino acids 50 to 90, amino acids 215 to 256 and/or amino acids 380 to 420 of SEQ ID NO:2.

A MAM domain further contains at least about 2 to 6, preferably, 3 to 5, more preferably 4 conserved cysteine residues. By alignment of a TANGO 239 family member with a MAM consensus sequence, conserved cysteine residues can be found. For example, as shown in FIG. 3, there is a first cysteine residue in the MAM consensus sequence that corresponds to a cysteine residue at amino acid 26 of the first MAM domain of TANGO 239 (SEQ ID NO:2); there is a second cysteine residue in the MAM consensus sequence that corresponds to a cysteine residue at amino acid 33 of TANGO 239 (SEQ ID NO:2); there is a third cysteine residue in the MAM consensus sequence that corresponds to a cysteine residue at amino acid 80 of TANGO 239 (SEQ ID NO:2); and/or there is a fourth cysteine residue in the MAM consensus sequence that corresponds to a cysteine residue at amino acid 167 of TANGO 239 (SEQ ID NO:2). In addition, conserved cysteine residues can be found at amino acids 170, 178, 246 and/or 327 of the second MAM domain of TANGO 239 (SEQ ID NO:2); and at amino acids 342, 349, 411 and/or 496 of the third MAM domain of TANGO 239 (SEQ ID NO:2). The MAM consensus sequence is available from the HMMer version 2.0 software as Accession Number PF00629. Software for HMM-based profiles is available from http://www.csc.ucsc.edu/research/compbio/sam.html and from http://genome.wustl.edu/eddy/hmmer.html. A MAM domain of TANGO 239 extends, for example, from about amino acids 26 to 169, about amino acids 170 to 329, about amino acids 342 to 498, and/or about amino acids 509 to 666 of SEQ ID NO:2.

Also included within the scope of the present invention are TANGO 239 proteins having a signal sequence. In certain embodiments, a TANGO 239 family member has the amino acid sequence of SEQ ID NO:1, and the signal sequence is located at amino acids 1 to 16, 1 to 17, 1 to 18, 1 to 19, and 1 to 20. In such embodiments of the invention, the domains and the mature protein resulting from cleavage of such signal peptides are also included herein. For example, the cleavage of a signal sequence consisting of amino acids 1 to 18 of SEQ ID NO:2 results in a mature TANGO 239 protein corresponding to amino acids 19 to 686 of SEQ ID NO:2. The signal sequence is normally cleaved during processing of the mature protein.

Various features of human TANGO 239, form 1 and form 2, and mouse TANGO are summarized below.

HUMAN TANGO 239 Form 1

A cDNA encoding human TANGO 239 was identified by screening an IL-1β stimulated astrocyte library. A clone, comprising human TANGO 239, was selected for complete sequencing based on its ability to direct the secretion of a protein of approximately 60 kDa in $^{35}$S labeled supernatants of 293T cells.

TANGO 239 includes a 3413 nucleotide cDNA (FIG. 1A-1D; SEQ ID NO:1). In one embodiment, TANGO 239 is referred to as TANGO 239, form 1. The open reading frame of this TANGO 239, form 1 cDNA comprises nucleotides 344 to 1990 of SEQ ID NO:1, and encodes a secreted protein comprising the 550 amino acids depicted in FIG. 1A-1D (SEQ ID NO:2).

It is noted that the nucleotide sequence depicted in SEQ ID NO:1 contains Sal I and Not I adapter sequences on the 5' and 3' ends (GTCGACCCACGCGTCCC, nucleotides 1 to 16 of SEQ ID NO:1 and GGGCGGCCGC of nucleotides 3404 to 3413 of SEQ ID NO:1, respectively). Thus, it is to be understood that the nucleic acid molecules of the invention include not only those sequences with such adaptor sequences but also the nucleic acid sequences described herein lacking the adaptor sequences.

The signal peptide prediction program SIGNALP (Nielsen et al. (1997) *Protein Engineering* 10:1-6) predicted that human TANGO 239, form 1 includes an 18 amino acid signal peptide (amino acids 1 to about amino acid 18 of SEQ ID NO:2) preceding the mature TANGO 239, form 1 protein (corresponding to about amino acid 19 to amino acid 550 of SEQ ID NO:2). Human TANGO 239, form 1 is predicted to have a molecular weight of approximately 61.5 kDa prior to cleavage of its signal peptide and a molecular weight of approximately 59.5 kDa subsequent to cleavage of its signal peptide.

Human TANGO 239, form 1 includes three MAM domains from about amino acids 24 to 169, amino acids 170 to 329, and amino acids 340 to 496 of SEQ ID NO:2.

FIG. 2 depicts a hydropathy plot of human TANGO 239, form 1, the details of which are described herein. As shown in the hydropathy plot, the hydrophobic region at the beginning of the plot which corresponds to about amino acids 1 to 18 of SEQ ID NO:2 is the signal sequence of TANGO 239, form 1 (SEQ ID NO:2).

A clone, EpDH233, which encodes human TANGO 239 form 1 was deposited as part of EpDHMix1 with the American Type Culture Collection (ATCC®, 10801 University Boulevard, Manassas, Va. 20110-2209) on Nov. 20, 1998 which was assigned Accession Number 98999. This deposit will be maintained under the terms of the Budapest Treaty on the International Recognition of the Deposit of Microorganisms for the Purposes of Patent Procedure. This deposit was made merely as a convenience to those of skill in the art and is not an admission that a deposit is required under 35 U.S.C. §112.

HUMAN TANGO 239 Form 2

A cDNA encoding full length human TANGO 239 was identified by screening an IL-1β stimulated astrocyte library. A clone comprising human TANGO 239 was selected for complete sequencing based on its ability to direct the secretion of a protein of approximately 102.9 kDa in $^{35}$S labeled supernatants of 293T cells.

Human TANGO 239 includes a 3413 nucleotide cDNA (FIG. 4A-4C; SEQ ID NO:3). In one embodiment, human TANGO 239 is referred to as TANGO 239, form 2. The open reading frame of this TANGO 239, form 2 cDNA comprises nucleotides 344 to 2395 (SEQ ID NO:3), and encodes a secreted protein comprising the 686 amino acid depicted in FIG. 4A-4C (SEQ ID NO:4). It is noted that the nucleotide sequence depicted in SEQ ID NO:3 contains Sal I adaptor sequences and adapter sequences on the 5' and 3' ends, respectively.

The signal peptide prediction program SIGNALP (Nielsen et al. (1997) *Protein Engineering* 10:1-6) predicted that human TANGO 239, form 2 includes an 18 amino acid signal peptide (amino acids 1 to about amino acid 18 of SEQ ID NO:4) preceding the mature TANGO 239, form 2 protein (corresponding to about amino acid 19 to amino acid 686 of SEQ ID NO:4). Human TANGO 239, form 2 is predicted to have a molecular weight of approximately 102.9 kDa prior to cleavage of its signal peptide and a molecular weight of approximately 100 kDa subsequent to cleavage of its signal peptide.

Human TANGO 239, form 2 includes four MAM domains from about amino acids 26 to 169, amino acids 170 to 329, amino acids 340 to 496, and amino acids 509 to 666 of SEQ ID NO:4.

Northern analysis of human TANGO 239 mRNA expression using TANGO 239, form 2 nucleotide sequence as a probe revealed that TANGO 239 mRNA was highly expressed in skeletal muscle, placenta, and peripheral blood leukocytes. Expression was moderate in colon, thymus, kidney. Weak expression was observed in the liver, small intestine, and lung. No expression was detected in the brain, heart and spleen.

Mouse TANGO 239

A mouse homologue of human TANGO 239 was identified. Mouse TANGO 239 was identified by analyzing the sequences of clones present in a mouse inflammation model cDNA library. This analysis led to the identification of a clone, jymua038a02, encoding a mouse TANGO 239. The mouse TANGO 239 cDNA of this clone is 1029 nucleotides long (FIG. 5; SEQ ID NO:5). It is noted that the nucleotide sequence depicted in SEQ ID NO:5 contains Sal I and Not I adapter sequences on the 5' and 3' ends, respectively. The open reading frame of this cDNA, nucleotides 209 to 370 of SEQ ID NO:5, encodes a 54 amino acid secreted protein (FIG. 5; SEQ ID NO:6).

In situ tissue screening was performed on mouse adult and embryonic tissue to analyze for the expression of mouse TANGO 239 mRNA. In summary, expression in the adult mouse appeared to be restricted to bone structures. The in situ screen only detected expression in developing bones of embryos starting at E14.5. Expression was weak but was clearly detectable in the skull, scapula, sternum, vertebrae, incisor teeth, and femur. Adult tissues did not include bone or cartilage. Photoemulsion technique will be necessary to determine whether expression is from osteoblasts, osteoclasts, or chondrocytes. No signal was detected in the following tissues: brain (included a sense control), spinal cord, eye and harderian gland, submandibular gland, white fat, brown fat, stomach, heart (included a sense control), lung (included a sense control), liver (included a sense control), kidney (included a sense control), adrenal gland, colon, small intestine, thymus, lymph node, spleen, pancreas (included a sense control), skeletal muscle, bladder, testes, ovaries, placenta (included a sense control). In the case of embryonic expression, the following results were obtained: at E13.5, no signal was observed. At E14.5, a weak signal was observed outlining the vertebrae, incisors, and femur (included a sense control). At E15.5, most developing bone structures appeared to be outlined including the skull, Meckel's cartilage, scapula, vertebrae, primordium of basisphenoid bone, and femur (included a sense control). At E16.5 and E18.5, most developing bone structures had a weak signal in a pattern which outline the bone structures (included a sense control). At P1.5, a weak signal was associated with many developing bone structures. The most noticeable structures included the skull, basisphenoid bone, vertebrae, Meckel's cartilage and/or incisor teeth of the upper and lower jaw, sternum, scapula, and femur (included a sense control).

Human and mouse TANGO 239 sequences exhibit considerable similarity at the protein, nucleic acid, and open reading frame levels. An alignment (made using the ALIGN software {Myers and Miller (1989) CABIOS, ver. 2.0}; BLOSUM 62 scoring matrix; gap penalties −12/−4), reveals a protein identity of 79.6%. The human and mouse TANGO 239 full length cDNAs are 58.8% identical, as assessed using the same software and parameters as indicated (without the BLOSUM 62 scoring matrix). In the respective ORFs, calculated in the same fashion as the full length cDNAs, human and mouse TANGO 239 are 77.2% identical.

Uses of TANGO 239 Nucleic Acids, Polypeptides, and Modulators Thereof

As discussed above, the MAM domains of human TANGO 239 have adhesion function. Thus, the human TANGO 239 proteins of the invention likely play a role in cellular adhesion and therefore, human TANGO 239 proteins, nucleic acid molecules and/or modulators can be used to modulate cellular adhesion.

As human TANGO 239 was originally identified in an astrocyte library, human TANGO 239 nucleic acids, proteins, and modulators thereof can be used to modulate the proliferation, activation, development, differentiation, and/or function of glial cells e.g., astrocytes. Human TANGO 239 nucleic acids, proteins and modulators thereof can be used to treat glial cell-related disorders, e.g., astrocytoma and glioblastoma As TANGO 239 exhibits expression in the lung, TANGO 239 polypeptides, nucleic acids, or modulators thereof, can be used to treat pulmonary (lung) disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

As TANGO 239 exhibits expression in the small intestine, TANGO 239 polypeptides, nucleic acids, or modulators thereof, can be used to treat intestinal disorders, such as ischemic bowel disease, infective enterocolitis, Crohn's disease, benign tumors, malignant tumors (e.g., argentaffinomas, lymphomas, adenocarcinomas, and sarcomas), malabsorption syndromes (e.g., celiac disease, tropical sprue, Whipple's disease, and abetalipoproteinemia), obstructive lesions, hernias, intestinal adhesions, intussusception, or volvulus.

As TANGO 239 exhibits expression in the spleen, TANGO 239 nucleic acids, proteins, and modulators thereof can be used to modulate the proliferation, differentiation, and/or function of cells that form the spleen, e.g., cells of the splenic connective tissue, e.g., splenic smooth muscle cells and/or endothelial cells of the splenic blood vessels. TANGO 239 nucleic acids, proteins, and modulators thereof can also be used to modulate the proliferation, differentiation, and/or function of cells that are processed, e.g., regenerated or phagocytized within the spleen, e.g., erythrocytes and/or B and T lymphocytes and macrophages. Thus TANGO 239 nucleic acids, proteins, and modulators thereof can be used to treat spleen, e.g., the fetal spleen, associated diseases and disorders. Examples of splenic diseases and disorders include e.g., splenic lymphoma and/or splenomegaly, and/or phagocytotic disorders, e.g., those inhibiting macrophage engulfment of bacteria and viruses in the bloodstream.

As TANGO 239 exhibits expression in the heart, TANGO 239 nucleic acids, proteins, and modulators thereof can be used to treat heart disorders, e.g., ischemic heart disease, atherosclerosis, hypertension, angina pectoris, Hypertrophic Cardiomyopathy, and congenital heart disease.

As TANGO 239 exhibits expression in bone structures, TANGO 239 nucleic acids, proteins, and modulators thereof can be used to modulate the proliferation, differentiation, and/or function of bone and cartilage cells, e.g., chondrocytes and osteoblasts, and to treat bone and/or cartilage associated diseases or disorders. Examples of bone and/or cartilage diseases and disorders include bone and/or cartilage injury due to for example, trauma (e.g., bone breakage, cartilage tearing), degeneration (e.g., osteoporosis), degeneration of joints, e.g., arthritis, e.g., osteoarthritis, and bone wearing.

Other TANGO 239 activities include at least one or more of the following activities: 1) modulation of cellular adhesion, either in vitro or in vivo; 2) regulation of cell trafficking and/or migration; 3) modulation of cellular proliferation; 4) modulation of inflammation; and/or 5) modulation of a signaling pathway. Thus, TANGO 239 proteins, nucleic acids and/or modulators can be used to treat a disorder characterized by aberrant TANGO 239 expression and/or an aberrant TANGO 239 activity.

Human TANGO 219

A cDNA encoding human TANGO 219 was identified by analyzing the sequences of clones present in a prostate stroma cDNA library. This analysis led to the identification of a clone, jthqc101c05, encoding human TANGO 219. The human TANGO 219 cDNA of this clone is 1268 nucleotides long (FIG. 6; SEQ ID NO:7). The open reading frame of this cDNA, nucleotides 106 to 552 of SEQ ID NO:7, encodes a 149 amino acid secreted protein (FIG. 6; SEQ ID NO:8).

In one embodiment of a nucleotide sequence of human TANGO 219, the nucleotide at position 186 is an guanine (G). In this embodiment, the amino acid at position 27 is glutamate (E). In another embodiment of a nucleotide sequence of human TANGO 219, the nucleotide at position 186 is a cytosine (C). In this embodiment, the amino acid at position 27 is aspartate (D). In another embodiment of a nucleotide sequence of human TANGO 219, the nucleotide at position 261 is guanine (G). In this embodiment, the amino acid at position 52 is glutamate (E). In another embodiment of a nucleotide sequence of human TANGO 219, the nucleotide at position 261 is cytosine (C). In this embodiment, the amino acid at position 52 is aspartate (D). In another embodiment of a nucleotide sequence of human TANGO 219, the nucleotide at position 309 is adenine (A). In this embodiment, the amino acid at position 68 is glutamate (E). In another embodiment of a nucleotide sequence of human TANGO 219, the nucleotide at position 309 is cytosine (C). In this embodiment, the amino acid at position 68 is aspartate (D).

The signal peptide prediction program SIGNALP (Nielsen et al. (1997) *Protein Engineering* 10:1-6) predicted that human TANGO 219 includes an 18 amino acid signal peptide (amino acid 1 to about amino acid 18 of SEQ ID NO:8) preceding the mature TANGO 219 protein corresponding to about amino acid 19 to amino acid 149 of SEQ ID NO:8. The TANGO 219 protein molecular weight is 17.0 kDa prior to the cleavage of the signal peptide, 14.8 kDa after cleavage of the signal peptide.

Northern analysis of TANGO 219 in human tissues revealed that an approximately 1.25 kB transcript is weakly expressed in the heart and not in other tissues tested such as, for example, brain, placenta, lung, liver, skeletal muscle, kidney, pancreas, stomach, thyroid, spinal cord, lymph node, adrenal gland, trachea, bone marrow, spleen, thymus, prostate, testes, ovary, small intestine, colon, and peripheral blood leukocytes.

The human gene for TANGO 219 was mapped on radiation hybrid panels to the long arm of chromosome 5, in the region q21-22. Flanking markers for this region are NIB916 and D5S492. The MANA2 (mannosidase, type2), APC (adenomatous polyposis coli), PST (polysialytransferase), CAST (calpastatin) genes also map to this region of the human chromosome. The LGMD1A (limb girdle muscular dystrophy) loci also maps to this region of the human chromosome. This region is syntenic to mouse chromosomes 11 and 18. The Q (quinky), pdw (proportional dwarf), and lyl1 (lymphoblastomic leukemia) loci also map to this region of the mouse chromosome. The Chr.11-fer (protein kinase, testis specific) Chr.18-mcc (mutated in colorectal cancers), pk (plucked), don1 (divergent of neuregulin 1) genes also map to this region of the mouse chromosome.

Clone EpT219, which encodes human TANGO 219, was deposited with the American Type Culture Collection (10801 University Boulevard, Manassas, Va. 20110-2209) on Sep. 25, 1998 and assigned Accession Number 98899. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 7:
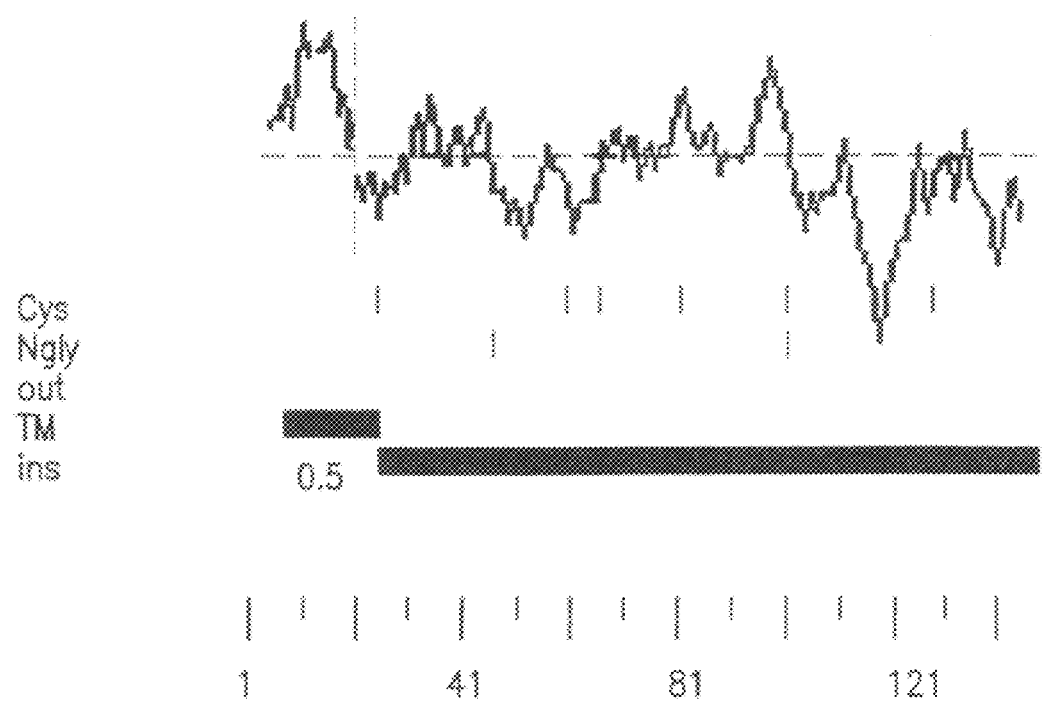
FIG. 7 depicts a hydropathy plot of human TANGO 219 (SEQ ID NO:8), the details of which are described herein. The amino acid sequence of TANGO 219 (SEQ ID NO:8) appears beneath the plot.

FIG. 7 depicts a hydropathy plot of human TANGO 219, the details of which are described herein.

Mouse TANGO 219

A mouse homolog of human TANGO 219 was identified. A cDNA encoding mouse TANGO 219 was identified by analyzing the sequences of clones present in a mouse cDNA library. This analysis led to the identification of a clone encoding mouse TANGO 219. The mouse TANGO 219 cDNA of this clone is 397 nucleotides long (FIG. 8; SEQ ID NO:9).

The open reading frame of this cDNA, comprises nucleotides 2 to 370 of SEQ ID NO:9, and encodes a secreted protein comprising the 123 amino acid sequence depicted in FIG. 8 (SEQ ID NO:10).

In one embodiment of a nucleotide sequence of mouse TANGO 219, the nucleotide at position 127 is an guanine (G). In this embodiment, the amino acid at position 42 is glutamate (E). In another embodiment of a nucleotide sequence of mouse TANGO 219, the nucleotide at position 127 is a cytosine (C). In this embodiment, the amino acid at position 42 is aspartate (D). In another embodiment of a nucleotide sequence of mouse TANGO 219, the nucleotide at position 154 is guanine (G). In this embodiment, the amino acid at position 51 is glutamate (E). In another embodiment of a nucleotide sequence of mouse TANGO 219, the nucleotide at position 154 is cytosine (C). In this embodiment, the amino acid at position 51 is aspartate (D). In another embodiment of a nucleotide sequence of mouse TANGO 219, the nucleotide at position 226 is adenine (A). In this embodiment, the amino acid at position 75 is glutamate (E). In another embodiment of a nucleotide sequence of mouse TANGO 219, the nucleotide at position 226 is cytosine (C). In this embodiment, the amino acid at position 75 is aspartate (D).

The signal peptide prediction program SIGNALP (Nielsen et al. (1997) *Protein Engineering* 10:1-6) predicted that mouse TANGO 219 includes a 40 amino acid signal peptide (amino acid 1 to about amino acid 40 of SEQ ID NO:10) preceding the mature mouse TANGO 219 protein (corresponding to about amino acid 41 to amino acid 123 of SEQ ID NO:10). The TANGO 219 protein molecular weight is 17.0 kDa prior to the cleavage of the signal peptide, 14.8 kDa after cleavage of the signal peptide.

Uses of TANGO 219 Nucleic acids, Polypeptides, and Modulators Thereof

As TANGO 219 was originally found in a prostate stroma library, TANGO 219 nucleic acids, proteins, and modulators thereof can be used to modulate the proliferation, differentiation, and/or function, e.g., secretory activity, of the prostate cells. Such molecules can also be useful for treatment of prostate diseases or disorders, e.g., acute or chronic prostatitis (and the resulting urinary tract infection), benign nodular enlargement, and prostatic carcinoma.

As TANGO 219 appears to be preferentially expressed in the heart and not in many other tissues, TANGO 219 nucleic acids, proteins, and modulators thereof can be used to modulate the proliferation, differentiation, and/or function of cardiac cells. Thus TANGO 219 plays a role in regulating cardiac function, including modulating cardiac rhythm and strength of contraction, and the heart's response to stress. Such molecules can also be useful for treatment of heart diseases or conditions, e.g., ischemic heart disease or atherosclerosis, or cerebrovascular accidents, or more particularly, treating or preventing conditions involving heart contraction, and the impulse generating nodes and cardiac muscle cells, e.g., ventricular fibrillation or myocardial infarction.

TANGO 232

A TANGO 232 family member includes a signal sequence. In certain embodiments, a TANGO 232 family member has the amino acid sequence of SEQ ID NO:14, and the signal sequence is located at amino acids 1 to 20, 1 to 21, 1 to 22, 1 to 23, or 1 to 24. In such embodiments of the invention, the domains and the mature protein resulting from cleavage of such signal peptides are also included herein. For example, the cleavage of a signal sequence consisting of amino acids 1-22 of SEQ ID NO:14, results in a mature TANGO 232 protein corresponding to amino acids 23 to 238 of SEQ ID NO:14. The signal sequence is normally cleaved during processing of the mature protein.

In another example, a TANGO 232 family member also includes one or more of the following domains: (1) an extracellular domain; (2) a transmembrane domain; and (3) a cytoplasmic domain.

In one embodiment, a TANGO 232 protein contains an extracellular domain of about amino acids 23-194 of SEQ ID NO:14. In another embodiment, a TANGO 232 protein contains a transmembrane domain of about amino acids 195-216 of SEQ ID NO:14. In another embodiment, a TANGO 232 protein contains a cytoplasmic domain of about amino acids 217-238 of SEQ ID NO:14.

TANGO 232 family members can also include a cysteine-rich domain. As used herein, a "cysteine-rich domain" includes at least about 30 to 70 amino acid residues, more preferably at least about 40 to 60 amino acid residues, and most preferably at least about 40 to 50 amino acid residues. Of these residues at least about five are cysteine residues. The cysteine-rich domain can also include at least the following consensus sequence: C-D-Y-D-Xaa(1)-C-R-H-L-Q-V-Xaa(2)-C-Xaa(3)-E-L-Q-Xaa(1)-Xaa(4)-Xaa(5)-P-Xaa(4)-Xaa(4)-C-L-C-P-G-L-S-Xaa(6)-Xaa(7)-Xaa(7)-Q-Xaa(2)-P-Xaa(8)-Xaa(2)-P-R-Xaa(4)-G (SEQ ID NO:55); wherein Xaa(1) is an amino acid with a basic side chain, e.g., R, H, or K; Xaa(2) is an amino acid with an uncharged polar side chain or a nonpolar side chain, e.g., S, P, or Q; Xaa(3) is an amino acid with a basic side chain or an uncharged polar side chain, e.g., Q or K; Xaa(4) is an amino acid with a nonpolar side chain, e.g., A, P, V, L or M; Xaa(5) is an amino acid with an acidic side chain or an uncharged polar side chain, e.g., G or E; Xaa(6) is an amino acid with a basic side chain or an uncharged polar side chain, e.g., S or R; Xaa(7) is an amino acid with an acidic side chain or a nonpolar side chain, e.g., P, E, A, or D; Xaa(8) is an amino acid with an acidic side chain, e.g., D or E.

The cysteine-rich domain of macaque TANGO 232 is located from amino acid residues 49 to 90 of SEQ ID NO:14, and the cysteine residues are at positions 49, 54, 61, 72, and 74.

In a preferred embodiment, a TANGO 232 polypeptide is a human polypeptide which includes a cysteine-rich domain as described herein. Preferably the human polypeptide is at least about 95%, 96%, 97%, or 98% identical to the macaque TANGO 232 amino acid sequence shown in SEQ ID NO:14.

Macaque TANGO 232

A cDNA encoding macaque TANGO 232 was identified by analyzing the sequences of clones present in a macaque adipose tissue cDNA library.

This analysis led to the identification of a clone, Atkfa110e6, encoding macaque TANGO 232. The cDNA of this clone is 1937 nucleotides long (FIG. 9; SEQ ID NO:11). It is noted that the nucleotide sequence depicted in SEQ ID NO:11 contains Sal I and Not I adapter sequences on the 5' and 3' ends, respectively.

The open reading frame of this cDNA, nucleotides 96 to 809 of SEQ ID NO:12, encodes a 238 amino acid transmembrane protein (FIG. 9; SEQ ID NO:12).

In one embodiment of a nucleotide sequence of macaque TANGO 232, the nucleotide at position 182 is an adenine (A). In this embodiment, the amino acid at position 29 is glutamate (E). In another embodiment of a nucleotide sequence of macaque TANGO 232, the nucleotide at position 182 is a cytosine (C). In this embodiment, the amino acid at position 29 is aspartate (D). In another embodiment of a nucleotide sequence of macaque TANGO 232, the nucleotide at position 185 is adenine (A). In this embodiment, the amino acid at position 30 is glutamate (E). In another embodiment of a nucleotide sequence of macaque TANGO 232, the nucleotide at position 185 is cytosine (C). In this embodiment, the amino acid at position 30 is aspartate (D). In another embodiment of a nucleotide sequence of macaque TANGO 232, the nucleotide at position 188 is guanine (G). In this embodiment, the amino acid at position 31 is glutamate (E). In another embodiment of a nucleotide sequence of macaque TANGO 232, the nucleotide at position 188 is cytosine (C). In this embodiment, the amino acid at position 31 is aspartate (D).

The signal peptide prediction program SIGNALP (Nielsen et al. (1997) *Protein Engineering* 10:1-6) predicted that macaque TANGO 232 includes an 22 amino acid signal peptide (amino acid 1 to about amino acid 22 of SEQ ID NO:12) preceding the mature macaque TANGO 232 protein (corresponding to about amino acid 23 to amino acid 238 of SEQ ID NO:12).

There are eight conserved cysteines in the extracellular domain at positions 48, 53, 60, 70, 73, 105, 152 and 183 of SEQ ID NO:12. Macaque TANGO 232 has a high proportion of charged amino acids in the predicted extracellular (22%, not including histidine) and cytoplasmic (27%) domains. Macaque TANGO 232 is predicted to have a molecular weight of 25.4 kDa prior to cleavage of its signal peptide and a molecular weight of 23.0 kDa subsequent to cleavage of its signal peptide.

A clone, EpT232m, which encodes macaque TANGO 232, was deposited with the American Type Culture Collection (10801 University Boulevard, Manassas, Va. 20110-2209) on Jan. 7, 1999 and assigned Accession Number 207045. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 10:
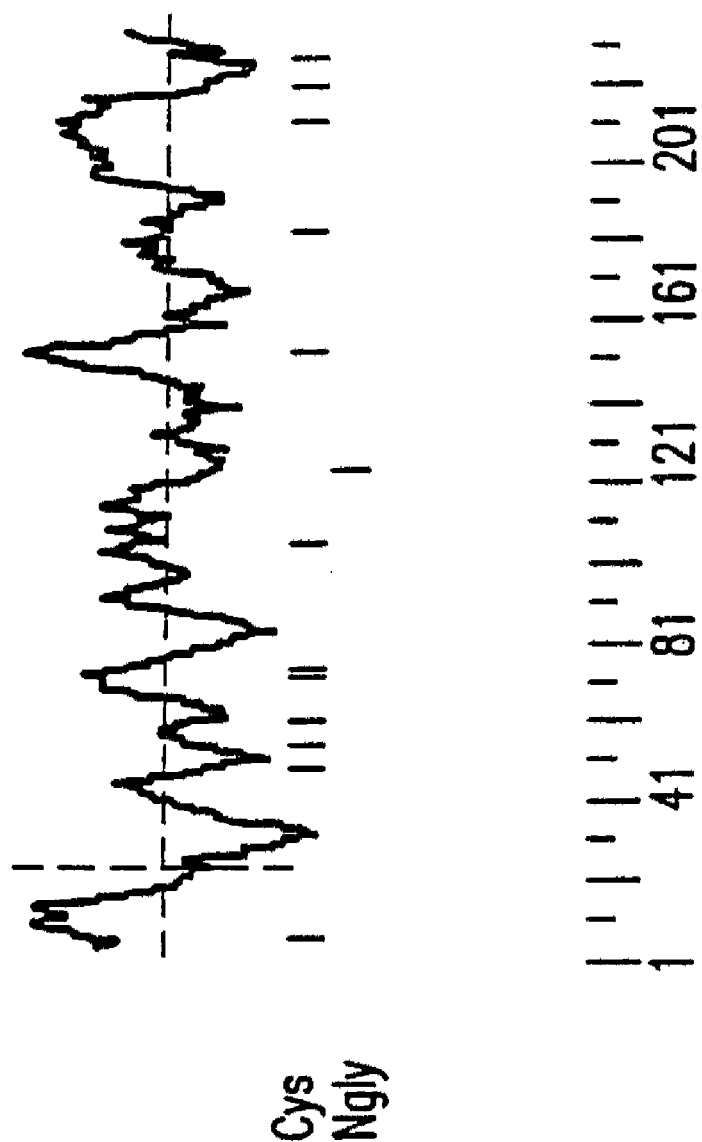
FIG. 10 depicts a hydropathy plot of macaque TANGO 232 (SEQ ID NO:12), the details of which are described herein.

FIG. 10 depicts a hydropathy plot of macaque TANGO 232, the details of which are described herein. The dashed vertical line separates the signal sequence (amino acids 1-22 of SEQ ID NO:12) on the left from the mature protein (amino acids 23-238 of SEQ ID NO:12) on the right.

In one embodiment, macaque TANGO 232 is predicted to be a transmembrane protein having a 172 amino acid extracellular domain (amino acids 23-194 of SEQ ID NO:12), a 22 amino acid transmembrane domain (amino acids 195-216 of SEQ ID NO:12), and a 22 amino acid cytoplasmic domain (amino acids 217-238 of SEQ ID NO:12). Alternatively, in another embodiment, a macaque TANGO 232 protein contains an extracellular domain at amino acid residues 217 to 238, a transmembrane domain at amino acid residues 195 to 216, and a cytoplasmic domain at amino acid residues 1 to 194 of SEQ ID NO:12.

An N-glycosylation site NATV is found from amino acids 132 to 135. A protein kinase C phosphorylation site TVR is found from amino acids 134 to 136. An N-myristoylation site GSEAAQ is found from amino acids 121 to 126. A second N-myristoylation site GLKPGG is found from amino acids 142 to 147. A third N-myristoylation site GLEGAD is found from amino acids 171 to 176. A fourth N-myristoylation site GVGTAL is found from amino acids 201 to 206.

FIG. 11 depicts an alignment of a portion of the macaque TANGO 232 amino acid sequence (amino acids 1-132 of SEQ ID NO:12) with a translation of a rabbit nucleotide sequence (GenBank Accession Number C83084; SEQ ID NO:45) and a mouse nucleotide sequence (clone jtmoa31f1; SEQ ID NO:18). This alignment defines a cysteine-rich domain that is conserved and which is described in detail herein. The arrows indicate the conserved cysteine residues at positions 49, 54, 61, 72, and 74. An additional cysteine residue at position 106 is conserved in the macaque and rabbit sequences.

Human TANGO 232

A clone, Athke96c4, encoding human TANGO 232 was identified. The cDNA of this clone is 1459 nucleotides long (FIG. 12; SEQ ID NO:13). It is noted that the nucleotide sequence depicted in SEQ ID NO:13 contains a Not I adapter sequence on the 3' end, respectively. In one embodiment, human TANGO 232 is referred to as human TANGO 232, form 1. The open reading frame of this human TANGO 232, form 1 cDNA comprises nucleotides 1 to 366 of SEQ ID NO:13, and encodes a polypeptide comprising the 122 amino acid sequence shown in FIG. 12 (SEQ ID NO:14).

Secretion assays indicate that the polypeptide encoded by human TANGO 232 is not secreted and thus, likely a transmembrane protein. The secretion assays were performed essentially as follows: $8 \times 10^5$ 293T cells were plated per well in a 6-well plate and the cells were incubated in growth medium (DMEM, 10% fetal bovine serum, penicillin/strepomycin) at 37° C., 5% $CO_2$ overnight. 293T cells were transfected with 2 µg of full-length TANGO 232 inserted in the pMET7 vector/well and 10 µg LipofectAMINE (GIBCO/BRL Cat. #18324-012)/well according to the protocol for GIBCO/BRL LipofectAMINE. The transfectant was removed 5 hours later and fresh growth medium was added to allow the cells to recover overnight. The medium was removed and each well was gently washed twice with DMEM without methionine and cysteine (ICN Cat. #16-424-54). 1 ml DMEM without methionine and cysteine with 50 µCi Trans-$^{35}$S (ICN Cat. #51006) was added to each well and the cells were incubated at 37° C., 5% $CO_2$ for the appropriate time period. A 150 µl aliquot of conditioned medium was obtained and 150 µl of 2×SDS sample buffer was added to the aliquot. The sample was heat-inactivated and loaded on a 4-20% SDS-PAGE gel. The gel was fixed and the presence of secreted protein was detected by autoradiography.

The signal peptide prediction program SIGNALP (Nielsen et al. (1997) *Protein Engineering* 10:1-6) predicted that human TANGO 232 form 1 does not appear to include a signal peptide. Accordingly, the mature human TANGO 232 form 1 protein corresponds to about amino acid 1 to about amino acid 122 of SEQ ID NO:14.

In one embodiment, human TANGO 232 form 1 protein is a transmembrane protein that contains an extracellular domain at amino acid residues 1 to 78, a transmembrane domain at amino acid residues 79 to 100, and a cytoplasmic domain at amino acid residues 101 to 122 of SEQ ID NO:14. Alternatively, in another embodiment, a human TANGO 232 form 1 protein contains an extracellular domain at amino acid residues 101 to 122, a transmembrane domain at amino acid residues 79 to 100, and a cytoplasmic domain at amino acid residues 1 to 78 of SEQ ID NO:14.

A clone, EpT232h, which encodes human TANGO 232, was deposited with the American Type Culture Collection (10801 University Boulevard, Manassas, Va. 20110-2209) on Jan. 7, 1999 and assigned Accession Number 207046. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIG. 13A-13D depicts an alignment of a portion of the cDNA sequence of macaque TANGO 232 (nucleotides 424 to 1937 of SEQ ID NO:11) and nucleotides 1 to 1459 of human TANGO 232 clone Athke96c4 (SEQ ID NO:13). An evaluation of the sequence similarity using the program FASTA (Pearson, W. R., and Lipman, D. J. (1988) *Proc. Natl. Acad. Sci. USA* 85:2444-2448) version 2.0u53 (July 1996) indicates that there is 83.4% identity between the two sequences.

FIG. 14 depicts an alignment of a portion of the amino acid sequence of macaque TANGO 232 (amino acids 93 to 238 of SEQ ID NO:12) and human TANGO 232 clone Athke96c4 (SEQ ID NO:14). An evaluation of the sequence similarity using the program FASTA (Pearson, W. R., and Lipman, D. J. (1988) *Proc. Natl. Acad. Sci. USA* 85:2444-2448) version 2.0u53 (July 1996) indicates that there is 94.9% identity between the two sequences.

Another cDNA clone, Arhoc109b10, encoding human TANGO 232 was identified. The cDNA of this clone is 1136 nucleotides long (FIG. 15; SEQ ID NO:15). It is noted that the nucleotide sequence depicted in SEQ ID NO: contains Sal I and Not I adapter sequences on the 5' and 3' ends, respectively.

In one embodiment, human TANGO 232 is referred to as human TANGO 232, form 2. The open reading frame of this human TANGO 232, form 2 cDNA, nucleotides 110 to 823 of SEQ ID NO:15, encodes a 238 amino acid transmembrane protein shown in FIG. 15 (SEQ ID NO:16).

In one embodiment of a nucleotide sequence of human TANGO 232 form 2, the nucleotide at position 196 is an adenine (A). In this embodiment, the amino acid at position 30 is glutamate (E). In another embodiment of a nucleotide sequence of human TANGO 232 form 2, the nucleotide at position 196 is a cytosine (C). In this embodiment, the amino acid at position 30 is aspartate (D). In another embodiment of a nucleotide sequence of human TANGO 232 form 2, the nucleotide at position 199 is adenine (A). In this embodiment, the amino acid at position 31 is glutamate (E). In another embodiment of a nucleotide sequence of human TANGO 232 form 2, the nucleotide at position 199 is cytosine (C). In this embodiment, the amino acid at position 31 is aspartate (D). In another embodiment of a nucleotide sequence of human TANGO 232 form 2, the nucleotide at position 202 is guanine (G). In this embodiment, the amino acid at position 32 is glutamate (E). In another embodiment of a nucleotide sequence of human TANGO 232 form 2, the nucleotide at position 202 is cytosine (C). In this embodiment, the amino acid at position 32 is aspartate (D).

The signal peptide prediction program SIGNALP (Nielsen et al. (1997) *Protein Engineering* 10:1-6) predicted that human TANGO 232 form 2 includes a 22 amino acid signal peptide (amino acid 1 to about amino acid 22 of SEQ ID NO:16) preceding the mature human TANGO 232 form 2 protein (corresponding to about amino acid 23 to amino acid 238 of SEQ ID NO:16).

In one embodiment, human TANGO 232 form 2 protein is a transmembrane protein that contains an extracellular domain at amino acid residues 23 to 194, a transmembrane domain at amino acid residues 195 to 216, and a cytoplasmic domain at amino acid residues 217 to 238 of SEQ ID NO:16. Alternatively, in another embodiment, a human TANGO 232 form 2 protein contains an extracellular domain at amino acid residues 217 to 238, a transmembrane domain at amino acid residues 195 to 216, and a cytoplasmic domain at amino acid residues 1 to 194 of SEQ ID NO:16.

The human gene for TANGO 232 was mapped on radiation hybrid panels to the long arm of chromosome 11, in the region q13. Flanking markers for this region are D11S1965 and WI-1409. The ARRB1 (arrestin, beta), GIF (gastric intrinsic factor), ACTN3 (actinin, alpha 3) genes also map to this region of the human chromosome. The 1-IBM (high bone mass), OPTB1 (osteoporosis, auto.rec.), OPPG (osteoporosis, pseudoglioma syndrome), BBS1 (Bardet-Biedl syndrome), FIND (Hartnup disorder), MKS2 (Meckel syndrome 2). This region is syntenic to mouse chromosome 7. The oc (osteosclerotic), dc (dancer), nmd (meuromuscular degeneration), ocd (osteochondrodystrophy) loci also map to this region of the mouse chromosome. The pcx (pyruvate decarboxylase), chk (choline kinase), gain (galanin) genes also map to this region of the mouse chromosome.

Mouse TANGO 232

A cDNA encoding mouse TANGO 232 was identified by analyzing the sequences of clones present in a mouse osteoblast, LPS stimulated cDNA library. This analysis led to the identification of a clone, jtmoa31f1, encoding mouse TANGO 232. The mouse TANGO 232 cDNA of this clone is 2221 nucleotides long (FIG. 16A-16B; SEQ ID NO:17). It is noted that the nucleotide sequence depicted in SEQ ID NO:17 contains a Sal I adapter sequence on the 5' end. The open reading frame of this cDNA, nucleotides 79 to 795 of SEQ ID NO:17, encodes the 239 amino acid transmembrane protein depicted in FIG. 16A-16B (SEQ ID NO:18).

In one embodiment of a nucleotide sequence of mouse TANGO 232, the nucleotide at position 171 is an adenine (A). In this embodiment, the amino acid at position 31 is glutamate (E). In another embodiment of a nucleotide sequence of mouse TANGO 232, the nucleotide at position 171 is a cytosine (C). In this embodiment, the amino acid at position 31 is aspartate (D). In another embodiment of a nucleotide sequence of mouse TANGO 232, the nucleotide at position 177 is adenine (A). In this embodiment, the amino acid at position 33 is glutamate (E). In another embodiment of a nucleotide sequence of mouse TANGO 232, the nucleotide at position 177 is cytosine (C). In this embodiment, the amino acid at position 33 is aspartate (D). In another embodiment of a nucleotide sequence of mouse TANGO 232, the nucleotide at position 180 is guanine (G). In this embodiment, the amino acid at position 34 is glutamate (E). In another embodiment of a nucleotide sequence of mouse TANGO 232, the nucleotide at position 180 is cytosine (C). In this embodiment, the amino acid at position 34 is aspartate (D).

The signal peptide prediction program SIGNALP (Nielsen et al. (1997) *Protein Engineering* 10:1-6) predicted that mouse TANGO 232 includes a 19 amino acid signal peptide (amino acid 1 to about amino acid 19 of SEQ ID NO:18) preceding the mature mouse TANGO 232 protein (corresponding to about amino acid 20 to amino acid 239 of SEQ ID NO:18).

In one embodiment, mouse TANGO 232 protein is a transmembrane protein that contains an extracellular domain at amino acid residues 20 to 192, a transmembrane domain at amino acid residues 193 to 216, and a cytoplasmic domain at amino acid residues 217 to 239 of SEQ ID NO:18. Alternatively, in another embodiment, a mouse TANGO 232 protein contains an extracellular domain at amino acid residues 217 to 239 of SEQ ID NO:18, a transmembrane domain at amino acid residues 193 to 216 of SEQ ID NO:18, and a cytoplasmic domain at amino acid residues 1 to 192 of SEQ ID NO:18.

In situ tissue screening was performed on mouse adult and embryonic tissue to analyze for the expression of mouse TANGO 232 mRNA. In summary, the embryonic signal pattern was suggestive of expression by developing muscle. Expression was observed in a layer just under the skin beginning at E14.5. At later ages expression was also observed outlining the ribs, skull, ear, and clavicle suggesting expression by or around some bone structures. Expression was also detected from the mesothelial cells outlining the pleural cavity. At E18.5, expression in the smooth muscle of the small intestine was also detected but was not observed at P1.5. Adult expression was observed in the skeletal and smooth muscle in a weak or moderate multifocal pattern. Expression was also observed in the muscle layer of the bladder and in the labyrinth region of the placenta. In particular, with respect to adult expression, the following results were obtained: A multifocal signal was observed in the skeletal and smooth muscle (diaphragm). In addition, a stronger signal was observed along the edge of the diaphragm. This signal may be from the peritoneum. A weak, multifocal signal which is predominately in the muscle portion of the bladder tissue. A signal is observed in the labyrinth zone of the placenta. No expression was observed in the following tissues: Brain, spinal cord, eye and harderian gland, submandibular gland, white fat, brown fat, stomach, heart, lung, liver, kidney, adrenal gland, colon, small intestine, thymus, lymph node, spleen, pancreas, testes, and the ovaries.

With respect to embryonic expression, at E13.5, no positive signal was detected. At E14.5, a weak signal was detected just under the skin along the back, stomach, and skull in a pattern suggestive of the muscle layer. Weak signal was also seen outlining the ribs. At E15.5, a signal was observed just under the skin along the back, leg, stomach, and chest. Signal was also seen outlining the ribs and along the skull and in the region of the ear. At E16.5, the signal was observed in the muscle layer just under the skin throughout the embryo. Signal was also seen outlining the ribs, regions of the skull, and muscles of the leg. The mesothelial cells lining the pleural cavity were also detected. The diaphragm did not appear to be positive. At E18.5, the signal pattern was very similar to that observed at E16.5 with most of the thin muscle layers being positive thus outlining many major structures. In addition, the small intestine was outlined indicating some smooth muscle expression. At P1.5, a signal in the region of the gut, heart, and head appears to have decreased. A moderate signal was still observed just under the skin.

Human and mouse TANGO 232 sequences exhibit considerable similarity at the protein, nucleic acid, and open reading frame levels. An alignment (made using the ALIGN software {Myers and Miller (1989) CABIOS, ver. 2.0}; BLOSUM 62 scoring matrix; gap penalties -12/-4), reveals a protein identity of 68.8%. The human and mouse TANGO 232 full length cDNAs are 69.1% identical, as assessed using the same software and parameters as indicated (without the BLOSUM 62 scoring matrix). In the respective ORFs, calculated in the same fashion as the full length cDNAs, human and mouse TANGO 232 are 72.6% identical.

Uses of TANGO 232 Nucleic Acids, Polypeptides, and Modulators Thereof

Because TANGO 232 is expressed in subcutaneous adipose tissue, TANGO 232 polypeptides, nucleic acids, and modulators of TANGO 232 expression or activity can be useful for modulation of adipocyte function, e.g., fat metabolism. Such molecules can also be used to treat disorders associated with abnormal fat metabolism, e.g., obesity, arteriosclerosis, or cachexia.

As mouse TANGO 232 was originally found in an LPS stimulated mouse primary osteoblast library, TANGO 232 nucleic acids, proteins, and modulators thereof can be used to modulate the proliferation, differentiation, and/or function of cells that form bone matrix, e.g., osteoblasts and osteoclasts, and can be used to modulate the formation of bone matrix. Thus, TANGO 232 nucleic acids, proteins, and modulators thereof can be used to treat cartilage and bone associated diseases and disorders, and can play a role in bone growth, formation, and remodeling. Examples of cartilage and bone associated diseases and disorders include e.g., bone cancer, achondroplasia, myeloma, fibrous dysplasia, scoliosis, osteoarthritis, osteosarcoma, and osteoporosis.

TANGO 232 exhibits weak homology to the F3 domain of Ephrin receptor and G-CSF receptor. G-CSF is the major growth factor involved in the production of neutrophilic granulocytes. G-CSF exerts its function via the activation of a membrane receptor that belongs to the super-family of hematopoietic receptors, also referred to as class I cytokine receptors. Thus, TANGO 232 polypeptides, nucleic acids, and modulators of TANGO 232 expression or activity can be useful for modulation of the function of the G-CSF receptor in normal granulopoiesis. TANGO 232 polypeptides, nucleic acids, and modulators of TANGO 232 expression or activity can be useful for modulation of G-CSF-induced STAT3 activation during basal granulopoiesis (low G-CSF) and "emergency" granulopoiesis (high G-CSF). Thus, TANGO 232 polypeptides, nucleic acids, and modulators of TANGO 232 expression or activity can be useful for the modulation of diseases characterized by disturbed myeloid maturation such as severe congenital neutropenia and acute myeloblastic leukemia. In addition, the TANGO 232 proteins, nucleic acids and/or modulators can be used for the treatment of a disorder characterized by aberrant TANGO 232 expression and/or an aberrant TANGO 232 activity, such as maturation signaling.

TANGO 281

The TANGO 281 proteins and nucleic acid molecules comprise families of molecules having certain conserved structural and functional features. In one example, a TANGO 281 family member consists of one or more of the following domains: (1) an extracellular domain; (2) a transmembrane domain; and (3) a cytoplasmic domain.

In another embodiment, a TANGO 281 protein contains an extracellular domain at amino acids 1 to about 123 or a mature extracellular domain at about amino acid residues 39 to 123, a transmembrane domain at about amino acid residues 124 to 148, and a cytoplasmic domain at about amino acid residues 149 to 245 of SEQ ID NO:20.

In another embodiment, a mature TANGO 281 protein contains about amino acid residues 39 to 245 of SEQ ID NO:20. In another embodiment, a TANGO 281 family contains an extracellular domain at amino acids 1 to about 112 or a mature extracellular domain at about amino acid residues 27 to 112, a transmembrane domain at about amino acid residues 113 to 137, and a cytoplasmic domain at about amino acid residues 138 to 213 of SEQ ID NO:20. In yet another embodiment, a mature TANGO 281 protein contains about amino acid residues 27 to 213 of SEQ ID NO:20.

In one embodiment, a TANGO 281 family member includes a signal sequence. In a preferred embodiment, a TANGO 281 family member has the amino acid sequence of SEQ ID NO:20, and the signal sequence is located at about amino acids 1 to 38. In an another preferred embodiment, a TANGO 281 family member has the amino acid sequence of SEQ ID NO:20, and the signal sequence is located at about amino acids 1 to 26.

A photosystem II 10 kd phosphoprotein (PSBH) domain has been identified in the TANGO 281 proteins. The domain is also present in the chloroplast gene PSBH that encodes a 9-10 kDa thylakoid membrane protein (PSII-H) which is associated with photosystem II. In one embodiment, a TANGO 281 family member includes one or more PSBH domains having an amino acid sequence that is at least about 55%, preferably at least about 65%, more preferably at least 75%, yet more preferably at least about 85%, and most preferably at least about 95% identical to amino acids 41 to 90 and/or amino acids 127 to 182 of SEQ ID NO:20, which are the PSBH domains of human TANGO 281.

In another embodiment, a TANGO 281 family member includes one or more PSBH domains having an amino acid sequence that is at least about 55%, preferably at least about 65%, more preferably at least about 75%, yet more preferably at least about 85%, and most preferably at least about 95% identical to amino acids 41 to 90 and/or amino acids 127 to 182 of SEQ ID NO:20, which are the PSBH domains of human TANGO 281 includes one or more PSBH domain consensus sequences described herein, and has at least one TANGO 281 biological activity as described herein.

In another embodiment, a TANGO 281 family member includes one or more PSBH domains having an amino acid sequence that is at least about 55%, preferably at least about 65%, more preferably at least 75%, yet more preferably at least about 85%, and most preferably at least about 95% to 98% identical to amino acids 42 to 91 and/or amino acids 128 to 183 of SEQ ID NO:22, which are the PSBH domains of mouse TANGO 281.

In another embodiment, a TANGO 281 family member includes one or more PSBH domains having an amino acid sequence that is at least about 55%, preferably at least about 65%, more preferably at least about 75%, yet more preferably at least about 85%, and most preferably at least about 95% identical to amino acids 42 to 91 and/or amino acids 128 to 183 of SEQ ID NO:22, which are the PSBH domains of mouse TANGO 281, includes one or more PSBH domain consensus sequences described herein, and has at least one TANGO 281 biological activity as described herein.

Human TANGO 281

A cDNA encoding human TANGO 281 was identified by analyzing the sequences of clones present in a human megakarocyte cDNA library. This analysis led to the identification of a clone, AThPb81d10, encoding human TANGO 281. The human TANGO 281 cDNA of this clone is 1812 nucleotides long (FIG. 17A-17B; SEQ ID NO:19). The open reading frame of this cDNA, nucleotides 65 to 799 of SEQ ID NO:19, encodes a 245 amino acid transmembrane protein (FIG. 17A-17B; SEQ ID NO:20).

The signal peptide prediction program SIGNALP (Nielsen, et al. (1997) *Protein Engineering* 10:1-6) predicted that human TANGO 281 includes an 38 amino acid signal peptide (amino acid 1 to amino acid 38 of SEQ ID NO:20) preceding the mature TANGO 281 protein (corresponding to amino acid 39 to amino acid 245 of SEQ ID NO:20). The molecular weight of TANGO 281 without post-translational modifications is 26.5 kDa prior to the cleavage of the signal peptide, 20.2 kDa after cleavage of the signal peptide.

Human TANGO 281 is a transmembrane protein which contains one or more of the following domains: (1) an extracellular domain; (2) a transmembrane domain; and (3) a cytoplasmic domain. The human TANGO 281 protein contains an extracellular domain at amino acids 1 to 123 or a mature extracellular domain at about amino acid residues 39 to 123, a transmembrane domain at amino acid residues 124 to 148, and a cytoplasmic domain at amino acid residues 149 to 245 of SEQ ID NO:20.

Figure 18:
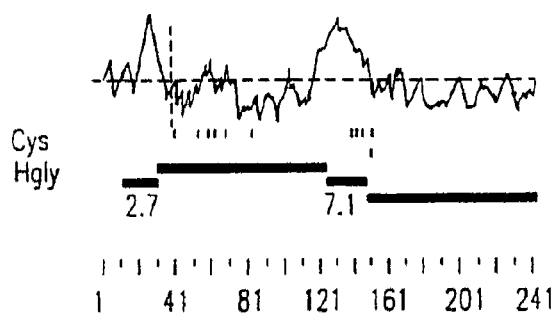
FIG. 18 depicts a hydropathy plot of human TANGO 281, the details of which are described herein. The dashed vertical line separates the signal sequence (amino acids 1 to 38 of SEQ ID NO:20) on the left from the mature protein (amino acids 39 to 245 of SEQ ID NO:20) on the right.

FIG. 18 depicts a hydropathy plot of human TANGO 281, the details of which are described herein. The dashed vertical line separates the signal sequence (amino acids 1 to 38 of SEQ ID NO:20) on the left from the mature protein (amino acids 38 to 245 of SEQ ID NO:20) on the right.

Human TANGO 281 comprises photosystem II 10 kD phosphoprotein (PSBH) domain sequences, which have been shown to be phosphorylated in a light-dependent reaction, from amino acids 41 to 90 and 127 to 182 of SEQ ID NO:20. FIG. 19 depicts an alignment between the PSBH domain (SEQ ID NO:46; Accession No. PF00737) and human TANGO 281 from amino acids 97 to 146 of SEQ ID NO:20.

An N-glycosylation site having the sequence NTTT is present in TANGO 281 at about amino acids 160 to 163 of SEQ ID NO:48. Two protein kinase C phosphorylation sites are present in human TANGO 281. The first has the sequence SVR (at amino acids 8 to 10), and the second has the sequence SSR (at amino acids 87 to 89). Three casein kinase II phosphorylation sites are present in human TANGO 281. The first has the sequence SIPE (at amino acids 49 to 52), the second has the sequence SCPD (at amino acids 53 to 56), and the third has the sequence SSLD (at amino acids 108 to 111). Human TANGO 281 has two N-myristylation sites. The first has the sequence GSCSSQ (at amino acids 60 to 65), and the second has the sequence GATVAI (at amino acids 119 to 124).

Nucleic acid base pairs 413 to 746 of human TANGO 281 (SEQ ID NO:19) have 81% identity to the nucleic acid sequence identified as Accession Number AV34245. Nucleic acid base pairs 438 to 746 of human TANGO 281 (SEQ ID NO:19) have 80% identity to a nucleic acid sequence referred to as "gene 31" described in PCT Publication No. WO 98/39446 (SEQ ID NO:49). "Gene 31" is characterized as being expressed primarily in brain and thymus, and to a lesser extent in such organs as liver, skin, bone and bone marrow.

Clone EpT281 was deposited with the American Type Culture Collection (10801 University Boulevard, Manassas, Va. 20110-2209) on Apr. 21, 1999 and assigned Accession Number 207222. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Mouse TANGO 281

A cDNA encoding mouse TANGO 281 was identified in a normal mouse megakaryocyte library by performing expression profiling on megakarocytes obtained from mice with a the deletion of the element of the gata-1 gene responsible for megakaryocyte-specific expression. This analysis led to the identification of a clone, Atmea49d3, encoding mouse TANGO 281. The mouse TANGO 281 cDNA of this clone is 1858 nucleotides long (FIG. 20A-20B; SEQ ID NO:21). The open reading frame of this cDNA, nucleotides 90 to 728 of SEQ ID NO:21, encodes a 213 amino acid transmembrane protein (FIG. 20A-20B; SEQ ID NO:22).

The signal peptide prediction program SIGNALP (Nielsen, et al. (1997) *Protein Engineering* 10:1-6) predicted that mouse TANGO 281 includes an 26 amino acid signal peptide (amino acid 1 to amino acid 26 of SEQ ID NO:22) preceding the mature TANGO 281 protein (corresponding to amino acid 27 to amino acid 213 of SEQ ID NO:22). The molecular weight of mouse TANGO 281 without post-translational modifications is 22.9 kDa prior to the cleavage of the signal peptide, 20.2 kDa after cleavage of the signal peptide.

Mouse TANGO 281 is a transmembrane protein which contains one or more of the following domains: (1) an extracellular domain; (2) a transmembrane domain; and (3) a cytoplasmic domain. The mouse TANGO 281 protein contains an extracellular domain at amino acid residues 27 to 112, a transmembrane domain at amino acid residues 113 to 137, and a cytoplasmic domain at amino acid residues 138 to 213 of SEQ ID NO:22.

Figure 21:
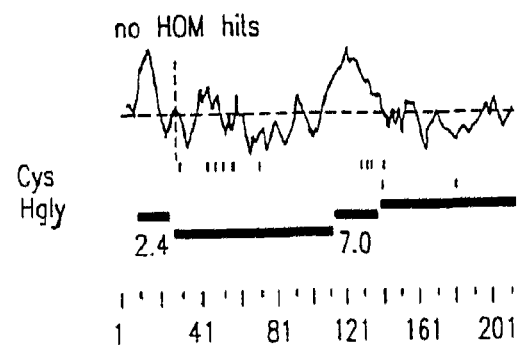
FIG. 21 depicts a hydropathy plot of mouse TANGO 281 (SEQ ID NO:22), the details of which are described herein. The dashed vertical line separates the signal sequence (amino acids 1 to 26 of SEQ ID NO:22) on the left from the mature protein (amino acids 27 to 213 of SEQ ID NO:22) on the right.

FIG. 21 depicts a hydropathy plot of mouse TANGO 281, the details of which are described herein. The dashed vertical line separates the signal sequence (amino acids 1 to 26 of SEQ ID NO:22) on the left from the mature protein (amino acids 27 to 213 of SEQ ID NO:22) on the right.

Mouse TANGO 281 comprises photosystem II 10 kD phosphoprotein (PSBH) domain sequences, which have been shown to be phosphorylated in a light-dependent reaction, from amino acids 42 to 91 and 128 to 183 of SEQ ID NO:22. Two N-glycosylation sites having the sequences NTTT (at amino acids 149 to 152) and NASS (at about amino 189 to 192) are present in TANGO 281. A glycosaminoglycan attachment site having the sequence SGFG is present in mouse TANGO 281, and protein kinase C phosphorylation site having the sequence SSR is present in mouse TANGO 281. Two casein kinase II phosphorylation sites are present in human TANGO 281. The first has the sequence TPAE (at amino acids 80 to 83), and the second has the sequence SSFD (at amino acids 97 to 100). Mouse TANGO 281 has two N-myristylation sites. The first has the sequence GSCSNQ (at amino acids 48 to 53), and the second has the sequence GATVAI (at amino acids 108 to 113).

Northern blot analysis of mouse TANGO 281 expression revealed two mRNA bands, one of approximately 1.8 kb and another approximately 1.4 kb. Expression of the 1.8 kb band was detected in the heart, spleen, lung and kidney, with the greatest abundance detected in the heart and lung, followed by the kidney and trace amounts in the spleen. Expression of the 1.4 kb band was detected in the brain, spleen, and lung. Expression of the 1.4 kb and 1.8 kb species of mouse TANGO 281 was detected in 7 day old normal mouse embryos. Neither the 1.4 kb or the 1.8 kb species of mouse TANGO 281 were detected in 11 day old normal mouse embryos. The 1.8 kb species of mouse TANGO 281 was detected in 15 day old normal mouse embryos at 20% the level detected in 7 day old normal mouse embryos. Expression of the 1.8 kb species detected in 17 day old normal mouse embryos was comparable to the level of expression detected in 7 day old normal mouse embryos. Expression of mouse TANGO 281 expression was greatly reduced in megakaryocytes obtained from gata-1 knockout mice.

In situ tissue screening was performed on mouse adult and embryonic tissues to analyze for the expression of mouse TANGO 281 mRNA. Mouse TANGO 281 expression was detected predominantly in the adult lymphoid tissues such as the thymus, lymph node, and spleen. In particular, mouse TANGO 281 expression was detected in the following adult tissues: a moderate, ubiquitous signal was detected in the submandibular gland; a strong, ubiquitous signal was detected in the adrenal gland; a strong, multifocal signal was detected in the medulla of the thymus and a moderate, ubiquitous signal was detected in the cortex of the thymus; a strong signal was detected in the lymph node; a strong signal was detected in the follicles of the spleen; a weak signal was detected in the mucosal epithelium of the bladder; a strong signal was detected in the ovaries; a ubiquitous signal was detected in the placenta; a moderate signal was detected in the muscle region of the stomach; a weak signal in a pattern outlining many of the large airways was detected in lung; a weak, ubiquitous signal was detected in the liver; and a weak, ubiquitous signal was detected in the kidney.

In the case of embryonic expression, mouse TANGO 281 expression was detected in the lung, stomach, thymus and submaxillary gland. In particular, at E16.5 a weak to moderate signal was detected in the intestine and stomach, and a moderate, ubiquitous signal was detected in the lung. At P1.5, a signal was detected in the lung, stomach, thymus, and submaxillary gland.

FIG. 22 depicts that there is an overall 66.5% identity between the precursor human TANGO 281 amino acid sequence and the precursor mouse TANGO 281 amino acid sequence.

Clone EpT281 was deposited with the American Type Culture Collection (10801 University Boulevard, Manassas, Va. 20110-2209) on Jun. 15, 1999 and assigned patent deposit Number PTA-224. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 281 Nucleic acids, Polypeptides, and Modulators Thereof

As TANGO 281 was originally found in a megakaryocyte library, TANGO 281 nucleic acids, proteins, and modulators thereof can be used to modulate the proliferation, differentiation, and/or function of megakaryocytes and platelets. TANGO 281 nucleic acids, proteins, and modulators thereof can be used to treat associated hematological diseases such as thrombocytopenia, platelet disorders and bleeding disorders (e.g., hemophilia). TANGO 281 nucleic acids, proteins, and modulators thereof can be used to modulate platelet aggregation and degranulation. Further, as TANGO 281 expression varies in mouse embryos during development, TANGO 281 nucleic acids, proteins, and modulators thereof can be used to modulate the development of cells, tissues or organs in embryos.

As TANGO 281 expression is greatly reduced in megakaryocytes obtained from gata-1 knockout mice compared normal mice, TANGO 281 is either a direct or indirect target of gata-1 and has profound biological implications. Gata-1 is a transcription factor involved in the development of hemapoietic cell lineages. Gata-1 expression is required for proper development of erythrocytes and megakaryocytes. Although deletion of the gata-1 gene is lethal at the embryonic stage due to a failure to form red blood cells, deletion of only the element of the gata-1 gene responsible for megakaryocyte-specific expression (a 10 kb region of genomic DNA containing a megakaryocyte specific DNase I hypersensitive) is not lethal and results in a reduction in gata-1 expression in the megakaryocyte without affecting gata-1 expression in red blood cells. The megakaryocytes of mice with this element of the gata-1 gene knocked out fail to develop into mature platelets, and the mice experience abnormal bleeding due to their profound thrombocytopenia. TANGO 281 nucleic acids, proteins, and modulators thereof can be used to treat disease and/or disorders associated with gata-1 dysfunction. In light of the reduced expression of TANGO 281 in gata-1 knockout mice, TANGO 281 expression can be utilized as a marker for modulators of gata-1 expression and/or activity.

As TANGO 281 is expressed in the heart, brain, spleen, lung, kidney, embryo and megakaryocytes, TANGO 281 nucleic acids, proteins, and modulators thereof can be used to treat disorders of these cells, tissues, or organs, e.g., ischemic heart disease or atherosclerosis, head trauma, brain cancer, splenic lymphoma, splenomegaly, lung cancer, cystic fibrosis, rheumatoid lung disease, glomerulonephritis, end stage renal disease, uremia, DiGeorge syndrome, thymoma, autoimmune disorders, atresia, Crohns's disease, and various embryonic disorders. TANGO 281 nucleic acids, proteins, and modulators thereof can be used to modulate the bleeding associated with uremia. Further, TANGO 281 nucleic acids, proteins, and modulators thereof can be used to, treat hypercoagulation associated with a damaged endothelium, e.g., pre-eclampsia, malignant hypertension, disseminated intravascular coagulopathy, renal transplant rejection, cyclosporin toxicity, microangiopathic hemolytic anemia, and thrombotic thrombocytopenic purpura.

Further, as TANGO 281 exhibits expression in the heart, TANGO 281 nucleic acids, proteins, and modulators thereof can be used to treat heart disorders, e.g., atherosclerosis, hypertension, hypotension, angina pectoris, cardiomyopathy, and congenital heart disease.

As TANGO 281 is expressed in lung, TANGO 281 nucleic acids, proteins, and modulators thereof can be used to modulate the proliferation, activation, development, differentiation, and/or function of lung cells. Thus, TANGO 281 polypeptides, nucleic acids, or modulators thereof, can be used to treat pulmonary (lung) disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

TANGO 281 exhibits homology to a gene referred to as "gene 31" (PCT Publication No. WO98/39446), which is expressed primarily in the brain and thymus. In light of this, TANGO 281 nucleic acids, proteins and modulators thereof can be utilized to ameliorate at least one symptom associated with central nervous (CNS) disorders, hematopoietic disorder, and disorders of the endocrine system.

In another example, as TANGO 281 exhibits homology to "gene 31" which is expressed in the brain and thymus, TANGO 281 polypeptides, nucleic acids, or modulators thereof, can be used to treat disorders of the brain, such as cerebral edema, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain.

Further, in light of TANGO 281's pattern of expression in mice, TANGO 281 expression can be utilized as a marker for specific tissues (e.g., lymphoid tissues such as the thymus and spleen) and/or cells (e.g., lymphocytes) in which INTERCEPT 281 is expressed. TANGO 281 nucleic acids can also be utilized for chromosomal mapping.

A236 (INTERCEPT 236)

The present invention is also based, at least in part, on the discovery of cDNA molecules encoding A236, all of which are predicted to be either wholly secreted or transmembrane proteins.

Members of the A236 family may have common structural domains. For example, A236 family members include a signal sequence. In one embodiment, a A236 protein contains a signal sequence of amino acids 1-18 of SEQ ID NO:24. The signal sequence is cleaved during processing of the mature protein. In certain embodiments, an A236 family member has the amino acid sequence of SEQ ID NO:24, and the signal sequence is located at amino acids 1 to 16, 1 to 17, 1 to 18, 1 to 19 or 1 to 20. In such embodiments of the invention, the domains and the mature protein resulting from cleavage of such signal peptides are also included herein. For example, the cleavage of a signal sequence consisting of amino acids 1 to 18 results in a mature A236 protein corresponding to amino acids 19 to 373 of SEQ ID NO:24. The signal sequence is normally cleaved during processing of the mature protein.

In another example, A236 family members also include one or more of the following domains: (1) an extracellular domain; (2) a transmembrane domain; and (3) a cytoplasmic domain.

A236 family members can include a immunoglobulin domain. Immunoglobulin domains are present in a variety of proteins and are involved in protein-protein and protein-ligand interaction. A consensus immunoglobulin domain has the sequence of SEQ ID NO:64. This consensus sequence is shown in FIG. 23A-23B where the more conserved residues in the consensus sequence are indicated by uppercase letters and the less conserved residues in the consensus sequence are indicated by lowercase letters. The immunoglobulin domains of human A236 are located at amino acids 28-113 and amino acids 146-210 of SEQ ID NO:24. The immunoglobulin domains of mouse A236 are located at amino acids 27-112 and amino acids 145-209 of SEQ ID NO:26.

HUMAN A236

A cDNA encoding human A236 was identified by analyzing the sequences of clones present in a human osteoblast cDNA library.

This analysis led to the identification of a clone, fthwa195d06, encoding human A236. The cDNA of this clone is 1948 nucleotides long (FIG. 23A-23B; SEQ ID NO:23). The 1119 nucleotide open reading frame of this cDNA, nucleotides 314-1432 of SEQ ID NO:23, encodes a 373 amino acid protein (FIG. 23A-23B; SEQ ID NO:24).

In one embodiment of a nucleotide sequence of human A236 the nucleotide at position 379 is a guanine (G). In this embodiment, the amino acid at position 22 is glutamate (E). In another embodiment of a nucleotide sequence of human A236, the nucleotide at position 379 is a cytosine (C). In this embodiment, the amino acid at position 22 is aspartate (D). In another embodiment of a nucleotide sequence of mouse A236, the nucleotide at position 397 is a guanine (G). In this embodiment, the amino acid at position 28 is a glutamate (E). In another embodiment of a nucleotide sequence of human A236, the nucleotide at position 397 is a cytosine (C). In this embodiment, the amino acid at position 28 is aspartate (D). In another embodiment of a nucleotide sequence of human A236, the nucleotide at position 400 is an adenine (A). In this embodiment, the amino acid at position 29 is a glutamate (E). In another embodiment of a nucleotide sequence of human A236, the nucleotide at position 400 is a cytosine (C). In this embodiment, the amino acid at position 29 is aspartate (D).

The presence of a methionine residue at amino acid residue positions 200, 233, and 362 of SEQ ID NO:24 indicate that there can be alternative forms of human A236 of 174 amino acids, 141 amino acids, and 12 amino acids of SEQ ID NO:24, respectively.

Another embodiment of the invention includes isolated nucleic acid molecules comprising a polynucleotide having a nucleotide sequence encoding the polypeptide having the human A236 amino acid sequence in SEQ ID NO:24, but lacking the N-terminal methionine residue. In this embodiment, the nucleotide sequence of human A236, nucleotides 317-1432 of SEQ ID NO:23, encodes a human A236 amino acid sequence comprising amino acids 2-373 of SEQ ID NO:24.

The signal peptide prediction program SIGNALP (Nielsen et al. (1997) *Protein Engineering* 10:1-6) predicted that human A236 includes an 18 amino acid signal peptide (amino acid 1 to about amino acid 18 of SEQ ID NO:24) preceding the mature human A236 protein (corresponding to about amino acid 19 to amino acid 373 of SEQ ID NO:24).

In one embodiment, human A236 has an extracellular domain which extends from about amino acid 19 to about amino acid 230, a transmembrane domain which extends from about amino acid 231 to about amino acid 255, and a cytoplasmic domain which extends from about amino acid 256 to amino acid 373 of SEQ ID NO:24. Alternatively, in another embodiment, a human A236 protein contains an extracellular domain at amino acid residues to 256 to 373, a transmembrane domain at amino acid residues 231 to 255, and a cytoplasmic domain at amino acid residues 19 to 230 of SEQ ID NO:24.

Human A236 includes immunoglobulin domains at amino acids 28-113 of SEQ ID NO:24 and amino acids 146-210 of SEQ ID NO:24. FIG. 25 depicts an alignment of the immunoglobulin domains of human A236 with a consensus immunoglobulin domain derived from a hidden Markov model (SEQ ID NO:50).

Human A236 that has not been post-translationally modified is predicted to have a molecular weight of 41.2 kDa prior to cleavage of its signal peptide and a molecular weight of 39.2 kDa subsequent to cleavage of its signal peptide.

N-glycosylation sites are present at amino acids 74-77, 197-200, and 352-355. Protein kinase C phosphorylation sites are present at amino acids 67-69, 110-112, 116-118, 296-298, 303-305, and 314-316. Casein kinase II phosphorylation sites are present at amino acids 19-22, 54-57, 157-160, 183-186, and 354-357. Tyrosine kinase phosphorylation sites are present at amino acids amino acids 102-109 and 257-264. N-myristoylation sites are present at amino acids 15-20, 146-151, 204-209, 211-216, 232-237, 240-245, 293-298, and 300-305.

Clone fthwa195d06, which encodes human A236, was deposited as INTERCEPT 236 with the American Type Culture Collection (10801 University Boulevard, Manassas, Va. 20110-2236) on May 7, 1999 and assigned Accession Number PTA-34. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 24:
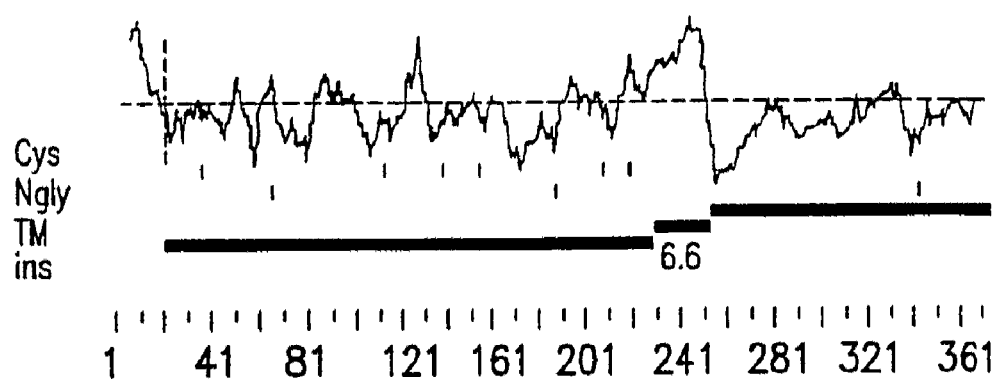
FIG. 24 depicts a hydropathy plot of human A236, the details of which are described herein.

FIG. 24 depicts a hydropathy plot of human A236, the details of which are described herein. The hydropathy plot indicates the presence of a signal sequence at the amino-terminus of human A236 and a transmembrane domain within human A236, suggesting that human A236 is a transmembrane protein.

When A236 was expressed in 293T cells the cells were found to secrete a 30 kD form of A236. Briefly, 293T cells (8×105 293T cells/well) were plated and incubated in growth medium (DMEM, 10% FBS, P/S) at 37_C, 5% CO2 overnight. The cells were then transfected with an expression vector capable of expressing human A236. The transfection was performed according to the LipofectAMINE protocol (Gibco/BRL; Gaithersburg, Md.) using 2 mg DNA and 10 ml LipofectAMINE for each well. After the cells were transfected for 5 hrs, the culture supernatant was replaced with fresh growth medium, and the cells were incubated overnight. Next, the cells were pulse labeled as follows. The cells were washed twice with DMEM lacking methionine and cysteine. Next, 1 ml DMEM lacking methionine and cysteine and 50 mCi Trans-35S (ICN Cat#51006) was added to each well. After incubation, 150 ml samples of cell culture supernatant were collected and mixed with an equal amount of 2×SDS gel sample buffer. The samples were boiled for 5 mins and then separated by SDS PAGE.

Mouse A236

A cDNA encoding mouse A236 was identified by analyzing the sequences of clones present in a mouse osteoblast cDNA library. The original mouse clone, jymuf004e01, was derived from lung.

This analysis led to the identification of a clone, jymuf004e01, encoding mouse A236. The cDNA of this clone is 1949 nucleotides long (FIG. 26A-26C; SEQ ID NO:25). The 1119 nucleotide open reading frame of this cDNA, nucleotides 304 to 1422 of SEQ ID NO:25, encodes a 373 amino acid protein (FIG. 26A-26C; SEQ ID NO:26).

In one embodiment of a nucleotide sequence of mouse A236 the nucleotide at position 366 is a guanine (G). In this embodiment, the amino acid at position 21 is glutamate (E). In another embodiment of a nucleotide sequence of mouse A236, the nucleotide at position 366 is a cytosine (C). In this embodiment, the amino acid at position 21 is aspartate (D). In another embodiment of a nucleotide sequence of mouse A236, the nucleotide at position 384 is a guanine (G). In this embodiment, the amino acid at position 27 is a glutamate (E). In another embodiment of a nucleotide sequence of mouse A236, the nucleotide at position 384 is a cytosine (C). In this embodiment, the amino acid at position 27 is aspartate (D). In another embodiment of a nucleotide sequence of mouse A236, the nucleotide at position 387 is an adenine (A). In this embodiment, the amino acid at position 28 is a glutamate (E). In another embodiment of a nucleotide sequence of mouse A236, the nucleotide at position 387 is a cytosine (C). In this embodiment, the amino acid at position 28 is aspartate (D).

The presence of a methionine residue at amino acid residue positions 199, and 232 of SEQ ID NO:26 indicate that there can be alternative forms of mouse A236 of 175 amino acids, and 142 amino acids of SEQ ID NO:26, respectively.

Figure 29:
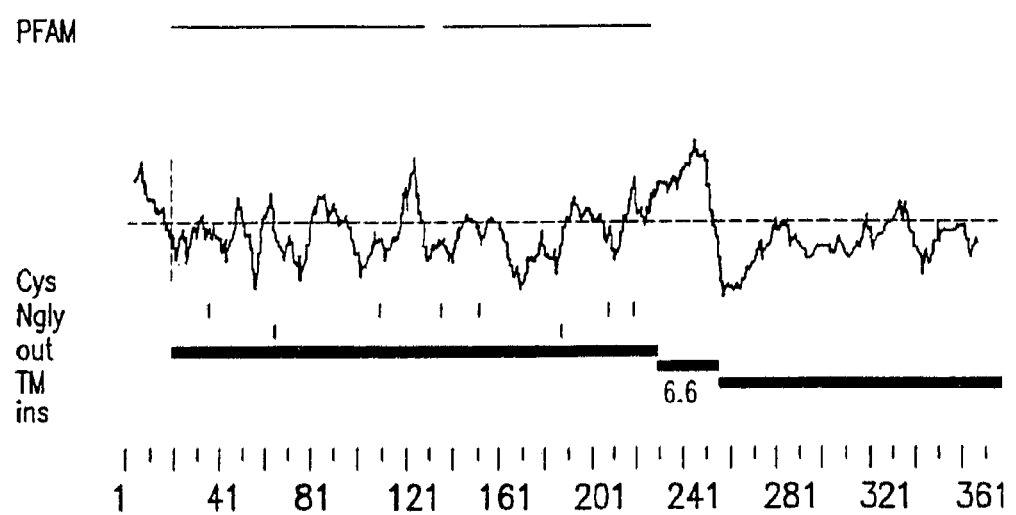
FIG. 29 depicts a hydropathy plot of mouse A236 (SEQ ID NO:26), the details of which are described herein.

FIG. 29 depicts a hydropathy plot of mouse A236, the details of which are described herein.

Another embodiment of the invention includes isolated nucleic acid molecules comprising a polynucleotide having a nucleotide sequence encoding the polypeptide having a mouse A236 amino acid sequence in SEQ ID NO:26, but lacking the N-terminal methionine residue. In this embodiment, the nucleotide sequence of mouse A236, nucleotides 317 to 1432 of SEQ ID NO:25, encodes the mouse A236 amino acid sequence comprising amino acids 2 to 373 of SEQ ID NO:26.

The signal peptide prediction program SIGNALP (Nielsen et al. (1997) *Protein Engineering* 10:1-6) predicted that mouse A236 includes an 17 amino acid signal peptide (amino acid 1 to about amino acid 17 of SEQ ID NO:26) preceding the mature mouse A236 protein (corresponding to about amino acid 18 to amino acid 373 of SEQ ID NO:26).

In one embodiment, mouse A236 has an extracellular domain which extends from about amino acid 18 to about amino acid 229, a transmembrane domain which extends from about amino acid 230 to about amino acid 254, and a cytoplasmic domain which extends from about amino acid 255 to amino acid 373 of SEQ ID NO:26. Alternatively, in another embodiment, a mouse A236 protein contains an extracellular domain at amino acid residues 255 to 373, a transmembrane domain at amino acid residues 230 to 254, and a cytoplasmic domain at amino acid residues 18 to 229 of SEQ ID NO:26.

Mouse A236 that has not been post-translationally modified is predicted to have a molecular weight of 41.2 kDa prior to cleavage of its signal peptide and a molecular weight of 39.2 kDa subsequent to cleavage of its signal peptide.

Mouse A236 includes immunoglobulin domains at amino acids 27-112 and amino acids 145-209 of SEQ ID NO:26.

A casein kinase II phosphorylation site is present at amino acids 18-21, 53-56, 182-185, and 354-357 of SEQ ID NO:157, respectively. N-myristoylation sites are present at amino acids 14-19, 145-150, 203, 208, 210, 215, 231-236, and 239-244, respectively. Protein kinase C phosphorylation sites are present at amino acids 66-68, 109-111, 115-117, 295-297, 302-304, and 313-315 of SEQ ID NO:157, respectively. A cyclic AMP phosphorylation site and cGMP-dependent protein kinase phosphorylation site is present at amino acids 256-259 of SEQ ID NO:157. ASN-glycosylation and N glycosylation sites are present at amino acids 73-76, and 196-199, respectively. A tyrosine kinase phosphorylation site is present at amino acids 101-108.

In situ tissue screening was performed on mouse adult and embryonic tissue to analyze the expression of mouse A236 mRNA. In summary, mouse A236 mRNA expression was detected by in situ hybridization in a few adult and numerous embryonic tissues. Adult expression was detected ubiquitously in brain and more restricted in placenta, uterus, and ovary. Embryonic expression was nearly ubiquitous with higher expression in brain, mandible, and the intestinal tract. Liver noticeably lacked expression during embryogenesis.

Human and mouse A236 sequences exhibit considerable similarity at the protein, nucleic acid, and open reading frame levels. An alignment (made using the ALIGN software (Myers and Miller (1989) CABIOS, ver. 2.0); BLOSUM 62 scoring matrix; gap penalties −12/−4), reveals a protein identity of 92.5%. The human and mouse A236 full length cDNAs are 83.57% identical, as assessed using the same software and parameters as indicated. In the respective ORFs, calculated in the same fashion as the full length cDNAs, human and mouse A236 are 87.81% identical. The nucleotide sequence (ORF) and amino acid sequence alignments of human and mouse A236 can be found in FIGS. 27A-27C, and FIG. 28, respectively.

Use of A236 Nucleic Acids, Polypeptides, and Modulators Thereof

A236 polypeptides, nucleic acids, and modulators thereof, can be used to modulate the function, morphology, proliferation and/or differentiation of cells in the tissues in which it is expressed. In addition, based on its homology to CAR (Bergelson et al. (1997) *Science* 275:1320-23) A236 may act as a entry mediator for coxsackie B viruses and adenovirus. Thus, compounds which interfere with virus binding to A236 or compounds which reduce A236 expression can be used to interfere with viral entry. A236 polypeptides, nucleic acids, and modulators thereof can be used to treat or prevent disorders associated with infection by the coxsackie B viruses and adenovirus, e.g., cardiac infection (e.g., myocarditis or dilated cardiomyopathy), central nervous system infection (e.g., non-specific febrile illness or meningoencephalitis), pancreatic infection (e.g., acute pancreatitis), respiratory infection (pneumonia), gastrointestinal infection, or type I diabetes.

As human A236 was originally found in a LPS stimulated human primary osteoblast library, A236 nucleic acids, proteins, and modulators thereof can be used to modulate the proliferation, differentiation, and/or function of cells that form bone matrix, e.g., osteoblasts and osteoclasts, and can be used to modulate the formation of bone matrix. Thus, A236 nucleic acids, proteins, and modulators thereof can be used to treat cartilage and bone associated diseases and disorders, and can play a role in bone growth, formation, and remodeling. Examples of cartilage and bone associated diseases and disorders include, e.g., bone cancer, achondroplasia, myeloma, fibrous dysplasia, scoliosis, osteoarthritis, osteosarcoma, and osteoporosis.

As the original mouse A236 clone, jymuf004e01, was derived from lung, A236 nucleic acids, proteins, and modulators thereof can be used to modulate the proliferation, activation, development, differentiation, and/or function of lung cells. Thus, A236 polypeptides, nucleic acids, or modulators thereof, can be used to treat pulmonary (lung) disorders, such as atelectasis, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchiolovlveolar carcinoma, bronchial carcinoid, hamartoma, and mesenchymal tumors).

A236 polypeptides, nucleic acids, and modulators thereof, can be used to modulate the function, morphology, proliferation and/or differentiation of cells in the tissues in which it is expressed. Such molecules can be used to treat disorders associated with abnormal or aberrant metabolism or function of cells in the tissues in which it is expressed. Tissues in which A236 is expressed include, for example, brain, placenta, uterus, ovaries, intestinal tract and the heart.

In another example, A236 polypeptides, nucleic acids, or modulators thereof, can be used to treat disorders of the brain, such as cerebral edema, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain.

In another example, A236 polypeptides, nucleic acids, or modulators thereof, can be used to treat pancreatic disorders, such as pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), or islet cell tumors (e.g., insulinomas, adenomas, Zollinger-Ellison syndrome, glucagonomas, and somatostatinoma).

Because A236 is expressed in the reproductive tract, particularly in the ovaries, the A236 polypeptides, nucleic acids and/or modulators thereof can be used to modulate the function, morphology, proliferation and/or differentiation of cells in the tissues in which it is expressed.

For example, the A236 polypeptides, nucleic acids and/or modulators thereof can be used modulate the function, morphology, proliferation and/or differentiation of the ovaries. For example, such molecules can be used to treat or modulate disorders associated with the ovaries, including, without limitation, ovarian tumors, McCune-Albright syndrome (polyostotic fibrous dysplasia). For example, the A236 polypeptides, nucleic acids and/or modulators can be used in the treatment of infertility.

The A236 polypeptides, nucleic acids and/or modulators thereof can be used to modulate the function, morphology, proliferation and/or differentiation of cells in the tissues of the reproductive tract other than the ovaries. For example, such molecules can be used to treat or modulate disorders associated with the female reproductive tract including, without limitation, uterine disorders, e.g., hyperplasia of the endometrium, uterine cancers (e.g., uterine leiomyomoma, uterine cellular leiomyoma, leiomyosarcoma of the uterus, malignant mixed mullerian Tumor of uterus, uterine Sarcoma), and dysfunctional uterine bleeding (DUB).

In another example, A236 polypeptides, nucleic acids, or modulators thereof, can be used to treat renal (kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal diseasemedullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

In another example, A236 polypeptides, nucleic acids, or modulators thereof, can be used to treat intestinal disorders, such as ischemic bowel disease, infective enterocolitis, Crohn's disease, benign tumors, malignant tumors (e.g., argentaffinomas, lymphomas, adenocarcinomas, and sarcomas), malabsorption syndromes (e.g., celiac disease, tropical sprue, Whipple's disease, and abetalipoproteinemia), obstructive lesions, hernias, intestinal adhesions, intussusception, or volvulus.

HUMAN TANGO 300

A cDNA encoding human TANGO 300 was identified by analyzing the sequences of clones present in a human fetal lung cDNA library.

This analysis led to the identification of a sequence encoding human TANGO 300. The cDNA of this clone is 1332 nucleotides long (FIG. 30A-30B; SEQ ID NO:27). The 1083 nucleotide open reading frame of this cDNA, nucleotide 31 to nucleotide 1113 of SEQ ID NO:27, encodes a 361 amino acid protein (FIG. 30A-30B; SEQ ID NO:28).

The signal peptide prediction program SIGNALP (Nielsen et al., 1997, *Protein Engineering* 10:1-6) predicted that human TANGO 300 includes a 20 amino acid signal peptide (amino acid 1 to about amino acid 20 of SEQ ID NO:28) preceding the mature human TANGO 300 protein (corresponding to about amino acid 21 to amino acid 361 of SEQ ID NO:28).

Human TANGO 300 is a transmembrane protein having an extracellular domain from about amino acid 21 to about amino acid 304, a transmembrane domain from about amino acid 305 to about amino acid 321, and a cytoplasmic domain from about amino acid 322 to amino acid 361 of SEQ ID NO:28.

Alternatively, in another embodiment, a human TANGO 300 protein contains an extracellular domain at amino acid residues 322 to amino acid 361, transmembrane domains at amino acid residues 305 to about amino acid 321, and a cytoplasmic domain at amino acid 21 to about amino acid 304 of SEQ ID NO:28.

Human TANGO 300 that has not been post-translationally modified is predicted to have a molecular weight of 40.6 kDa prior to cleavage of its signal peptide and a molecular weight of 38.5 kDa subsequent to cleavage of its signal peptide.

Within human TANGO 300, protein kinase C phosphorylation sites are present at amino acids 74 to 76, 89 to 91, 307 to 309, and 359 to 361. Casein kinase II phosphorylation sites are present at amino acids 34 to 37, 41 to 44, 74 to 77, 153 to 156, and 169 to 172. Tyrosine kinase phosphorylation sites are present at amino acids 111 to 117 and 236 to 243. N-myristylation sites are present at amino acids 25 to 30 and 170 to 175.

Clone AthX672i5, which encodes human TANGO 300, was deposited as EpT300 with the American Type Culture Collection (ATCC® 10801 University Boulevard, Manassas, Va. 20110-2236) on Jun. 30, 1999 and assigned Accession Number PTA-293. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 31:
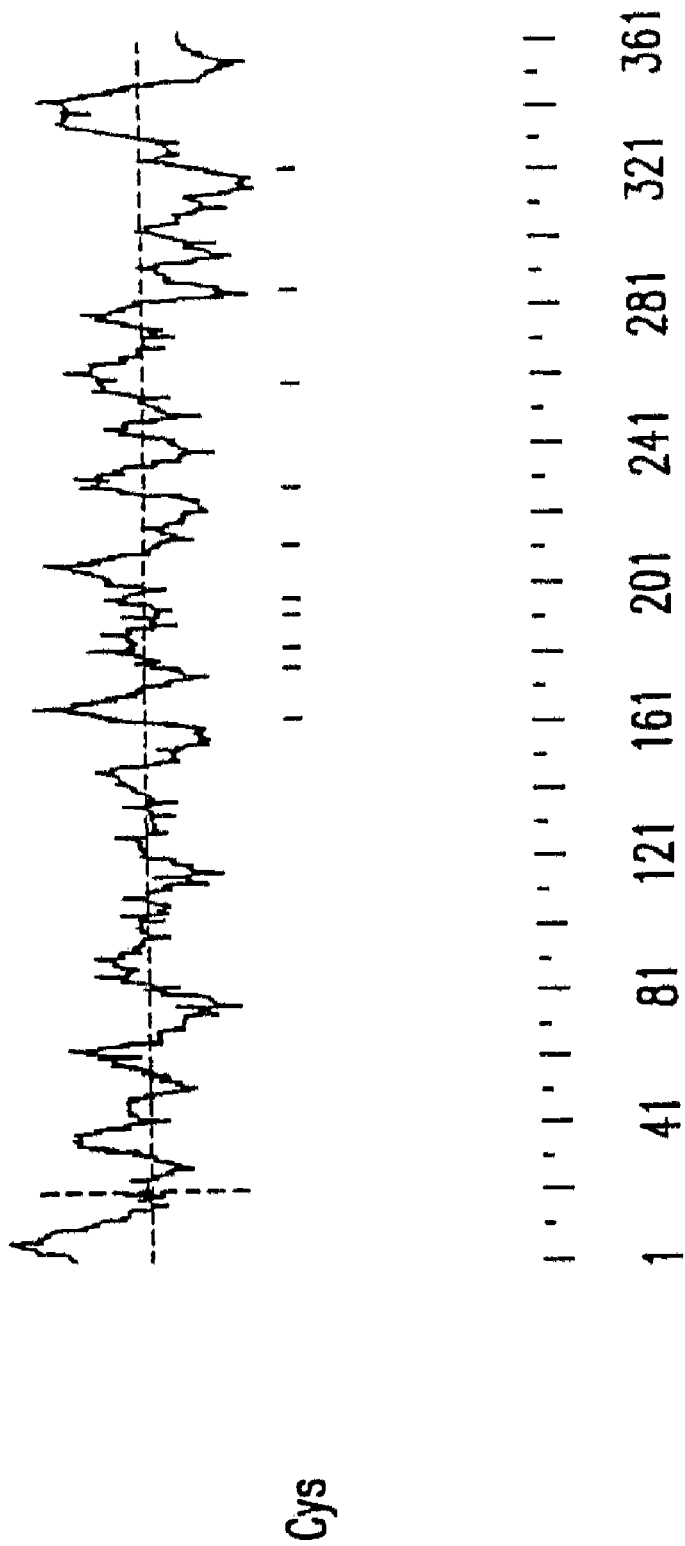
FIG. 31 depicts a hydropathy plot of human TANGO 300 (SEQ ID NO:28), the details of which are described herein.

FIG. 31 depicts a hydropathy plot of human TANGO 300, the details of which are described herein. The hydropathy plot indicates that human TANGO 300 has a signal peptide at its amino terminus and an internal hydrophobic region, suggesting that human TANGO 300 is a transmembrane protein.

MOUSE TANGO 300

A clone, jthub009c07, containing mouse TANGO 300 was also identified. The cDNA of this clone is 1400 nucleotides long (FIG. 32A-32C; SEQ ID NO:29). The 1155 nucleotide open reading frame of this cDNA, nucleotide 41 to nucleotide 1195 of SEQ ID NO:29, encodes a 385 amino acid protein (FIG. 32A-32C; SEQ ID NO:30).

The signal peptide prediction program SIGNALP (Nielsen et al., 1997, *Protein Engineering* 10:1-6) predicted that mouse TANGO 300 includes a 19 amino acid signal peptide (amino acid 1 to about amino acid 19 of SEQ ID NO:30) preceding the mature mouse TANGO 300 protein (corresponding to about amino acid 20 to amino acid 385 of SEQ ID NO:30).

Mouse TANGO 300 is a transmembrane protein having an extracellular domain which extends from about amino acid 20 to about amino acid 318, a transmembrane domain which extends from about amino acid 319 to about amino acid 335, and a cytoplasmic domain which extends from about amino acid 336 to amino acid 385 of SEQ ID NO:30.

Alternatively, in another embodiment, a mouse TANGO 300 protein contains an extracellular domain at amino acid residues 336 to amino acid 385, transmembrane domains at amino acid residues 319 to about amino acid 335, and a cytoplasmic domain at amino acid 20 to about amino acid 318 of SEQ ID NO:30.

Mouse TANGO 300 that has not been post-translationally modified is predicted to have a molecular weight of 43.1 kDa prior to cleavage of its signal peptide and a molecular weight of 41.0 kDa subsequent to cleavage of its signal peptide.

Within mouse TANGO 300, protein kinase C phosphorylation sites are present at amino acids 85 to 87 and 378 to 380. Casein kinase II phosphorylation sites are present at amino acids 22 to 25, 37 to 40, 149 to 152, 165 to 168 and 287 to 290. A tyrosine kinase phosphorylation site is present at amino acids 107 to 113. N-myristylation sites are present at amino acids 29 to 34, 89 to 94, 166 to 171 and 207 to 212. A N-glycosylation site is present at amino acids 136 to 139.

Figure 33:
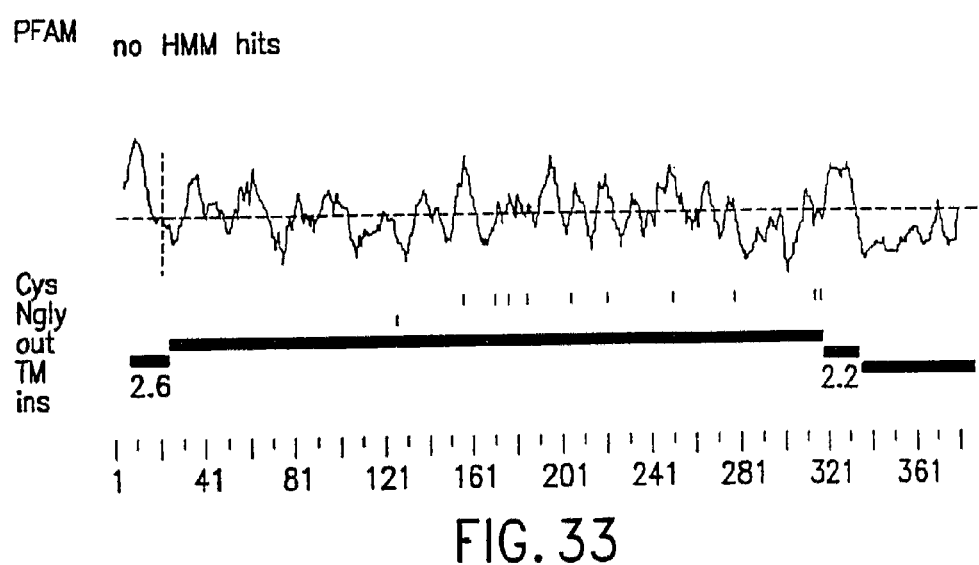
FIG. 33 depicts a hydropathy plot of mouse TANGO 300 (SEQ ID NO:30), the details of which are described herein.

FIG. 33 depicts a hydropathy plot of mouse TANGO 300, the details of which are described herein. The hydropathy plot indicates that mouse TANGO 300 has a signal peptide at its amino terminus and an internal hydrophobic region, suggesting that mouse TANGO 300 is a transmembrane protein.

FIG. 34A-34C depicts an alignment of the open reading frame (ORF) nucleotide sequence of human TANGO 300 (SEQ ID NO:27) and the ORF nucleotide sequence of mouse TANGO 300 (SEQ ID NO:29). This alignment was created using BESTFIT (BLOSUM 62 scoring matrix; gap open penalty of 12; frame shift penalty of 5; gap extend penalty of 4). In this alignment, the sequences are 77.7% identical. FIG. 35 depicts an alignment of the amino acid sequence of human TANGO 300 (SEQ ID NO:28) and the amino acid sequence of mouse TANGO 300 (SEQ ID NO:30). This alignment was created using BESTFIT (BLOSUM 62 scoring matrix; gap open penalty of 12; frame shift penalty of 5; gap extend penalty of 4). In this alignment, the sequences are 69.6% identical. The complete cDNA sequences of human and mouse TANGO 300 are 75.8% identical.

Use of TANGO 300 Nucleic Acids, Polypeptides, and Modulators Thereof

TANGO 300 polypeptides, nucleic acids, and modulators thereof can be used to modulate the function, morphology, proliferation and/or differentiation of cells in the tissues in which they are expressed.

Further, in light of TANGO 300's presence in a fetal lung cDNA library, TANGO 300 expression can be utilized as a marker for specific tissues (e.g., lung) and/or cells (e.g., pulmonary) in which TANGO 300 is expressed. TANGO 300 nucleic acids can also be utilized for chromosomal mapping.

Human TANGO 353

A cDNA encoding human TANGO 353 was identified by analyzing the sequences of clones present in a mixed lymphocyte reaction library for sequences that encode a wholly secreted or transmembrane protein. This analysis led to the identification of a clone, jthLa031g12 encoding human TANGO 353. The human TANGO 353 cDNA of this clone is 1239 nucleotides long (FIG. 36; SEQ ID NO:31). The open reading frame of this cDNA, nucleotides 76 to 765 of SEQ ID NO:31, encodes a 230 amino acid transmembrane protein (FIG. 36; SEQ ID NO:32).

Figure 37:
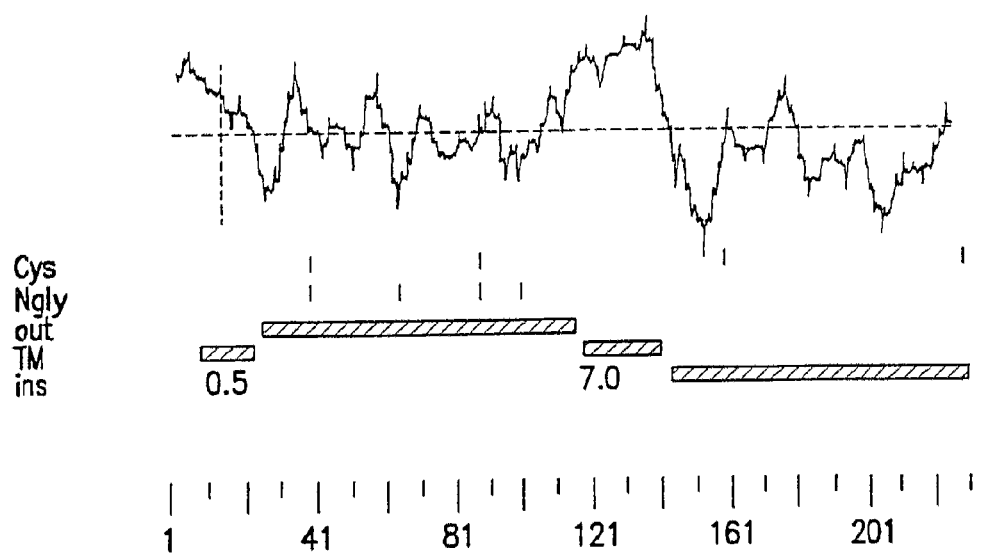
FIG. 37 depicts a hydropathy plot of human TANGO 353, the details of which are described herein. The dashed vertical line separates the signal sequence (amino acids 1 to 14 of SEQ ID NO:32) on the left from the mature protein (amino acids 15 to 230 of SEQ ID NO:32) on the right.

FIG. 37 depicts a hydropathy plot of human TANGO 353, the details of which are described herein.

The signal peptide prediction program SIGNALP (Nielsen et al., 1997, Protein Engineering 10:1-6) predicted that human TANGO 353 includes a 14 amino acid signal peptide (amino acid 1 to amino acid 14 of SEQ ID NO:32) preceding the mature human TANGO 353 protein (corresponding to amino acid 15 to amino acid 230 of SEQ ID NO:32). The molecular weight of human TANGO 353 protein without post-translational modifications is 24.8 kDa prior to the cleavage of the signal peptide and 23.3 kDa after cleavage of the signal peptide. The presence of a methionine residue at positions 39, 170 and 184 indicates that there can be alternative forms of human TANGO 353 of 192 amino acids, 61 amino acids, and 47 amino acids of SEQ ID NO:32, respectively.

Human TANGO 353 is a transmembrane protein which can include one or more of the following domains: (1) an extracellular domain; (2) a transmembrane domain; and (3) a cytoplasmic domain. The human TANGO 353 protein contains an extracellular domain at amino acid residues 15 to 116, a transmembrane domain at amino acid residues 117 to 141, and a cytoplasmic domain at amino acid residues 142 to 230 of SEQ ID NO:32.

Alternatively, in another embodiment, a human TANGO 353 protein contains a cytoplasmic domain at amino acid residues 15 to 116, a transmembrane domain at amino acid residues 117 to 141, and an extracellular domain at amino acid residues 142 to 230 of SEQ ID NO:32.

In one embodiment, a TANGO 353 protein contains a signal sequence of about amino acids 1 to 14 of SEQ ID NO:32. In certain embodiments, a TANGO 353 family member has the amino acid sequence of SEQ ID NO:32, and the signal sequence is located at amino acids 1 to 12, 1 to 13, 1 to 14, 1 to 15 or 1 to 16. In such embodiments of the invention, the extracellular domain and the mature protein resulting from cleavage of such signal peptides are also included herein. For example, the cleavage of a signal sequence consisting of amino acids 1 to 12 results in an extracellular domain consisting of amino acids 13 to 116 of SEQ ID NO:32 and the mature TANGO 353 protein corresponding to amino 13 to 230.

A TANGO 353 family member can include one or more of the following domains: (1) an extracellular domain; (2) a transmembrane domain; and (3) a cytoplasmic domain. Thus, in one embodiment, an TANGO 353 protein contains an extracellular domain of about amino acids 1 to 116 of SEQ ID NO:32, or a mature extracellular domain of about amino acids 15 to 116 of SEQ ID NO:32. In another embodiment, a TANGO 353 protein contains a transmembrane domain of about amino acids 117 to 141 of SEQ ID NO:32. In another embodiment, a TANGO 353 protein contains a cytoplasmic domain of about amino acids 142 to 230 of SEQ ID NO:32. In yet another embodiment, a TANGO 353 protein is a mature protein containing an extracellular, transmembrane and cytoplasmic domain of about amino acids 15 to 230 of SEQ ID NO:32.

In one embodiment of a nucleotide sequence of human TANGO 353, the nucleotide at position 68 is thymine (T). In this embodiment, the amino acid at position 23 is valine (V). In an alternative embodiment, a species variant of human TANGO 353 has a nucleotide at position 68 which is cytosine (C). In this embodiment, the amino acid at position 23 is alanine (A), i.e., a conservative substitution.

In one embodiment of a nucleotide sequence of human TANGO 353, the nucleotide at position 77 is adenine (A). In this embodiment, the amino acid at position 26 is tyrosine (Y). In an alternative embodiment, a species variant of human TANGO 353 has a nucleotide at position 77 which is thymine (T). In this embodiment, the amino acid at position 26 is phenylalanine (F), i.e., a conservative substitution.

In one embodiment of a nucleotide sequence of human TANGO 353, the nucleotide at position 203 is guanine (G). In this embodiment, the amino acid at position 68 is arginine (R). In an alternative embodiment, a species variant of human TANGO 353 has a nucleotide at position 203 which is adenine (A). In this embodiment, the amino acid at position 68 is histidine (H), i.e., a conservative substitution.

In one embodiment of a nucleotide sequence of human TANGO 353, the nucleotide at position 309 is cytosine (C). In this embodiment, the amino acid at position 103 is aspartate (D). In an alternative embodiment, a species variant of human TANGO 353 has a nucleotide at position 309 which is guanine (G). In this embodiment, the amino acid at position 103 is glutamate (E), i.e., a conservative substitution.

Four N-glycosylation sites are present in human TANGO 353. The first has the sequence NFTL (at amino acid residues 48 to 51), the second has the sequence NLSG (at amino acid residues 73 to 76), the third has the sequence NQSQ (at amino acid residues 97 to 100), and the fourth has the sequence NVSF (at amino acid residues 109 to 112). Human TANGO 353 has one cAMP- and cGMP-dependent protein kinase phosphorylation site with the sequence KRPT (at amino acid residues 209 to 212). Five protein kinase C phosphorylation sites are present in human TANGO 353. The first has the sequence SIR (at amino acid residues 19 to 21), the second has the sequence SSK (at amino acid residues 78 to 80), the third hag the sequence SAK (at amino acids 180 to 182), the fourth has the sequence TRK (at amino acid residues 207 to 209), and the fifth has the sequence TFR (at amino acid residues 225 to 227). Human TANGO 353 has four casein kinase II phosphorylation sites. The first has the sequence SSQE (at amino acid residues 28 to 31), the second has the sequence TMPE (at amino acid residues 183 to 186), the third has the sequence TLDD (at amino acid residues 191 to 194), and the fourth has the sequence SSPE (at amino acid residues 216 to 219). Human TANGO 353 has two N-myristylation sites. The first has the sequence GNFPGA (at amino acid residues 42 to 47) and the second has the sequence GVTFNL (at amino acid residues 69 to 74).

Clone EpT353, which encodes human TANGO 353, was deposited with the American Type Culture Collection (10801 University Boulevard, Manassas, Va. 20110-2209) on Jun. 29, 1999 and assigned Accession Number PTA-292. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 353 Nucleic Acids, Polypeptides, and Modulators Thereof

As TANGO 353 was originally found in a mixed lymphocyte library, TANGO 353 nucleic acids, proteins, and modulators thereof can be utilized to diagnose disorders and/or modulate processes involved in lymphocyte development, differentiation and activity, including, but not limited to development, differentiation and activation of T cells, including T helper, T cytotoxic and non-specific T killer cell types and subtypes, and B cells, immune functions associated with such cells, and amelioration of one or more symptoms associated with abnormal function of such cell types. Such disorders can include, but are not limited to, autoimmune disorders (e.g., autoimmune thyroiditis, Type I diabetes mellitus, insulin-resistant diabetes, autoimmune anemia, multiple sclerosis, rheumatoid arthritis, lupus or sclerodoma, allergy, including allergic rhinitis and food allergies, asthma, psoriasis, graft rejection, transplantation rejection, graft versus host disease, pathogenic susceptibilities), inflammatory disorders (e.g., bacterial or viral infections, wound healing and inflammatory bowel disease and arthritis), apoptotic disorders, and cytotoxic disorders, septic shock, cachexia, and proliferative disorders (e.g., B cell cancers stimulated by TNF).

Other TANGO 353 associated disorders can include TNF related disorders (e.g., acute myocarditis, myocardial infarction, congestive heart failure, T cell disorders (e.g., dermatitis, fibrosis)), immunological differentiative and apoptotic disorders (e.g., hyper-proliferative syndromes such as systemic lupus erythematosus (lupus)), and disorders related to angiogenesis (e.g., tumor formation and/or metastasis, cancer). Modulators of TANGO 353 expression and/or activity can be used to treat such disorders.

As TANGO 353 is expressed in mixed lymphocyte cultures, and hence likely expressed in bone marrow, TANGO 353 nucleic acids, proteins, and modulators thereof can be used to diagnose disorders associated with cells in the bone marrow and/or modulate the proliferation, differentiation, and/or function of cells that appear in the bone marrow, e.g., stem cells (e.g., hematopoietic stem cells), and blood cells, e.g., erythrocytes, platelets, and leukocytes. Thus TANGO 353 nucleic acids, proteins, and modulators thereof can be used to treat bone marrow, blood, and hematopoietic associated diseases and disorders, e.g., acute myeloid leukemia, hemophilia, leukemia, anemia (e.g., sickle cell anemia), and thalassemia.

As TANGO 353 is a transmembrane protein, TANGO 353 nucleic acids, proteins and modulators thereof can be utilized to modulate intercellular signaling cascades, or alternatively.

TANGO 353 expression can be utilized as a marker (e.g., an in situ marker) for specific tissues (e.g., spleen) and/or cells (e.g., lymphocytes) in which TANGO 353 is expressed. TANGO 353 nucleic acids can also be utilized for chromosomal mapping, or as chromosomal markers, e.g., in radiation hybrid mapping.

Human TANGO 393

A cDNA encoding human TANGO 393 was identified by analyzing the sequences of clones present in a human fetal hypothalamus cDNA library for sequences containing signal peptides. This analysis led to the identification of a clone, jthhb039 ft39, encoding full-length human TANGO 393. The human cDNA of this clone is 1778 nucleotides long (FIGS. 38A-38B; SEQ ID NO:33). The open reading frame of this cDNA, nucleotides 40 to 1458 of SEQ ID NO:33, encodes a 473 amino acid human TANGO 393 transmembrane protein (FIG. 38A-38B; SEQ ID NO:34).

Figure 39:
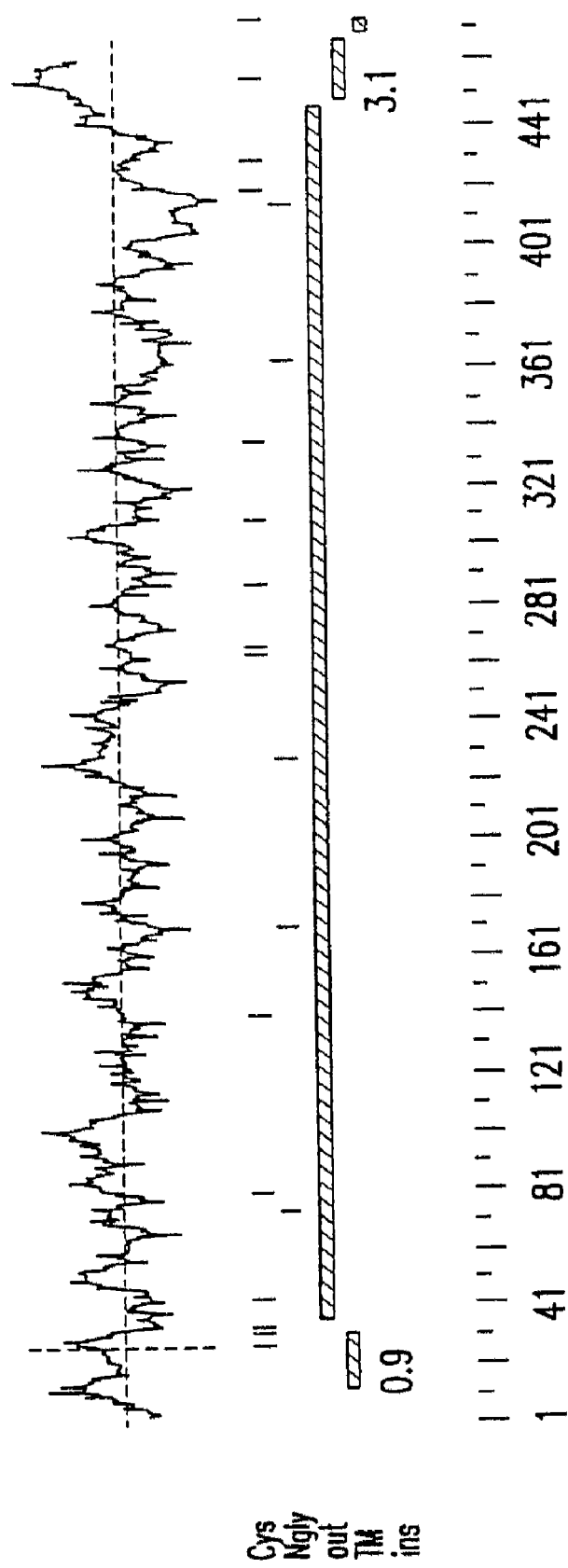
FIG. 39 depicts a hydropathy plot of human TANGO 393 (SEQ ID NO:34), the details of which are described herein. The dashed vertical line separates the signal sequence (amino acids 1 to 26 of SEQ ID NO:34) on the left from the nature protein (amino acids 27 to 473 of SEQ ID NO:34) on the right.

FIG. 39 depicts a hydropathy plot of human TANGO 393, the details of which are described herein. The dashed vertical line separates the signal sequence (amino acids 1 to 26 of SEQ ID NO:34) on the left from the mature protein (amino acids 27 to 473 of SEQ ID NO:34) on the right.

The signal peptide prediction program SIGNALP (Nielsen, et al. (1997) *Protein Engineering* 10:1-6) predicted that human TANGO 393 includes an 26 amino acid signal peptide (amino acid 1 to amino acid 26 of SEQ ID NO:34) preceding the mature protein (corresponding to amino acid 27 to amino acid 473 of SEQ ID NO:34). The molecular weight of human TANGO 393 without post-translational modifications is 50.7 kDa prior to the cleavage of the signal peptide, 47.8 kDa after cleavage of the signal peptide. The presence of a methionine residue at position 229 indicates that there can be alternative forms of human TANGO 393 of 245 amino acids of SEQ ID NO:34.

Human TANGO 393 is a transmembrane protein which contains one or more of the following domains: (1) an extracellular domain; (2) a transmembrane domain; and (3) a cytoplasmic domain; and (4) a leucine-rich domain. The human TANGO 393 protein contains an extracellular domain at amino acids 27 to 447, a transmembrane domain at amino acid residues 448 to 467, and a cytoplasmic domain at amino acid residues 468 to 473 of SEQ ID NO:34.

Alternatively, in another embodiment, a human TANGO 393 protein contains a cytoplasmic domain at amino acids 27 to 447, a transmembrane domain at amino acid residues 448 to 467, and a extracellular domain at amino acid residues 468 to 473 of SEQ ID NO:34.

In another embodiment, human TANGO 393 protein contains a signal sequence of about amino acids 1 to 26 of SEQ ID NO:34. In one embodiment, a TANGO 393 protein contains an extracellular domain at amino acids 1 to about 447 of SEQ ID NO:34 or a mature extracellular domain at about amino acid residues 27 to 447, a transmembrane domain at about amino acid residues 448 to 467, and a cytoplasmic domain at about amino acid residues 468 to 473 of SEQ ID NO:34. In another embodiment, a TANGO 393 family member contains an extracellular domain at amino acids 1 to about 26 or a mature extracellular domain at about amino acid residues 27 to 449, a transmembrane domain at about amino acid residues 450 to 467, and a cytoplasmic domain at about amino acid residues 468 to 473 of SEQ ID NO:34.

A TANGO 393 family member can include one or more leucine-rich-repeat (LRR) domains. A leucine-rich-repeat domain typically has the following degenerate consensus sequence: x-L-x-x-L-x-L-x-x-[NCT]-x-L-x-x-x-L-x-x-x-x-L-x-x-L, wherein L is a leucine residue and can be replaced by any aliphatic residue, "x" is any amino acid, and [NCT] is either an asparagine, cysteine or threonine, respectively. Leucine-rich-repeat domains most frequently appear in tandem repeats. The degenerate leucine-rich-repeat domains are characteristic of a diverse set of signaling proteins that are involved in cell signaling, cell growth and cell differentiation. Defects in leucine-rich-repeat genes have been shown to cause various diseases which include but are not limited to Bernard-Soulier disease, a bleeding disorder. Furthermore, leucine-rich-repeat genes are involved in the pathogenesis of diseases, for example, the leucine-rich-repeat of type-1 human immunodeficiency virus Rev protein is the trans-activating region of the virus (Kobe and Deisenhofer, 1994, TIBS, 19:415-421).

In one embodiment, a TANGO 393 family member has the amino acid sequence of SEQ ID NO:34 and, preferably, a leucine-rich-repeat domain consensus sequence is located at about amino acid positions 26 to 57, 58 to 81, 82 to 105, 106 to 130, 131 to 154, 155 to 178, 179 to 202, 203 to 226, 227 to 250, and/or 260 to 310 of human TANGO 393 (SEQ ID NO:34). In another embodiment, a TANGO 393 family member has the amino acid sequence of SEQ ID NO:36 and, preferably, a leucine-rich-repeat domain is located at about amino acid positions 26 to 57, 58 to 81, 82 to 105, 106 to 130, 131 to 154, 155 to 178, 179 to 202, 203 to 226, 227 to 250, and/or 260 to 310 of mouse TANGO 393 (SEQ ID NO:36).

In another embodiment, a TANGO 393 family member includes one or more leucine-rich-repeat domain consensus sequences having an amino acid sequence that is at least about 55%, preferably at least about 65%, more preferably at least 75%, yet more preferably at least about 85%, and most preferably at least about 95% identical to amino acids 26 to 57, 58 to 81, 82 to 105, 106 to 130, 131 to 154, 155 to 178, 179 to 202, 203 to 226, 227 to 250, and/or 260 to 310 of human TANGO 393 of SEQ ID NO:34. In another embodiment, a TANGO 393 family member includes one or more leucine-rich-repeat domains having an amino acid sequence that is at least about 55%, preferably at least about 65%, more preferably at least 75%, yet more preferably at least about 85%, and most preferably at least about 95% identical to amino acid positions 26 to 57, 58 to 81, 82 to 105, 106 to 130, 131 to 154, 155 to 178, 179 to 202, 203 to 226, 227 to 250, and/or 260 to 310 of mouse TANGO 393 SEQ ID NO:36.

In another embodiment, a TANGO 393 family member includes one or more leucine-rich-repeat domain consensus sequences having an amino acid sequence that is at least about 55%, preferably at least about 65%, more preferably at least 75%, yet more preferably at least about 85%, and most preferably at least about 95% identical to amino acids 26 to 57, 58 to 81, 82 to 105, 106 to 130, 131 to 154, 155 to 178, 179 to 202, 203 to 226, 227 to 250, and/or 260 to 310 of human TANGO 393 of SEQ ID NO:34, and has at least one TANGO 393 biological activity as described herein. In yet another embodiment, a TANGO 393 family member includes one or more leucine-rich-repeat domains having an amino acid sequence that is at least about 55%, preferably at least about 65%, more preferably at least 75%, yet more preferably at least about 85%, and most preferably at least about 95% identical to amino acid positions 26 to 57, 58 to 81, 82 to 105, 106 to 130, 131 to 154, 155 to 178, 179 to 202, 203 to 226, 227 to 250, and/or 260 to 310 of mouse TANGO 393 (SEQ ID NO:36), and has at least one TANGO 393 biological activity as described herein.

In one embodiment of a nucleotide sequence of human TANGO 393, the nucleotide at position 5 is adenine (A). In this embodiment, the amino acid at position 2 is lysine (K). In an alternative embodiment, a species variant of human TANGO 393 has a nucleotide at position 5 which is guanine (G). In this embodiment, the amino acid at position 2 is arginine (R), i.e., a conservative substitution.

In one embodiment of a nucleotide sequence of human TANGO 393, the nucleotide at position 17 is cytosine (C). In this embodiment, the amino acid at position 6 is alanine (A). In an alternative embodiment, a species variant of human TANGO 393 has a nucleotide at position 17 which is thymidine (T). In this embodiment, the amino acid at position 6 is valine (V), i.e., a conservative substitution.

In one embodiment of a nucleotide sequence of human TANGO 393, the nucleotide at position 55 is cytosine (C). In this embodiment, the amino acid at position 19 is glutamine (Q). In an alternative embodiment, a species variant of human TANGO 393 has a nucleotide at position 55 which is guanine (G). In this embodiment, the amino acid at position 19 is glutamate (E), i.e., a conservative substitution.

In one embodiment of a nucleotide sequence of human TANGO 393, the nucleotide at position 118 is adenine (A). In this embodiment, the amino acid at position 40 is threonine (T). In an alternative embodiment, a species variant of human TANGO 393 has a nucleotide at position 118 which is thymine (T). In this embodiment, the amino acid at position 40 is serine (S), i.e., a conservative substitution.

Human TANGO 393 has LRR from amino acids 26 to 57, 58 to 81, 82 to 105, 106 to 130, 131 to 154, 155 to 178, 179 to 202, 203 to 226, 227 to 250, and 260 to 310 of SEQ ID NO:34. These repeats are spaced in beta-alpha folds in the structure of the protein, so as to create a hydrophobic face that induces particular folding of the protein.

Human TANGO 393 has five N-glycosylation sites. The first has a sequence of NLTI (at amino acids 82-85), the second has a sequence of NLTH (at amino acids 179 to 182), the third has a sequence of NLSA (at amino acids 237 to 240), the fourth has a sequence of NGSG (at amino acids 372 to 375), and the fifth has a sequence of NRTR (at amino acids 423 to 426). Human TANGO 393 has one Glycosaminoglycan attachment site, the sequence of which is SGGG (at amino acids 436 to 439). Human TANGO 393 has one cAMP and cGMP-dependent protein kinase phosphorylation site, the sequence of which is KRAS (at amino acids 2 to 5). Human TANGO 393 has five protein kinase C phosphorylation sites, where the first has a sequence SQR of (at amino acids 59 to 61), the second has a sequence SFR of (at amino acids 76 to 78), the third has a sequence TFR of (at amino acids 173 to 175), the fourth has a sequence TGR of (at amino acids 321 to 323), and the fifth has a sequence SRK of (at amino acids 420 to 422). Human TANGO 393 has five casein kinase H phosphorylation sites, where the first has a sequence of TFRD (at amino acids 173 to 176), the second has a sequence of SVPE (at amino acids 192 to 195), the third has a sequence of SSSE (at amino acids 281 to 284), the fourth has a sequence of TDEE (at amino acids 325 to 328), and the fifth has a sequence of SVLE (at amino acids 345 to 348). Human TANGO 393 has eleven N-myristylation sites, where the first has the sequence GACVCY (at amino acids 29 to 34), the second has the sequence GEPAAS (at amino acids 54 to 59), and the third has the sequence GNRISH (at amino acids 66 to 71), the fourth has the sequence GLFRGL (at amino acids 148 to 153), and the fifth has the sequence GNRISS (at amino acids 187 to 192), the sixth has the sequence GCAVAT (at amino acids 308 to 313), and the seventh has the sequence GLPKCC (at amino acids 331 to 336), the eighth has the sequence GTLPGS (at amino acids 385 to 390), and the ninth has the sequence GQAGSG (at amino acids 432 to 437), the tenth has the sequence GGGTGD (at amino acids 438 to 443), and the eleventh has the sequence GALPSL (at amino acids 448 to 453). Human TANGO 393 has a Leucine zipper pattern which has the amino acid sequence LHLDRCGLQELG-PGLFRGLAAL (at amino acids 135 to 156).

Human TANGO 393 maps by homology to ESTs to Chromosome 22 between D22S420 and D22S446.

Clone EpT393, which encodes human TANGO 393, was deposited with the American Type Culture Collection (10801 University Boulevard, Manassas, Va. 20110-2209) on Jun. 29, 1999 and assigned Accession Number PTA-295. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Mouse TANGO 393

A cDNA encoding mouse TANGO 393 was identified in an analysis of a fetal hypothalamus library for screening encoding signal peptides. This analysis led to the identification of a clone, jtmoa038d08, encoding mouse TANGO 393. The mouse cDNA of this clone is 1946 nucleotides long (FIG. 40A-40B; SEQ ID NO:35). The open reading frame is from nucleotides 226 to 1644 of SEQ ID NO:35, encodes a 473 amino acid mouse TANGO 393 transmembrane protein (FIG. 40A-40B; SEQ ID NO:36).

Figure 41:
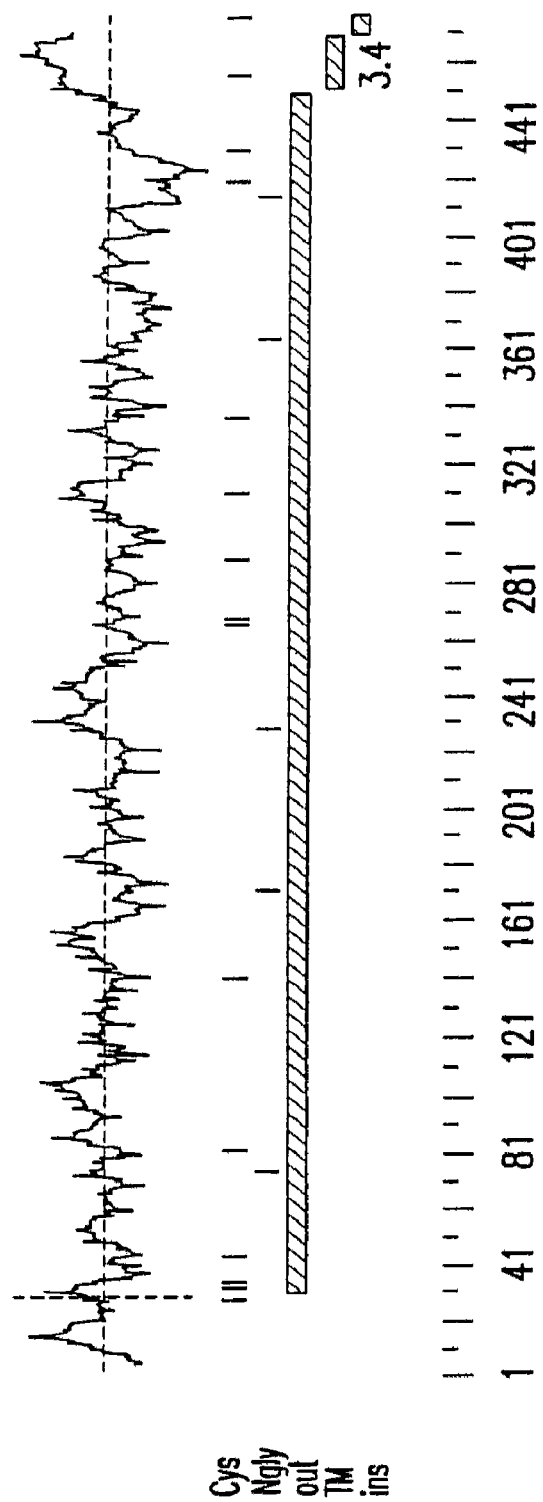
FIG. 41 depicts a hydropathy plot of mouse TANGO 393 (SEQ ID NO:36), the details of which are described herein. The dashed vertical line separates the signal sequence (amino acids 1 to 26 of SEQ ID NO:36) on the left from the mature protein (amino acids 27 to 473 of SEQ ID NO:36) on the right.

FIG. 41 depicts a hydropathy plot of mouse TANGO 393, the details of which are described herein. The dashed vertical line separates the signal sequence (amino acids 1 to 26 of SEQ ID NO:36) on the left from the mature protein (amino acids 27 to 473 of SEQ ID NO:36) on the right.

The signal peptide prediction program SIGNALP (Nielsen, et al. (1997) *Protein Engineering* 10:1-6) predicted that mouse TANGO 393 includes an 26 amino acid signal peptide (amino acid 1 to amino acid 26 of SEQ ID NO:36) preceding the mature protein (corresponding to amino acid 27 to amino acid 473 of SEQ ID NO:36). The molecular weight of mouse TANGO 393 without post-translational modifications is 51.0 kDa prior to the cleavage of the signal peptide, 48.1 kDa after cleavage of the signal peptide. The presence of a methionine residue at positions 229, 240 and 247 indicates that there can be alternative forms of mouse TANGO 393 of 245 amino acids, 234 amino acids, and 227 amino acids of SEQ ID NO:36, respectively.

Mouse TANGO 393 is a transmembrane protein which contains one or more of the following domains: (1) an extracellular domain; (2) a transmembrane domain; (3) a cytoplasmic domain; and (4) leucine-rich repeat domain. The mouse TANGO 393 protein contains an extracellular domain at amino acids 27 to 449, a transmembrane domain at amino acid residues 450 to 467, and a cytoplasmic domain at amino acid residues 468 to 473 of SEQ ID NO:36.

In another embodiment, mouse TANGO 393 protein contains a signal sequence of about amino acids 1 to 26 of SEQ ID NO:36. Alternatively, in another embodiment, a mouse TANGO 393 protein contains a cytoplasmic domain at amino acids 27 to 449, a transmembrane domain at amino acid residues 450 to 467, and an extracellular domain at amino acid residues 468 to 473 of SEQ ID NO:36.

In one embodiment of a nucleotide sequence of mouse TANGO 393, the nucleotide at position 5 is adenine (A). In this embodiment, the amino acid at position 2 is lysine (K). In an alternative embodiment, a species variant of mouse TANGO 393 has a nucleotide at position 5 which is guanine (G). In this embodiment, the amino acid at position 2 is arginine (R), i.e., a conservative substitution.

In one embodiment of a nucleotide sequence of mouse TANGO 393, the nucleotide at position 59 is cytosine (C). In this embodiment, the amino acid at position 20 is alanine (A). In an alternative embodiment, a species variant of mouse TANGO 393 has a nucleotide at position 59 which is thymidine (T). In this embodiment, the amino acid at position 20 is valine (V), i.e., a conservative substitution.

In one embodiment of a nucleotide sequence of mouse TANGO 393, the nucleotide at position 118 is adenine (A). In this embodiment, the amino acid at position 40 is threonine (T). In an alternative embodiment, a species variant of mouse TANGO 393 has a nucleotide at position 118 which is thymidine (T). In this embodiment, the amino acid at position 40 is serine (S), i.e., a conservative substitution.

In one embodiment of a nucleotide sequence of mouse TANGO 393, the nucleotide at position 178 is cytosine (C). In this embodiment, the amino acid at position 60 is glutamine (Q). In an alternative embodiment, a species variant of mouse TANGO 393 has a nucleotide at position 178 which is guanine (G). In this embodiment, the amino acid at position 60 is glutamate (E), i.e., a conservative substitution.

Mouse TANGO 393 has five N-glycosylation sites. The first has a sequence of NLTI (at amino acids 82-85), the second has a sequence of NLTH (at amino acids 179 to 182), the third has a sequence of NLSM (at amino acids 237 to 240), the fourth has a sequence of NGSG (at amino acids 372 to 375), and the fifth has a sequence of NRTR (at amino acids 423 to 426). Mouse TANGO 393 has one Glycosaminoglycan attachment site, the sequence of which is SGTG (at amino acids 439 to 442). Mouse TANGO 393 has one cAMP- and cGMP-dependent protein kinase phosphorylation site, the sequence of which is KRAS (at amino acids 2 to 5). Mouse TANGO 393 has four protein kinase C phosphorylation sites, where the first has a sequence SQR of (at amino acids 59 to 61), the second has a sequence SCR of (at amino acids 79 to 81), the third has a sequence TFR of (at amino acids 173 to 175), and the fourth has a sequence SRK of (at amino acids 420 to 422). Mouse TANGO 393 has eight casein kinase II phosphorylation sites, where the first has a sequence of TLLE (at amino acids 105 to 108), the second has a sequence of TFRD (at amino acids 173 to 176), the third has a sequence of SVPE (at amino acids 192 to 195), the fourth has a sequence of SSSE (at amino acids 281 to 284), the fifth has a sequence of SDLE (at amino acids 304 to 307), the sixth has a sequence of TDEE (at amino acids 325 to 328), the seventh has a sequence of SVLE (at amino acids 345 to 348), and the eighth has a sequence of SSAE (at amino acids 389 to 392). Mouse TANGO 393 has ten N-myristylation sites, where the first has the sequence GACVCY (at amino acids 29 to 34), the second has the sequence GIPAAS (at amino acids 54 to 59), and the third has the sequence GNRISH (at amino acids 66 to 71), the fourth has the sequence GLFRGL (at amino acids 148 to 153), and the fifth has the sequence GCAVAS (at amino acids 308 to 313), the sixth has the sequence GTLPSS (at amino acids 385 to 390), and the seventh has the sequence GLPTTG (at amino acids 407 to 412), the eighth has the sequence GQAGSG (at amino acids 432 to 437), and the ninth has the sequence GTGDAE (at amino acids 440 to 445), and the tenth has the sequence GALPAL (at amino acids 448 to 453). Mouse TANGO 393 has a prokaryotic membrane lipoprotein lipid attachment site with the sequence of SHVPAASFQSC (at amino acids 70 to 80). Mouse TANGO 393 has a Leucine zipper pattern which has the amino acid sequence LHLDRCGLRELGPGLFRGLAAL (at amino acids 135 to 156).

Mouse TANGO 393 has LRR from amino acids 26 to 57, 58 to 81, 82 to 105, 106 to 130, 131 to 154, 155 to 178, 179 to 202, 203 to 226, 227 to 250, and 260 to 310 of SEQ ID NO:36. These repeats are spaced in beta-alpha folds in the structure of the protein, so as to create a hydrophobic face that induces particular folding of the protein.

FIG. 42A-42C depicts an alignment of the open reading frames of human TANGO 393 (SEQ ID NO:33) and mouse TANGO 393 (SEQ ID NO:35) demonstrating an identity of 82.8%. The algorithm used to align the sequences was the ALIGN program which calculates a global alignment of two sequences. (Version 2.0u, Myers and Miller, 1989)

FIG. 43 depicts an alignment of the immature proteins of human TANGO 393 (SEQ ID NO:34) and mouse TANGO 393 (SEQ ID NO:36) demonstrating an identity of 89.2%. The algorithm used to align the sequences was the ALIGN program which calculates a global alignment of two sequences. (Version 2.0u, Myers and Miller, 1989)

Uses of TANGO 393 Nucleic Acids, Polypeptides, and Modulators Thereof

As both mouse and human TANGO 393 clones were originally identified in a fetal hypothalamus library, TANGO 393 nucleic acids, proteins, and modulators thereof can be used to diagnose disorders and/or modulate the proliferation, differentiation, and/or function of endocrine cells, in particular hypothalamus, cells. TANGO 393 nucleic acids, proteins and modulators thereof can be utilized to modulate processes involved in hypothalamus development, differentiation and activity, including, but not limited to development, and differentiation and activation of hypothalamus tissues and cells as well as any function associated with such cells, and amelioration of one or more symptoms associated with abnormal function of such cell types. Such disorders can include, but are not limited to, malignant or benign hypothalamus cell growth.

Furthermore, as the hypothalamus is the master regulator of the entire endocrine system, as such, TANGO 393 nucleic acids, proteins and modulators thereof can be used as a therapeutic agent to treat mammals with abnormal hypothalamic function wherein the mammal exhibits abnormal whole animal homeostasis, appetite-related disorders, obesity, cachexia, food intake disorders, stress responsiveness disorders, adrenal function disorders, pituitary disorders and adrenal disorders. Further, TANGO 393 proteins, nucleic acids, or modulators thereof, can be used to treat disorders of the adrenal cortex, such as hypoadrenalism (e.g., primary chronic or acute adrenocortical insufficiency, and secondary adrenocortical insufficiency), hyperadrenalism (Cushing's syndrome, primary hyper-aldosteronism, adrenal virilism, and adrenal hyperplasia), or neoplasia (e.g., adrenal adenoma and cortical carcinoma). In another example, TANGO 393 polypeptides, nucleic acids, or modulators thereof, can be used to treat disorders of the thyroid gland, which is partially regulated by the hypothalamus, such as hyperthyroidism (e.g., diffuse toxic hyperplasia, toxic multinodular goiter, toxic adenoma, and acute or subacute thyroiditis), hypothyroidism (e.g., cretinism and myxedema), thyroiditis (e.g., Hashimoto's thyroiditis, subacute granulomatous thyroiditis, subacute lymphocytic thyroiditis, Riedel's thyroiditis), Graves' disease, goiter (e.g., simple diffuse goiter and multinodular goiter), or tumors (e.g., adenoma, papillary carcinoma, follicular carcinoma, medullary carcinoma, undifferentiated malignant carcinoma, Hodgkin's disease, and non-Hodgkin's lymphoma).

TANGO 393 exhibits homology to genes which contain sequences referred to as Leucine Rich Repeats (LRR), for example, SLIT-1, leucine-rich α-2-Glycoprotein and Platelet Glycoprotein V precursor. As such, TANGO 393 nucleic acids, proteins and modulators thereof can be used to treat subjects with defects in leucine-rich-repeat genes shown to cause various diseases, including but not limited to Bernard-Soulier disease, a bleeding disorder. Further, as TANGO 393 has homology to Platelet Glycoprotein V (GPV) precursor, TANGO 393 nucleic acids, proteins and modulators thereof can be used to diagnose disorders and/or modulate platelet activity, thrombin activity, von Willebrand Factor assembly and activation, or ADP/epinephrine-, cathepsin G-, and TRAP-induced decrease in platelet surface GPV expression.

Furthermore, TANGO 393 proteins, nucleic acids and modulators thereof can be used to modulate the pathogenesis of infectious diseases, for example, diseases that are affected by the expression of leucine-rich-repeat proteins such as the type-1 human immunodeficiency virus (HIV-1) Rev protein, which is the trans-activating region of the virus (Kobe and Deisenhofer, 1994, TIBS, 19:415-421).

LRR containing proteins are tissue organizers, wherein they orient and order collagen fibrils during ontogeny and are involved in pathological processes such as wound healing, tissue repair, and tumor stroma formation. These properties are rooted in their bifunctional character: the protein moiety binding collagen fibrils at strategic loci, the microscopic gaps between staggered fibrils, and the highly charged glycosaminoglycans extending out to regulate interfibrillar distances and thereby establishing the exact topology of fibrillar collagens in tissues. Therefore, TANGO 393 nucleic acids, proteins and modulators thereof can be used to disrupt intercellular and intracellular protein interactions or cellular signaling in tissues or cells, for example in the hypothalamus. More particularly, the TANGO 393 nucleic acids, proteins and modulators thereof can be used to modulate wound healing (e.g., platelet activation), tissue repair and tumor stroma formation as well. Furthermore, TANGO 393 nucleic acids, proteins and modulators thereof can be used to diagnose disorders and/or modulate the function of the hypothalamus as it relates to control of endocrine function, regulation of whole animal homeostasis and modulation of diurnal requirements, appetite as related to obesity or cachexia, and generally weight control in mammals.

Proteins with LRR also interact with soluble growth factors, modulate their functional activity, and bind to cell surface receptors. The latter interaction affects cell cycle progression in a variety of cellular systems and could explain changes in the expression of these gene products around the invasive neoplastic cells and in regenerating tissues. See Generally, Iozzo, 1997, Crit. Rev. Biochem. Mol. Biol., 32(2): 141-74. As such, TANGO 393 nucleic acids, proteins and modulators thereof can be used to modulate disorders associated with aberrant expression of TANGO 393 in cancerous (e.g., tumor) cells that do not normally express TANGO 393. Such disorders can include, for example, ones associated with tumor cell migration and progression to metastasis.

As TANGO 393 exhibits homology to the SLIT-1 proteins, TANGO 393 proteins, nucleic acids and modulators thereof may participate in the formation and maintenance of the nervous and endocrine systems by e.g., protein-protein interactions. Northern blot analysis has revealed that the human SLIT-1, -2, and -3 mRNAs are exclusively expressed in the brain, spinal cord, and thyroid, respectively. In situ hybridization studies indicated that the rat SLIT-1 mRNA is specifically expressed in the neurons of fetal and adult forebrains (Itoh et al., Brain Res Mol Brain Res 1998 Nov. 20; 62(2): 175-86.) This suggests a role for TANGO 393 nucleic acids, proteins and modulators thereof in brain development and neural function. Therefore, the TANGO 393 nucleic acids, proteins and modulators thereof may be useful to disrupt protein interaction or cellular signaling in brain tissues or cells. In particular, TANGO 393 protein, nucleic acids and modulators thereof could be useful to treat neural related disorders or neural damage, such as for regenerative neural repair after damage by trauma, degeneration, or inflammation e.g., multiple sclerosis, spinal cord injuries, infarction, infection, malignancy, exposure to toxic agents, nutritional deficiency, paraneoplastic syndromes, and degenerative nerve diseases including but not limited to Alzheimer's disease, Parkinson's disease, Huntington's Chorea, amyotrophic lateral sclerosis, progressive supra-nuclear palsy, and other dementia.

TANGO 393 expression can be utilized as a marker (e.g., an in situ marker) for specific tissues (e.g., the hypothalamus) and/or cells (e.g., hypothalamic cells) in which TANGO 393 is expressed. TANGO 393 nucleic acids can also be utilized for chromosomal mapping, or as chromosomal markers, e.g., in radiation hybrid mapping.

Human TANGO 402

A cDNA encoding human TANGO 402 was identified by analyzing the sequences of clones present in a human 9 week fetus library for sequences that encode wholly secreted or transmembrane proteins. This analysis led to the identification of a clone, jthga055h07, encoding human TANGO 402. The human TANGO 402 cDNA of this clone is 1348 nucleotides long (FIG. 44; SEQ ID NO:37). The open reading frame of this cDNA, nucleotides 87 to 707 of SEQ ID NO:37, encodes a 207 amino acid transmembrane protein (FIG. 44; SEQ ID NO:38).

Figure 45:
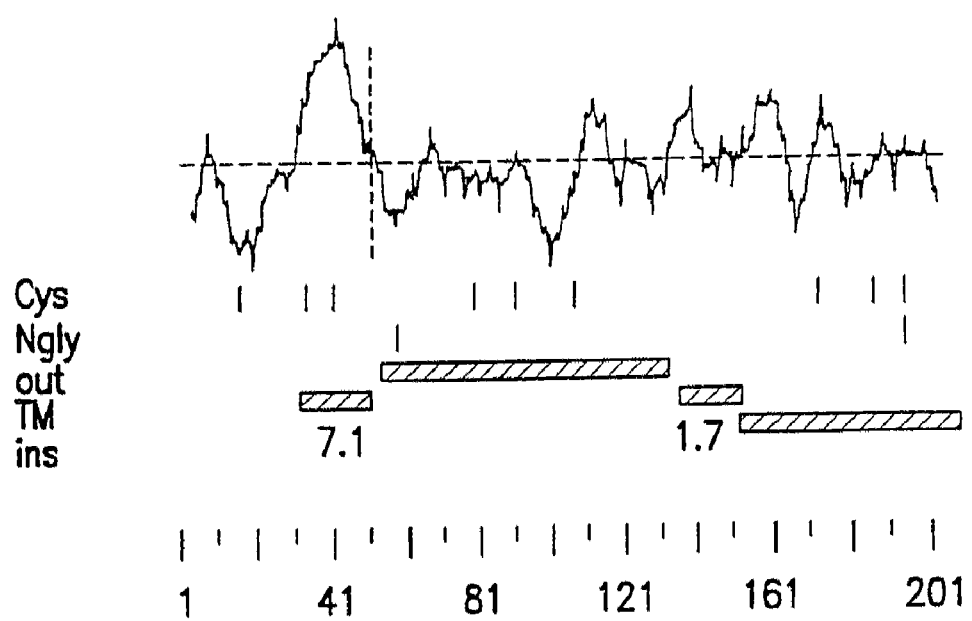
FIG. 45 depicts a hydropathy plot of human TANGO 402 (SEQ ID NO:38), the details of which are described herein. The dashed vertical line separates the signal sequence (amino acids 1 to 50 of SEQ ID NO:38) on the left from the mature protein (amino acids 51 to 207 of SEQ ID NO:38) on the right.

FIG. 45 depicts a hydropathy plot of human TANGO 402, the details of which are described herein.

The signal peptide prediction program SIGNALP (Nielsen et al., 1997, *Protein Engineering* 10:1-6) predicted that human TANGO 402 includes a 50 amino acid signal peptide (amino acid 1 to amino acid 50 of SEQ ID NO:38) preceding the mature human TANGO 402 protein (corresponding to amino acid 51 to amino acid 207 of SEQ ID NO:38). The molecular weight of human TANGO 402 protein without post-translational modifications is 24.0 kDa prior to the cleavage of the signal peptide, 18.1 kDa after cleavage of the signal peptide.

Human TANGO 402 protein is a transmembrane protein that contains an extracellular domain at amino acids 1 to 133 or a mature extracellular domain at amino acid residues 51 to 133, a transmembrane domain at amino acid residues 134 to 151, and a cytoplasmic domain at amino acid residues 152 to 207 of SEQ ID NO:38.

Alternatively, in another embodiment, a human TANGO 402 protein contains a cytoplasmic domain at amino acids 1 to 133 or a mature cytoplasmic domain at amino acid residues 51 to 133, a transmembrane domain at amino acid residues 134 to 151, and an extracellular domain at amino acid residues 152 to 207 of SEQ ID NO:38.

In another embodiment, a TANGO 402 protein contains a signal sequence of about amino acids 1 to 50 of SEQ ID NO:38. The signal sequence is usually cleaved during processing of the mature protein. In the case of, e.g., transmembrane 4-type proteins, the signal peptide is generally not cleaved, but becomes a transmembrane-anchoring domain of the polypeptide.

A TANGO 402 family member can include of one or more of the following domains: (1) an extracellular domain; (2) a transmembrane domain; and (3) a cytoplasmic domain. In one embodiment, a TANGO 402 protein contains an extracellular domain at amino acids 1 to about 133 or a mature extracellular domain at about amino acid residues 51 to 133, a transmembrane domain at about amino acid residues 134 to 151, and a cytoplasmic domain at about amino acid residues 152 to 207 of SEQ ID NO:38.

A TANGO 402 family member can include a signal sequence. In certain embodiments, a TANGO 402 family member has the amino acid sequence of SEQ ID NO:38, and the signal sequence is located at amino acids 1 to 48, 1 to 49, 1 to 50, 1 to 51 or 1 to 52. In such embodiments of the invention, the extracellular domain and the mature protein resulting from cleavage of such signal peptides are also included herein. For example, the cleavage of a signal sequence consisting of amino acids 1 to 48 results in an extracellular domain consisting of amino acids 49 to 133 and the mature TANGO 402 protein corresponding to amino 49 to 207 of SEQ ID NO:38.

A TANGO 402 family member can include a C-type lectin domain or a C-type lectin-like domain.

A C-type lectin domain typically has the following consensus sequence: C-[LIVMFATG]-x(5,12)-[WL]-x-[DNSR]-x(2)-C-x(5,6)-[FYWLIVSTA]-[LIVSTA]-C, wherein C is a cysteine residue, [LIVMFATG] is a leucine, isoleucine, methionine, phenylalanine, alanine, threonine or glycine residue, x is any amino acid and the number in parentheses indicates the number of amino acids, [WL] is either a tryptophan or leucine residue, [DNSR] is a aspartic acid, asparagine, serine or arginine residue, [FYWLIVSTA] is a phenylalanine, tyrosine, tryptophan, leucine, isoleucine, valine, serine, threonine or alanine residue, and [LIVSTA] is a leucine, isoleucine, valine, serine, threonine or alanine residue. C-type lectin domains contain four cysteines, which are involved in two disulfide bonds, and are about 110 to 130 amino acid residues. C-type lectin domains typically function as calcium-dependent carbohydrate-recognition domains and have been found in various proteins including, but not limited to, asialoglycoprotein receptors (ASGPR), pulmonary surfactant-associated protein A (SP-A), mannan-binding proteins, L-selectin, neurocan, and tetranectin. These proteins have various functions including, for example, cell adhesion (i.e., L-selectin). ASGPR mediates the endocytosis of plasma glycoprotein to which the terminal salic acid-residue in their carbohydrated moieties has been removed. SP-A binds to surfactant phospholipids and contributes to lower the surface tension at the air-liquid interface in the alveoli of the lung.

A C-type lectin-like domain as described herein has the following consensus sequence: C-[LIVMFATG]-x-(5,12)-[DNSR]-x(2)-C-x(5,6)-[LIVSTA]-C, wherein C is a cysteine residue, [LIVMFATG] is a leucine, isoleucine, methionine, phenylalanine, alanine, threonine or glycine residue, "x" is any amino acid and the number in parentheses indicates the number of amino acids [DNSR] is an aspartic acid, asparagine, serine or arginine residue, and [LIVSTA] is a leucine, isoleucine, valine, serine, threonine or alanine residue. In one embodiment, a TANGO 402 family member has the amino acid sequence of SEQ ID NO:38 and, preferably, a C-type lectin-like domain is located at about amino acid positions 104 to 193, wherein the consensus sequence is at about amino acid positions 172 to 193 of SEQ ID NO:38.

In another embodiment, a TANGO 402 family member includes one or more C-type lectin-like domains having an amino acid sequence that is at least about 55%, preferably at least about 65%, more preferably at least 75%, yet more preferably at least about 85%, and most preferably at least about 95% identical to amino acids 104 to 193 of SEQ ID NO:38.

In another embodiment, a TANGO 402 family member includes one or more C-type lectin-like domains having an amino acid sequence that is at least about 55%, preferably at least about 65%, more preferably at least 75%, yet more preferably at least about 85%, and most preferably at least about 95% identical to amino acids 104 to 193 of SEQ ID NO:38, and has at least one TANGO 402 biological activity as described herein.

In another embodiment, a TANGO 402 family member includes one or more C-type lectin-like domains having an amino acid sequence that is at least about 55%, preferably at least about 65%, more preferably at least 75%, yet more preferably at least about 85%, and most preferably at least about 95% identical to amino acids 104 to 193 of SEQ ID NO:38 and includes a cysteine residue N-terminal to the consensus sequence. In yet another embodiment, a TANGO 402 family member includes one or more C-type lectin-like domain having an amino acid sequence that is at least about 55%, preferably at least about 65%, more preferably at least 75%, yet more preferably at least about 85%, and most preferably at least about 95% identical to amino acids 104 to 193 of SEQ ID NO:38, includes a cysteine residue N-terminal to the consensus sequence, and has at least one TANGO 402 biological activity as described herein.

In another embodiment, the C-type lectin-like domain of TANGO 402 is a C-type lectin domain, which has the following consensus sequence: C-[LIVMFATG]-x(5,12)-[WL]-x-[DNSR]-x(2)-C-x(5,6)-[FYWLIVSTA]-[LIVSTA]-C, wherein C is a cysteine residue, [LIVMFATG] is a leucine, isoleucine, methionine, phenylalanine, alanine, threonine or glycine residue, x is any amino acid, [WL] is either a tryptophan or leucine residue, [DNSR] is a aspartic acid, asparagine, serine or arginine residue, [FYWLIVSTA] is a phenylalanine, tyrosine, tryptophan, leucine, isoleucine, valine, serine, threonine or alanine residue, and [LIVSTA] is a leucine, isoleucine, valine, serine, threonine or alanine residue. In this embodiment, a TANGO 402 family member includes one or more C-type lectin-like domains having an amino acid sequence that is at least about 55%, preferably at least about 65%, more preferably at least 75%, yet more preferably at least about 85%, and most preferably at least about 95% identical to amino acids 104 to 193 of SEQ ID NO:38.

In one embodiment of a nucleotide sequence of human TANGO 402, the nucleotide at position 28 is cytosine (C). In this embodiment, the amino acid at position 10 is leucine (L). In an alternative embodiment, a species variant of human TANGO 402 has a nucleotide at position 28 which is guanine (G). In this embodiment, the amino acid at position 10 is valine (V), i.e., a conservative substitution.

In one embodiment of a nucleotide sequence of human TANGO 402, the nucleotide at position 58 is cytosine (C). In this embodiment, the amino acid at position 20 is glutamine (A). In an alternative embodiment, a species variant of human TANGO 402 has a nucleotide at position 58 which is guanine (G). In this embodiment, the amino acid at position 20 is glutamate (E), i.e., a conservative substitution.

In one embodiment of a nucleotide sequence of human TANGO 402, the nucleotide at position 61 is adenine (A). In this embodiment, the amino acid at position 21 is lysine (K). In an alternative embodiment, a species variant of human TANGO 402 has a nucleotide at position 61 which is guanine (G). In this embodiment, the amino acid at position 21 is arginine (R), i.e., a conservative substitution.

In one embodiment of a nucleotide sequence of human TANGO 402, the nucleotide at position 64 is thymine (T). In this embodiment, the amino acid at position 22 is serine (S). In an alternative embodiment, a species variant of human TANGO 402 has a nucleotide at position 64 which is adenine (A). In this embodiment, the amino acid at position 22 is threonine (T), i.e., a conservative substitution.

Two N-glycosylation sites are present in human TANGO 402. The first has the sequence NISS (at amino acid residues 67 to 70) and the second has the sequence NGTS (at amino acid residues 202 to 205). Six protein kinase C phosphorylation sites are present in human TANGO 402. The first has the sequence SFK (at amino acid residues 11 to 13), the second has the sequence SFK (at amino acid residues 95 to 97), the third has the sequence TWK (at amino acid residues 98 to 100), the fourth has the sequence SQR (at amino acid residues 102 to 104), the fifth has the sequence SLK (at amino acid residues 128 to 130), and the sixth has the sequence TFK (at amino acid residues 188 to 190). Three casein kinase II phosphorylation sites are present in human TANGO 402. The first has the sequence TGID (at amino acid residues 49 to 52), the second has the sequence TWKE (at amino acid residues 98 to 101), and the third has the sequence SQRD (at amino acid residues 102 to 105). Human TANGO 402 has a tyrosine kinase phosphorylation site having the sequence KSKDFSLY at amino acid residues 21 to 28). Human TANGO 402 has an N-myristylation site having the sequence GLYVTF at amino acid residues 138 to 143.

Human TANGO 402 includes a C-type lectin (CTL)-like domain at amino acid residues 104 to 193 of SEQ ID NO:38. CTL domains have been shown to function as a calcium-dependent carbohydrate-recognition domain.

Human TANGO 402 is homologous to human lectin-like oxidized LDL receptor 1 (LOX-1), which is the receptor for oxidized lipoprotein (Sawamura et al., 1997, Science, 386: 73-77). LOX-1 is involved in oxidized low-density lipoprotein (Ox-LDL) uptake and subsequent foam cell transformation in macrophages and smooth muscle cells in the atherosclerotic intima (Kume et al., 1998, Cir. Res., 83:322-327; Yamada, et al., 1998, Cell. Mol. Life. Sci., 54(7):628-640; Moriwaki et al., 1998, Artherioscler. Thromb. Vasc. Biol., 18(10):1541-1547; Napase et al., 1998, J. Biol. Chem., 273(50):33702-33707).

FIG. 46 depicts an alignment of the human TANGO 402 amino acid sequence (SEQ ID NO:38) with the human LOX-1 amino acid sequence (SEQ ID NO:47; Accession Number AB010710). As shown in the figure, the amino acid sequence of LOX-1 is 25.1% identical to the amino acid sequence of human TANGO 402 (SEQ ID NO:38).

FIG. 47A-47B depicts an alignment of the open reading frames of human TANGO 402 (nucleotide 87 to nucleotide 707 of SEQ ID NO:37) and LOX-1 (SEQ ID NO:54), which are 42.0% identical. The overall nucleic acid sequence identity between human TANGO 402 (SEQ ID NO:37) and LOX-1 (SEQ ID NO:54) is 44.0%.

Clone EpT402, which encodes human TANGO 402, was deposited with the American Type Culture Collection (10801 University Boulevard, Manassas, Va. 20110-2209) on Jun. 29, 1999 and assigned Accession Number PTA-294. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 402 Nucleic Acids, Polypeptides, and Modulators Thereof

As TANGO 402 was originally found in a human fetal library, TANGO 402 nucleic acids, proteins, and modulators thereof can be used to diagnose disorders associated with cells, tissues, and/or organs in the embryo or fetus, or modulate the proliferation, development, differentiation, and/or function of cells, tissues, and/or organs in the embryo or fetus.

In addition, as TANGO 402 is homologous to LOX-1, TANGO 402 nucleic acids, proteins and modulators thereof can be utilized to diagnose disorders, modulate development, differentiation, proliferation and/or activity of immune cells, such as macrophages and endothelial cells, e.g., the phagocytosis of aged/apoptotic cells by endothelial cells. TANGO 402 nucleic acids, proteins and modulators thereof can be utilized to treat, inhibit and/or prevent disorders and diseases associated with the aberrant activity of the cells, tissues or organs in which TANGO 402 is expressed, e.g. endothelial activity. TANGO 402 nucleic acids, proteins and modulations thereof can also be used to diagnose disorders and/or modulate symptoms associated with atherosclerosis (e.g., atherosclerotic cardiovascular disease) and Alzheimer's disease. TANGO 402 nucleic acids, proteins and modulators thereof can be used to diagnose disorders associated with host immune defenses and/or modulate host immune defenses, e.g., modulating the activation of macrophages. TANGO 402 nucleic acids, proteins and modulators thereof can be utilized to treat and/or prevent obesity, diabetes, and inflammatory disorders (e.g., asthma, arthritis, multiple sclerosis, allergies, hepatitis and infections).

TANGO 402 nucleic acids, proteins and modulators thereof can be used to modulate e.g., (1) the ability to modulate, e.g., prevent, lipid deposition, e.g., in arteries, and thus modulate, e.g., prevent, intimal thickening; (2) the ability to modulate, e.g., induce or prevent, changes in cells, e.g., transformation of cells (e.g., macrophages and smooth muscle cells) into foam cells and functional alteration of cells (e.g., endothelial cells, e.g., intimal neovascular endothelial cells); (3) the ability to bind and phagocytose cells, e.g., aged and apoptotic cells; and (4) the ability to remove debris, e.g., apoptotic cells, from blood vessel walls.

In another example, TANGO 402 nucleic acids, proteins and modulators thereof can be used to modulate e.g., (1) the ability to modulate homeostasis, e.g., vascular homeostasis, e.g., by modulating, e.g., preventing the impairment of, nitric oxide production; (2) the ability to modulate, e.g., inhibit, the expression of molecules, e.g., adhesion molecules (e.g., leukocyte adhesion molecules) and growth factors (e.g., smooth-muscle growth factors); (3) the ability to alter, e.g., increase, expression in response to stimuli, e.g., TNF, shear stress, and pathophysiological stimuli relevant to disorders (e.g., atherosclerosis and inflammation).

In yet another example, TANGO 402 nucleic acids, proteins and modulators thereof can be used to modulate e.g., (1) the ability to form, e.g., stabilize, promote, facilitate, inhibit, or disrupt, cell-extracellular matrix interactions, e.g., adhesion between cells and extracellular matrix; (2) the ability to form, e.g., stabilize, promote, facilitate, inhibit, or disrupt, cell to cell and cell to blood product interaction, e.g., between leukocytes and platelets or leukocytes and vascular endothelial cells; and (3) the ability to recognize large molecules, e.g., carbohydrates.

In light of the fact that TANGO 402 is homologous to LOX-1, TANGO 402 nucleic acids, proteins and modulators thereof have biological activities that can also include the ability to perform one or more of the functions of LOX-1 described, for example, in the following: Sawamura et al. (1997) *Nature*. 386:73-77; Kataoka et al. (1999) *Circulation*. 99:3110-3117; and Kita (1999) *Circulation Research*. 84:1113-1115, the contents of each of which is incorporated herein by reference in its entirety.

Moreover, due to TANGO 402's homology to LOX-1, as evidenced by the presence of similar domains and mapping coordinates between the two molecules, TANGO 402 nucleic acids, proteins and modulators thereof can be used to modulate or treat disorders in which LOX-1 plays a role, some of which are described in the following references: Sawamura et al. (1997) *Nature*. 386:73-77; Kataoka et al. (1999) *Circulation*. 99:3110-3117; and Kita (1999) *Circulation Research*. 84:1113-1115, the contents of each of which is incorporated herein by reference in its entirety.

Furthermore, TANGO 402 nucleic acids, proteins and modulators thereof can modulate or treat atherosclerosis, e.g., by binding to oxidatively modified low density lipoprotein (Ox-LDL) and its lipid constituents, thus preventing lipid deposition and intimal thickening in the arteries, and thus preventing the induction of endothelial expression of leukocyte adhesion molecules and smooth-muscle growth factors (both which are implicated in atherogenesis).

In another example, TANGO 402 nucleic acids, proteins and modulators thereof modulate or treat immune related diseases and disorders. As LOX-1 is implicated in inflammation, and as LOX-1 has highest homology with the NKR-P1 family of proteins, which are involved in target-cell recognition and natural killer cell activation, TANGO 402-nucleic acids, proteins and modulators thereof can be used to diagnose disorders and/or modulate or treat inflammatory disorders such as bacterial infection, psoriasis, septicemia, cerebral malaria, inflammatory bowel disease, multiple sclerosis, arthritis (e.g., rheumatoid arthritis, osteoarthritis), and allergic inflammatory disorders (e.g., asthma, psoriasis), and processes. Further, TANGO 402 nucleic acids, proteins and modulators thereof can be used to identify, diagnose and/or modulate or treat immune disorders including, e.g., autoimmune disorders (e.g., arthritis, graft rejection (e.g., allograft rejection), and T cell autoimmune disorders (e.g., AIDS)) and inflammatory disorders.

TANGO 402 nucleic acids, proteins and modulators thereof be used to identify, diagnose and/or modulate or treat TNF-related disorders, as LOX-1 expression is induced by tumor necrosis factors. Such disorders include, e.g., acute myocarditis, myocardial infarction, congestive heart failure, T cell disorders (e.g., dermatitis, fibrosis)), differentiative and apoptotic disorders, and disorders related to angiogenesis (e.g., tumor formation and/or metastasis, cancer). As LOX-1 expression is upregulated in hypertensive rats, and as LOX-1 levels are downregulated in patients treated with ACE (angiotensin converting enzyme) inhibitors, TANGO 402 can also play a role in treating hypertension and congestive heart failure.

As both TANGO 402 has C-type lectin domains or C-type lectin-like domains, and is similar in that respect to the selectins, which are implicated in cell-cell recognition (including endothelial-leukocyte adhesion), TANGO 402 nucleic acids, proteins and modulators thereof can be used to identify, diagnose and/or modulate or treat cell adhesion or cell migration/motility related disorders. Such disorders include, e.g., disorders associated with adhesion and migration of cells, e.g., platelet aggregation disorders (e.g., Glanzmann's thromboasthemia, which is a bleeding disorders characterized by failure of platelet aggregation in response to cell stimuli), inflammatory disorders (e.g., leukocyte adhesion deficiency, which is a disorder associated with impaired migration of neutrophils to sites of extravascular inflammation), disorders associated with abnormal tissue migration during embryo development, and tumor metastasis.

As TANGO 402 has a C-type lectin domain or C-type lectin-like domain, TANGO 402 nucleic acids, proteins and modulators thereof can be used to diagnose C-type lectin disorders and/or modulate calcium-dependent carbohydrate recognition. TANGO 402 proteins exhibit homology to lectins. In light of this, TANGO 402 nucleic acids, proteins and modulators thereof can be utilized to modulate cell-cell, cell-extracellular matrix (ECM) interactions, cell adhesion, cell migration and cell signaling. TANGO 402 nucleic acids, proteins and modulators thereof can be utilized to treat and/or prevent disorders and diseases associated with aberrant cell-cell, cell-ECM interactions, cell migration, cell adhesion and cell-signaling, as well as treating and preventing tumor cell metastasis. TANGO 402 nucleic acids, proteins and modulators thereof can also be utilized to treat and/or prevent the migration of cancerous and precancerous cells (e.g., tumor migration).

TANGO 402 nucleic acids, proteins and modulators thereof can also be used to modulate cell proliferation, e.g., abnormal cell proliferation. Such modulation may, for example, be via modulation of one or more elements involved in signal transduction cascades.

TANGO 402 expression can be utilized as a marker (e.g., an in situ marker) for specific tissues (e.g., fetal tissues) and/or cells (e.g., fetal cells) in which TANGO 402 is expressed. TANGO 402 nucleic acids can also be utilized for chromosomal mapping, or as chromosomal markers, e.g., in radiation hybrid mapping.

HUMAN TANGO 351

A cDNA encoding human TANGO 351 was identified by analyzing the sequences of clones present in a human fetal kidney library for sequences that encode wholly secreted or transmembrane proteins. This analysis led to the identification of a clone, jthKa90d12, encoding human TANGO 351. The human TANGO 351 cDNA of this clone is 3345 nucleotides long (FIG. 48A-48C; SEQ ID NO:39). The open reading frame of this cDNA, nucleotides 143 to 1588 of SEQ ID NO:39, encodes a 482 amino acid transmembrane protein ((FIG. 48A-48C; SEQ ID NO:40).

Figure 49:
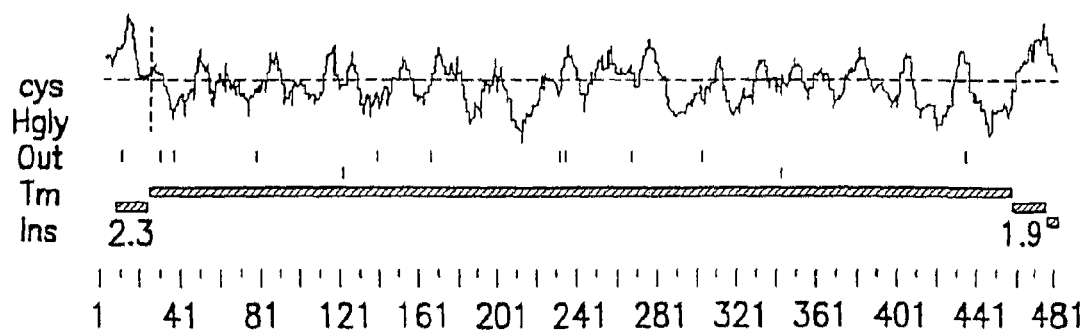
FIG. 49 depicts a hydropathy plot of human TANGO 351, the details of which are described herein. The dashed vertical line separates the signal sequence (amino acids 1 to 24 of SEQ ID NO:40 on the left from the mature protein (amino acids 25 to 482 of SEQ ID NO:40) on the right.

FIG. 49 depicts a hydropathy plot of human TANGO 351, the details of which are described herein.

The signal peptide prediction program SIGNALP (Nielsen et al., 1997, Protein Engineering 10:1-6) predicted that human TANGO 351 includes a 24 amino acid signal peptide (amino acid 1 to amino acid 24 of SEQ ID NO:40) preceding the mature TANGO 351 protein (corresponding to amino acid 25 to amino acid 482 of SEQ ID NO:40). In instances wherein the signal peptide is cleaved, the molecular weight of TANGO 351 protein without post-translational modifications is 53.4 kDa prior to the cleavage of the signal peptide, and 51.1 kDa after cleavage of the signal peptide.

Human TANGO 351 protein is a transmembrane protein that contains an extracellular domain at amino acid residues 25 to 458, a transmembrane domain at amino acid residues 459 to 476, and a cytoplasmic domain at amino acid residues 477 to 482 of SEQ ID NO:40.

In instances wherein the signal peptide is not cleaved, human TANGO 351 has extracellular domains at amino acid residues contains an extracellular domain at amino acid residues 1 to 458, a transmembrane domain at amino acid residues 459 to 476, and a cytoplasmic domain at amino acid residues 477 to 482 of SEQ ID NO:40. In this embodiment, the mature TANGO 351 protein corresponds to amino acids 25 to 482 of SEQ ID NO:40.

In certain embodiments, a TANGO 351 family member has the amino acid sequence of SEQ ID NO:40, and the signal sequence is located at amino acids 1 to 22, 1 to 23, 1 to 24, 1 to 25 or 1 to 26. In such embodiments of the invention, the domains and the mature protein resulting from cleavage of such signal peptides are also included herein. For example, the cleavage of a signal sequence consisting of amino acids 1 to 24 results in an extracellular domain consisting of amino acids 25 to 458 of SEQ ID NO:40 and the mature TANGO 351 protein corresponding to amino acids 25 to 482 of SEQ ID NO:40.

Alternatively, in another embodiment, a human TANGO 351 protein contains a cytoplasmic domain at amino acid residues 25 to 458, a transmembrane domain at amino acid residues 459 to 476, and an extracellular domain at amino acid residues 477 to 482 of SEQ ID NO:40.

In one embodiment a cDNA sequence of human TANGO 351 has a nucleotide at position 153 which is cytosine (C). In this embodiment, the cDNA contains an open reading frame encoding a polypeptide having an amino acid at position 4 that is alanine (A). In an alternative/embodiment, a species variant cDNA sequence of human TANGO 351 has a nucleotide at position 153 which is thymine (T). In this embodiment, the cDNA contains an open reading frame encoding a polypeptide having an amino acid at position 4 that is valine (V), i.e., a conservative substitution.

In another embodiment a cDNA sequence of human TANGO 351 has a nucleotide at position 165 which is adenine (A). In this embodiment, the cDNA contains an open reading frame encoding a polypeptide having an amino acid at position 8 that is tyrosine (Y). In an alternative embodiment, a species variant cDNA sequence of human TANGO 351 has a nucleotide at position 165 which is thymine (T). In this embodiment, the cDNA contains an open reading frame encoding a polypeptide having an amino acid at position 8 that is phenylalanine (F), i.e., a conservative substitution.

In another embodiment a cDNA sequence of human TANGO 351 has a nucleotide at position 269 which is guanine (G). In this embodiment, the cDNA contains an open reading frame encoding a polypeptide having an amino acid at position 43 that is aspartate (D). In an alternative embodiment, a species variant cDNA sequence of human TANGO 351 has a nucleotide at position 269 which is adenine (A). In this embodiment, the cDNA contains an open reading frame encoding a polypeptide having an amino acid at position 43 that is asparagine (N), i.e., a conservative substitution.

In another embodiment a cDNA sequence of human TANGO 351 has a nucleotide at position 273 which is guanine (G). In this embodiment, the cDNA contains an open reading frame encoding a polypeptide having an amino acid at position 44 that is arginine (R). In an alternative embodiment, a species variant cDNA sequence of human TANGO 351 has a nucleotide at position 273 which is adenine (A). In this embodiment, the cDNA contains an open reading frame encoding a polypeptide having an amino acid at position 44 that is lysine (K), i.e., a conservative substitution.

Two N-glycosylation sites are present in TANGO 351. The first has the sequence NQTR (at amino acid residues 131 to 134) and the second has the sequence NFSE (at amino acid residues 353 to 356).

Two cAMP- and cGMP-dependent protein kinase phosphorylation sites are present in TANGO 351. The first has the sequence RRAS (at amino acid residues 94 to 97) and the second has the sequence KRPT (at amino acid residues 424 to 427).

TANGO 351 has seven protein kinase C phosphorylation sites. The first has the sequence TGR (at amino acid residues 62 to 64), the second has the sequence SRR (at amino acid residues 119 to 121), the third has the sequence TGR (at amino acid residues 127 to 129), the fourth has the sequence SAR (at amino acid residues 159 to 161), the fifth has the sequence SPR (at amino acid residues 193 to 195), the sixth has the sequence STR (at amino acid residues 323 to 325), and the seventh has the sequence TER (at amino acid resides 370 to 372).

Six casein kinase II phosphorylation sites are present in TANGO 351. The first has the sequence TEAD (at amino acid residues 104 to 107), the second has the sequence TMHE amino acid residues 173 to 176), the third has the sequence SGCE (at amino acid residues 268 to 271), the fourth has the sequence TPMD (at amino acid residues 342 to 345), the fifth has the sequence TERD (at amino acid residues 370 to 373), and the sixth has the sequence SSPD (at amino acid residues 417 to 420).

TANGO 351 has three tyrosine kinase phosphorylation sites. The first has the sequence RGATEADY (at amino acid residues 101 to 108), the second has the sequence RLVEELY (at amino acid residues 195 to 201), and the third has the sequence RSWEGYY (at amino acid residues 290 to 296). Four N-myristylation sites are present in TANGO 351. The first has the sequence GATEAD (at amino acid residues 102 to 107), the second has the sequence GTPSTR (at amino acid residues 320 to 325), the third has the sequence GGAGAW (at amino acid residues 361 to 366), and the fourth has the sequence GQRPTD (at amino acid residues 410 to 415).

TANGO 351 has a prokaryotic membrane lipoprotein lipid attachment site with the sequence HLGGWWVSSGC (at amino acid residues 260 to 270).

Clone EpT351, which encodes human TANGO 351, was deposited with the American Type Culture Collection (10801 University Boulevard, Manassas, Va. 20110-2209) on Jul. 23, 1999 and assigned Accession Number PTA-424. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 351 Nucleic Acids, Polypeptides, and Modulators Thereof

As TANGO 351 was originally found in a human fetal kidney library, TANGO 351 nucleic acids, proteins and modulators thereof can be used to modulate the proliferation, development, differentiation, and/or function of kidney cells and the kidney. TANGO 351 nucleic acids, proteins and modulators thereof can be used to modulate or treat renal disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal diseasemedullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy), acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

In view of the fact that TANGO 351 is expressed in fetal cells, TANGO 351 nucleic acids, proteins and modulators thereof can be used for the development of an embryo and/or fetus.

TANGO 351 expression can be utilized as a marker (e.g., an in situ marker) for specific tissues (e.g., the kidney) and/or cells (e.g., renal cells) in which TANGO 351 is expressed. TANGO 351 nucleic acids can also be utilized for chromosomal mapping, or as chromosomal markers, e.g., in radiation hybrid mapping.

HUMAN TANGO 509

A cDNA encoding human TANGO 509 was identified by analyzing the sequences of clones present in a mammary epithelium library for sequences that encode wholly secreted or transmembrane proteins. This analysis led to the identification of a clone, jthvb017h11, encoding human TANGO 509. The human TANGO 509 cDNA of this clone is 3575 nucleotides long (FIG. 50A-50C; SEQ ID NO:41). The open reading frame of this cDNA, nucleotides 59 to 928 of (SEQ ID NO:41), encodes a 290 amino acid transmembrane protein (FIG. 50A-50C; SEQ ID NO:42).

Figure 51:
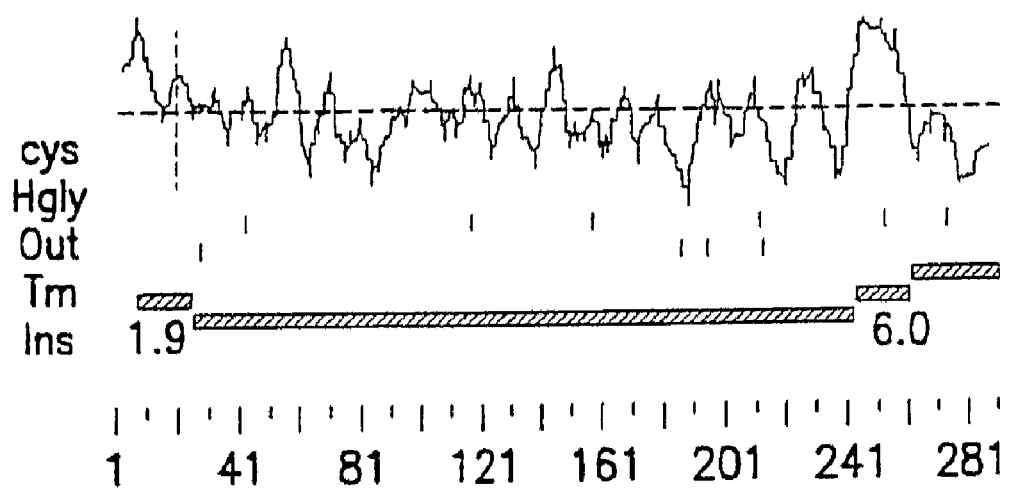
FIG. 51 depicts a hydropathy plot of human TANGO 509 (SEQ ID NO:42), the details of which are described herein. The dashed vertical line separates the signal sequence (amino acids 1 to 18 of SEQ ID NO:42) on the left from the mature protein (amino acids 19 to 290 of SEQ ID NO:42) on the right.

FIG. 51 depicts a hydropathy plot of human TANGO 509, the details of which are described herein.

The signal peptide prediction program SIGNALP (Nielsen et al., 1997, Protein Engineering 10:1-6) predicted that human TANGO 509 includes a 18 amino acid signal peptide (amino acid 1 to amino acid 18 of SEQ ID NO:42) preceding the mature TANGO 509 protein (corresponding to amino acid 19 to amino acid 290 of SEQ ID NO:42). In instances wherein the signal peptide is cleaved, the molecular weight of TANGO 509 protein without post-translational modifications is 33.3 kDa prior to the cleavage of the signal peptide, and 31.0 kDa after cleavage of the signal peptide.

Human TANGO 509 protein is a transmembrane protein that contains an extracellular domain at amino acid residues 260 to 290, a transmembrane domain at amino acid residues 241 to 259, and a cytoplasmic domain at amino acid residues 19 to 240 of SEQ ID NO:42.

In instances wherein the signal peptide is not cleaved, human TANGO 509 contains an extracellular domain at amino acid residues 260 to 290, a transmembrane domain at amino acid residues 241 to 259, and a cytoplasmic domain at amino acid residues 1 to 240 of SEQ ID NO:42.

Alternatively, in another embodiment, a human TANGO 509 protein contains a cytoplasmic domain at amino acid residues 260 to 290, a transmembrane domain at amino acid residues 241 to 259, and an extracelluar domain at amino acid residues 19 to 240 of SEQ ID NO:42.

A human TANGO 509 family member can include one or more of the following domains: (1) an extracellular domain; (2) a transmembrane domain; and (3) a cytoplasmic domain. In one embodiment, a human TANGO 509 protein contains an extracellular domain at about amino acid residues 19 to 240, a transmembrane domain at about amino acid residues 241 to 259, and a cytoplasmic domain at about amino acid residues 260 to 290 of SEQ ID NO:42. In this embodiment, the mature TANGO 509 protein corresponds to amino acids 19 to 290 of SEQ ID NO:42.

A human TANGO 509 family member can include a signal sequence. In certain embodiments, a human TANGO 509 family member has the amino acid sequence of SEQ ID NO:42, and the signal sequence is located at about amino acids 1 to 16, 1 to 17, 1 to 18, 1 to 19, or 1 to 20. In such embodiments of the invention, the domains and the mature protein resulting from cleavage of such signal peptides are also included herein. For example, the cleavage of a signal sequence consisting of amino acids 1 to 18 results in a mature human TANGO 509 protein corresponding to amino acids 19 to 290 of SEQ ID NO:42.

A human TANGO 509 family member can include one or more Ig-like domains. A TANGO 509 Ig-like domain as described herein has the following consensus sequence, beginning about 1 to 15 amino acid residues, more preferably about 3 to 10 amino acid residues, and most preferably about 5 amino acid residues from the domain C-terminus: [FY]-Xaa-C, wherein [FY] is either a phenylalanine or a tyrosine residue (preferably tyrosine), where "Xaa" is any amino acid, and C is a cysteine residue. In one embodiment, a human TANGO 509 family member includes one or more Ig-like domains having an amino acid sequence that is at least about 55%, preferably at least about 65%, more preferably at least 75%, yet more preferably at least about 85%, and most preferably at least about 95% identical to amino acids 33 to 116 or 148 to 211 of SEQ ID NO:42.

In another embodiment, a human TANGO 509 family member includes one or more TANGO 509 Ig-like domains having an amino acid sequence that is at least about 55%, preferably at least about 65%, more preferably at least about 75%, yet more preferably at least about 85%, and most preferably at least about 95% identical to amino acids 33 to 116 or 148 to 211 of SEQ ID NO:42, and has a conserved cysteine residue about 8 residues downstream from the N-terminus of the Ig-like domain. In another embodiment, a human TANGO 509 family member includes one or more TANGO 509 Ig-like domains having an amino acid sequence that is at least 55%, preferably at least about 65%, more preferably at least about 75%, yet more preferably at least about 85%, and most preferably at least about 95% identical to amino acids 33 to 116 or 148 to 211 of SEQ ID NO:42, has a conserved cysteine residue about 8 residues downstream from the N-terminus of the Ig-like domain and has a conserved cysteine within the consensus sequence that forms a disulfide with said first conserved cysteine.

In yet another embodiment, a human TANGO 509 family member includes one or more TANGO 509 Ig-like domains having an amino acid sequence that is at least 55%, preferably at least about 65%, more preferably at least about 75%, yet more preferably at least about 85%, and most preferably at least about 95% identical to amino acids 33 to 116 or 148 to 211 of SEQ ID NO:42, and has a conserved cysteine residue about 8 residues downstream from the N-terminus of the Ig-like domain which has a conserved cysteine within the consensus sequence that forms a disulfide with said first conserved cysteine, and has at least one human TANGO 509 biological activity as described herein.

In another embodiment, the Ig-like domain of human TANGO 509 is an Ig-like domain which has the following consensus sequence at the C-terminus of the domain: [FY]-Xaa-C-Xaa-[VAIF]-COO—, wherein [FY] is either a phenylalanine or a tyrosine residue (preferably tyrosine), where "Xaa" is any amino acid, C is a cysteine residue, [VA] is a valine, an alanine, an isoleucine or phenylalanine residue, and COO— is the C-terminus of the domain. In this embodiment, a human TANGO 509 family member includes one or more of these Ig-like domains having an amino acid sequence that is at least about 55%, preferably at least about 65%, more preferably at least 75%, yet more preferably at least about 85%, and most preferably at least about 95% identical to amino acids 33 to 116 or 148 to 211 of SEQ ID NO:42.

In one embodiment a cDNA sequence of human TANGO 509 has a nucleotide at position 69 which is thymidine (T). In this embodiment, the cDNA contains an open reading frame encoding a polypeptide having an amino acid at position 4 that is phenylalanine (F). In an alternative embodiment, a species variant cDNA sequence of human TANGO 509 has a nucleotide at position 69 which is adenine (A). In this embodiment, the cDNA contains an open reading frame encoding a polypeptide having an amino acid at position 4 that is tyrosine (Y), i.e., a conservative substitution.

In another embodiment a cDNA sequence of human TANGO 509 has a nucleotide at position 72 which is cytosine (C). In this embodiment, the cDNA contains an open reading frame encoding a polypeptide having an amino acid at position 5 that is alanine (A). In an alternative embodiment, a species variant cDNA sequence of human TANGO 509 has a nucleotide at position 72 which is thymine (T). In this embodiment, the cDNA contains an open reading frame encoding a polypeptide having an amino acid at position 5 that is valine (V), i.e., a conservative substitution.

In another embodiment a cDNA sequence of human TANGO 509 has a nucleotide at position 132 which is adenine (A). In this embodiment, the cDNA contains an open reading frame encoding a polypeptide having an amino acid at position 25 that is lysine (K). In an alternative embodiment, a species variant cDNA sequence of human TANGO 509 has a nucleotide at position 132 which is guanine (G). In this embodiment, the cDNA contains an open reading frame encoding a polypeptide having an amino acid at position 25 that is arginine (R), i.e., a conservative substitution.

In another embodiment a cDNA sequence of human TANGO 509 has a nucleotide at position 191 which is guanine (G). In this embodiment, the cDNA contains an open reading frame encoding a polypeptide having an amino acid at position 45 that is glutamate (E). In an alternative embodiment, a species variant cDNA sequence of human TANGO 509 has a nucleotide at position 191 which is cytosine (C). In this embodiment, the cDNA contains an open reading frame encoding a polypeptide having an amino acid at position 45 that is glutamine (Q), i.e., a conservative substitution.

Human TANGO 509 has four N-glycosylation sites with the first sequence NMTI (at amino acid residues 35 to 38), the second has the sequence NVTS (at amino acid residues 192 to 195), the third has the sequence NTTT (at amino acid residues 200 to 203), and the fourth has the sequence NHTA (at amino acid residues 219 to 222).

Two cAMP and cGMP-dependent protein kinase phosphorylation sites are present in human TANGO 509. The first has the sequence KRIT (at amino acid residues 124 to 127), and the second has the sequence KKQS.

Seven protein kinase C phosphorylation sites are present in human TANGO 509. The first has the sequence SYR (at amino acid residues 80 to 82), the second has the sequence TVK (at amino acid residues 127 to 129), the third has the sequence SGK (at amino acid residues 176 to 178), the fourth has the sequence SKR (at amino acid residues 184 to 186), the fifth has the sequence TLR (at amino acid residues 196 to 198), the sixth has the sequence TFR (at amino acid residues 210 to 212), and the seventh has the sequence SKK (at amino acid residues 279 to 281).

Human TANGO 509 has five casein kinase II phosphorylation sites. The first has the sequence SEHE (at amino acid residues 149 to 152), the second has the sequence TSSD (at amino acid residues 168 to 171), the third has the sequence SKRE (at amino acid residues 184 to 187), the fourth has the sequence TTNE (at amino acid residues 202 to 205 SEQ ID NO:68), and the fifth has the sequence THLE (at amino acid residues 285 to 288 SEQ ID NO:68).

Human TANGO 509 has a tyrosine kinase phosphorylation site with the sequence KLQDAGVY (at amino acid residues 105 to 112). Human TANGO 509 has four N-myristoylation sites. The first has the sequence GSNMTI (at amino acid residues 33 to 38), the second has the sequence GVYRCM (at amino acid residues 110 to 115), the third has the sequence GVALTF (at amino acid residues 252 to 257), and fourth has the sequence GIQDTN (at amino acid residues 273 to 278).

FIG. 52 depicts an alignment of the human TANGO 509 amino acid sequence (SEQ ID NO:42) with the butyrophilin-like amino acid sequence (SEQ ID NO:48; Accession Number: AF142780). The alignment shows that there is a 33.0% overall amino acid sequence identity between TANGO 509 and Butyrophilin-like protein. The Butyrophilin-like protein is expressed in dendritic cells which are involved in such processes as antigen presentation and immune stimulation. As such TANGO 509 proteins, nucleic acids and modulators thereof could be useful in immune modulation, for example in antigen presentation and immune stimulation.

Clone EpT509, which encodes human TANGO 509, was deposited with the American Type Culture Collection (10801 University Boulevard, Manassas, Va. 20110-2209) on Aug. 5, 1999 and assigned Accession Number PTA-438. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

MOUSE TANGO 509

A cDNA encoding mouse TANGO 509 was identified by analyzing the sequences of clones present in an alveolar macrophage cell line library. This analysis led to the identification of a clone, jtmca053b03, encoding mouse TANGO 509. The mouse TANGO 509 cDNA of this clone is 3637 nucleotides long (FIG. 53; SEQ ID NO:43). The open reading frame of this cDNA, nucleotides 49 to 918 of SEQ ID NO:43, encodes a 290 amino acid transmembrane protein (FIG. 53; SEQ ID NO:44).

Figure 54:
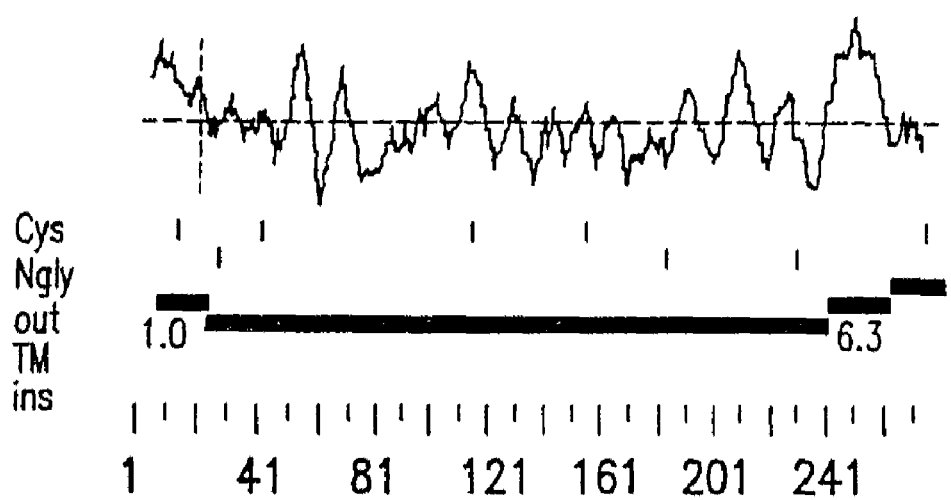
FIG. 54 depicts a hydropathy plot of mouse TANGO 509 (SEQ ID NO:44), the details of which are described herein. The dashed vertical line separates the signal sequence (amino acids 1 to 18 of SEQ ID NO:44) on the left from the mature protein (amino acids 19 to 290 of SEQ ID NO:44) on the right.

FIG. 54 depicts a hydropathy plot of mouse TANGO 509, the details of which are described herein.

The signal peptide prediction program SIGNALP (Nielsen et al., 1997, Protein Engineering 10:1-6) predicted that mouse TANGO 509 includes a 18 amino acid signal peptide (amino acid 1 to amino acid 18 of SEQ ID NO:44) preceding the mature TANGO 509 protein (corresponding to amino acid 19 to amino acid 290 of SEQ ID NO:44). In instances wherein the signal peptide is cleaved, the molecular weight of TANGO 509 protein without post-translational modifications is 33.3 kDa prior to the cleavage of the signal peptide, and 31.0 kDa after cleavage of the signal peptide.

Mouse TANGO 509 protein is a transmembrane protein that contains an extracellular domain at amino acid residues 261 to 290, a transmembrane domain at amino acid residues 240 to 260, and a cytoplasmic domain at amino acid residues 19 to 239 of SEQ ID NO:44.

In instances wherein the signal peptide is not cleaved, mouse TANGO 509 contains an extracellular domain at amino acid residues 261 to 290, a transmembrane domain at amino acid residues 240 to 260, and a cytoplasmic domain at amino acid residues 1 to 239 of SEQ ID NO:44.

Alternatively, in another embodiment, a mouse TANGO 509 protein contains a cytoplasmic domain at amino acid residues 261 to 290, a transmembrane domain at amino acid residues 240 to 260, and an extracellular domain at amino acid residues 19 to 239 of SEQ ID NO:44.

A mouse TANGO 509 family member can include one or more of the following domains: (1) an extracellular domain; (2) a transmembrane domain; and (3) a cytoplasmic domain. In one embodiment, a mouse TANGO 509 protein contains an extracellular domain consisting of amino acids 19 to 239, a transmembrane domain at amino acids 240 to 260, a cytoplasmic domain at amino acids 261 to 290 and a mature mouse TANGO 509 protein at amino acids 19 to 290 of SEQ ID NO:44.

A mouse TANGO 509 family member can include a signal sequence. In certain embodiments, a TANGO 509 family member has the amino acid sequence of SEQ ID NO:44, and the signal sequence is located at about amino acids 1 to 16, 1 to 17, 1 to 18, 1 to 19, or 1 to 20. In such embodiments of the invention, the domains and the mature protein resulting from cleavage of such signal peptides are also included herein. For example, the cleavage of a signal sequence consisting of amino acids 1 to 18 results in a mature mouse TANGO 509 protein corresponding to amino acids 19 to 290 of SEQ ID NO:44.

A mouse TANGO 509 family member can include one or more Ig-like domains. A mouse TANGO 509 Ig-like domain as described herein has the following consensus sequence, beginning about 1 to 15 amino acid residues, more preferably about 3 to 10 amino acid residues, and most preferably about 5 amino acid residues from the domain C-terminus: [FY]-Xaa-C, wherein [FY] is either a phenylalanine or a tyrosine residue (preferably tyrosine), where "Xaa" is any amino acid, and C is a cysteine residue. In one embodiment, a mouse TANGO 509 family member includes one or more such Ig-like domains having an amino acid sequence that is at least about 55%, preferably at least about 65%, more preferably at least about 75%, yet more preferably at least about 85%, and most preferably at least about 95% identical to amino acids 33 to 116 of SEQ ID NO:44.

In another embodiment, a mouse TANGO 509 family member includes one or more mouse TANGO 509 Ig-like domains having an amino acid sequence that is at least about 55%, preferably at least about 65%, more preferably at least about 75%, yet more preferably at least about 85%, and most preferably at least about 95% identical to amino acids 33 to 116 of SEQ ID NO:44, and has a conserved cysteine residue about 8 residues downstream from the N-terminus of the Ig-like domain. In another embodiment, a mouse TANGO 509 family member includes one or more mouse TANGO 509 Ig-like domains having an amino acid sequence that is at least 55%, preferably at least about 65%, more preferably at least about 75%, yet more preferably at least about 85%, and most preferably at least about 95% identical to amino acids 33 to 116 of SEQ ID NO:44, has a conserved cysteine residue about 8 residues downstream from the N-terminus of the Ig-like domain, and has a conserved cysteine within the consensus sequence that forms a disulfide with said first conserved cysteine.

In yet another embodiment, a mouse TANGO 509 family member includes one or more Ig-like domains having an amino acid sequence that is at least 55%, preferably at least about 65%, more preferably at least about 75%, yet more preferably at least about 85%, and most preferably at least about 95% identical to amino acids 33 to 116 of SEQ ID NO:44, and has a conserved cysteine residue about 8 residues downstream from the N-terminus of the Ig-like domain, has a conserved cysteine within the consensus sequence that forms a disulfide with said first conserved cysteine, and has at least one mouse TANGO 509 biological activity as described herein.

In another embodiment, the Ig-like domain of mouse TANGO 509 is an Ig domain which has the following consensus sequence at the C-terminus of the domain: [FY]-Xaa-C-Xaa-[VAIF]-COO—, wherein [FY] is either a phenylalanine or a tyrosine residue (preferably tyrosine), where "Xaa" is any amino acid, C is a cysteine residue, [VA] is a valine, an alanine, an isoleucine or phenylalanine residue, and COO— is the C-terminus of the domain. In this embodiment, a mouse TANGO 509 family member includes one or more Ig-like domains having an amino acid sequence that is at least about 55%, preferably at least about 65%, more preferably at least 75%, yet more preferably at least about 85%, and most preferably at least about 95% identical to amino acids 33 to 116 of SEQ ID NO:44.

In one embodiment a cDNA sequence of mouse TANGO 509 has a nucleotide at position 65 which is thymidine (T). In this embodiment, the cDNA contains an open reading frame encoding a polypeptide having an amino acid at position 4 that is phenylalanine (F). In an alternative embodiment, a species variant cDNA sequence of mouse TANGO 509 has a nucleotide at position 65 which is adenine (A). In this embodiment, the cDNA contains an open reading frame encoding a polypeptide having an amino acid at position 4 that is tyrosine (Y), i.e., a conservative substitution.

In another embodiment a cDNA sequence of mouse TANGO 509 has a nucleotide at position 68 which is cytosine (C). In this embodiment, the cDNA contains an open reading frame encoding a polypeptide having an amino acid at position 5 that is alanine (A). In an alternative embodiment, a species variant cDNA sequence of mouse TANGO 509 has a nucleotide at position 68 which is thymine (T). In this embodiment, the cDNA contains an open reading frame encoding a polypeptide having an amino acid at position 5 that is valine (V), i.e., a conservative substitution.

In another embodiment a cDNA sequence of mouse TANGO 509 has a nucleotide at position 128 which is adenine (A). In this embodiment, the cDNA contains an open reading frame encoding a polypeptide having an amino acid at position 25 that is lysine (K). In an alternative embodiment, a species variant cDNA sequence of mouse TANGO 509 has a nucleotide at position 128 which is guanine (G). In this embodiment, the cDNA contains an open reading frame encoding a polypeptide having an amino acid at position 25 that is arginine (R), i.e., a conservative substitution.

In another embodiment a cDNA sequence of mouse TANGO 509 has a nucleotide at position 132 which is cytosine (C). In this embodiment, the cDNA contains an open reading frame encoding a polypeptide having an amino acid at position 26 that is aspartate (D). In an alternative embodiment, a species variant cDNA sequence of mouse TANGO 509 has a nucleotide at position 132 which is adenine (A). In this embodiment, the cDNA contains an open reading frame encoding a polypeptide having an amino acid at position 45 that is glutamate (E), i.e., a conservative substitution.

Mouse TANGO 509 has six N-glycosylation sites with the first sequence NVTM (at amino acid residues 35 to 38), the second has the sequence NVTS (at amino acid residues 191 to 194), the third has the sequence NATA (at amino acid residues 199 to 202), the fourth has the sequence NHTA (at amino acid residues 218 to 221), the fifth has the sequence NRTH (at amino acid residues 236 to 239), and the sixth has the sequence NDTQ (at amino acid residues 283 to 286).

Mouse TANGO 509 has one cAMP and cGMP-dependent protein kinase phosphorylation site, having the sequence KRIT (at amino acid residues 124 to 127).

Mouse TANGO 509 has five protein kinase C phosphorylation sites. The first has the sequence TLK (at amino acid residues 127 to 129), the second has the sequence SGK (at amino acid residues 175 to 177), the third has the sequence TSR (at amino acid residues 182 to 184), the fourth has the sequence SLR (at amino acid residues 195 to 197), and the fifth has the sequence SSK (at amino acid residues 278 to 280).

Mouse TANGO 509 has five casein kinase II phosphorylation sites. The first has the sequence SEHE (at amino acid residues 148 to 151), the second has the sequence TNSD (at amino acid residues 167 to 170), the third has the sequence SRTE (at amino acid residues 183 to 186), the fourth has the sequence TAND (at amino acid residues 201 to 204), and the fifth has the sequence TQFE (at amino acid residues 285 to 288).

Mouse TANGO 509 has a tyrosine kinase phosphorylation site with the sequence KLQDAGVY (at amino acid residues 105 to 112).

Mouse TANGO 509 has five N-myristoylation sites. The first has the sequence GIIFTA (at amino acid residues 6 to 11), the second has the sequence GSNVTM (at amino acid residues 33 to 38), the third has the sequence GVYCCI (at amino acid residues 110 to 115 SEQ ID NO:78), the fourth has the sequence GMLLNV (at amino acid residues 187 to 192), the fifth has the sequence GQNHTA (at amino acid residues 216 to 221), and the sixth has the sequence GVEDTS (at amino acid residues 273 to 278).

FIG. 55 depicts an alignment of the mouse TANGO 509 amino acid sequence (SEQ ID NO:44) with the butyrophilin-like protein amino acid sequence (SEQ ID NO:48; Accession Number AF142780). The alignment shows that there is a 31.9% overall amino acid sequence identity between mouse TANGO 509 and the butyrophilin-like protein. This alignment was performed using the ALIGN alignment program with a PAM120 scoring matrix, a gap length penalty of 12, and a gap penalty of 4.

Uses of TANGO 509 Nucleic Acids, Polypeptides, and Modulators Thereof

As human TANGO 509 was originally found in a mammary epithelial library, TANGO 509 nucleic acids, proteins, and modulators thereof can be used to modulate the proliferation, activation, development, differentiation, and/or function of mammary cells, tissues and/or organs, e.g., tissues and cells of mammary epithelium origin. TANGO 509 nucleic acids, proteins and modulators thereof can be used to treat mammary-related disorders, e.g., breast cancer.

TANGO 509 exhibits homology to butyrophilin (BTN). BTN is the major protein associated with fat droplets in the milk of many species. BTN has immunoglobulin-like domains and is specifically expressed on the apical surface of mammary epithelial cells during lactation and becomes incorporated as an integral protein into the membrane of the milk fat globule during the budding and secretion of fat droplets into milk. As such, TANGO 509 nucleic acids, proteins and modulators thereof can be utilized to modulate fat secretion, e.g., fat secretion by the mammary epithelium, and milk secretion. In addition, such TANGO 509 compositions and modulators thereof can be used to bind to and, e.g., enhance, deplete or purify milk-associated factors. Further, TANGO 509 nucleic acids, proteins and modulators thereof can be utilized to treat mammary epithelium secretory diseases and/or disorders.

As mouse TANGO 509 was isolated from an alveolar macrophage library, and in light of the fact that TANGO 509 family members have characteristics of immunoglobulin superfamily proteins which are cell surface molecules involved in signal transduction and cellular proliferation, TANGO 509 nucleic acids, proteins and modulators thereof can be utilized to modulate the development and progression of cancerous and non-cancerous cell proliferative disorders, such as deregulated proliferation (such as hyperdysplasia, hyper-IgM syndrome, or lymphoproliferative disorders), cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia), cancers such as neoplasms or tumors (such as carcinomas, sarcomas, adenomas or myeloid lymphoma tumors, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon sarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hematoma, bile duct carcinoma, melanoma, choriocarcinoma, semicoma, embryonal carcinoma, Wilms' tumor, cervical cancer, testicular tumor, lung carcinoma, small cell carcinoma, bladder carcinoma, epithelial carcinoma, glioma, astrocytoma, medulloblastoma, craniopharyngioma, ependynoma, pinealoma, hemangioblastoma, retinoblastoma), leukemias, (e.g. acute lymphocytic leukemia), acute myelocytic leukemia (myelolastic, promyelocytic, myelomonocytic, monocytic and erythroleukemia), chronic leukemias (chronic myelocytic (granulocytic) leukemia and chronic lymphocytic leukemia), or polycythemia vera, or lymphomas (Hodgkin's disease and non-Hodgkin's diseases), multiple myelomas and Waldenström's macroglobulinemia.

As TANGO 509 proteins exhibit similarity to immunoglobulin domains, TANGO 509 nucleic acids, proteins and modulators thereof can be utilized to modulate immune activation. For example, antagonists to TANGO 509 action, such as peptides, antibodies or small molecules that decrease or block TANGO 509 activity, e.g., binding to extracellular matrix components, e.g., integrins, or that prevent TANGO 509 signaling, can be used as immune system activation blockers. In another example, agonists that mimic TANGO 509 activity, such as peptides, antibodies or small molecules, can be used to induce immune system activation. Antibodies may activate or inhibit the cell adhesion, proliferation and activation, and may help in treating infection, autoimmunity, inflammation, and cancer by affecting these cellular processes. TANGO 509 nucleic acids, proteins and modulators thereof can also be utilized to modulate intercellular signaling in the immune system, e.g., modulate intercellular signal transduction in immune stimulation or suppression and modulate immune cell membrane adhesion to ECM components, during development, e.g., late stages of development.

As TANGO 509 family members exhibit homology with the immune co-stimulatory molecules, CD80 and CD86, TANGO 509 nucleic acids, proteins and modulators thereof can be used for modulation of lymphocyte activation, cytokine secretion, e.g., IL-2, B-cell selection and maturation, as well as T-cell selection and maturation. TANGO 509 nucleic acids, proteins and modulators thereof can also be used to treat subjects infected with a pathogen, or to modulate autoimmune diseases, e.g., rheumatoid arthritis, Morbus Bechterew, Sjogren's Syndrome, and ulcerative colitis.

Furthermore, TANGO 509 nucleic acids, proteins and modulators thereof can be used for immune cell receptor co-stimulation via CD28 to modulate IL-2 expression in addition to modulating the expression of other lymphokines. Moreover, TANGO 509 nucleic acids, proteins and modulators thereof can be used to modulate diseases of the immune system, in particular AIDS, asthma or chronic viral diseases such as hepatitis C virus or hepatitis B virus infections, or to modulate the immune system in cancer patients, or patients undergoing organ or tissue transplantation procedures, or inflammatory disorders, e.g., bacterial or viral infection, psoriasis, septicemia, arthritis, allergic reactions.

TANGO 509 expression can be utilized as a marker (e.g., an in situ marker) for specific tissues (e.g., the mammary glands) and/or cells (e.g., mammary epithelial cells) in which TANGO 509 is expressed. TANGO 509 nucleic acids can also be utilized for chromosomal mapping, or as chromosomal markers, e.g., in radiation hybrid mapping.

TABLE 1

Summary of Nucleotide Sequence Information of TANGO 239, TANGO 219, TANGO 232, TANGO 281, A236 (INTERCEPT 236), TANGO 300, TANGO 353, TANGO 393, TANGO 402, TANGO 351 and TANGO 509 Nucleic Acids.

| GENE | FIGURE | (OPEN READING FRAME) and cDNA | POLYPEPTIDE | ATCC ® ACCESSION NUMBER |
|---|---|---|---|---|
| h TANGO 239, form 1 | 1 | (344 to 1990), 3413 base pair (b.p).; SEQ ID NO: 1 | 550 amino acids (a.a.); SEQ ID NO: 2 | 98999 |
| h TANGO 239, form 2 | 4 | (344-2401), 3413 b.p.; SEQ ID NO: 3 | 686 a.a.; SEQ ID NO: 4 | |
| m TANGO 239 | 5 | (209-370), 1029 b.p.; SEQ ID NO: 5 | 54 a.a.; SEQ ID NO: 6 | |
| h TANGO 219 | 6 | (106 to 552), 1268 b.p.; SEQ ID NO: 7 | 149 a.a.; SEQ ID NO: 8 | 98899 |
| m TANGO 219 | 8 | (2 to 370), 397 b.p.; SEQ ID NO: 9 | 123 a.a.; SEQ ID NO: 10 | |
| macaque TANGO 232 | 9 | (96 to 809), 1932 b.p.; SEQ ID NO: 11 | 238 a.a.; SEQ ID NO: 12 | 207045 |
| h TANGO 232, form 1 | 12 | (1 to 366), 1459 b.p.; SEQ ID NO: 13 | 122 a.a.; SEQ ID NO: 14 | 207046 |
| h TANGO 232, form 2 | 15 | (110 to 823), 238 b.p.; SEQ ID NO: 15 | 238 a.a.; SEQ ID NO: 16 | |
| m TANGO 232 | 16 | (79 to 795), 2221 b.p.; SEQ ID NO: 17 | 239 a.a.; SEQ ID NO: 18 | |
| h TANGO 281 | 17 | (65 to 799); 1812 b.p.; SEQ ID NO: 19 | 245 a.a.; SEQ ID NO: 20 | 207222 |
| m TANGO 281 | 20 | (90 to 728), 1858 b.p.; SEQ ID NO: 21 | 213 a.a.; SEQ ID NO: 22 | PTA-224 |
| h A236 (h INTERCEPT 236) | 23 | (314 to 1432), 1948 b.p.; SEQ ID NO: 23 | 373 a.a.; SEQ ID NO: 24 | PTA-34 |
| m A236 (m INTERCEPT 236) | 26 | (304 to 1422), 1949 b.p.; SEQ ID NO: 25 | 373 a.a.; SEQ ID NO: 26 | |
| h TANGO 300 | 30 | (31 to 1113), 1332 b.p.; SEQ ID NO: 27 | 361 a.a.; SEQ ID NO: 28 | PTA-293 |
| m TANGO 300 | 32 | (41 to 1195), 1400 b.p.; SEQ ID NO: 29 | 385 a.a.; SEQ ID NO: 30 | |
| h TANGO 353 | 36 | (76 to 765), 1239 b.p.; SEQ ID NO: 31 | 230 a.a.; SEQ ID NO: 32 | PTA-292 |
| h TANGO 393 | 38 | (40 to 1458), 1778 b.p.; SEQ ID NO: 33 | 473 a.a.; SEQ ID NO: 34 | PTA-295 |
| m TANGO 393 | 40 | (226 to 1644), 1946 b.p.; SEQ ID NO: 35 | 473 a.a.; SEQ ID NO: 36 | PTA-294 |

TABLE 1-continued

Summary of Nucleotide Sequence Information of TANGO 239, TANGO 219, TANGO 232, TANGO 281, A236 (INTERCEPT 236), TANGO 300, TANGO 353, TANGO 393, TANGO 402, TANGO 351 and TANGO 509 Nucleic Acids.

| GENE | FIGURE | (OPEN READING FRAME) and cDNA | POLYPEPTIDE | ATCC ® ACCESSION NUMBER |
|---|---|---|---|---|
| h TANGO 402 | 44 | (87 to 707), 1348 b.p.; SEQ ID NO: 37 | 207 a.a.; SEQ ID NO: 38 | |
| h TANGO 351 | 48 | (143 to 1588), 3345 b.p.; SEQ ID NO: 39 | 482 a.a.; SEQ ID NO: 40 | PTA-424 |
| h TANGO 509 | 50 | (59 to 928), 3575 b.p.; SEQ ID NO: 41 | 290 a.a.; SEQ ID NO: 42 | PTA-438 |
| m TANGO 509 | 53 | (49 to 918), 3637 b.p.; SEQ ID NO: 43 | 290 a.a.; SEQ ID NO: 44 | |

Various aspects of the invention are described in further detail in the following subsections:

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

In instances wherein the nucleic acid molecule is a cDNA or RNA, e.g., mRNA, molecule, such molecules can include a poly A "tail", or, alternatively, can lack such a 3' tail. Although cDNA or RNA nucleotide sequences may be depicted herein with such tail sequences, it is to be understood that cDNA nucleic acid molecules of the invention are also intended to include such sequences lacking the depicted poly A tails.

All or a portion of the nucleic acid sequences of SEQ ID NO:1, 3, 5, 7, 9, 11, 13, 15, 17, 19, 21, 23, 25, 27, 29, 31, 33, 35, 37, 39, 41, 43, or a complement thereof, can be used as molecular weight markers when compared to a comparably sized nucleic acid sequence. Likewise, all or a portion of the amino acid sequences encoded by SEQ ID NO:1, 3, 5, 7, 9, 11, 13, 15, 17, 19, 21, 23, 25, 27, 29, 31, 33, 35, 37, 39, 41 or a complement thereof can be used as molecular weight markers, in particular as molecular weight markers on SDS-PAGE electrophoresis.

A nucleic acid molecule of the present invention, e.g., a nucleic acid molecule having the nucleotide sequence of SEQ ID NO:1, 3, 5, 7, 9, 11, 13, 15, 17, 19, 21, 23, 25, 27, 29, 31, 33, 35, 37, 39, 41, or a complement thereof, can be isolated using standard molecular biology techniques and the sequence information provided herein. Using all or a portion of the nucleic acid sequences of SEQ ID NO:1, 3, 5, 7, 9, 11, 13, 15, 17, 19, 21, 23, 25, 27, 29, 31, 33, 35, 37, 39, or 41, as a hybridization probe, nucleic acid molecules of the invention can be isolated using standard hybridization and cloning techniques (e.g., as described in Sambrook et al., eds., *Molecular Cloning: A Laboratory Manual, 2nd ed., Cold Spring Harbor Laboratory*, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 3, 5, 7, 9, 11, 13, 15, 17, 19, 21, 23, 25, 27, 29, 31, 33, 35, 37, 39, 41, or a portion thereof. A nucleic acid molecule which is complementary to a given nucleotide sequence is one which is sufficiently complementary to the given nucleotide sequence that it can hybridize to the nucleotide sequence under the conditions set forth herein, thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologs in other cell types, e.g., from other tissues, as well as homologs from other mammals. The probe/primer typically comprises substantially purified oligonucleotide. In one embodiment, the oligonucleotide typically comprises a region of nucleotide sequence that hybridizes under stringent conditions to at least about 12, preferably about 25, more preferably about 50, 75, 100, 125, 150, 175, 200, 250, 300, 350 or 400 contiguous nucleotides of the sense or anti-sense sequence of SEQ ID NO:1, 3, 5, 7, 9, 11, 13, 15, 17, 19, 21, 23, 25, 27, 29, 31, 33, 35, 37, 39, 41, of a naturally occurring mutant of SEQ ID NO:1, 3, 5, 7, 9, 11, 13, 15, 17, 19, 21, 23, 25, 27, 29, 31, 33, 35, 37, 39, 41. In another embodiment, the oligonucleotide comprises a region of nucleotide sequence that hybridizes under stringent conditions to at least 400, preferably 450, 500, 530, 550, 600, 700, 800, 900, 1000 or 1150 consecutive oligonucleotides of the sense or antisense sequence of SEQ ID NO:1, 3, 5, 7, 9, 11, 13, 15, 17, 19, 21, 23, 25, 27, 29, 31, 33, 35, 37, 39, 41, of a naturally occurring mutant of SEQ ID NO:1, 3, 5, 7, 9, 11, 13, 15, 17, 19, 21, 23, 25, 27, 29, 31, 33, 35, 37, 39, 41.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NO:1, 3, 5, 7, 9, 11, 13, 15, 17, 19, 21, 23, 25, 27, 29, 31, 33, 35, 37, 39, 41 or 43, expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO: SEQ ID NO:1, 3, 5, 7, 9, 11, 13, 15, 17, 19, 21, 23, 25, 27, 29, 31, 33, 35, 37, 39, 41 or 43 due to degeneracy of the genetic code and thus encode the same protein as that encoded by the nucleotide sequence of SEQ ID NO:1, 3, 5, 7, 9, 11, 13, 15, 17, 19, 21, 23, 25, 27, 29, 31, 33, 35, 37, 39, 41 or 43.

In addition to the nucleotide sequences of SEQ ID NO:1, 3, 5, 7, 9, 11, 13, 15, 17, 19, 21, 23, 25, 27, 29, 31, 33, 35, 37, 39, 41 or 43, it will be appreciated by those skilled in the art that DNA sequence polymorphisms that lead to changes in the amino acid sequence may exist within a population (e.g., the human population). Such genetic polymorphisms may exist among individuals within a population due to natural allelic variation.

An allele is one of a group of genes which occur alternatively at a given genetic locus. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention.

An allele is one of a group of genes which occur alternatively at a given genetic locus. As used herein, the phrase "allelic variant" refers to a nucleotide sequence which occurs at a given locus or to a polypeptide encoded by the nucleotide sequence.

For example, human TANGO 393 maps by homology to ESTs to Chromosome 22 between D22S420 and D22S446; the human gene for TANGO 219 was mapped on radiation hybrid panels to the long arm of chromosome 5, in the region q21-22; and human gene for TANGO 232 was mapped on radiation hybrid panels to the long arm of chromosome 11, in the region q13.

Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention. In one embodiment, polymorphisms that are associated with a particular disease and/or disorder are used as markers to diagnose said disease or disorder. In a preferred embodiment, polymorphisms are used as a marker to diagnose abnormal coronary function such as atherosclerosis.

Moreover, nucleic acid molecules encoding proteins of the invention from other species (homologs), which have a nucleotide sequence which differs from that of the human or mouse protein described herein are intended to be within the scope of the invention. Nucleic acid molecules corresponding to natural allelic variants and homologs of a cDNA of the invention can be isolated based on their identity to the human nucleic acid molecule disclosed herein using the human cDNA, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 500, 600, 700, 800, 900, 1000, 1100, 1200, 1300, 1400, 1500, 1600, 1700, 1800, 1900 or 2000 contiguous nucleotides in length and hybridizes under stringent conditions to the nucleic acid molecule comprising the nucleotide sequence, preferably the coding sequence, of SEQ ID NO:1, 3, 5, 7, 9, 11, 13, 15, 17, 19, 21, 23, 25, 27, 29, 31, 33, 35, 37, 39, 41 or 43, or a complement thereof.

Accordingly, in another embodiment, an isolated nucleic acid molecule of the invention is at least 25, 50, 100, 200, 300, 400, 500, 600, 700, 800 or 900 contiguous nucleotides in length and hybridizes under stringent conditions to the nucleic acid molecule comprising the nucleotide sequence, preferably the coding sequence, of SEQ ID NO:1, 3, 5, 7, 9, 11, 13, 15, 17, 19, 21, 23, 25, 27, 29, 31, 33, 35, 37, 39, 41 or 43, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C. followed by one or more washes in 0.2×SSC, 0.1% SDS at 50-65° C. Another non-limiting example of stringent hybridization conditions are hybridization in 50% formamide, Denhardt's solution, and 6× sodium chloride/sodium citrate (SSC) at about 42° C., followed by removal of the hybridization buffer and subsequently one or more washes in 0.2×SSC, 0.1% SDS at 50-65° C. Preferably, an isolated nucleic acid molecule of the invention that hybridizes under stringent conditions to the sequence of SEQ ID NO:1, 3, 5, 7, 9, 11, 13, 15, 17, 19, 21, 23, 25, 27, 29, 31, 33, 35, 37, 39, 41 or 43 or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., mouse and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:2, 4, 6, 8, 10, 12, 14, 16, 18, 20, 22, 24, 26, 28, 30, 32, 34, 36, 38, 40, 42, and 44, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:2, 4, 6, 8, 10, 12, 14, 16, 18, 20, 22, 24, 26, 28, 30, 32, 34, 36, 38, 40, 42, and 44.

An isolated nucleic acid molecule encoding a variant protein can be created by introducing one or more nucleotide substitutions, additions or deletions into the nucleotide sequence of SEQ ID NO:1, 3, 5, 7, 9, 11, 13, 15, 17, 19, 21, 23, 25, 27, 29, 31, 33, 35, 37, 39, 41 or 43, such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein-protein interactions with proteins in a signaling pathway of the polypeptide of the invention; (2) the ability to bind a ligand of the polypeptide of the invention (i.e., in transmembrane proteins of the invention or alternatively, secreted proteins which are the ligand for a cellular receptor); or (3) the ability to bind to an intracellular target protein of the polypeptide of the invention. In yet another preferred embodiment, the mutant polypeptide can be assayed for the ability to modulate cellular proliferation, cellular migration, motility or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, (1988), *Nature* 334:585-591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987, 071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411-1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al. (1989) *Nucleic Acids Res.* 17:5973-88). PNA monomers are then coupled in a stepwise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

In still other embodiments, the nucleotides of the invention including variants and derivatives can be used as vaccines, for example by genetic immunization. Genetic immunization is particularly advantageous as it stimulates a cytotoxic T-cell response but does not utilize live attenuated vaccines, which can revert to a virulent form and infect the host causing the very infection sought to be prevented. As used herein, genetic immunization comprises inserting the nucleotides of the invention into a host, such that the nucleotides are taken up by cells of the host and the proteins encoded by the nucleotides are translated. These translated proteins are then either secreted or processed by the host cell for presentation to immune cells and an immune reaction is stimulated. Preferably, the immune reaction is a cytotoxic T cell response, however, a humoral response or macrophage stimulation is also useful in preventing future infections. The skilled artisan will appreciate that there are various methods for introducing foreign nucleotides into a host animal and subsequently into cells for genetic immunization, for example, by intramuscular injection of about 50 mg of plasmid DNA encoding the proteins of the invention solubilized in 50 ml of sterile saline solution, with a suitable adjuvant (Weiner and Kennedy (1999) *Scientific American* 7:50-57; Lowrie et al., (1999) *Nature* 400:269-271).

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NO: 2, 4, 6, 8, 10, 12, 14, 16, 18, 20, 22, 24, 26, 28, 30, 32, 34, 36, 38, 40, 42, and 44, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:2, 4, 6, 8, 10, 12, 14, 16, 18, 20, 22, 24, 26, 28, 30, 32, 34, 36, 38, 40, 42, and 44. Other useful proteins are substantially identical (e.g., at least about 45%, preferably 55%, 65%, 75%, 85%, 95%, or 99%) to any of SEQ ID NO:2, 4, 6, 8, 10, 12, 14, 16, 18, 20, 22, 24, 26, 28, 30, 32, 34, 36, 38, 40, 42, and 44, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or I for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

In another embodiment, the protein of the invention can be expressed as a dimer of itself. In this embodiment, a first domain of the protein is fused in frame to the same domain by a linker region. The linker can be a short flexible segment of amino acids, for example GGPGG or GPPGG, or a longer segment as needed. Alternatively, the first domain of the protein can be fused to a second domain of the protein, which is different than the first domain.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused with sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands. The immunoglobulin fusion protein can, for example, comprise a portion of a polypeptide of the invention fused with the amino-terminus or the carboxyl-terminus of an immunoglobulin constant region, as disclosed in U.S. Pat. No. 5,714,147, U.S. Pat. No. 5,116,964, U.S. Pat. No. 5,514, 582, and U.S. Pat. No. 5,455,165.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention SEQ ID NO:14, 34 or 78 can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811-7815; Delgrave et al. (1993) *Protein Engineering* 6(3):327-331).

The polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). In one embodiment, the polypeptides of the invention exhibit reduced levels of O-linked glycosylation and/or N-linked glycosylation relative to endogenously expressed TANGO 239, TANGO 219, TANGO 232, TANGO 281, A236 (INTERCEPT 236), TANGO 300, TANGO 353, TANGO 393, TANGO 402, TANGO 351 and TANGO 509 polypeptides. In another embodiment, the polypeptides of the invention do not exhibit O-linked glycosylation or N-linked glycosylation.

The polypeptides of the invention can, for example, include modifications that can increase such attributes as stability, half-life, ability to enter cells and aid in administration, e.g., in vivo administration of the polypeptides of the invention. For example, polypeptides of the invention can comprise a protein transduction domain of the HIV TAT protein as described in Schwarze, et al. (1999 *Science* 285: 1569-1572), thereby facilitating delivery of polypeptides of the invention into cells.

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:2, 4, 6, 8, 10, 12, 14, 16, 18, 20, 22, 24, 26, 28, 30, 32, 34, 36, 38, 40, 42, and 44, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 2, 8, 20, and 23 and are hydropathy plots of the proteins of the invention. These plots or similar analyses can be used to identify hydrophilic regions. In certain embodiments, the nucleic acid molecules of the invention are present as part of nucleic acid molecules comprising nucleic acid sequences that contain or encode heterologous (e.g., vector, expression vector, or fusion protein) sequences. These nucleotides can then be used to express proteins which can be used as immunogens to generate an immune response, or more particularly, to generate polyclonal or monoclonal antibodies specific to the expressed protein.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions; which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature*

321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899-903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In addition, the TANGO 239, TANGO 219, TANGO 232, TANGO 281, A236 (INTERCEPT 236), TANGO 300, TANGO 353, TANGO 393, TANGO 402, TANGO 351 and TANGO 509 gene sequences and gene products, including peptide fragments and fusion proteins thereof, and antibodies directed against said gene products and peptide fragments thereof, have applications for purposes independent of the role of the gene products, as described above. For example, gene products of the invention, including peptide fragments, as well as specific antibodies thereto, can be used for construction of fusion proteins to facilitate recovery, detection, or localization of another protein of interest. In addition, genes and gene products of the invention can be used for genetic mapping. Finally, TANGO 239, TANGO 219, TANGO 232, TANGO 281, A236 (INTERCEPT 236), TANGO 300, TANGO 353, TANGO 393, TANGO 402, TANGO 351 and TANGO 509 nucleic acids and gene products have generic uses, such as supplemental sources of nucleic acids, proteins and amino acids for food additives or cosmetic products.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-4 ("IL-4"), interleukin-6 ("IL-6"), interleukin-7 ("IL-7"), granulocyte macrophase colony stimulating factor ("GM-CSF"), granulocyte colony stimulating factor ("G-CSF"), interleukin-10 ("IL-10"), interleukin-12 ("IL-12"), interleukin-15 ("IL-15"), interferon-γ ("IFN-γ"), interferon-α ("IFN-α"), or other immune factors or growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with chemotherapeutic agents.

Alternatively, an antibody of the invention can be conjugated to a second antibody to form an "antibody heteroconjugate" as described by Segal in U.S. Pat. No. 4,676,980 or alternatively, two antibodies can be conjugated to each other to create a bispecific heteromers, or an "antibody heteropolymer" as described in Taylor et al., in U.S. Pat. Nos. 5,470,570 and 5,487,890.

An antibody with or without a therapeutic moiety conjugated to it can be used as a therapeutic that is administered alone or in combination with cytotoxic factor(s) and/or cytokine(s).

In yet a further aspect, the invention provides substantially purified antibodies or fragments thereof, including human or non-human antibodies or fragments thereof, which antibodies or fragments specifically bind to a polypeptide of the invention comprising an amino acid sequence selected from the group consisting of: the amino acid sequence of SEQ ED NOs:2, 4, 6, 8, 10, 12, 14, 16, 18, 20, 22, 24, 26, 28, 30, 32, 34, 36, 38, 40, 42, or 44, or the amino acid sequence encoded by the cDNA insert of the plasmid deposited on Oct. 1, 1999 with the ATCC® and having the deposit number 98999, 98899, 207045, 207046, 207222, PTA-34, PTA-34, PTA-224, PTA-293, PTA-292, PTA-295, PTA-294, PTA-424, and PTA-438; a fragment of at least 15 contiguous amino acid residues of the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438; an amino acid sequence which is at least 95% identical to the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NOs:1, 3, 5, 7, 9, 11, 13, 15, 17, 19, 21, 23, 25, 27, 29, 31, 33, 35, 37, 39, 41, 43 or to the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides human or non-human antibodies or fragments thereof, which antibodies or fragments specifically bind to a polypeptide comprising an amino acid sequence selected from the group consisting of: the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438; a fragment of at least 15 contiguous amino acid residues of the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438; an amino acid sequence which is at least 95% identical to the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NOs:1, 3, 5, 7, 9, 11, 13, 15, 17, 19, 21, 23, 25, 27, 29, 31, 33, 35, 37, 39, 41, 43 or to the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide of the invention comprising an amino acid sequence selected from the group consisting of: the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438; a fragment of at least 15 contiguous amino acid residues of the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438; an amino acid sequence which is at least 95% identical to the amino acid sequence of SEQ ID NOs:2, 4, 6, 8, 10, 12, 14, 16, 18, 20, 22, 24, 26, 28, 30, 32, 34, 36, 38, 40, 42, or 44 or the amino acid sequence encoded by the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NOs:1, 3, 5, 7, 9, 11, 13, 15, 17, 19, 21, 23, 25, 27, 29, 31, 33, 35, 37, 39, 41, 43 or the cDNA insert of the plasmid deposited with the ATCC® deposit number 98999, 98899, 207045, 207046, 207222, PTA-34, PTA-34, PTA-224, PTA-293, PTA-292, PTA-295, PTA-294, PTA-424, and PTA-438, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof specifically bind to a signal peptide, a secreted sequence, an extracellular domain, a transmembrane or a cytoplasmic domain cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind to a secreted sequence, or alternatively, to an extracellular domain of the amino acid sequence of the invention. Examples of preferred epitopes, i.e., epitopes in extracellular domains of polypeptides of the invention, can be identified using hydropathy plots as shown in FIGS.: 2, 7, 10, 18, 21, 24, 29, 31, 33, 37, 39, 41, 45, 49, 51 and 54.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes TANGO 239, TANGO 219, TANGO 232, TANGO 281, A236 (INTERCEPT 236), TANGO 300, TANGO 353, TANGO 393, TANGO 402, TANGO 351 and TANGO 509, the method comprising immunizing a mammal with a polypeptide. The polypeptide used as an immunogen comprises an amino acid sequence selected from the group consisting of: the amino acid sequence of any one of SEQ ID NOs:2, 4, 6, 8, 10, 12, 14, 16, 18, 20, 22, 24, 26, 28, 30, 32, 34, 36, 38, 40, 42, or 44 or an amino acid sequence encoded by the cDNA of a clone deposited as ATCC® deposit number 98999, 98899, 207045, 207046, 207222, PTA-34, PTA-34, PTA-224, PTA-293, PTA-292, PTA-295, PTA-294, PTA-424, and PTA-438; a fragment of at least 15 contiguous amino acid residues of the amino acid sequence of any one of SEQ ID NOs:2, 4, 6, 8, 10, 12, 14, 16, 18, 20, 22, 24, 26, 28, 30, 32, 34, 36, 38, 40, 42, or 44 an amino acid sequence which is at least 95% identical to the amino acid sequence of any one of SEQ ID NOs:2, 4, 6, 8, 10, 12, 14, 16, 18, 20, 22, 24, 26, 28, 30, 32, 34, 36, 38, 40, 42, or 44 wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of any one of SEQ ID NOs: 1, 3, 5, 7, 9, 11, 13, 15, 17, 19, 21, 23, 25, 27, 29, 31, 33, 35, 37, 39, 41, or 43, or the cDNA of a clone deposited at ATCC® deposit number 98999, 98899, 207045, 207046, 207222, PTA-34, PTA-34, PTA-224, PTA-293, PTA-292, PTA-295, PTA-294, PTA-424, and PTA-438, or a complement thereof, under conditions of hybridization of 6×SSC at 45° C. and washing in 0.2×SSC, 0.1% SDS at 65° C. After immunization, a sample is collected from the mammal that contains an antibody that specifically recognizes the immunogen. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn 1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and, the a-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., TANGO 239, TANGO 219, TANGO 232, TANGO 281, A236 (INTERCEPT 236), TANGO 300, TANGO 353, TANGO 393, TANGO 402, TANGO 351 and TANGO 509) gene within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene (e.g., TANGO 239, TANGO 219, TANGO 232, TANGO 281, A236 (INTERCEPT 236), TANGO 300, TANGO 353, TANGO 393, TANGO 402, TANGO 351 and TANGO 509) and controls, modulates or activates the endogenous gene. For example, endogenous genes of the invention which are normally "transcriptionally silent", i.e., genes which are normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous genes of the invention may be activated by insertion of a promiscuous regulatory element that works across cell types.

A heterologous regulatory element may be inserted into a stable cell line or cloned microorganism, such that it is operatively linked with and activates expression of endogenous TANGO 239, TANGO 219, TANGO 232, TANGO 281, A236 (INTERCEPT 236), TANGO 300, TANGO 353, TANGO 393, TANGO 402, TANGO 351 and TANGO 509 genes, using techniques, such as targeted homologous recombination, which are well known to those of skill in the art, and described e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. In addition to particular gene expression and/or polypeptide expression phenotypes, the transgenic animals of the invention can exhibit any of the phenotypes (e.g., processes, disorder symptoms and/or disorders), as are described in the sections above. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986) and Wakayama et al., (1999), *Proc. Natl. Acad. Sci. USA,* 96:14984-14989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

Antibodies or antibodies conjugated to therapeutic moieties can be administered to an individual alone or in combination with cytotoxic factor(s), chemotherapeutic drug(s), and/or cytokine(s). If the latter, preferably, the antibodies are administered first and the cytotoxic factor(s), chemotherapeutic drug(s) and/or cytokine(s) are administered thereafter within 24 hours. The antibodies and cytotoxic factor(s), chemotherapeutic drug(s) and/or cytokine(s) can be administered by multiple cycles depending upon the clinical response of the patient. Further, the antibodies and cytotoxic factor(s), chemotherapeutic drug(s) and/or cytokine(s) can be administered by the same or separate routes, for example, by intravenous, intranasal or intramuscular administration. Cytotoxic factors include, but are not limited to, TNF-$\alpha$, TNF-$\beta$, IL-1, IFN-$\gamma$ and IL-2. Chemotherapeutic drugs include, but are not limited to, 5-fluorouracil (5FU), vinblastine, actinomycin D, etoposide, cisplatin, methotrexate and doxorubicin. Cytokines include, but are not limited to, IL-2, IL-3, IL-4, IL-5, IL-6, IL-7, IL-8, IL-9, IL-10 and IL-12.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328, 470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used to (i) modulate cellular proliferation; (ii) modulate cellular differentiation; and/or (iii) modulate cellular adhesion. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869) or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15-25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919-924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223-27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Furthermore, the nucleic acid sequences disclosed herein can be used to perform searches against "mapping databases", e.g., BLAST-type search, such that the chromosome position of the gene is identified by sequence homology or identity with known sequence fragments which have been mapped to chromosomes.

In the instant case, the human gene for TANGO 219 was mapped on radiation hybrid panels to the long arm of chromosome 5, in the region q21-22. Flanking markers for this region are NIB916 and D5S492. The MANA2 (mannosidase, type2), APC (adenomatous polyposis coli), PST (polysialytransferase), CAST (calpastatin) genes also map to this region of the human chromosome. The LGMD1A (limb girdle muscular dystrophy) loci also maps to this region of the human chromosome. This region is syntenic to mouse chromosomes 11 and 18. The Q (quinky), pdw (proportional dwarf), and lyl1 (lymphoblastomic leukemia) loci also map to this region of the mouse chromosome. The Chr.11-fer (protein kinase, testis specific) Chr.18-mcc (mutated in colorectal cancers), pk (plucked), don1 (divergent of neuregulin 1) genes also map to this region of the mouse chromosome.

In the instant case, the human gene for TANGO 232 was mapped on radiation hybrid panels to the long arm of chromosome 11, in the region q13. Flanking markers for this region are D11S1965 and WI-1409. The ARRB1 (arrestin, beta), GIF (gastric intrinsic factor), ACTN3 (actinin, alpha 3) genes also map to this region of the human chromosome. The HBM (high bone mass), OPTB1 (osteoporosis, auto.rec.), OPPG (osteoporosis, pseudoglioma syndrome), BBS1 (Bardet-Biedl syndrome), FIND (Hartnup disorder), MKS2 (Meckel syndrome 2) This region is syntenic to mouse chromosome 7. The oc (osteosclerotic), dc (dancer), nmd (neuromuscular degeneration), ocd (osteochondrodystrophy) loci also map to this region of the mouse chromosome. The pcx (pyruvate decarboxylase), chk (choline kinase), galn (galanin) genes also map to this region of the mouse chromosome.

In the instant case, human TANGO 393 maps by homology to ESTs to Chromosome 22 between D22S420 and D22S446.

In addition, a polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37-41 and Van Keuren et al. (1986) *Hum. Genet.* 74:34-40. Alternatively, the presence of the polypeptide in the somatic cell hybrids can be determined by assaying an activity or property of the polypeptide, for example, enzymatic activity, as described in Bordelon-Riser et al. (1979) *Somatic Cell Genetics* 5:597-613 and Owerbach et al. (1978) *Proc. Natl. Acad. Sci. USA* 75:5640-5644.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 3, 5, 7, 9, 11, 13, 15, 17, 19, 21, 23, 25, 27, 29, 31, 33, 35, 37, 39, 41, or 43 can comfortably provide positive individual identification with a panel of perhaps 10 to 1,000 primers which each yield a noncoding amplified sequence of 100 bases. If predicted coding sequences of any of SEQ ID NO:1, 3, 5, 7, 9, 11, 13, 15, 17, 19, 21, 23, 25, 27, 29, 31, 33, 35, 37, 39, 41, or 43 are used, a more appropriate number of primers for positive individual identification would be 500-2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention, such as a proliferative disorder, e.g., psoriasis or cancer, or an angiogenic disorder. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 3, 5, 7, 9, 11, 13, 15, 17, 19, 21, 23, 25, 27, 29, 31, 33, 35, 37, 39, 41, or 43 or a portion thereof, such as an oligonucleotide of at least 15, 30, 50, 100, 250 or 500 contiguous nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or $F(ab')_2$) can be used The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the sequences of the invention.

For example, kits can be used to determine if a subject is suffering from or is at increased risk of disorders such as immunological disorders, e.g., autoimmune disorders (e.g., arthritis, graft rejection (e.g., allograft rejection), T cell disorders (e.g., AIDS) and inflammatory disorders (e.g., bacterial infection, psoriasis, septicemia, cerebral malaria, inflammatory bowel disease, arthritis (e.g., rheumatoid arthritis, osteoarthritis), and allergic inflammatory disorders (e.g., asthma, psoriasis), neurological disorders, eye disorders and embryonic disorders, which are associated with aberrant expression of a polypeptide of the invention.

In another example, kits can be used to determine if a subject is suffering from or is at risk for brain-related disorders, inflammations, and tumors, and to treat injury or trauma to the brain, which are associated with aberrant activity and/or expression of a polypeptide of the invention.

In another example, kits can be used to determine if a subject is suffering from or is at risk for ion transport disorders which are associated with aberrant expression of a polypeptide of the invention. In another example, kits can be used to determine if a subject is suffering from or is at risk a disorder which is associated with aberrant expression of a polypeptide of the invention. In another example, kits can be used to determine if a subject is suffering from or is at risk for a disorder associated with aberrant expression of a polypeptide of the invention.

The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., an immunologic disorder, or embryonic disorders. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as disorders discussed, for example, in sections above relating to uses of the sequences of the invention.

In another example, prognostic assays described herein can be used to identify a subject having or at risk of developing related disorders associated with expression of polypeptides of the invention.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a gene (see, e.g., Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh, et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., preferably peripheral blood leukocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyl-transferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention/(e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention, as discussed, for example, in sections above relating to uses of the sequences of the invention. For example, disorders characterized by aberrant expression or activity of the polypeptides of the invention include immunologic disorders, prostate disorders, endothelial cell disorders, developmental disorders, embryonic disorders, and neurological disorders. The nucleic acids, polypeptides, and modulators thereof of the invention can be used to treat immunologic diseases and disorders (e.g., monocyte disorders and platelet disorders), prostate disorders, embryonic disorders, and neurological disorders, as well as other disorders described herein.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject.

The prophylactic agents described herein, for example, can be used to treat a subject at risk of developing disorders such as disorders discussed for example, in Sections above relative to the uses of the sequences of the invention. For example, an antagonist of an TANGO 239, TANGO 219, TANGO 232, TANGO 281, A236 (INTERCEPT 236), TANGO 300, TANGO 353, TANGO 393, TANGO 402, TANGO 351 or TANGO 509 protein may be used to modulate or treat an immunological disorder. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell.

In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

This invention is further illustrated by the following examples which should not be construed as limiting. The contents of all references, patents and published patent applications cited throughout this application are hereby incorporated by reference.

Deposit of Clones

A clone encoding human TANGO 239 was deposited on Nov. 20, 1998 with the American Type Culture Collection under ATCC® Accession Number 98999, (also referred to herein as mix EpDHMix1) from which each clone comprising a particular cDNA clone is obtainable. This deposit is a mixture of five strains, each carrying one recombinant plasmid harboring a particular cDNA clone.

A clone encoding human TANGO 219 (clone EpT219) was deposited with the American Type Culture Collection (Manassas, Va.) on Sep. 25, 1998 as Accession Number 98899, as part of a composite deposit representing a mixture of five strains, each carrying one recombinant plasmid harboring a particular cDNA clone.

A clone containing cDNA molecules encoding human TANGO 281 (clone EpT 281) was deposited with the American Type Culture Collection, 10801 University Boulevard, Manassas, Va., 20110-2209, on Apr. 21, 1999 as Accession Number 207222, as part of a composite deposit representing a mixture of strains, each carrying one recombinant plasmid harboring a particular cDNA clone.

A clone containing cDNA molecules encoding TANGO 353 (clone EpT353), was deposited with the American Type Culture Collection (Manassas, Va.) on Jun. 29, 1999 as Accession Number PTA-292, as part of a composite deposit representing a mixture of three strains, each carrying one recombinant plasmid harboring a particular cDNA clone.

A clone containing cDNA molecules encoding TANGO 393 (clone EpT393), was deposited with the American Type Culture Collection (Manassas, Va.) on Jun. 29, 1999 as Accession Number PTA-295, as part of a composite deposit representing a mixture of four strains, each carrying one recombinant plasmid harboring a particular cDNA clone.

A clone containing cDNA molecules encoding TANGO 351 (clone 351), was deposited with the American Type Culture Collection (Manassas, Va.) on Jul. 23, 1999 as Accession Number PTA-424, as part of a composite deposit representing a mixture of five strains, each carrying one recombinant plasmid harboring a particular cDNA clone.

A clone containing cDNA molecules encoding TANGO 509 (509), was deposited with the American Type Culture Collection (Manassas, Va.) on Jul. 29, 1999 as Accession Number PTA-455, Accession Number PTA-438, and Accession Number PTA-438 respectively, as part of a composite deposit representing a mixture of five strains, each carrying one recombinant plasmid harboring a particular cDNA clone.

To distinguish the strains and isolate a strain harboring a particular cDNA clone, one can first streak out an aliquot of the mixture to single colonies on nutrient medium (e.g., LB plates) supplemented with 100 µg/ml ampicillin, grow single colonies, and then extract the plasmid DNA using a standard minipreparation procedure.

A clone containing cDNA molecules encoding TANGO 402 (clone EpT402), was deposited with the American Type Culture Collection (Manassas, Va.) on Jun. 29, 1999 as Accession Number PTA-294, as part of a composite deposit representing a mixture of two strains, each carrying one recombinant plasmid harboring a particular cDNA clone.

One can digest a sample of the DNA minipreparation with a combination of the restriction enzymes Sal I and Not I and resolve the resultant products on a 0.8% agarose gel using standard DNA electrophoresis conditions. The digest will liberate a fragment as follows:

TANGO 239 (EpDH233) 3.0 kb and 3.4 kb
TANGO 219: 1.3 kb
TANGO 393 (EpT393): 1.8 kb
TANGO 353 (EpT353): 1.3 kb
TANGO 351 (351): 3.4 kb.

TANGO 509 (509): 3.6 kb

TANGO 402 (EpT402): 1.4 kb

The TANGO 281 DNA mini-preparation can be digested with a combination of the restriction enzymes SalI, NotI, XbaI and EcorV and the resultant products resolved on a 0.8% agarose gel using standard DNA electrophoresis conditions. The digest liberates fragments as follows:

Human TANGO 281 (clone EpT281): 0.9 kb and 0.9 kb (human TANGO 281 Has an XbaI cut site at about by 900).

The identity of each of the strains can be inferred from the DNA fragments liberated.

All publications, patents and patent applications mentioned in this specification are herein incorporated by reference into the specification to the same extent as if each individual publication, patent or patent application was specifically and individually indicated to be incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

<160> NUMBER OF SEQ ID NOS: 55

<210> SEQ ID NO 1
<211> LENGTH: 3413
<212> TYPE: DNA
<213> ORGANISM: Homo sapiens
<220> FEATURE:
<221> NAME/KEY: CDS
<222> LOCATION: (344)...(1990)

<400> SEQUENCE: 1

```
gtcgacccac gcgtcccggg ctggcctttc aaagtgtgca gttgtctcct ccctgtccag        60
ccccatcgtc gcccaggacc agctgggccg cggtctgacc tgaggctgct gctcagcgcc       120
ggggcgctgg cgctctccat tcgagcacct tccagcatac cgctcggctc cgggagccgc       180
tctgcaaagt tgggcagctc agagcgcaag ctttgcctct cgacttctcc ctccttgggt       240
ccccggcgcc cccgcctccc acgatccctt tcactaggag cagccagtcc cagcgggctg       300
gcaacttgca ccccttccta gtcatcctcc ctgaaacgcg acc atg ctg tta agg        355
                                              Met Leu Leu Arg
                                                1 ggc gtc ctc ctg gcg ttg caa gcc ctg cag ctc gcc ggt gcc ctc gac        403
Gly Val Leu Leu Ala Leu Gln Ala Leu Gln Leu Ala Gly Ala Leu Asp
 5                  10                  15                  20 ctg ccc gct ggg tcc tgt gcc ttt gaa gag agc act tgc ggc ttt gac        451
Leu Pro Ala Gly Ser Cys Ala Phe Glu Glu Ser Thr Cys Gly Phe Asp
                25                  30                  35 tcc gtg ttg gcc tct ctg ccg tgg att tta aat gag gaa ggc cat tac        499
Ser Val Leu Ala Ser Leu Pro Trp Ile Leu Asn Glu Glu Gly His Tyr
            40                  45                  50 att tat gtg gat acc tcc ttt ggc aag cag ggg gag aaa gct gtg ctg        547
Ile Tyr Val Asp Thr Ser Phe Gly Lys Gln Gly Glu Lys Ala Val Leu
        55                  60                  65 cta agt cct gac tta cag gct gag gaa tgg agc tgc ctc cgt ttg gtc        595
Leu Ser Pro Asp Leu Gln Ala Glu Glu Trp Ser Cys Leu Arg Leu Val
    70                  75                  80 tac cag ata acc aca tct tcg gag tct ctg tca gat ccc agc cag ctg        643
Tyr Gln Ile Thr Thr Ser Ser Glu Ser Leu Ser Asp Pro Ser Gln Leu
 85                  90                  95                 100 aac ctc tac atg aga ttt gaa gat gaa agc ttt gat cgc ttg ctt tgg        691
Asn Leu Tyr Met Arg Phe Glu Asp Glu Ser Phe Asp Arg Leu Leu Trp
                105                 110                 115 tca gct aag gaa cct tca gac agc tgg ctc ata gcc agc ttg gat ttg        739
Ser Ala Lys Glu Pro Ser Asp Ser Trp Leu Ile Ala Ser Leu Asp Leu
            120                 125                 130 caa aac agt tcc aag aaa ttc aag att tta ata gaa ggt gta cta gga        787
Gln Asn Ser Ser Lys Lys Phe Lys Ile Leu Ile Glu Gly Val Leu Gly
```

-continued

```
                 135                 140                 145
cag gga aac aca gcc agc atc gca cta ttt gaa atc aag atg aca acc      835
Gln Gly Asn Thr Ala Ser Ile Ala Leu Phe Glu Ile Lys Met Thr Thr
    150                 155                 160 ggc tac tgt att gaa tgt gac ttt gaa gaa aat cat ctc tgt ggc ttt      883
Gly Tyr Cys Ile Glu Cys Asp Phe Glu Glu Asn His Leu Cys Gly Phe
165                 170                 175                 180 gtg aac cgc tgg aat ccc aat gtg aac tgg ttt gtt gga gga gga agt      931
Val Asn Arg Trp Asn Pro Asn Val Asn Trp Phe Val Gly Gly Gly Ser
                185                 190                 195 att cgg aat gtc cac tcc att ctc cca cag gat cac acc ttc aag agt      979
Ile Arg Asn Val His Ser Ile Leu Pro Gln Asp His Thr Phe Lys Ser
            200                 205                 210 gaa ctg ggc cac tac atg tac gtg gac tca gtt tat gtg aag cac ttc     1027
Glu Leu Gly His Tyr Met Tyr Val Asp Ser Val Tyr Val Lys His Phe
        215                 220                 225 cag gag gtg gca cag ctc atc tcc ccg ttg acc acg gcc ccc atg gct     1075
Gln Glu Val Ala Gln Leu Ile Ser Pro Leu Thr Thr Ala Pro Met Ala
    230                 235                 240 ggc tgc ctg tca ttt tat tac cag atc cag cag ggg aat gac aat gtc     1123
Gly Cys Leu Ser Phe Tyr Tyr Gln Ile Gln Gln Gly Asn Asp Asn Val
245                 250                 255                 260 ttt tcc ctt tac act cgg gat gtg gct ggc ctt tac gag gaa atc tgg     1171
Phe Ser Leu Tyr Thr Arg Asp Val Ala Gly Leu Tyr Glu Glu Ile Trp
                265                 270                 275 aaa gca gac agg cca ggg aat gct gcc tgg aac ctt gcg gag gtc gag     1219
Lys Ala Asp Arg Pro Gly Asn Ala Ala Trp Asn Leu Ala Glu Val Glu
            280                 285                 290 ttc aat gct cct tac ccc atg gag gtt att ttt gaa gtt gct ttc aat     1267
Phe Asn Ala Pro Tyr Pro Met Glu Val Ile Phe Glu Val Ala Phe Asn
        295                 300                 305 ggt ccc aag gga ggt tat gtt gcc ctg gat gat att tca ttc tct cct     1315
Gly Pro Lys Gly Gly Tyr Val Ala Leu Asp Asp Ile Ser Phe Ser Pro
    310                 315                 320 gtt cac tgc cag aat cag aca gaa ctt ctg ttc agt gcc gtg gaa gcc     1363
Val His Cys Gln Asn Gln Thr Glu Leu Leu Phe Ser Ala Val Glu Ala
325                 330                 335                 340 agc tgc aat ttt gag caa gat ctc tgc aac ttt tac caa gat aaa gaa     1411
Ser Cys Asn Phe Glu Gln Asp Leu Cys Asn Phe Tyr Gln Asp Lys Glu
                345                 350                 355 ggt cca ggt tgg acc cga gtg aaa gta aaa cca aac atg tat cgg gct     1459
Gly Pro Gly Trp Thr Arg Val Lys Val Lys Pro Asn Met Tyr Arg Ala
            360                 365                 370 gga gac cac act aca ggc tta ggg tat tac ctg cta gcc aac aca aag     1507
Gly Asp His Thr Thr Gly Leu Gly Tyr Tyr Leu Leu Ala Asn Thr Lys
        375                 380                 385 ttc aca tct cag cct ggc tac att gga agg ctc tat ggg ccc tcc cta     1555
Phe Thr Ser Gln Pro Gly Tyr Ile Gly Arg Leu Tyr Gly Pro Ser Leu
    390                 395                 400 cca gga aac ttg cag tat tgt ctg cgt ttt cat tat gcc atc tat gga     1603
Pro Gly Asn Leu Gln Tyr Cys Leu Arg Phe His Tyr Ala Ile Tyr Gly
405                 410                 415                 420 ttt tta aaa atg agt gac acc cta gca gtt tac atc ttt gaa gag aac     1651
Phe Leu Lys Met Ser Asp Thr Leu Ala Val Tyr Ile Phe Glu Glu Asn
                425                 430                 435 cat gtg gtt caa gag aag atc tgg tct gtg ttg gag tcc cca agg ggt     1699
His Val Val Gln Glu Lys Ile Trp Ser Val Leu Glu Ser Pro Arg Gly
            440                 445                 450 gtt tgg atg caa gct gaa atc acc ttt aag aag ccc atg cct acc aag     1747
Val Trp Met Gln Ala Glu Ile Thr Phe Lys Lys Pro Met Pro Thr Lys
```

| | | |
|---|---|---|
| gtg gtt ttc atg agc cta tgc aaa agt ttc tgg gac tgt ggg ctt gta<br>Val Val Phe Met Ser Leu Cys Lys Ser Phe Trp Asp Cys Gly Leu Val<br>470                            475                          480 | | 1795 |
| gcc ctg gat gac att aca ata caa ttg gga agc tgc tca tct tca gag<br>Ala Leu Asp Asp Ile Thr Ile Gln Leu Gly Ser Cys Ser Ser Ser Glu<br>485                            490                          495                    500 | | 1843 |
| aaa ctt cca cct cac ctg gag agt gta ctt tcg agc aag atg aat gta<br>Lys Leu Pro Pro His Leu Glu Ser Val Leu Ser Ser Lys Met Asn Val<br>                  505                          510                          515 | | 1891 |
| cat tta ctc agg aga aaa gaa acc gga gca gct ggc aca gga gga ggg<br>His Leu Leu Arg Arg Lys Glu Thr Gly Ala Ala Gly Thr Gly Gly Gly<br>                520                          525                          530 | | 1939 |
| gag aaa ctc cca ctt cct aca cag gac caa agg gag atc aca cta ctg<br>Glu Lys Leu Pro Leu Pro Thr Gln Asp Gln Arg Glu Ile Thr Leu Leu<br>535                            540                          545 | | 1987 |
| ggg taggctacta catgtacatt gaggcctccc atatggtgta tggacaaaaa<br>Gly | | 2040 |
| gcacgcctct tgtccaggcc tctgcgagga gtctctggaa acactgctt gaccttttc | | 2100 |
| taccacatgt atggaggggg cactggcctg ctgagtgttt atctgaaaaa ggaagaagac | | 2160 |
| agtgaagagt ccctcttatg gaggagaaga ggtgaacaga gcatttcctg gctacgagca | | 2220 |
| ctgattgaat acagctgtga gaggcaacac cagataattt ttgaagccat tcgaggagta | | 2280 |
| tcaataagaa gtgatattgc cattgatgat gttaaatttc aggcaggacc ctgtggagaa | | 2340 |
| atggaagata caactcaaca atcatcagga tattctgagg acttaaatga aattgagtat | | 2400 |
| taagaaatga tctgcattgg atttactaga cgaaaaccat acctctcttc aatcaaaatg | | 2460 |
| aaaacaaagc aaatgaatac tggacagtct taacaatttt ataagttata aaatgacttt | | 2520 |
| agagcaccct ccttcattac ttttgcaaaa acatactgac tcagggctct tttttttctt | | 2580 |
| ttgcatatga caactgttac tagaaataca ggctactggt tttgcataga tcattcatct | | 2640 |
| taatttggt accagttaaa aatacaaatg tactatattg tagtcatttt aaagtacaca | | 2700 |
| aagggcacaa tcaaaatgag atgcactcat ttaaatctgc attcagtgaa tgtattggga | | 2760 |
| gaaaaatagg tcttgcaggt ttcctttga attttaagta tcataaatat ttttaagta | | 2820 |
| aataatacgg ggtgtcagta atatctgcag aatgaatgca gtctttcatg ctaatgagtt | | 2880 |
| agtctggaaa aataaagtct tatttctat gttttattca tagaaatgga gtattaattt | | 2940 |
| ttaatatttt caccatatgt gataacaaag gatctttcat gaatgtccaa gggtaagtca | | 3000 |
| gtattaatta atgctgtatt acaaggcaat gctaccttct ttattccccc tttgaactac | | 3060 |
| ctttgaagtc actatgagca catggataga aatttaactt ttttttgtaa agcaagctta | | 3120 |
| aaatgtttat gtatacatac ccagcaactt ttataaatgt gttaaacaat tttactgatt | | 3180 |
| tttataataa atattttggt aagattttga ataatatgaa ttcaggcaga tatactaaac | | 3240 |
| tgctttatt tacttgttta gaaaattgta tatatatgtt tgtgtatcct aacagctgct | | 3300 |
| atgaaattat aaaattacct aataaaaata atttgaaaat caaaaaaaa aaaaaaaaa | | 3360 |
| aaaaaaaaa aaaaaaaaa aaaaaaaaa aaaaaaaaa aaaaaggggg ggg | | 3413 |

<210> SEQ ID NO 2
<211> LENGTH: 549
<212> TYPE: PRT
<213> ORGANISM: Homo sapiens

<400> SEQUENCE: 2

Met Leu Leu Arg Gly Val Leu Leu Ala Leu Gln Ala Leu Gln Leu Ala

```
               1               5                  10                 15
Gly Ala Leu Asp Leu Pro Ala Gly Ser Cys Ala Phe Glu Glu Ser Thr
                    20                  25                 30

Cys Gly Phe Asp Ser Val Leu Ala Ser Leu Pro Trp Ile Leu Asn Glu
                35                  40                 45

Glu Gly His Tyr Ile Tyr Val Asp Thr Ser Phe Gly Lys Gln Gly Glu
            50                  55                 60

Lys Ala Val Leu Leu Ser Pro Asp Leu Gln Ala Glu Glu Trp Ser Cys
65                  70                  75                 80

Leu Arg Leu Val Tyr Gln Ile Thr Thr Ser Ser Glu Ser Leu Ser Asp
                    85                  90                 95

Pro Ser Gln Leu Asn Leu Tyr Met Arg Phe Glu Asp Glu Ser Phe Asp
                100                 105                110

Arg Leu Leu Trp Ser Ala Lys Glu Pro Ser Asp Ser Trp Leu Ile Ala
                115                 120                125

Ser Leu Asp Leu Gln Asn Ser Ser Lys Lys Phe Lys Ile Leu Ile Glu
                130                 135                140

Gly Val Leu Gly Gln Gly Asn Thr Ala Ser Ile Ala Leu Phe Glu Ile
145                 150                 155                160

Lys Met Thr Thr Gly Tyr Cys Ile Glu Cys Asp Phe Glu Glu Asn His
                    165                 170                175

Leu Cys Gly Phe Val Asn Arg Trp Asn Pro Asn Val Asn Trp Phe Val
                180                 185                190

Gly Gly Gly Ser Ile Arg Asn Val His Ser Ile Leu Pro Gln Asp His
                195                 200                205

Thr Phe Lys Ser Glu Leu Gly His Tyr Met Tyr Val Asp Ser Val Tyr
            210                 215                220

Val Lys His Phe Gln Glu Val Ala Gln Leu Ile Ser Pro Leu Thr Thr
225                 230                 235                240

Ala Pro Met Ala Gly Cys Leu Ser Phe Tyr Tyr Gln Ile Gln Gln Gly
                    245                 250                255

Asn Asp Asn Val Phe Ser Leu Tyr Thr Arg Asp Val Ala Gly Leu Tyr
                260                 265                270

Glu Glu Ile Trp Lys Ala Asp Arg Pro Gly Asn Ala Ala Trp Asn Leu
            275                 280                285

Ala Glu Val Glu Phe Asn Ala Pro Tyr Pro Met Glu Val Ile Phe Glu
                290                 295                300

Val Ala Phe Asn Gly Pro Lys Gly Gly Tyr Val Ala Leu Asp Asp Ile
305                 310                 315                320

Ser Phe Ser Pro Val His Cys Gln Asn Gln Thr Glu Leu Leu Phe Ser
                    325                 330                335

Ala Val Glu Ala Ser Cys Asn Phe Glu Gln Asp Leu Cys Asn Phe Tyr
                340                 345                350

Gln Asp Lys Glu Gly Pro Gly Trp Thr Arg Val Lys Val Lys Pro Asn
            355                 360                365

Met Tyr Arg Ala Gly Asp His Thr Thr Gly Leu Gly Tyr Tyr Leu Leu
                370                 375                380

Ala Asn Thr Lys Phe Thr Ser Gln Pro Gly Tyr Ile Gly Arg Leu Tyr
385                 390                 395                400

Gly Pro Ser Leu Pro Gly Asn Leu Gln Tyr Cys Leu Arg Phe His Tyr
                    405                 410                415

Ala Ile Tyr Gly Phe Leu Lys Met Ser Asp Thr Leu Ala Val Tyr Ile
                420                 425                430
```

```
                Phe Glu Glu Asn His Val Val Gln Glu Lys Ile Trp Ser Val Leu Glu
                    435                 440                 445
                Ser Pro Arg Gly Val Trp Met Gln Ala Glu Ile Thr Phe Lys Lys Pro
                    450                 455                 460
                Met Pro Thr Lys Val Val Phe Met Ser Leu Cys Lys Ser Phe Trp Asp
                465                 470                 475                 480
                Cys Gly Leu Val Ala Leu Asp Asp Ile Thr Ile Gln Leu Gly Ser Cys
                                485                 490                 495
                Ser Ser Ser Glu Lys Leu Pro Pro His Leu Glu Ser Val Leu Ser Ser
                            500                 505                 510
                Lys Met Asn Val His Leu Leu Arg Arg Lys Glu Thr Gly Ala Ala Gly
                            515                 520                 525
                Thr Gly Gly Gly Glu Lys Leu Pro Leu Pro Thr Gln Asp Gln Arg Glu
                        530                 535                 540
                Ile Thr Leu Leu Gly
                545

<210> SEQ ID NO 3
<211> LENGTH: 3413
<212> TYPE: DNA
<213> ORGANISM: Homo sapiens
<220> FEATURE:
<221> NAME/KEY: CDS
<222> LOCATION: (344)...(2401)

<400> SEQUENCE: 3
gtcgacccac gcgtcccggg ctggcctttc aaagtgtgca gttgtctcct ccctgtccag      60
ccccatcgtc gcccaggacc agctgggccg cggtctgacc tgaggctgct gctcagcgcc     120
ggggcgctgg cgctctccat tcgagcacct tccagcatac cgctcggctc cgggagccgc     180
tctgcaaagt tgggcagctc agagcgcaag cttttgcctct cgacttctcc ctccttgggt     240
ccccggcgcc cccgcctccc acgatccctt tcactaggag cagccagtcc cagcgggctg     300
gcaacttgca ccccttccta gtcatcctcc ctgaaacgcg acc atg ctg tta agg      355
                                                Met Leu Leu Arg
                                                  1 ggc gtc ctc ctg gcg ttg caa gcc ctg cag ctc gcc ggt gcc ctc gac      403
Gly Val Leu Leu Ala Leu Gln Ala Leu Gln Leu Ala Gly Ala Leu Asp
  5                  10                  15                  20 ctg ccc gct ggg tcc tgt gcc ttt gaa gag agc act tgc ggc ttt gac      451
Leu Pro Ala Gly Ser Cys Ala Phe Glu Glu Ser Thr Cys Gly Phe Asp
                 25                  30                  35 tcc gtg ttg gcc tct ctg ccg tgg att tta aat gag gaa ggc cat tac      499
Ser Val Leu Ala Ser Leu Pro Trp Ile Leu Asn Glu Glu Gly His Tyr
             40                  45                  50 att tat gtg gat acc tcc ttt ggc aag cag ggg gag aaa gct gtg ctg      547
Ile Tyr Val Asp Thr Ser Phe Gly Lys Gln Gly Glu Lys Ala Val Leu
         55                  60                  65 cta agt cct gac tta cag gct gag gaa tgg agc tgc ctc cgt ttg gtc      595
Leu Ser Pro Asp Leu Gln Ala Glu Glu Trp Ser Cys Leu Arg Leu Val
     70                  75                  80 tac cag ata acc aca tct tcg gag tct ctg tca gat ccc agc cag ctg      643
Tyr Gln Ile Thr Thr Ser Ser Glu Ser Leu Ser Asp Pro Ser Gln Leu
 85                  90                  95                 100 aac ctc tac atg aga ttt gaa gat gaa agc ttt gat cgc ttg ctt tgg      691
Asn Leu Tyr Met Arg Phe Glu Asp Glu Ser Phe Asp Arg Leu Leu Trp
                105                 110                 115 tca gct aag gaa cct tca gac agc tgg ctc ata gcc agc ttg gat ttg      739
Ser Ala Lys Glu Pro Ser Asp Ser Trp Leu Ile Ala Ser Leu Asp Leu
            120                 125                 130
```

```
caa aac agt tcc aag aaa ttc aag att tta ata gaa ggt gta cta gga       787
Gln Asn Ser Ser Lys Lys Phe Lys Ile Leu Ile Glu Gly Val Leu Gly
        135                 140                 145 cag gga aac aca gcc agc atc gca cta ttt gaa atc aag atg aca acc       835
Gln Gly Asn Thr Ala Ser Ile Ala Leu Phe Glu Ile Lys Met Thr Thr
150                 155                 160 ggc tac tgt att gaa tgt gac ttt gaa gaa aat cat ctc tgt ggc ttt       883
Gly Tyr Cys Ile Glu Cys Asp Phe Glu Glu Asn His Leu Cys Gly Phe
165                 170                 175                 180 gtg aac cgc tgg aat ccc aat gtg aac tgg ttt gtt gga gga gga agt       931
Val Asn Arg Trp Asn Pro Asn Val Asn Trp Phe Val Gly Gly Gly Ser
            185                 190                 195 att cgg aat gtc cac tcc att ctc cca cag gat cac acc ttc aag agt       979
Ile Arg Asn Val His Ser Ile Leu Pro Gln Asp His Thr Phe Lys Ser
        200                 205                 210 gaa ctg ggc cac tac atg tac gtg gac tca gtt tat gtg aag cac ttc      1027
Glu Leu Gly His Tyr Met Tyr Val Asp Ser Val Tyr Val Lys His Phe
    215                 220                 225 cag gag gtg gca cag ctc atc tcc ccg ttg acc acg gcc ccc atg gct      1075
Gln Glu Val Ala Gln Leu Ile Ser Pro Leu Thr Thr Ala Pro Met Ala
230                 235                 240 ggc tgc ctg tca ttt tat tac cag atc cag cag ggg aat gac aat gtc      1123
Gly Cys Leu Ser Phe Tyr Tyr Gln Ile Gln Gln Gly Asn Asp Asn Val
245                 250                 255                 260 ttt tcc ctt tac act cgg gat gtg gct ggc ctt tac gag gaa atc tgg      1171
Phe Ser Leu Tyr Thr Arg Asp Val Ala Gly Leu Tyr Glu Glu Ile Trp
            265                 270                 275 aaa gca gac agg cca ggg aat gct gcc tgg aac ctt gcg gag gtc gag      1219
Lys Ala Asp Arg Pro Gly Asn Ala Ala Trp Asn Leu Ala Glu Val Glu
        280                 285                 290 ttc aat gct cct tac ccc atg gag gtt att ttt gaa gtt gct ttc aat      1267
Phe Asn Ala Pro Tyr Pro Met Glu Val Ile Phe Glu Val Ala Phe Asn
    295                 300                 305 ggt ccc aag gga ggt tat gtt gcc ctg gat gat att tca ttc tct cct      1315
Gly Pro Lys Gly Gly Tyr Val Ala Leu Asp Asp Ile Ser Phe Ser Pro
310                 315                 320 gtt cac tgc cag aat cag aca gaa ctt ctg ttc agt gcc gtg gaa gcc      1363
Val His Cys Gln Asn Gln Thr Glu Leu Leu Phe Ser Ala Val Glu Ala
325                 330                 335                 340 agc tgc aat ttt gag caa gat ctc tgc aac ttt tac caa gat aaa gaa      1411
Ser Cys Asn Phe Glu Gln Asp Leu Cys Asn Phe Tyr Gln Asp Lys Glu
            345                 350                 355 ggt cca ggt tgg acc cga gtg aaa gta aaa cca aac atg tat cgg gct      1459
Gly Pro Gly Trp Thr Arg Val Lys Val Lys Pro Asn Met Tyr Arg Ala
        360                 365                 370 gga gac cac act aca ggc tta ggg tat tac ctg cta gcc aac aca aag      1507
Gly Asp His Thr Thr Gly Leu Gly Tyr Tyr Leu Leu Ala Asn Thr Lys
    375                 380                 385 ttc aca tct cag cct ggc tac att gga agg ctc tat ggg ccc tcc cta      1555
Phe Thr Ser Gln Pro Gly Tyr Ile Gly Arg Leu Tyr Gly Pro Ser Leu
390                 395                 400 cca gga aac ttg cag tat tgt ctg cgt ttt cat tat gcc atc tat gga      1603
Pro Gly Asn Leu Gln Tyr Cys Leu Arg Phe His Tyr Ala Ile Tyr Gly
405                 410                 415                 420 ttt tta aaa atg agt gac acc cta gca gtt tac atc ttt gaa gag aac      1651
Phe Leu Lys Met Ser Asp Thr Leu Ala Val Tyr Ile Phe Glu Glu Asn
            425                 430                 435 cat gtg gtt caa gag aag atc tgg tct gtg ttg gag tcc cca agg ggt      1699
His Val Val Gln Glu Lys Ile Trp Ser Val Leu Glu Ser Pro Arg Gly
        440                 445                 450
```

|  |  |
|---|---|
| gtt tgg atg caa gct gaa atc acc ttt aag aag ccc atg cct acc aag<br>Val Trp Met Gln Ala Glu Ile Thr Phe Lys Lys Pro Met Pro Thr Lys<br>455 460 465 | 1747 |
| gtg gtt ttc atg agc cta tgc aaa agt ttc tgg gac tgt ggg ctt gta<br>Val Val Phe Met Ser Leu Cys Lys Ser Phe Trp Asp Cys Gly Leu Val<br>470 475 480 | 1795 |
| gcc ctg gat gac att aca ata caa ttg gga agc tgc tca tct tca gag<br>Ala Leu Asp Asp Ile Thr Ile Gln Leu Gly Ser Cys Ser Ser Ser Glu<br>485 490 495 500 | 1843 |
| aaa ctt cca ccc tca cct gga gag tgt act ttc gag caa gat gaa tgt<br>Lys Leu Pro Pro Ser Pro Gly Glu Cys Thr Phe Glu Gln Asp Glu Cys<br>505 510 515 | 1891 |
| aca ttt act cag gag aaa aga aac cgg agc agc tgg cac agg agg agg<br>Thr Phe Thr Gln Glu Lys Arg Asn Arg Ser Ser Trp His Arg Arg Arg<br>520 525 530 | 1939 |
| gga gaa act ccc act tcc tac aca gga cca aag gga gat cac act act<br>Gly Glu Thr Pro Thr Ser Tyr Thr Gly Pro Lys Gly Asp His Thr Thr<br>535 540 545 | 1987 |
| ggg gta ggc tac tac atg tac att gag gcc tcc cat atg gtg tat gga<br>Gly Val Gly Tyr Tyr Met Tyr Ile Glu Ala Ser His Met Val Tyr Gly<br>550 555 560 | 2035 |
| caa aaa gca cgc ctc ttg tcc agg cct ctg cga gga gtc tct gga aaa<br>Gln Lys Ala Arg Leu Leu Ser Arg Pro Leu Arg Gly Val Ser Gly Lys<br>565 570 575 580 | 2083 |
| cac tgc ttg acc ttt ttc tac cac atg tat gga ggg gcc act ggc ctg<br>His Cys Leu Thr Phe Phe Tyr His Met Tyr Gly Gly Gly Thr Gly Leu<br>585 590 595 | 2131 |
| ctg agt gtt tat ctg aaa aag gaa gaa gac agt gaa gag tcc ctc tta<br>Leu Ser Val Tyr Leu Lys Lys Glu Glu Asp Ser Glu Glu Ser Leu Leu<br>600 605 610 | 2179 |
| tgg agg aga aga ggt gaa cag agc att tcc tgg cta cga gca ctg att<br>Trp Arg Arg Arg Gly Glu Gln Ser Ile Ser Trp Leu Arg Ala Leu Ile<br>615 620 625 | 2227 |
| gaa tac agc tgt gag agg caa cac cag ata att ttt gaa gcc att cga<br>Glu Tyr Ser Cys Glu Arg Gln His Gln Ile Ile Phe Glu Ala Ile Arg<br>630 635 640 | 2275 |
| gga gta tca ata aga agt gat att gcc att gat gat gtt aaa ttt cag<br>Gly Val Ser Ile Arg Ser Asp Ile Ala Ile Asp Asp Val Lys Phe Gln<br>645 650 655 660 | 2323 |
| gca gga ccc tgt gga gaa atg gaa gat aca act caa caa tca tca gga<br>Ala Gly Pro Cys Gly Glu Met Glu Asp Thr Thr Gln Gln Ser Ser Gly<br>665 670 675 | 2371 |
| tat tct gag gac tta aat gaa att gag tat taagaaatga tctgcattgg<br>Tyr Ser Glu Asp Leu Asn Glu Ile Glu Tyr<br>680 685 | 2421 |
| atttactaga cgaaaaccat acctctcttc aatcaaaatg aaaacaaagc aaatgaatac | 2481 |
| tggacagtct taacaatttt ataagttata aaatgacttt agagcaccct ccttcattac | 2541 |
| ttttgcaaaa acatactgac tcagggctct ttttttcttt ttgcatatga caactgttac | 2601 |
| tagaaataca ggctactggt tttgcataga tcattcatct taattttggt accagttaaa | 2661 |
| aatacaaatg tactatattg tagtcatttt aaagtacaca aagggcacaa tcaaaatgag | 2721 |
| atgcactcat ttaaatctgc attcagtgaa tgtattggga gaaaaatagg tcttgcaggt | 2781 |
| ttccttttga atttttaagta tcataaatat ttttttaagta aataatacgg ggtgtcagta | 2841 |
| atatctgcag aatgaatgca gtctttcatg ctaatgagtt agtctggaaa aataaagtct | 2901 |
| tattttctat gttttattca tagaaatgga gtattaattt ttaatatttt caccatatgt | 2961 |
| gataacaaag gatctttcat gaatgtccaa gggtaagtca gtattaatta atgctgtatt | 3021 |

-continued

```
acaaggcaat gctaccttct ttattccccc tttgaactac ctttgaagtc actatgagca   3081
catggataga aatttaactt ttttttgtaa agcaagctta aaatgtttat gtatacatac   3141
ccagcaactt ttataaatgt gttaaacaat tttactgatt tttataataa atattttggt   3201
aagattttga ataatatgaa ttcaggcaga tatactaaac tgcttttatt tacttgttta   3261
gaaaattgta tatatatgtt tgtgtatcct aacagctgct atgaaattat aaaattaccct  3321 aataaaaata atttgaaaat caaaaaaaaa aaaaaaaaaa aaaaaaaaaa aaaaaaaaa   3381 aaaaaaaaaa aaaaaaaaaa aaaaaagggg gg                               3413
```

<210> SEQ ID NO 4
<211> LENGTH: 686
<212> TYPE: PRT
<213> ORGANISM: Homo sapiens

<400> SEQUENCE: 4

```
Met Leu Leu Arg Gly Val Leu Ala Leu Gln Ala Leu Gln Leu Ala
 1               5                  10                  15

Gly Ala Leu Asp Leu Pro Ala Gly Ser Cys Ala Phe Glu Glu Ser Thr
                20                  25                  30

Cys Gly Phe Asp Ser Val Leu Ala Ser Leu Pro Trp Ile Leu Asn Glu
            35                  40                  45

Glu Gly His Tyr Ile Tyr Val Asp Thr Ser Phe Gly Lys Gln Gly Glu
    50                  55                  60

Lys Ala Val Leu Leu Ser Pro Asp Leu Gln Ala Glu Glu Trp Ser Cys
65                  70                  75                  80

Leu Arg Leu Val Tyr Gln Ile Thr Thr Ser Glu Ser Leu Ser Asp
                85                  90                  95

Pro Ser Gln Leu Asn Leu Tyr Met Arg Phe Glu Asp Glu Ser Phe Asp
            100                 105                 110

Arg Leu Leu Trp Ser Ala Lys Glu Pro Ser Asp Ser Trp Leu Ile Ala
        115                 120                 125

Ser Leu Asp Leu Gln Asn Ser Ser Lys Lys Phe Lys Ile Leu Ile Glu
    130                 135                 140

Gly Val Leu Gly Gln Gly Asn Thr Ala Ser Ile Ala Leu Phe Glu Ile
145                 150                 155                 160

Lys Met Thr Thr Gly Tyr Cys Ile Glu Cys Asp Phe Glu Glu Asn His
                165                 170                 175

Leu Cys Gly Phe Val Asn Arg Trp Asn Pro Asn Val Asn Trp Phe Val
            180                 185                 190

Gly Gly Gly Ser Ile Arg Asn Val His Ser Ile Leu Pro Gln Asp His
        195                 200                 205

Thr Phe Lys Ser Glu Leu Gly His Tyr Met Tyr Val Asp Ser Val Tyr
    210                 215                 220

Val Lys His Phe Gln Glu Val Ala Gln Leu Ile Ser Pro Leu Thr Thr
225                 230                 235                 240

Ala Pro Met Ala Gly Cys Leu Ser Phe Tyr Tyr Gln Ile Gln Gln Gly
                245                 250                 255

Asn Asp Asn Val Phe Ser Leu Tyr Thr Arg Asp Val Ala Gly Leu Tyr
            260                 265                 270

Glu Glu Ile Trp Lys Ala Asp Arg Pro Gly Asn Ala Ala Trp Asn Leu
        275                 280                 285

Ala Glu Val Glu Phe Asn Ala Pro Tyr Pro Met Glu Val Ile Phe Glu
    290                 295                 300
```

-continued

```
Val Ala Phe Asn Gly Pro Lys Gly Gly Tyr Val Ala Leu Asp Asp Ile
305                 310                 315                 320

Ser Phe Ser Pro Val His Cys Gln Asn Gln Thr Glu Leu Leu Phe Ser
                325                 330                 335

Ala Val Glu Ala Ser Cys Asn Phe Glu Gln Asp Leu Cys Asn Phe Tyr
            340                 345                 350

Gln Asp Lys Glu Gly Pro Gly Trp Thr Arg Val Lys Val Lys Pro Asn
        355                 360                 365

Met Tyr Arg Ala Gly Asp His Thr Thr Gly Leu Gly Tyr Tyr Leu Leu
    370                 375                 380

Ala Asn Thr Lys Phe Thr Ser Gln Pro Gly Tyr Ile Gly Arg Leu Tyr
385                 390                 395                 400

Gly Pro Ser Leu Pro Gly Asn Leu Gln Tyr Cys Leu Arg Phe His Tyr
                405                 410                 415

Ala Ile Tyr Gly Phe Leu Lys Met Ser Asp Thr Leu Ala Val Tyr Ile
            420                 425                 430

Phe Glu Glu Asn His Val Val Gln Glu Lys Ile Trp Ser Val Leu Glu
        435                 440                 445

Ser Pro Arg Gly Val Trp Met Gln Ala Glu Ile Thr Phe Lys Lys Pro
    450                 455                 460

Met Pro Thr Lys Val Val Phe Met Ser Leu Cys Lys Ser Phe Trp Asp
465                 470                 475                 480

Cys Gly Leu Val Ala Leu Asp Asp Ile Thr Ile Gln Leu Gly Ser Cys
                485                 490                 495

Ser Ser Ser Glu Lys Leu Pro Pro Ser Pro Gly Glu Cys Thr Phe Glu
            500                 505                 510

Gln Asp Glu Cys Thr Phe Thr Gln Glu Lys Arg Asn Arg Ser Ser Trp
        515                 520                 525

His Arg Arg Arg Gly Glu Thr Pro Thr Ser Tyr Thr Gly Pro Lys Gly
    530                 535                 540

Asp His Thr Thr Gly Val Gly Tyr Tyr Met Tyr Ile Glu Ala Ser His
545                 550                 555                 560

Met Val Tyr Gly Gln Lys Ala Arg Leu Leu Ser Arg Pro Leu Arg Gly
                565                 570                 575

Val Ser Gly Lys His Cys Leu Thr Phe Phe Tyr His Met Tyr Gly Gly
            580                 585                 590

Gly Thr Gly Leu Leu Ser Val Tyr Leu Lys Lys Glu Glu Asp Ser Glu
        595                 600                 605

Glu Ser Leu Leu Trp Arg Arg Gly Glu Gln Ser Ile Ser Trp Leu
    610                 615                 620

Arg Ala Leu Ile Glu Tyr Ser Cys Glu Arg Gln His Gln Ile Ile Phe
625                 630                 635                 640

Glu Ala Ile Arg Gly Val Ser Ile Arg Ser Asp Ile Ala Ile Asp Asp
                645                 650                 655

Val Lys Phe Gln Ala Gly Pro Cys Gly Glu Met Glu Asp Thr Thr Gln
            660                 665                 670

Gln Ser Ser Gly Tyr Ser Glu Asp Leu Asn Glu Ile Glu Tyr
        675                 680                 685

<210> SEQ ID NO 5
<211> LENGTH: 1029
<212> TYPE: DNA
<213> ORGANISM: Homo sapiens
<220> FEATURE:
<221> NAME/KEY: CDS
<222> LOCATION: (209)...(370)
```

<400> SEQUENCE: 5

```
gtcgacccac gcgtccgccg ggctacgagt ggccggacgc tacagccttg cgcagcgcgc      60
tctgctcctc agactcttcg aatttgagca gcctgtggca tcccccagca ggtccccag     120
ctccttgcct agcaccctcc cttccctagg agcagcgggc cacagtgagc cagcagccct     180
cgcgggtcct cctgcctgaa gttcaact atg cta cta gaa ggg gtc ctg ctg       232
                                Met Leu Leu Glu Gly Val Leu Leu
                                  1               5
gta gtg caa gcc ttg cag ctt gcc aat gcc cta gac ctg ccc gct ggc       280
Val Val Gln Ala Leu Gln Leu Ala Asn Ala Leu Asp Leu Pro Ala Gly
         10                  15                  20
tcc tgc gcc ttt gaa gaa gac acg tgt ggc ttt gac tcc gtg ttt gcg       328
Ser Cys Ala Phe Glu Glu Asp Thr Cys Gly Phe Asp Ser Val Phe Ala
 25                  30                  35                  40
ttt ctg cct tgg ata cta aat gag gaa ggt aag ggg act tcg               370
Phe Leu Pro Trp Ile Leu Asn Glu Glu Gly Lys Gly Thr Ser
                 45                  50
tagaaagatg ctcgaggtga actttcttca cgtcttgttc ctcccaaccc cccggaagta     430
aagatatctt ggagttactt ccctttggga ggaaaagtgt gtgagtcatg aaacctcctt     490
ccaactctcc tgcagcaaag agtggccagg aaaccacgg gaaggggc ggaggggaac       550
agctgtgtac ctggctctga gcatgcgctc ctaccccag cacacccta tgaaagggac     610
aaggggatt ctgctaatga ttgttgcccc tagccgtgtg ccccctgcag gctgatagcc     670
ttgctagtct cagtggctac ttgccccgagc tgagattgtc aaacggacta gctcacagga   730
agctttgcag aaattttcca cacggttgtg agcgtcctct gtgctaagct ctcccacttt    790
ggtccaccca cagcagtttt acctgtgatt catcctttcc cattgtatct aattcagcac    850
tggacaaaag agttaactcc accacggagt ccctgaagcc actgggctag gccaattga    910
tcagtcacat tactctgcac cgctgggtt ccggtgacaa cgtttaagtg aaaaggagtc    970
tgtgatgtgt tttcttaccc ttcattgtta cagtaaaaaa aaaaaaaaag ggcggccgc  1029
```

<210> SEQ ID NO 6
<211> LENGTH: 54
<212> TYPE: PRT
<213> ORGANISM: Homo sapiens

<400> SEQUENCE: 6

```
Met Leu Leu Glu Gly Val Leu Leu Val Val Gln Ala Leu Gln Leu Ala
  1               5                  10                  15
Asn Ala Leu Asp Leu Pro Ala Gly Ser Cys Ala Phe Glu Glu Asp Thr
             20                  25                  30
Cys Gly Phe Asp Ser Val Phe Ala Phe Leu Pro Trp Ile Leu Asn Glu
         35                  40                  45
Glu Gly Lys Gly Thr Ser
     50
```

<210> SEQ ID NO 7
<211> LENGTH: 1440
<212> TYPE: DNA
<213> ORGANISM: Homo sapiens

<400> SEQUENCE: 7

```
atgcagatcc cgcgcgccgc tcttctcccg ctgctgctgc tgctgctggc ggcgcccgcc      60
tcggcgcagt gtcccgggc cggccgctcg gcgcctttgg ccgccgggtg cccagaccgc     120
tgcgagccgg cgcgctgccc gccgcagccg gagcactgcg agggcggccg ggcccgggac     180
```

-continued

```
gcgtgcggct gctgcgaggt gtgcggcgcg cccgagggcg ccgcgtgcgg cctgcaggag      240
ggcccgtgcg gcgagggggct gcagtgcgtg gtgcccttcg gggtgccagc ctcggccacg     300
gtgcggcggc gcgcgcaggc cggcctctgt gtgtgcgcca gcagcgagcc ggtgtgcggc      360
agcgacgcca acacctacgc caacctgtgc cagctgcgcg ccgccagccg ccgctccgag      420
aggctgcacc ggccgccggt catcgtcctg cagcgcggag cctgcggcca agggcaggaa     480
gatcccaaca gtttgcgcca taaatataac tttatcgcgg acgtggtgga gaagatcgcc     540
cctgccgtgg ttcatatcga attgtttcgc aagcttccgt tttctaaacg agaggtgccg     600
gtggctagtg ggtctgggtt tattgtgtcg gaagatggac tgatcgtgac aaatgcccac     660
gtggtgacca acaagcaccg ggtcaaagtt gagctgaaga acggtgccac ttacgaagcc     720
aaaatcaagg atgtggatga aaagcagac atcgcactca tcaaaattga ccaccagggc     780
aagctgcctg tcctgctgct tggccgctcc tcagagctgc ggccgggaga gttcgtggtc     840
gccatcggaa gcccgttttc ccttcaaaac acagtcacca ccgggatcgt gagcaccacc     900
cagcgaggcg gcaaagagct ggggctccgc aactcagaca tggactacat ccagaccgac     960
gccatcatca actatggaaa ctcgggaggc ccgttagtaa acctggacgg tgaagtgatt    1020
ggaattaaca ctttgaaagt gacagctgga atctcctttg caatcccatc tgataagatt    1080
aaaaagttcc tcacggagtc ccatgaccga caggccaaag aaaagccat caccaagaag     1140 aagtatattg gtatccgaat gatgtcactc acgtccagca agccaaaga gctgaaggac     1200 cggcaccggg acttcccaga cgtgatctca ggagcgtata taattgaagt aattcctgat    1260
accccagcag aagctggtgg tctcaaggaa aacgacgtca taatcagcat caatggacag    1320
tccgtggtct ccgccaatga tgtcagcgac gtcattaaaa gggaaagcac cctgaacatg    1380
gtggtccgca ggggtaatga agatatcatg atcacagtga ttcccgaaga aattgaccca    1440
```

<210> SEQ ID NO 8
<211> LENGTH: 149
<212> TYPE: PRT
<213> ORGANISM: Homo sapiens

<400> SEQUENCE: 8

```
Met Val Ser Phe Arg Lys Ile Phe Ile Leu Gln Leu Val Gly Leu Val
1               5                   10                  15

Leu Thr Tyr Asp Phe Thr Asn Cys Asp Phe Glu Lys Ile Lys Ala Ala
            20                  25                  30

Tyr Leu Ser Thr Ile Ser Lys Asp Leu Ile Thr Tyr Met Ser Gly Thr
        35                  40                  45

Lys Ser Thr Glu Phe Asn Asn Thr Val Ser Cys Ser Asn Arg Pro His
    50                  55                  60

Cys Leu Thr Glu Ile Gln Ser Leu Thr Phe Asn Pro Thr Ala Gly Cys
65                  70                  75                  80

Ala Ser Leu Ala Lys Glu Met Phe Ala Met Lys Thr Lys Ala Ala Leu
                85                  90                  95

Ala Ile Trp Cys Pro Gly Tyr Ser Glu Thr Gln Ile Asn Ala Thr Gln
            100                 105                 110

Ala Met Lys Lys Arg Arg Lys Arg Lys Val Thr Thr Asn Lys Cys Leu
        115                 120                 125

Glu Gln Val Ser Gln Leu Gln Gly Leu Trp Arg Arg Phe Asn Arg Pro
    130                 135                 140

Leu Leu Lys Gln Gln
145
```

<210> SEQ ID NO 9
<211> LENGTH: 1044
<212> TYPE: DNA
<213> ORGANISM: Unknown
<220> FEATURE:
<223> OTHER INFORMATION: Mouse

<400> SEQUENCE: 9

```
atgcaggcgc gagcgctgca gctctccggg acgcccgtgc gccagctgca gaagggcgcc      60
tgcccgttgg gtctccacca gctgagcagc ccgcgctaca agttcaactt cattgctgac     120
gtggtggaga agatcgcacc agccgtggtc cacatagagc tcttcctgag cacccgctg      180
tttggccgca acgtgcccct gtccagcggt tctggcttca tcatgtcaga ggccggcctg     240
atcatcacca atgccacgt ggtgtccagc aacagtgctg ccccgggcag gcagcagctc      300
aaggtgcagc tacagaatgg ggactcctat gaggccacca tcaaagacat cgacaagaag     360
tcggacattg ccaccatcaa gatccatccc aagaaaaagc tccctgtgtt gttgctgggt     420
cactcggccg acctgcggcc tggggagttt gtggtggcca tcggcagtcc cttcgcccta     480
cagaacacag tgacaacggg catcgtcagc actgcccagc ggggagggcag ggagctgggc     540
ctccgggact ccgacatgga ctacatccag acggatgcca tcatcaacta cgggaactcc     600
gggggaccac tggtgaacct ggatggcgag gtcattggca tcaacacgct caaggtcacg     660
gctggcatct cctttgccat ccctcagac cgcatcacac ggttcctcac agagttccaa      720
gacaagcaga tcaaagactg aagaagcgc ttcatcggca tacggatgcg gacgatcaca      780
ccaagcctgg tggatgagct gaaggccagc aacccggact cccagaggt cagcagtgga     840
atttatgtgc aagaggttgc gccgaattca ccttctcaga gaggcggcat ccaagatggt     900
gacatcatcg tcaaggtcaa cggggcgtcct ctagtggact cgagtgagct gcaggaggcc     960
gtgctgaccg agtctcctct cctactggag gtgcggcggg ggaacgacga cctcctcttc    1020
agcatcgcac ctgaggtggt catg                                            1044
```

<210> SEQ ID NO 10
<211> LENGTH: 123
<212> TYPE: PRT
<213> ORGANISM: Unknown
<220> FEATURE:
<223> OTHER INFORMATION: Mouse

<400> SEQUENCE: 10

```
Leu Ile Pro Asp Thr Phe Leu Val Ser Phe Pro Ile Pro Ile Pro
 1               5                  10                  15

Phe Pro Val Pro Phe Ile Gln Phe Leu Ile Ser Gly Gly Phe Asn Leu
            20                  25                  30

Leu Ser Leu Ser Asn Cys Ala Ala Cys Glu Gln Pro Ala Cys Leu Leu
        35                  40                  45

Lys Ile Glu Tyr Tyr Thr Leu Asn Pro Ile Pro Gly Cys Pro Ser Leu
    50                  55                  60

Pro Asp Lys Thr Phe Ala Arg Arg Thr Arg Glu Ala Leu Asn Asp His
65                  70                  75                  80

Cys Pro Gly Tyr Pro Glu Thr Glu Arg Asn Asp Gly Thr Gln Glu Met
                85                  90                  95

Ala Gln Glu Val Gln Asn Ile Cys Leu Asn Gln Thr Ser Gln Ile Leu
            100                 105                 110

Arg Leu Trp Tyr Ser Phe Met Gln Ser Pro Glu
        115                 120
```

```
<210> SEQ ID NO 11
<211> LENGTH: 1937
<212> TYPE: DNA
<213> ORGANISM: Homo sapiens
<220> FEATURE:
<221> NAME/KEY: CDS
<222> LOCATION: (96)...(809)

<400> SEQUENCE: 11
gtcgacccac gcgtccgctt ggggatccct cagcttaaca cccacagaca tcggctggtg      60
gattcccgct gcatcaaggc ctacccactg tctcc atg ctg ggc tct ccc tgc       113
                                     Met Leu Gly Ser Pro Cys
                                       1               5 ctt ctg tgg ctc ctg gcc gtg acc ttc ttg gtt ccc aga gct cag ccc      161
Leu Leu Trp Leu Leu Ala Val Thr Phe Leu Val Pro Arg Ala Gln Pro
             10                  15                  20 ttg gcc cct caa gac ttt gaa gaa gag gaa gaa gat gag act gag acg      209
Leu Ala Pro Gln Asp Phe Glu Glu Glu Glu Glu Asp Glu Thr Glu Thr
         25                  30                  35 gcg tgg ccg cct ttg ccg gct gtc ccc tgc gac tac gac cac tgc cga      257
Ala Trp Pro Pro Leu Pro Ala Val Pro Cys Asp Tyr Asp His Cys Arg
     40                  45                  50 cac ctg cag gtg ccc tgt aag gag cta cag agg gcc ggg ccg gcg gcc      305
His Leu Gln Val Pro Cys Lys Glu Leu Gln Arg Ala Gly Pro Ala Ala
 55                  60                  65                  70 tgc ctg tgc cca gga ctc tct agc cct gcc cag ccg ccc gac ccg ccg      353
Cys Leu Cys Pro Gly Leu Ser Ser Pro Ala Gln Pro Pro Asp Pro Pro
                 75                  80                  85 cgc atg gga gaa gtg agc att gtg gcc gaa gag ggc cgc gca gtg gtc      401
Arg Met Gly Glu Val Ser Ile Val Ala Glu Glu Gly Arg Ala Val Val
             90                  95                 100 cac tgg tgt gcc ccc ttc tcc ccg gtc ctc cac tac tgg ctg ctg ctt      449
His Trp Cys Ala Pro Phe Ser Pro Val Leu His Tyr Trp Leu Leu Leu
        105                 110                 115 tgg gac ggc agc gag gct gcg cag aag ggg ccc tcg ctg aac gct acg      497
Trp Asp Gly Ser Glu Ala Ala Gln Lys Gly Pro Ser Leu Asn Ala Thr
    120                 125                 130 gtc cgc aga gcc gaa ctg aag ggg ctg aag cca ggg ggc gtt tat gtc      545
Val Arg Arg Ala Glu Leu Lys Gly Leu Lys Pro Gly Gly Val Tyr Val
135                 140                 145                 150 gtt tgc gtg gtg gcc gct aac gag gct ggg gca agc cgc gtg cct gag      593
Val Cys Val Val Ala Ala Asn Glu Ala Gly Ala Ser Arg Val Pro Glu
                155                 160                 165 gct gga aga gag ggc ctc gag ggg gcc gac atc cct gcc ttc ggg cct      641
Ala Gly Arg Glu Gly Leu Glu Gly Ala Asp Ile Pro Ala Phe Gly Pro
            170                 175                 180 tgc agc cgc ttt gca gtg ccg ccc aac ccc cgc act ctg gtc cac gcc      689
Cys Ser Arg Phe Ala Val Pro Pro Asn Pro Arg Thr Leu Val His Ala
        185                 190                 195 gcc gtc ggg gtg ggc acg gcc ctg gcc ctg ctg agc tgt gcc gcc ctg      737
Ala Val Gly Val Gly Thr Ala Leu Ala Leu Leu Ser Cys Ala Ala Leu
    200                 205                 210 gtg tgg cac ttc tgc cta cgc gat cgc tgg ggc tgc ccg cgc cga gcc      785
Val Trp His Phe Cys Leu Arg Asp Arg Trp Gly Cys Pro Arg Arg Ala
215                 220                 225                 230 gtc gcc cga gca gca ggg gcg ctc tgaaagggc ctgggggcat ctcgggcaca       839
Val Ala Arg Ala Ala Gly Ala Leu
                235 gccagcccca cctgcggcgt tcagcccggc tcctggaaag aggggaaccc gctgcctcca      899
```

```
gggagggttg  gacggtgagc  tgggagccag  ccccaggctc  tagagccaca  gcagagtcat      959
ggttctctgg  gctgagcgct  tgtttaggtc  cggaacttgg  tgctgtttcc  tggctgaggt     1019
ctgggaaaga  atagaaaggg  gccccccaatt tttcttttt   aacggtcaga  tagtaaataa     1079
tgtaaccttt  gcggtttaag  aggataaaat  ggagaatatt  atgtgggtat  ttatatgacc     1139
tttgtaacca  tttataaagg  aaaaaccaca  cgacatagta  atgcgaacct  agagtagcag     1199
ctactccgga  agctgaaatg  ggaggatctc  ttgagcccag  gagtttgagt  ccagtccagc     1259
cagggcaaca  cagccagacg  cccttgtgtt  ttgttttgtt  ttgttttttg  agaagaagtc     1319
tccctctgtt  acacagggtg  gattgcaatg  acacgatata  tgtcggttca  ctgcaacctc     1379
cacctcctag  gttcaagtga  ttctcccgta  tcagcatcct  aagtagttgg  ggttacaggt     1439
gcccacgacc  atgcccggct  aattattgtg  ttttttttagt agagatgggt  tttcaccatg     1499
ttggtcagcc  tggtctcaaa  ctcctgacct  caggtactcc  acccaccttg  gcctcccaaa     1559
gtgctgggat  tacaggcgtg  agccacggtg  cccaggcaga  ccccccttctt  taaagatgta    1619 aaatcattct  tagtccgtgg  gccttacaaa  tcaggtcact  ggcccattgc  ttgtagttag     1679
ttgatccata  tcatgcaccc  tcaaaacggc  tctgtcaatg  agtgtcttca  gtgggattct     1739
gagaataaat  ttatattctt  gctaggtaga  acaaaacaaa  aatgacagta  atatcaagga     1799
atttctcatc  ccttttttc   cctccatttg  tatttattgc  atatccactg  taaaaacatt     1859
aaaggatctt  taaagaaaa   aaaaaaaaaa  aaaaaaaaaa  aaaaaaaaaa  aaaaaaaaaa     1919
aaaaaagggg  gcggccgc                                                      1937
```

<210> SEQ ID NO 12
<211> LENGTH: 238
<212> TYPE: PRT
<213> ORGANISM: Homo sapiens

<400> SEQUENCE: 12

```
Met Leu Gly Ser Pro Cys Leu Leu Trp Leu Leu Ala Val Thr Phe Leu
 1               5                  10                  15

Val Pro Arg Ala Gln Pro Leu Ala Pro Gln Asp Phe Glu Glu Glu Glu
            20                  25                  30

Glu Asp Glu Thr Glu Thr Ala Trp Pro Pro Leu Pro Ala Val Pro Cys
        35                  40                  45

Asp Tyr Asp His Cys Arg His Leu Gln Val Pro Cys Lys Glu Leu Gln
    50                  55                  60

Arg Ala Gly Pro Ala Ala Cys Leu Cys Pro Gly Leu Ser Ser Pro Ala
65                  70                  75                  80

Gln Pro Pro Asp Pro Pro Arg Met Gly Glu Val Ser Ile Val Ala Glu
                85                  90                  95

Glu Gly Arg Ala Val Val His Trp Cys Ala Pro Phe Ser Pro Val Leu
            100                 105                 110

His Tyr Trp Leu Leu Leu Trp Asp Gly Ser Glu Ala Ala Gln Lys Gly
        115                 120                 125

Pro Ser Leu Asn Ala Thr Val Arg Arg Ala Glu Leu Lys Gly Leu Lys
    130                 135                 140

Pro Gly Gly Val Tyr Val Val Cys Val Val Ala Ala Asn Glu Ala Gly
145                 150                 155                 160

Ala Ser Arg Val Pro Glu Ala Gly Arg Glu Gly Leu Glu Gly Ala Asp
                165                 170                 175

Ile Pro Ala Phe Gly Pro Cys Ser Arg Phe Ala Val Pro Pro Asn Pro
            180                 185                 190
```

```
Arg Thr Leu Val His Ala Ala Val Gly Val Gly Thr Ala Leu Ala Leu
    195                 200                 205

Leu Ser Cys Ala Ala Leu Val Trp His Phe Cys Leu Arg Asp Arg Trp
    210                 215                 220

Gly Cys Pro Arg Arg Ala Val Ala Arg Ala Ala Gly Ala Leu
225                 230                 235

<210> SEQ ID NO 13
<211> LENGTH: 1459
<212> TYPE: DNA
<213> ORGANISM: Homo sapiens
<220> FEATURE:
<221> NAME/KEY: CDS
<222> LOCATION: (1)...(366)

<400> SEQUENCE: 13 gtc gac cca cgc gtc cgc gag gct gcg cag aag ggg ccc ccg ctg aac      48
Val Asp Pro Arg Val Arg Glu Ala Ala Gln Lys Gly Pro Pro Leu Asn
1               5                   10                  15 gct acg gtc cgc aga gcc gaa ctg aag ggg ctg aag cca ggg ggc att      96
Ala Thr Val Arg Arg Ala Glu Leu Lys Gly Leu Lys Pro Gly Gly Ile
                20                  25                  30 tat gtc gtt tgc gta gtg gcc gct aac gag gcc ggg gca agc cgc gtg     144
Tyr Val Val Cys Val Val Ala Ala Asn Glu Ala Gly Ala Ser Arg Val
            35                  40                  45 ccc cag gct gga gga gag ggc ctc gag ggg gcc gac atc cct gcc ttc     192
Pro Gln Ala Gly Gly Glu Gly Leu Glu Gly Ala Asp Ile Pro Ala Phe
        50                  55                  60 ggg cct tgc agc cgc ctt gcg gtg ccg ccc aac ccc cgc act ctg gtc     240
Gly Pro Cys Ser Arg Leu Ala Val Pro Pro Asn Pro Arg Thr Leu Val
65                  70                  75                  80 cac gcg gcc gtc ggg gtg ggc acg gcc ctg gcc ctg cta agc tgt gcc     288
His Ala Ala Val Gly Val Gly Thr Ala Leu Ala Leu Leu Ser Cys Ala
                85                  90                  95 gcc ctg gtg tgg cac ttc tgc ctg cgc gat cgc tgg ggc tgc ccg cgc     336
Ala Leu Val Trp His Phe Cys Leu Arg Asp Arg Trp Gly Cys Pro Arg
            100                 105                 110 cga gcc gcc gcc cga gcc gca ggg gcg ctc tgaaagggggc tgggggcat       386
Arg Ala Ala Ala Arg Ala Ala Gly Ala Leu
        115                 120 ctcgggcaca  dacagcccca  cctggggcgc  tcagcctggc  cccgggaaa   gaggaaaacc    446
cgctgcctcc  agggagggct  ggacggcgag  ctgggagcca  gccccaggct  ccagggccac    506
ggcggagtca  tggttctcag  gactgagcgc  ttgtttaggt  ccggtacttg  gcgctttgtt    566
tcctggctga  ggtctgggaa  ggaatagaaa  ggggccccca  attttttttt  aagcggccag    626
ataataaata  atgtaacctt  tgcggtttaa  gaggataaaa  tggaggatat  tattatgtgg    686
gtatttatat  gacctttgta  accatttaaa  aatgtaaaaa  cgacctgact  tagtaatgcg    746
aacctatagt  agcagctact  ccagaggctg  aaatgggagg  atctcttgag  cccaggagtt    806
ggagtccagt  ccagccaggg  caacacagcc  agacgccctt  gtttttttatt  ttgttttgtt    866
ttggtttttt  gttttttgag  gagtttccct  ctgtcacaca  agctggaggg  caatggcgcc    926
atctcagctc  actgcaacgt  ccacctcctg  ggttcaggcg  attctcctgc  ctcagcatcc    986
taattggtgg  gtacctgtgg  tcccagctac  tccggaggct  gaggcaggag  aatggcgtga   1046
gcccgggagg  cggatcttgc  agtgagcgga  gattgcgcca  ctgcactcca  gcctgggtga   1106
cagagcaaga  ctccctctca  aaagaaaaag  aaaaagatg   taaaaaccat  tcttagtttg   1166
tgggccttac  aaatcaggcc  actggcccat  tgcttgtagt  tagttgatcc  atgtcatgca   1226
```

```
cccctaaaaat ggctctgtca ctgtgagtgg cttcagtagg attttgagaa taagttttata    1286 ttcttgctag gtaaaacaaa acaaaaacga cagtaatacc aaggaatctc cccccccttt     1346
taccctccat ttgtgtttat tgcatatcca ctataacaac attaaaggac ctttaaaagg     1406
aaaaaaaaaa aaaaaaaaaa aaaaaaaaaa aaaaaaaaa aagggggcggc cgc              1459
```

```
<210> SEQ ID NO 14
<211> LENGTH: 122
<212> TYPE: PRT
<213> ORGANISM: Homo sapiens

<400> SEQUENCE: 14
```

| | | | | | | | | | | | | | | |
|---|---|---|---|---|---|---|---|---|---|---|---|---|---|---|
|Val|Asp|Pro|Arg|Val|Arg|Glu|Ala|Ala|Gln|Lys|Gly|Pro|Pro|Leu|Asn|
|1| | | |5| | | | |10| | | | |15|

| | | | | | | | | | | | | | | |
|---|---|---|---|---|---|---|---|---|---|---|---|---|---|---|
|Ala|Thr|Val|Arg|Arg|Ala|Glu|Leu|Lys|Gly|Leu|Lys|Pro|Gly|Gly|Ile|
| | | |20| | | | |25| | | | |30| |

Tyr Val Val Cys Val Val Ala Ala Asn Glu Ala Gly Ala Ser Arg Val
              35                  40                  45

Pro Gln Ala Gly Gly Glu Gly Leu Glu Gly Ala Asp Ile Pro Ala Phe
         50                  55                  60

Gly Pro Cys Ser Arg Leu Ala Val Pro Pro Asn Pro Arg Thr Leu Val
65                  70                  75                  80

His Ala Ala Val Gly Val Gly Thr Ala Leu Ala Leu Leu Ser Cys Ala
                 85                  90                  95

Ala Leu Val Trp His Phe Cys Leu Arg Asp Arg Trp Gly Cys Pro Arg
             100                 105                 110

Arg Ala Ala Ala Arg Ala Ala Gly Ala Leu
         115                 120

```
<210> SEQ ID NO 15
<211> LENGTH: 1136
<212> TYPE: DNA
<213> ORGANISM: Homo sapiens
<220> FEATURE:
<221> NAME/KEY: CDS
<222> LOCATION: (110)...(823)

<400> SEQUENCE: 15
gtcgacccac gcgtccggca cagcctgaga tcttggggat ccctcagcct aacacccaca    60
gacgtcagct ggtggattcc cgctgcatca aggcctaccc actgtctcc atg ctg ggc   118
                                                      Met Leu Gly
                                                        1 tct ccc tgc ctt ctg tgg ctc ctg gcc gtg acc ttc ttg gtt ccc aga     166
Ser Pro Cys Leu Leu Trp Leu Leu Ala Val Thr Phe Leu Val Pro Arg
  5                   10                  15 gct cag ccc ttg gcc cct caa gac ttt gaa gaa gag gag gca gat gag     214
Ala Gln Pro Leu Ala Pro Gln Asp Phe Glu Glu Glu Glu Ala Asp Glu
 20                  25                  30                  35 act gag acg gcg tgg ccg cct ttg ccg gct gtc ccc tgc gac tac gac     262
Thr Glu Thr Ala Trp Pro Pro Leu Pro Ala Val Pro Cys Asp Tyr Asp
             40                  45                  50 cac tgc cga cac ctg cag gtg ccc tgc aag gag cta cag agg gtc ggg     310
His Cys Arg His Leu Gln Val Pro Cys Lys Glu Leu Gln Arg Val Gly
         55                  60                  65 ccg gcg gcc tgc ctg tgc cca gga ctc tcc agc ccc gcc cag ccg ccc     358
Pro Ala Ala Cys Leu Cys Pro Gly Leu Ser Ser Pro Ala Gln Pro Pro
     70                  75                  80 gac ccg ccg cgc atg gga gaa gtg cgc att gcg gcc gaa gag ggc cgc     406
Asp Pro Pro Arg Met Gly Glu Val Arg Ile Ala Ala Glu Glu Gly Arg
 85                  90                  95
```

```
gca gtg gtc cac tgg tgt gcc ccc ttc tcc ccg gtc ctc cac tac tgg      454
Ala Val Val His Trp Cys Ala Pro Phe Ser Pro Val Leu His Tyr Trp
100                 105                 110                 115 ctg ctg ctt tgg gac ggc agc gag gct gcg cag aag ggg ccc ccg ctg      502
Leu Leu Leu Trp Asp Gly Ser Glu Ala Ala Gln Lys Gly Pro Pro Leu
                120                 125                 130 aac gct acg gtc cgc aga gcc gaa ctg aag ggg ctg aag cca ggg ggc      550
Asn Ala Thr Val Arg Arg Ala Glu Leu Lys Gly Leu Lys Pro Gly Gly
            135                 140                 145 att tat gtc gtt tgc gta gtg gcc gct aac gag gcc ggg gca agc cgc      598
Ile Tyr Val Val Cys Val Val Ala Ala Asn Glu Ala Gly Ala Ser Arg
        150                 155                 160 gtg ccc cag gct gga gga gag ggc ctc gag ggg gcc gac atc cct gcc      646
Val Pro Gln Ala Gly Gly Glu Gly Leu Glu Gly Ala Asp Ile Pro Ala
    165                 170                 175 ttc ggg cct tgc agc cgc ctt gcg gtg ccg ccc aac ccc cgc act ctg      694
Phe Gly Pro Cys Ser Arg Leu Ala Val Pro Pro Asn Pro Arg Thr Leu
180                 185                 190                 195 gtc cac gcg gcc gtc ggg gtg ggc acg gcc ctg gcc ctg cta agc tgt      742
Val His Ala Ala Val Gly Val Gly Thr Ala Leu Ala Leu Leu Ser Cys
                200                 205                 210 gcc gcc ctg gtg tgg cac ttc tgc ctg cgc gat cgc tgg ggc tgc ccg      790
Ala Ala Leu Val Trp His Phe Cys Leu Arg Asp Arg Trp Gly Cys Pro
            215                 220                 225 cgc cga gcc gcc gcc cga gcc gca ggg gcg ctc tgaaaggggc ctgggggcat    843
Arg Arg Ala Ala Ala Arg Ala Ala Gly Ala Leu
        230                 235 ctcgggcaca gacagcccca cctggggcgc tcagcctggc ccccgggaaa gaggaaaacc    903
cgctgcctcc agggagggct ggacggcgag ctgggagcca gccccaggct ccagggccac    963
ggcggagtca tggttctcag gactgagcgc ttgtttaggt ccggtacttg gcgctttgtt   1023
tcctggctga ggtctgggaa ggaatagaaa ggggcccccca attttttttt aagcggccag   1083
ataataaata atgtaacctt tgcggtttaa aaaaaaaaa aaagggcggc cgc           1136

<210> SEQ ID NO 16
<211> LENGTH: 238
<212> TYPE: PRT
<213> ORGANISM: Homo sapiens

<400> SEQUENCE: 16

Met Leu Gly Ser Pro Cys Leu Leu Trp Leu Leu Ala Val Thr Phe Leu
1               5                   10                  15

Val Pro Arg Ala Gln Pro Leu Ala Pro Gln Asp Phe Glu Glu Glu
            20                  25                  30

Ala Asp Glu Thr Glu Thr Ala Trp Pro Pro Leu Pro Ala Val Pro Cys
        35                  40                  45

Asp Tyr Asp His Cys Arg His Leu Gln Val Pro Cys Lys Glu Leu Gln
    50                  55                  60

Arg Val Gly Pro Ala Ala Cys Leu Cys Pro Gly Leu Ser Ser Pro Ala
65                  70                  75                  80

Gln Pro Pro Asp Pro Arg Met Gly Glu Val Arg Ile Ala Ala Glu
            85                  90                  95

Glu Gly Arg Ala Val Val His Trp Cys Ala Pro Phe Ser Pro Val Leu
                100                 105                 110

His Tyr Trp Leu Leu Leu Trp Asp Gly Ser Glu Ala Ala Gln Lys Gly
            115                 120                 125

Pro Pro Leu Asn Ala Thr Val Arg Arg Ala Glu Leu Lys Gly Leu Lys
```

```
                  130                 135                 140
Pro Gly Gly Ile Tyr Val Val Cys Val Val Ala Asn Glu Ala Gly
145                 150                 155                 160

Ala Ser Arg Val Pro Gln Ala Gly Gly Glu Gly Leu Glu Gly Ala Asp
                165                 170                 175

Ile Pro Ala Phe Gly Pro Cys Ser Arg Leu Ala Val Pro Pro Asn Pro
                180                 185                 190

Arg Thr Leu Val His Ala Ala Val Gly Val Gly Thr Ala Leu Ala Leu
            195                 200                 205

Leu Ser Cys Ala Ala Leu Val Trp His Phe Cys Leu Arg Asp Arg Trp
        210                 215                 220

Gly Cys Pro Arg Arg Ala Ala Arg Ala Ala Gly Ala Leu
225                 230                 235

<210> SEQ ID NO 17
<211> LENGTH: 2221
<212> TYPE: DNA
<213> ORGANISM: Homo sapiens
<220> FEATURE:
<221> NAME/KEY: CDS
<222> LOCATION: (79)...(795)

<400> SEQUENCE: 17
cgtccgggcc tctccgcctg atagccacgg atatctgggg gcaaaccctc actgtgacga       60
ggcctaccca ctgactcc atg ttg ggc tct ctt tcc ctt ctg tgg ctg gca      111
                   Met Leu Gly Ser Leu Ser Leu Leu Trp Leu Ala
                    1               5                   10 gcc atg acc acc tcc ttg gtt tcc caa cct cag atc ttg acc ctg gaa      159
Ala Met Thr Thr Ser Leu Val Ser Gln Pro Gln Ile Leu Thr Leu Glu
             15                  20                  25 gac tac cag gaa ggg gaa gag gat gat gtg aca gta gct aca cct tcc      207
Asp Tyr Gln Glu Gly Glu Glu Asp Asp Val Thr Val Ala Thr Pro Ser
         30                  35                  40 tta gct gtc cgt tgc gac tat gac cgt tgc cgc cac ctg cag gtg tcc      255
Leu Ala Val Arg Cys Asp Tyr Asp Arg Cys Arg His Leu Gln Val Ser
     45                  50                  55 tgc cag gag ctg cag aag gtt ggg cca gta gcc tgc ctg tgc cca ggg      303
Cys Gln Glu Leu Gln Lys Val Gly Pro Val Ala Cys Leu Cys Pro Gly
 60                  65                  70                  75 ctc tcc agg gaa gat caa cag cca gag cct cct cgc ctg gga gaa gtg      351
Leu Ser Arg Glu Asp Gln Gln Pro Glu Pro Pro Arg Leu Gly Glu Val
                 80                  85                  90 caa ata atg gct gaa gaa ggc tac gca gtg gtt cac tgg tgt gct ccc      399
Gln Ile Met Ala Glu Glu Gly Tyr Ala Val Val His Trp Cys Ala Pro
             95                 100                 105 ttc tct cca gtc agc cac tac tgg ctt ctg ctt tgg gaa agc aac ggg      447
Phe Ser Pro Val Ser His Tyr Trp Leu Leu Leu Trp Glu Ser Asn Gly
         110                 115                 120 gct cca cag aag agt gcc cct ctc aat gct aca gtt cga aga gca gag      495
Ala Pro Gln Lys Ser Ala Pro Leu Asn Ala Thr Val Arg Arg Ala Glu
     125                 130                 135 ctg aag gga cta aag cct ggg gtt gct tat gtc ctt tgc gtg gtg gct      543
Leu Lys Gly Leu Lys Pro Gly Val Ala Tyr Val Leu Cys Val Val Ala
 140                 145                 150                 155 gct aat gac gca ggt gag agc aat gtt cct ggg gca gaa gtc gag ggt      591
Ala Asn Asp Ala Gly Glu Ser Asn Val Pro Gly Ala Glu Val Glu Gly
                 160                 165                 170 cct gag aac tgg act ggc cct tcc ttt ggg ccc tgt cgc aag ttt atc      639
Pro Glu Asn Trp Thr Gly Pro Ser Phe Gly Pro Cys Arg Lys Phe Ile
             175                 180                 185
```

```
atg ccg cct aag cct gtt acc ctg gtc tat gca gcc gtg gga gtg ggc      687
Met Pro Pro Lys Pro Val Thr Leu Val Tyr Ala Ala Val Gly Val Gly
        190                 195                 200 aca gcc tta gct ctg ctg agc tgt gca gcc ctg gtt tgg cat ttc tgc      735
Thr Ala Leu Ala Leu Leu Ser Cys Ala Ala Leu Val Trp His Phe Cys
    205                 210                 215 ctt cgt gag cga tgg ggt tgc ccc cga cgt caa ggt atg gcc caa gcg      783
Leu Arg Glu Arg Trp Gly Cys Pro Arg Arg Gln Gly Met Ala Gln Ala
220                 225                 230                 235 tca gaa gct ctc tgacaggagt cccctcgact acaaacaact catctggaga          835
Ser Glu Ala Leu gcccaaccca ctcccaggag gagtgtgggg cttgttgcca cctggcaacc agaggcacag    895
ccaagccaga gcggaagccc aggcaattag cctcagcact gagggcttgg ttagtcccta    955
actggtcact atgttccttc cctgttgggg gttagaaaaa gtagcaatta ttccttggag   1015
gtctgatgaa aatgatttaa gctttatggg tttgaagggg taaaattaca gacattatac   1075
atgaacttat atatagccag ttaaaatgga gctatttaaa ggcctggcat ggtggtttac   1135
aattttggtc tccagcgccc tggaggcaga ggcaggcgga tctgagtttc ggggcagcc    1195 tgatctacat agaaagattc caggccaacc cagataatat agtgagaccc tgtctcaaaa   1255
agagtaaaac agaagcaaaa caaacaaaag gtggggcggg atagagagat tgttcagcag   1315
ttaagaatac tggctatttt tccagaggac agaatttat tcctagcatc cacatggcag   1375
ctcacaacca tctgtaattc catttccagg agatccagtg tctaattctg acctctgcca   1435
gcatcaggca catacatacg cacacataca tacatacata catacataca cacacacaca   1495
cacacacaca cacacacaga gagagacaaa acactcatac acataaaata aaaattaatt   1555
tgaagtgtag ctgtttaaaa atgtaaactg ttcatagctc ataggtctct cacagcaagc   1615
agcagactac atttggcctg ttggctgatt tgccaacacc tatcattctc aaagggactt   1675
tgtgactgtc ggtggcttcc ctgcatattt tgagaataag ctgagttttg ccaacacctg   1735
ttattctgaa aaggactctg cgactgtggg tggcttccac gcatgttttg agaataagca   1795
gggtagatgt ggagactgga gctctgtctt tctgctactt gttgtttcct tcctaaggat   1855
gatcctgctc agactccacc tggggctatg gaagctgggg attaaaaatc agcatgggct   1915
ggaggagaca gggcccaagc ttctggctac ataagttagt ggtcttgttt gttttggggg   1975 ttttttgtttg tttgtttttt caagacaggg tttctctgtg tagctctggc tgtcctggaa   2035
ctcactttgt agaccaggct ggcctcgaac tcagaaatcc gcctgcctct gcctcccaag   2095
tgctgggatt aaaggcatgc gccaccaccg cccagcagtg gttttatttg taactaacag   2155
tttataccaa tgactcccca caactttgtg taattgtttt tccactgtat taacattaaa   2215
gggaat                                                               2221

<210> SEQ ID NO 18
<211> LENGTH: 239
<212> TYPE: PRT
<213> ORGANISM: Homo sapiens

<400> SEQUENCE: 18

Met Leu Gly Ser Leu Ser Leu Leu Trp Leu Ala Ala Met Thr Thr Ser
1               5                   10                  15

Leu Val Ser Gln Pro Gln Ile Leu Thr Leu Glu Asp Tyr Gln Glu Gly
                20                  25                  30

Glu Glu Asp Asp Val Thr Val Ala Thr Pro Ser Leu Ala Val Arg Cys
            35                  40                  45
```

```
Asp Tyr Asp Arg Cys Arg His Leu Gln Val Ser Cys Gln Glu Leu Gln
        50                  55                  60

Lys Val Gly Pro Val Ala Cys Leu Cys Pro Gly Leu Ser Arg Glu Asp
 65                  70                  75                  80

Gln Gln Pro Glu Pro Pro Arg Leu Gly Glu Val Gln Ile Met Ala Glu
                85                  90                  95

Glu Gly Tyr Ala Val Val His Trp Cys Ala Pro Phe Ser Pro Val Ser
            100                 105                 110

His Tyr Trp Leu Leu Leu Trp Glu Ser Asn Gly Ala Pro Gln Lys Ser
        115                 120                 125

Ala Pro Leu Asn Ala Thr Val Arg Arg Ala Glu Leu Lys Gly Leu Lys
    130                 135                 140

Pro Gly Val Ala Tyr Val Leu Cys Val Val Ala Ala Asn Asp Ala Gly
145                 150                 155                 160

Glu Ser Asn Val Pro Gly Ala Glu Val Glu Gly Pro Glu Asn Trp Thr
                165                 170                 175

Gly Pro Ser Phe Gly Pro Cys Arg Lys Phe Ile Met Pro Pro Lys Pro
            180                 185                 190

Val Thr Leu Val Tyr Ala Ala Val Gly Val Gly Thr Ala Leu Ala Leu
        195                 200                 205

Leu Ser Cys Ala Ala Leu Val Trp His Phe Cys Leu Arg Glu Arg Trp
    210                 215                 220

Gly Cys Pro Arg Arg Gln Gly Met Ala Gln Ala Ser Glu Ala Leu
225                 230                 235

<210> SEQ ID NO 19
<211> LENGTH: 1801
<212> TYPE: DNA
<213> ORGANISM: Homo sapiens

<400> SEQUENCE: 19
gtcgacccac gcgtccggcg gaggttgtgg ctgcaccgtg gtcctgggct tggtcctggg      60
cttgatgcgt ctgtttgtcc gtccgtccgt ccgtcccgcc atggctgcgc cggcgccctc     120
tccgtggacc ctttcgctgc tgctgttgtt gctactgccg tctccgggtg cccatggcga     180
gctgtgcagg cccttcggtg aagacaattc gatcccagag tcctgtcctg acttctgttg     240
tggctcctgt tccagccaat actgctgctc tgacgtgctg aagaaaatcc agtggaatga     300
ggaaatgtgc cctgagccag agtccagcag attttccgcc cacccggaga caccagaaca     360
gctgggttca gcgctgaagt atcagtccag tcttgacagt gacaacatgc cagggttcgg     420
agcgaccgtg gccatcggcc tgaccgtctt cgtggtgttt atcgctacca tcattgtgtg     480
ctttacctgc tcctgctgct gtctatataa gatgtgctgc cgcccacgac ctgtcgtgtc     540
caacaccaca actactaccg tggttcacac cgcttaccct cagcctcaac ctgtggcccc     600
cagctatcct ggaccaacat accagggcta ccatcccatg cccccccagc caggaatgcc     660
agcagcaccc tacccaacgc agtaccctcc accctacctg gcccagccca cagggccacc     720
agcctatcat gagacgttgg ctggagccag ccagcctcca tacaacccgg cctacatgga     780 tccccccaaag gcagttccct gagcctgccc ccagcctctt ggctaacatt tgattatgt      840 catgtgtgtg tgagtgctat gcagagttct ttactgctgt ctgtggtgcg tgtgccttgt     900
ctagacatgt ggcttcctct gctgatgacc aggtaggcac aaatcttacc agtgctggtt     960
gggaccaatc tgttttcttc ctcacttgaa attgtaattt ctgaaatttc aagtaaatta    1020
aaaacaatag ggtaggaggt atttcccgct tcaccccaag gtgaccagcc atagcctgcc    1080
```

```
acacatagga gagcaagctt tttgtgggtc catgtcctgc tttggggagt agccagctag      1140
ctgctgctat gggtttattc ccagggcttg gctgcattta gctggacaga gaacaagggg      1200
cctcagtggc agtgggtcag tgactgatgt cagagcacac taggcagaga gccccgtccg      1260
tctccatcag ctgtctgtct ggacggtccc actgtctttc ctgggactat gtagagggcc      1320
acatgtattc actattcagg ctccagtggc ttccaggcca ggggcctctg tctactacac      1380
actctggttt ctccctacag tgtcttttta cgattagcca aacatattgc ctgttttttg      1440
tatccagatg tgtgataatt ggtgaggttg aaatccttgg ttcctggaga acaggaaacc      1500
tgacctctga cagtccgttt cccttgacac cagcttcata gaatacctga ctcctgtact      1560
acagtccagt ttgttccagt agcagggaca ccagggccag gggttatctg gaccaagggt      1620
gggggtggag agcctggatg gtagctctgg accagatgtg aatgcctcca tattccctgt      1680
tggttcctgt ttcactggct gttttagttt tgtgttaatt ggtgtttctg agcattcaaa      1740
ctccgcaccc tcgtttataa taaatgaata tttggaaaaa aaaaaaaaaa aaaaaaaaa      1800 a                                                                     1801

<210> SEQ ID NO 20
<211> LENGTH: 245
<212> TYPE: PRT
<213> ORGANISM: Homo sapiens

<400> SEQUENCE: 20

Met Arg Leu Phe Val Arg Pro Ser Val Arg Pro Ala Met Ala Ala Pro
 1               5                  10                  15

Ala Pro Ser Pro Trp Thr Leu Ser Leu Leu Leu Leu Leu Leu Leu Pro
             20                  25                  30

Ser Pro Gly Ala His Gly Glu Leu Cys Arg Pro Phe Gly Glu Asp Asn
         35                  40                  45

Ser Ile Pro Glu Ser Cys Pro Asp Phe Cys Cys Gly Ser Cys Ser Ser
     50                  55                  60

Gln Tyr Cys Cys Ser Asp Val Leu Lys Lys Ile Gln Trp Asn Glu Glu
 65                  70                  75                  80

Met Cys Pro Glu Pro Glu Ser Ser Arg Phe Ser Ala His Pro Glu Thr
                 85                  90                  95

Pro Glu Gln Leu Gly Ser Ala Leu Lys Tyr Gln Ser Ser Leu Asp Ser
            100                 105                 110

Asp Asn Met Pro Gly Phe Gly Ala Thr Val Ala Ile Gly Leu Thr Val
        115                 120                 125

Phe Val Val Phe Ile Ala Thr Ile Ile Val Cys Phe Thr Cys Ser Cys
    130                 135                 140

Cys Cys Leu Tyr Lys Met Cys Cys Arg Pro Arg Pro Val Val Ser Asn
145                 150                 155                 160

Thr Thr Thr Thr Thr Val Val His Thr Ala Tyr Pro Gln Pro Gln Pro
                165                 170                 175

Val Ala Pro Ser Tyr Pro Gly Pro Thr Tyr Gln Gly Tyr His Pro Met
            180                 185                 190

Pro Pro Gln Pro Gly Met Pro Ala Ala Pro Tyr Pro Thr Gln Tyr Pro
        195                 200                 205

Pro Pro Tyr Leu Ala Gln Pro Thr Gly Pro Pro Ala Tyr His Glu Thr
    210                 215                 220

Leu Ala Gly Ala Ser Gln Pro Pro Tyr Asn Pro Ala Tyr Met Asp Pro
225                 230                 235                 240
```

Pro Lys Ala Val Pro
              245

<210> SEQ ID NO 21
<211> LENGTH: 1858
<212> TYPE: DNA
<213> ORGANISM: Mus musculus

<400> SEQUENCE: 21

```
gtcgacccac gcgtccgcgc ggaggttgcg gcggcaccgt ggtcttgggc ttggtccgtc     60
tgttcgtccg tccgttggtc tgtcccgcca tggctgcgcc ggcgccctct ctgtggaccc    120
tattgctgct gctgttgctg ctgccgccgc ctccgggtgc ccatggtgag ctgtgcaggc    180
cctttggtga agacaattcg atcccagtgt tctgtcctga tttctgttgt ggttcctgtt    240
ccaaccaata ctgctgctcg gacgtgctga ggaaaatcca gtggaatgag gaaatgtgtc    300
ctgagccaga gtccagcaga ttttccaccc ccgcggagga gacacccgaa catctgggtt    360
cagcgctgaa atttcgatcc agttttgaca gtgaccctat gtcagggttc ggagcgaccg    420
tcgccattgg cgtgaccatc tttgtggtgt ttattgccac tatcatcatc tgcttcacct    480
gctcctgctg ctgtctgtat aagatgtgct gcccccaacg ccctgtcgtg accaacacca    540
caactactac cgtggttcat gcccctttacc ctcagcctca acctcaacct gtggccccca    600
gctatcctgg accaacatac cagggctacc atcccatgcc ccccccagcc aggaatgcca    660
gcagcaccct acccaacgca gtacccacca ccctacctgg cccagcccac agggccgcca    720
ccctaccatg agtccttggc tggagccagc cagcctccat acaacccgac ctacatggat    780
tccctaaaga caattccctg aacctgcccc cagcctcttt ggctgccatt tatgtcgtgt    840
gtgagtgagt gatacgcaga gttctttact gctgtctgtg gtgtgtgtgc cttgtctaga    900
catgtggctt cctctgctgt tgaccaggta ggcgcaagtc ttaccagtgt gggtcgggac    960
caacctgttt tcttcctcac ttgaaattgt actttctgaa atttcaagca aattaaaaac   1020
aataaggtag gaggtatttc ccacgtcacc ccaaggtgac cagccatggc ctgtcatact   1080
taggagagca agcttttttgc gggtacagag caggcttttgg ggggtaacca gctagctgct   1140
gctaggcctt tattcccagg gtttggctgc attggcagtg aggcaggtgg ctgggggtga   1200
caccaggtga caaggggact cagtggcagg gggtcacacc aggcagaaca ccatacactc   1260
tccatcagct gtctgtctgg atgtcactgt ccttcccggg gctgtataga gggccacatg   1320
tgttcactat tcaggctcca ctgggggaat tttcctacct ttgctggctt ggctcctgct   1380
cccaggccag ggacctcggt ctgtctacta cacactctgg tttctccctg cactgtcttt   1440
ttactgttag ccaaacattt tgcctgtttt ctgtctccag atgtgtgata attggtgtga   1500
ggttgaaatc cctggttcct ggaggacaga caacctgacc tccgactgtc agtttccctt   1560
gacaccatct tcatagaaat acctgactcc tgtaccacag tccagtttgt cccagtagca   1620
gggacaccaa ggccaatggg ttatctggac caaaggtggg gtggagggcc tagatggtat   1680
ctccggccca gatgtgaata cctccatatt ccctgttggt tcctgtttca ctggctgttt   1740
tagctttgtg ttgattggtg tttctgagca ttcagactcc gcaccctcat ttctaataaa   1800
tgcaacattg gaaaaaaaaa aaaaaaaaaa aaaaaaaaaa aaaaaaaagg gcggccgc      1858
```

<210> SEQ ID NO 22
<211> LENGTH: 213
<212> TYPE: PRT
<213> ORGANISM: Mus musculus

<400> SEQUENCE: 22

```
Met Ala Ala Pro Ala Pro Ser Leu Trp Thr Leu Leu Leu Leu Leu
  1               5                  10                  15

Leu Leu Pro Pro Pro Gly Ala His Gly Glu Leu Cys Arg Pro Phe
         20                  25                  30

Gly Glu Asp Asn Ser Ile Pro Val Phe Cys Pro Asp Cys Cys Gly
         35                  40                  45

Ser Cys Ser Asn Gln Tyr Cys Cys Ser Asp Val Leu Arg Lys Ile Gln
 50                  55                  60

Trp Asn Glu Glu Met Cys Pro Glu Pro Glu Ser Ser Arg Phe Ser Thr
 65              70                  75                      80

Pro Ala Glu Glu Thr Pro Glu His Leu Gly Ser Ala Leu Lys Phe Arg
             85                  90                  95

Ser Ser Phe Asp Ser Asp Pro Met Ser Gly Phe Gly Ala Thr Val Ala
            100                 105                 110

Ile Gly Val Thr Ile Phe Val Val Phe Ile Ala Thr Ile Ile Cys
            115                 120                 125

Phe Thr Cys Ser Cys Cys Leu Tyr Lys Met Cys Cys Pro Gln Arg
        130                 135                 140

Pro Val Val Thr Asn Thr Thr Thr Thr Val Val His Ala Pro Tyr
145                 150                 155                 160

Pro Gln Pro Gln Pro Gln Pro Val Ala Pro Ser Tyr Pro Gly Pro Thr
                165                 170                 175

Tyr Gln Gly Tyr His Pro Met Pro Pro Ala Arg Asn Ala Ser Ser
            180                 185                 190

Thr Leu Pro Asn Ala Val Pro Thr Thr Leu Pro Gly Pro Ala His Arg
            195                 200                 205

Ala Ala Thr Leu Pro
            210

<210> SEQ ID NO 23
<211> LENGTH: 1948
<212> TYPE: DNA
<213> ORGANISM: Homo sapiens
<220> FEATURE:
<221> NAME/KEY: CDS
<222> LOCATION: (314)...(1432)
<220> FEATURE:
<221> NAME/KEY: misc_feature
<222> LOCATION: 1894, 1907
<223> OTHER INFORMATION: n = A,T,C or G

<400> SEQUENCE: 23
cgcttactcc tttgccttcg caaacaggga aaagtgttcc acgaagcggt agcgcctttc      60
cgcctcgcgt tttcctccct gaccctggtc ccggctcccg tccggcgcc agctggtggg     120 gcgagcgccg ggagcccatc tgcccccagg ggcacggggc gcggggccgg ctcccgcccg     180
gcacatggct gcagccacct cgcgcgcacc ccgaggcgcc gcgcccagct cgcccgaggt     240
ccgtcggagg cgcccggccg ccccggagcc aagcagcaac tgagcgggga agcgcccgcg     300 tccgggatc ggg atg tcc ctc ctc ctt ctc ctc ttg cta gtt tcc tac        349
          Met Ser Leu Leu Leu Leu Leu Leu Leu Val Ser Tyr
            1               5                  10 tat gtt gga acc ttg ggg act cac act gag atc aag aga gtg gca gag     397
Tyr Val Gly Thr Leu Gly Thr His Thr Glu Ile Lys Arg Val Ala Glu
            15                  20                  25 gaa aag gtc act ttg ccc tgc cac cat caa ctg ggg ctt cca gaa aaa     445
Glu Lys Val Thr Leu Pro Cys His His Gln Leu Gly Leu Pro Glu Lys
        30                  35                  40
```

```
gac act ctg gat att gaa tgg ctg ctc acc gat aat gaa ggg aac caa    493
Asp Thr Leu Asp Ile Glu Trp Leu Leu Thr Asp Asn Glu Gly Asn Gln
 45              50                  55                  60 aaa gtg gtg atc act tac tcc agt cgt cat gtc tac aat aac ttg act    541
Lys Val Val Ile Thr Tyr Ser Ser Arg His Val Tyr Asn Asn Leu Thr
                     65                  70                  75 gag gaa cag aag ggc cga gtg gcc ttt gct tcc aat ttc ctg gca gga    589
Glu Glu Gln Lys Gly Arg Val Ala Phe Ala Ser Asn Phe Leu Ala Gly
             80                  85                  90 gat gcc tcc ttg cag att gaa cct ctg aag ccc agt gat gag ggc cgg    637
Asp Ala Ser Leu Gln Ile Glu Pro Leu Lys Pro Ser Asp Glu Gly Arg
         95                 100                 105 tac acc tgt aag gtt aag aat tca ggg cgc tac gtg tgg agc cat gtc    685
Tyr Thr Cys Lys Val Lys Asn Ser Gly Arg Tyr Val Trp Ser His Val
     110                 115                 120 atc tta aaa gtc tta gtg aga cca tcc aag ccc aag tgt gag ttg gaa    733
Ile Leu Lys Val Leu Val Arg Pro Ser Lys Pro Lys Cys Glu Leu Glu
125                 130                 135                 140 gga gag ctg aca gaa gga agt gac ctg act ttg cag tgt gag tca tcc    781
Gly Glu Leu Thr Glu Gly Ser Asp Leu Thr Leu Gln Cys Glu Ser Ser
                145                 150                 155 tct ggc aca gag ccc att gtg tat tac tgg cag cga atc cga gag aaa    829
Ser Gly Thr Glu Pro Ile Val Tyr Tyr Trp Gln Arg Ile Arg Glu Lys
            160                 165                 170 gag gga gag gat gaa cgt ctg cct ccc aaa tct agg att gac tac aac    877
Glu Gly Glu Asp Glu Arg Leu Pro Pro Lys Ser Arg Ile Asp Tyr Asn
        175                 180                 185 cac cct gga cga gtt ctg ctg cag aat ctt acc atg tcc tac tct gga    925
His Pro Gly Arg Val Leu Leu Gln Asn Leu Thr Met Ser Tyr Ser Gly
    190                 195                 200 ctg tac cag tgc aca gca ggc aac gaa gct ggg aag gaa agc tgt gtg    973
Leu Tyr Gln Cys Thr Ala Gly Asn Glu Ala Gly Lys Glu Ser Cys Val
205                 210                 215                 220 gtg cga gta act gta cag tat gta caa agc atc ggc atg gtt gca gga   1021
Val Arg Val Thr Val Gln Tyr Val Gln Ser Ile Gly Met Val Ala Gly
                225                 230                 235 gca gtg aca ggc ata gtg gct gga gcc ctg ctg att ttc ctc ttg gtg   1069
Ala Val Thr Gly Ile Val Ala Gly Ala Leu Leu Ile Phe Leu Leu Val
            240                 245                 250 tgg ctg cta atc cga agg aaa gac aaa gaa aga tat gag gaa gaa gag   1117
Trp Leu Leu Ile Arg Arg Lys Asp Lys Glu Arg Tyr Glu Glu Glu Glu
        255                 260                 265 aga cct aat gaa att cga gaa gat gct gaa gct cca aaa gcc cgt ctt   1165
Arg Pro Asn Glu Ile Arg Glu Asp Ala Glu Ala Pro Lys Ala Arg Leu
    270                 275                 280 gtg aaa ccc agc tcc tct tcc tca ggc tct cgg agc tca cgc tct ggt   1213
Val Lys Pro Ser Ser Ser Ser Gly Ser Arg Ser Ser Arg Ser Gly
285                 290                 295                 300 tct tcc tcc act cgc tcc aca gca aat agt gcc tca cgc agc cag cgg   1261
Ser Ser Ser Thr Arg Ser Thr Ala Asn Ser Ala Ser Arg Ser Gln Arg
                305                 310                 315 aca ctg tca act gac gca gca ccc cag cca ggg ctg gcc acc cag gca   1309
Thr Leu Ser Thr Asp Ala Ala Pro Gln Pro Gly Leu Ala Thr Gln Ala
            320                 325                 330 tac agc cta gtg ggg cca gag gtg aga ggt tct gaa cca aag aaa gtc   1357
Tyr Ser Leu Val Gly Pro Glu Val Arg Gly Ser Glu Pro Lys Lys Val
        335                 340                 345 cac cat gct aat ctg acc aaa gca gaa acc aca ccc agc atg atc ccc   1405
His His Ala Asn Leu Thr Lys Ala Glu Thr Thr Pro Ser Met Ile Pro
    350                 355                 360
```

```
                                                            -continued
agc cag agc aga gcc ttc caa acg gtc tgaattacaa tggacttgac         1452
Ser Gln Ser Arg Ala Phe Gln Thr Val
365                 370 tcccacgctt tcctaggagt cagggtcttt ggactcttct cgtcattgga gctcaagtca  1512
ccagccacac aaccagatga gaggtcatct aagtagcagt gagcattgca cggaacagat  1572
tcagatgagc attttcctta taatacca aacaagcaaa aggatgtaag ctgattcatc    1632
tgtaaaaagg catcttattg tgcctttaga ccagagtaag ggaaagcagg agtccaaatc  1692
tatttgttga ccaggacctg tggtgaagaa aggttgggga aaggtgaggt gaatatacct  1752
aaaactttta atgtgggata ttttgtatca gtgctttgat tcacaatttt caagaggaaa  1812
tgggatgctg tttgtaaatt ttctatgcat ttctgcaaac ttattggatt attagttatt  1872
cagacagtca agcagaaccc ncagccttat tacncctgtc tacaccatgt actgagctaa  1932
ccacttttaa gaaact                                                 1948

<210> SEQ ID NO 24
<211> LENGTH: 373
<212> TYPE: PRT
<213> ORGANISM: Homo sapiens

<400> SEQUENCE: 24

Met Ser Leu Leu Leu Leu Leu Leu Val Ser Tyr Tyr Val Gly Thr
1               5                   10                  15

Leu Gly Thr His Thr Glu Ile Lys Arg Val Ala Glu Glu Lys Val Thr
                20                  25                  30

Leu Pro Cys His His Gln Leu Gly Leu Pro Glu Lys Asp Thr Leu Asp
            35                  40                  45

Ile Glu Trp Leu Leu Thr Asp Asn Gly Asn Gln Lys Val Val Ile
50                  55                  60

Thr Tyr Ser Ser Arg His Val Tyr Asn Asn Leu Thr Glu Glu Gln Lys
65                  70                  75                  80

Gly Arg Val Ala Phe Ala Ser Asn Phe Leu Ala Gly Asp Ala Ser Leu
                85                  90                  95

Gln Ile Glu Pro Leu Lys Pro Ser Asp Glu Gly Arg Tyr Thr Cys Lys
            100                 105                 110

Val Lys Asn Ser Gly Arg Tyr Val Trp Ser His Val Ile Leu Lys Val
        115                 120                 125

Leu Val Arg Pro Ser Lys Pro Lys Cys Glu Leu Glu Gly Glu Leu Thr
130                 135                 140

Glu Gly Ser Asp Leu Thr Leu Gln Cys Glu Ser Ser Gly Thr Glu
145                 150                 155                 160

Pro Ile Val Tyr Tyr Trp Gln Arg Ile Arg Glu Lys Glu Gly Glu Asp
                165                 170                 175

Glu Arg Leu Pro Pro Lys Ser Arg Ile Asp Tyr Asn His Pro Gly Arg
            180                 185                 190

Val Leu Leu Gln Asn Leu Thr Met Ser Tyr Ser Gly Leu Tyr Gln Cys
        195                 200                 205

Thr Ala Gly Asn Glu Ala Gly Lys Glu Ser Cys Val Val Arg Val Thr
    210                 215                 220

Val Gln Tyr Val Gln Ser Ile Gly Met Val Ala Gly Ala Val Thr Gly
225                 230                 235                 240

Ile Val Ala Gly Ala Leu Leu Ile Phe Leu Leu Val Trp Leu Leu Ile
                245                 250                 255

Arg Arg Lys Asp Lys Glu Arg Tyr Glu Glu Glu Glu Arg Pro Asn Glu
            260                 265                 270
```

```
Ile Arg Glu Asp Ala Glu Ala Pro Lys Ala Arg Leu Val Lys Pro Ser
        275                 280                 285

Ser Ser Ser Gly Ser Arg Ser Arg Ser Gly Ser Ser Thr
    290                 295                 300

Arg Ser Thr Ala Asn Ala Ser Arg Ser Gln Arg Thr Leu Ser Thr
305                 310                 315                 320

Asp Ala Ala Pro Gln Pro Gly Leu Ala Thr Gln Ala Tyr Ser Leu Val
                325                 330                 335

Gly Pro Glu Val Arg Gly Ser Glu Pro Lys Lys Val His His Ala Asn
                340                 345                 350

Leu Thr Lys Ala Glu Thr Thr Pro Ser Met Ile Pro Ser Gln Ser Arg
                355                 360                 365

Ala Phe Gln Thr Val
        370

<210> SEQ ID NO 25
<211> LENGTH: 1949
<212> TYPE: DNA
<213> ORGANISM: Mus musculus
<220> FEATURE:
<221> NAME/KEY: CDS
<222> LOCATION: (304)...(1422)

<400> SEQUENCE: 25
gtcgacccac gcgtccggtt ccacgaagcg gtagctcctt gccgcctcgc cttctcctcc      60
ctaaccctgg gccggcccc cgtcccggcg cgagctggtg gagccagggc tagaagccct     120
cggtgccccc ggagcgcagc gcgcagggga cccgggcgcg gggccagcgc cgcacatgg     180 ctgcagcccc ccgcgcgcac cccgaggcgc cgcgccctgc tcacagaagg tccgtcggct    240
gggctcggtc gccctgcagc caggctgcgc tgagccggga agtgcccgtg tccggagatc    300 ggg atg tcc ctc ttc ttc ctc tgg cta gta tcc tat tat gtt gga acg     348
    Met Ser Leu Phe Phe Leu Trp Leu Val Ser Tyr Tyr Val Gly Thr
        1               5                   10                  15 ctg gga act cac act gag atc aag aga gtg gca gag gaa aag gtt acc     396
Leu Gly Thr His Thr Glu Ile Lys Arg Val Ala Glu Glu Lys Val Thr
                20                  25                  30 ttg ccc tgt cac cat caa ctg ggg ctt ccc gag aaa gac acc ctg gac     444
Leu Pro Cys His His Gln Leu Gly Leu Pro Glu Lys Asp Thr Leu Asp
            35                  40                  45 att gaa tgg ctg ctc acc gat aat gaa ggg aac caa aaa gtg gtt att     492
Ile Glu Trp Leu Leu Thr Asp Asn Glu Gly Asn Gln Lys Val Val Ile
        50                  55                  60 acg tat tcc agc cgt cat gtc tac aat aac ttg acc gag gag cag aag     540
Thr Tyr Ser Ser Arg His Val Tyr Asn Asn Leu Thr Glu Glu Gln Lys
    65                  70                  75 ggc cga gtg gcc ttc gct tcc aac ttc ctg gca gga gat gct tcc ctg     588
Gly Arg Val Ala Phe Ala Ser Asn Phe Leu Ala Gly Asp Ala Ser Leu
80                  85                  90                  95 cag att gag cct ctg aaa ccc agt gat gaa ggc aga tac acc tgc aag     636
Gln Ile Glu Pro Leu Lys Pro Ser Asp Glu Gly Arg Tyr Thr Cys Lys
                100                 105                 110 gtg aag aat tca gga cgc tat gtc tgg agc cat gtc atc ttg aaa gtg     684
Val Lys Asn Ser Gly Arg Tyr Val Trp Ser His Val Ile Leu Lys Val
            115                 120                 125 cta gtg aga cca tcc aag ccc aag tgt gag ctg gaa gga gag ccg acc     732
Leu Val Arg Pro Ser Lys Pro Lys Cys Glu Leu Glu Gly Glu Pro Thr
        130                 135                 140 gaa gga agt gac ctg acg ctg cag tgt gag tct gcc tct gga act aag     780
Glu Gly Ser Asp Leu Thr Leu Gln Cys Glu Ser Ala Ser Gly Thr Lys
```

```
                Glu Gly Ser Asp Leu Thr Leu Gln Cys Glu Ser Ala Ser Gly Thr Lys
                145                 150                 155 ccc att gtg tat tat tgg cag cga atc cgg gag aag gag gga gaa gat         828
Pro Ile Val Tyr Tyr Trp Gln Arg Ile Arg Glu Lys Glu Gly Glu Asp
160                 165                 170                 175 gaa cac ctg cca ccc aaa tcc aga att gat tac aac aac cct ggc cga         876
Glu His Leu Pro Pro Lys Ser Arg Ile Asp Tyr Asn Asn Pro Gly Arg
                180                 185                 190 gtg ctg ctg cag aat ctc acc atg gcc tcc tct ggg ctt tac cag tgc         924
Val Leu Leu Gln Asn Leu Thr Met Ala Ser Ser Gly Leu Tyr Gln Cys
                195                 200                 205 aca gca ggc aac gag gct gga aag gag agc tgt gtg gta cgg gtg act         972
Thr Ala Gly Asn Glu Ala Gly Lys Glu Ser Cys Val Val Arg Val Thr
210                 215                 220 gta cag tat gtg cag agc att ggc atg gtg gca gga gca gtg aca ggc        1020
Val Gln Tyr Val Gln Ser Ile Gly Met Val Ala Gly Ala Val Thr Gly
    225                 230                 235 ata gtg gca gga gcc ctg ctc att ttc ctc ctg ata tgg ctg cta ata        1068
Ile Val Ala Gly Ala Leu Leu Ile Phe Leu Leu Ile Trp Leu Leu Ile
240                 245                 250                 255 cga agg aaa agc aaa gac aga tac gag gaa gaa gac aga cct aat gaa        1116
Arg Arg Lys Ser Lys Asp Arg Tyr Glu Glu Glu Asp Arg Pro Asn Glu
                260                 265                 270 atc cga gaa gac gcc gaa gcg ccc cga gcc cgc ctt gtg aag cct agc        1164
Ile Arg Glu Asp Ala Glu Ala Pro Arg Ala Arg Leu Val Lys Pro Ser
                275                 280                 285 tcc tct tcc tca ggc tcc cgg agc tca cgc tct ggc tcc tcc tcc acc        1212
Ser Ser Ser Ser Gly Ser Arg Ser Ser Arg Ser Gly Ser Ser Ser Thr
                290                 295                 300 cgc tcc acc ggg aac agt gcc tcc aga agc cag cgg acg ctg tcg agt        1260
Arg Ser Thr Gly Asn Ser Ala Ser Arg Ser Gln Arg Thr Leu Ser Ser
305                 310                 315 gaa gca gcg ccg cag cag ccc ggg cta gcc ccg cag gca tac agc ctc        1308
Glu Ala Ala Pro Gln Gln Pro Gly Leu Ala Pro Gln Ala Tyr Ser Leu
320                 325                 330                 335 ata gga ccg gaa gtg aga ggt tct gaa cca aag aaa gtc cac cat acg        1356
Ile Gly Pro Glu Val Arg Gly Ser Glu Pro Lys Lys Val His His Thr
                340                 345                 350 acc ctg acc aaa gca gaa acc aca ctc agc aca acg ccc agc cag agc        1404
Thr Leu Thr Lys Ala Glu Thr Thr Leu Ser Thr Thr Pro Ser Gln Ser
                355                 360                 365 aaa gcc ttc caa act gtc tgacttagag tggacttgac ttgcgcttgc               1452
Lys Ala Phe Gln Thr Val
            370 cccaaagtca ggatcttagc ctagtcactg gagctcgtcc accagccacg caagcccctc      1512 agccagatac gatctcactt aagtagctgc agaaatggca cggaccagtt ctgatgagta      1572 ccctccttat ataggatacc aaacaaacac aaggacggag gctgaccatc tatctctaaa      1632 ggcacctcac tgtgccttca gacagagtgg aggggaggag gggcccaagc ttatttggtg      1692 aaaataaagg gaaaggtgag gctgcacaca cctgaaacat cttacctagg atgttgcaag      1752 tcaccacagt caagaagaag cgggaatctc gtagatcaat tttctattca tttctgcaaa     1812 tttattggat tagtgtgatt attcagatag tcaaaacaga agcccacgcc ttataatata      1872 cctatctgca acatgtactg ggagaactgc gtttaagaaa ttcacattaa aaaaaaaaa      1932 aaaaaaaggg cggccgc                                                     1949

<210> SEQ ID NO 26
<211> LENGTH: 373
```

```
<212> TYPE: PRT
<213> ORGANISM: Mus musculus

<400> SEQUENCE: 26

Met Ser Leu Phe Phe Leu Trp Leu Val Ser Tyr Tyr Val Gly Thr Leu
 1               5                  10                  15

Gly Thr His Thr Glu Ile Lys Arg Val Ala Glu Lys Val Thr Leu
             20                  25                  30

Pro Cys His His Gln Leu Gly Leu Pro Glu Lys Asp Thr Leu Asp Ile
             35                  40                  45

Glu Trp Leu Leu Thr Asp Asn Glu Gly Asn Gln Lys Val Val Ile Thr
 50                  55                  60

Tyr Ser Ser Arg His Val Tyr Asn Asn Leu Thr Glu Glu Gln Lys Gly
65                   70                  75                  80

Arg Val Ala Phe Ala Ser Asn Phe Leu Ala Gly Asp Ala Ser Leu Gln
                 85                  90                  95

Ile Glu Pro Leu Lys Pro Ser Asp Glu Gly Arg Tyr Thr Cys Lys Val
                100                 105                 110

Lys Asn Ser Gly Arg Tyr Val Trp Ser His Val Ile Leu Lys Val Leu
            115                 120                 125

Val Arg Pro Ser Lys Pro Lys Cys Glu Leu Glu Gly Glu Pro Thr Glu
130                 135                 140

Gly Ser Asp Leu Thr Leu Gln Cys Glu Ser Ala Ser Gly Thr Lys Pro
145                 150                 155                 160

Ile Val Tyr Tyr Trp Gln Arg Ile Arg Glu Lys Glu Gly Glu Asp Glu
                165                 170                 175

His Leu Pro Pro Lys Ser Arg Ile Asp Tyr Asn Asn Pro Gly Arg Val
                180                 185                 190

Leu Leu Gln Asn Leu Thr Met Ala Ser Ser Gly Leu Tyr Gln Cys Thr
            195                 200                 205

Ala Gly Asn Glu Ala Gly Lys Glu Ser Cys Val Val Arg Val Thr Val
210                 215                 220

Gln Tyr Val Gln Ser Ile Gly Met Val Ala Gly Ala Val Thr Gly Ile
225                 230                 235                 240

Val Ala Gly Ala Leu Leu Ile Phe Leu Leu Ile Trp Leu Leu Ile Arg
                245                 250                 255

Arg Lys Ser Lys Asp Arg Tyr Glu Glu Asp Arg Pro Asn Glu Ile
            260                 265                 270

Arg Glu Asp Ala Glu Ala Pro Arg Ala Arg Leu Val Lys Pro Ser Ser
            275                 280                 285

Ser Ser Ser Gly Ser Arg Ser Ser Arg Ser Gly Ser Ser Thr Arg
290                 295                 300

Ser Thr Gly Asn Ser Ala Ser Arg Ser Gln Arg Thr Leu Ser Ser Glu
305                 310                 315                 320

Ala Ala Pro Gln Gln Pro Gly Leu Ala Pro Gln Ala Tyr Ser Leu Ile
                325                 330                 335

Gly Pro Glu Val Arg Gly Ser Gly Pro Lys Lys Val His His Thr Thr
                340                 345                 350

Leu Thr Lys Ala Glu Thr Thr Leu Ser Thr Thr Pro Ser Gln Ser Lys
            355                 360                 365

Ala Phe Gln Thr Val
            370

<210> SEQ ID NO 27
<211> LENGTH: 1332
```

<212> TYPE: DNA
<213> ORGANISM: Homo sapiens
<220> FEATURE:
<221> NAME/KEY: CDS
<222> LOCATION: (31)...(1113)

<400> SEQUENCE: 27

```
ccaagaattc ggcacgagga gaggccggcc atg gcc agc ctg ggg ctg ctg ctc        54
                                 Met Ala Ser Leu Gly Leu Leu Leu
                                  1               5 ctg ctc tta ctg aca gca ctg cca ccg ctg tgg tcc tcc tca ctg cct       102
Leu Leu Leu Leu Thr Ala Leu Pro Pro Leu Trp Ser Ser Ser Leu Pro
         10                  15                  20 ggg ctg gac act gct gaa agt aaa gcc acc att gca gac ctg atc ctg       150
Gly Leu Asp Thr Ala Glu Ser Lys Ala Thr Ile Ala Asp Leu Ile Leu
 25                  30                  35                  40 tct gcg ctg gag aga gcc acc gtc ttc cta gaa cag agg ctg cct gaa       198
Ser Ala Leu Glu Arg Ala Thr Val Phe Leu Glu Gln Arg Leu Pro Glu
                 45                  50                  55 atc aac ctg gat ggc atg gtg ggg gtc cga gtg ctg gaa gag cag cta       246
Ile Asn Leu Asp Gly Met Val Gly Val Arg Val Leu Glu Glu Gln Leu
             60                  65                  70 aaa agt gtc cgg gag aag tgg gcc cag gag ccc ctg ctg caa ccg ctg       294
Lys Ser Val Arg Glu Lys Trp Ala Gln Glu Pro Leu Leu Gln Pro Leu
 75                  80                  85 agc ctg cgc gtg ggg atg ctg ggg gag aag ctg gag gct gcc atc cag       342
Ser Leu Arg Val Gly Met Leu Gly Glu Lys Leu Glu Ala Ala Ile Gln
         90                  95                 100 aga tcc ctc cac tac ctc aag ctg agt gat ccc aag tac cta aga gag       390
Arg Ser Leu His Tyr Leu Lys Leu Ser Asp Pro Lys Tyr Leu Arg Glu
105                 110                 115                 120 ttc cag ctg acc ctc cag ccc ggg ttt tgg aag ctc cca cat gcc tgg       438
Phe Gln Leu Thr Leu Gln Pro Gly Phe Trp Lys Leu Pro His Ala Trp
                125                 130                 135 atc cac act gat gcc tcc ttg gtg tac ccc acg ttc ggg ccc cag gac       486
Ile His Thr Asp Ala Ser Leu Val Tyr Pro Thr Phe Gly Pro Gln Asp
            140                 145                 150 tca ttc tca gag gag aga agt gac gtg tgc ctg gtg cag ctg ctg gga       534
Ser Phe Ser Glu Glu Arg Ser Asp Val Cys Leu Val Gln Leu Leu Gly
            155                 160                 165 acc ggg acg gac agc agc gag ccc tgc ggc ctc tca gac ctc tgc agg       582
Thr Gly Thr Asp Ser Ser Glu Pro Cys Gly Leu Ser Asp Leu Cys Arg
170                 175                 180 agc ctc atg acc aag ccc ggc tgc tca ggc tac tgc ctg tcc cac caa       630
Ser Leu Met Thr Lys Pro Gly Cys Ser Gly Tyr Cys Leu Ser His Gln
185                 190                 195                 200 ctg ctc ttc ttc ctc tgg gcc aga atg agg ggg tgc aca cag gga cca       678
Leu Leu Phe Phe Leu Trp Ala Arg Met Arg Gly Cys Thr Gln Gly Pro
                205                 210                 215 ctc caa cag agc cag gac tat atc aac ctc ttc tgc gcc aac atg atg       726
Leu Gln Gln Ser Gln Asp Tyr Ile Asn Leu Phe Cys Ala Asn Met Met
            220                 225                 230 gac ttg aac cgc aga gct gag gcc atc gga tac gcc tac cct acc cgg       774
Asp Leu Asn Arg Arg Ala Glu Ala Ile Gly Tyr Ala Tyr Pro Thr Arg
            235                 240                 245 gac atc ttc atg gaa aac atc atg ttc tgt gga atg ggc ggc ttc tcc       822
Asp Ile Phe Met Glu Asn Ile Met Phe Cys Gly Met Gly Gly Phe Ser
250                 255                 260 gac ttc tac aag ctc cgg tgg ctg gag gcc att ctc agc tgg cag aaa       870
Asp Phe Tyr Lys Leu Arg Trp Leu Glu Ala Ile Leu Ser Trp Gln Lys
265                 270                 275                 280
```

-continued

| | | | | | | | | | | | | | | |
|---|---|---|---|---|---|---|---|---|---|---|---|---|---|---|
|cag|cag|gaa|gga|tgc|ttc|ggg|gag|cct|gat|gct|gaa|gat|gaa|gaa tta|918
|Gln|Gln|Glu|Gly|Cys|Phe|Gly|Glu|Pro|Asp|Ala|Glu|Asp|Glu|Glu Leu
| | | |285| | | | |290| | | |295| | |

```
tct aaa gct att caa tat cag cag cat ttt tcg agg aga gtg aag agg    966
Ser Lys Ala Ile Gln Tyr Gln Gln His Phe Ser Arg Arg Val Lys Arg
        300                 305                 310 cga gaa aaa caa ttt cca gat ggc tgc tcc tcc cac aac aca gcc aca   1014
Arg Glu Lys Gln Phe Pro Asp Gly Cys Ser Ser His Asn Thr Ala Thr
        315                 320                 325 gca gtg gca gcc ctg ggt ggc ttc cta tac atc ctg gca gaa tac ccc   1062
Ala Val Ala Ala Leu Gly Gly Phe Leu Tyr Ile Leu Ala Glu Tyr Pro
        330                 335                 340 cca gca aac aga gag cca cac cca tcc aca ccg cca cca agc agc       1110
Pro Ala Asn Arg Glu Pro His Pro Ser Thr Pro Pro Pro Ser Ser
345                 350                 355                 360 cgc tgagacggac ggttccatgc cagctgcctg gaggaggaac agacccecttt       1163
Arg agtcctcatc ccttagatcc tggagggcac ggatcacatc ctgggaagaa ggcatctgga  1223
ggataagcaa agccaccccg acacccaatc ttggaagccc tgagtaggca gggccagggt  1283
aggtgggggc cggagggac ccaggtgtga acggatgaat aaagttcaa               1332

<210> SEQ ID NO 28
<211> LENGTH: 361
<212> TYPE: PRT
<213> ORGANISM: Homo sapiens

<400> SEQUENCE: 28

Met Ala Ser Leu Gly Leu Leu Leu Leu Leu Leu Thr Ala Leu Pro
 1               5                   10                  15

Pro Leu Trp Ser Ser Ser Leu Pro Gly Leu Asp Thr Ala Glu Ser Lys
                20                  25                  30

Ala Thr Ile Ala Asp Leu Ile Leu Ser Ala Leu Glu Arg Ala Thr Val
            35                  40                  45

Phe Leu Glu Gln Arg Leu Pro Glu Ile Asn Leu Asp Gly Met Val Gly
        50                  55                  60

Val Arg Val Leu Glu Glu Gln Leu Lys Ser Val Arg Glu Lys Trp Ala
65                  70                  75                  80

Gln Glu Pro Leu Leu Gln Pro Leu Ser Leu Arg Val Gly Met Leu Gly
                85                  90                  95

Glu Lys Leu Glu Ala Ala Ile Gln Arg Ser Leu His Tyr Leu Lys Leu
                100                 105                 110

Ser Asp Pro Lys Tyr Leu Arg Glu Phe Gln Leu Thr Leu Gln Pro Gly
            115                 120                 125

Phe Trp Lys Leu Pro His Ala Trp Ile His Thr Asp Ala Ser Leu Val
        130                 135                 140

Tyr Pro Thr Phe Gly Pro Gln Asp Ser Phe Ser Glu Glu Arg Ser Asp
145                 150                 155                 160

Val Cys Leu Val Gln Leu Leu Gly Thr Gly Thr Asp Ser Ser Glu Pro
                165                 170                 175

Cys Gly Leu Ser Asp Leu Cys Arg Ser Leu Met Thr Lys Pro Gly Cys
            180                 185                 190

Ser Gly Tyr Cys Leu Ser His Gln Leu Leu Phe Leu Trp Ala Arg
            195                 200                 205

Met Arg Gly Cys Thr Gln Gly Pro Leu Gln Gln Ser Gln Asp Tyr Ile
        210                 215                 220

Asn Leu Phe Cys Ala Asn Met Met Asp Leu Asn Arg Arg Ala Glu Ala
```

```
                225                 230                 235                 240
Ile Gly Tyr Ala Tyr Pro Thr Arg Asp Ile Phe Met Glu Asn Ile Met
            245                 250                 255

Phe Cys Gly Met Gly Gly Phe Ser Asp Phe Tyr Lys Leu Arg Trp Leu
            260                 265                 270

Glu Ala Ile Leu Ser Trp Gln Lys Gln Gln Glu Gly Cys Phe Gly Glu
            275                 280                 285

Pro Asp Ala Glu Asp Glu Glu Leu Ser Lys Ala Ile Gln Tyr Gln Gln
            290                 295                 300

His Phe Ser Arg Arg Val Lys Arg Arg Glu Lys Gln Phe Pro Asp Gly
305                 310                 315                 320

Cys Ser Ser His Asn Thr Ala Thr Ala Val Ala Ala Leu Gly Gly Phe
            325                 330                 335

Leu Tyr Ile Leu Ala Glu Tyr Pro Pro Ala Asn Arg Glu Pro His Pro
            340                 345                 350

Ser Thr Pro Pro Pro Ser Ser Arg
            355                 360

<210> SEQ ID NO 29
<211> LENGTH: 1400
<212> TYPE: DNA
<213> ORGANISM: Mus musculus
<220> FEATURE:
<221> NAME/KEY: CDS
<222> LOCATION: (41)...(1195)

<400> SEQUENCE: 29
gtcgacccac gcgtccgcat ccaccagcag aaatcctgtc atg gcg aga ctc ggg      55
                                            Met Ala Arg Leu Gly
                                              1               5 ctg ctt ctc ctc ctg ctg ctg gcc ctg cca cca cac ttc tcc tca gtg     103
Leu Leu Leu Leu Leu Leu Leu Ala Leu Pro Pro His Phe Ser Ser Val
                 10                  15                  20 tca tgg cca gac act gca cag ggc acc atg gca aac ttg atc ctg act     151
Ser Trp Pro Asp Thr Ala Gln Gly Thr Met Ala Asn Leu Ile Leu Thr
             25                  30                  35 gca tta gaa aaa gcc acc ttg ttc ttg gag gac agg ctg ccc aca atc     199
Ala Leu Glu Lys Ala Thr Leu Phe Leu Glu Asp Arg Leu Pro Thr Ile
         40                  45                  50 aac ctg gat ggt gtg gtg ggc ttc caa gtg ctg gaa gtg caa ctc cga     247
Asn Leu Asp Gly Val Val Gly Phe Gln Val Leu Glu Val Gln Leu Arg
     55                  60                  65 gga gtt cag gaa aaa tgg gct cac aag ccc ttg ctg cag cct ctc agc     295
Gly Val Gln Glu Lys Trp Ala His Lys Pro Leu Leu Gln Pro Leu Ser
 70                  75                  80                  85 atg cgc gct gga cag atg gcc aac aca ctg tct gct ctc ctc caa aaa     343
Met Arg Ala Gly Gln Met Ala Asn Thr Leu Ser Ala Leu Leu Gln Lys
                 90                  95                 100 tcc atc ttc tac ctc aag cag agt gac ccc acg tac cta aga gag ttc     391
Ser Ile Phe Tyr Leu Lys Gln Ser Asp Pro Thr Tyr Leu Arg Glu Phe
             105                 110                 115 cag cca agc att cag cct ggg ttt tgg aag ttg ccc aat gac tgg aca     439
Gln Pro Ser Ile Gln Pro Gly Phe Trp Lys Leu Pro Asn Asp Trp Thr
         120                 125                 130 cgc acc aat gcc tcc cta gtc tac ccc tgg ctg gaa ccc ctg gac tct     487
Arg Thr Asn Ala Ser Leu Val Tyr Pro Trp Leu Glu Pro Leu Asp Ser
     135                 140                 145 ttc tca gag gaa agc agc gat gtg tgc ctg gtg caa cta cta gga aca     535
Phe Ser Glu Glu Ser Ser Asp Val Cys Leu Val Gln Leu Leu Gly Thr
150                 155                 160                 165
```

```
ggg aca gac agc agc cag cct tgc agg ctc tcc aac ttc tgc aga acc         583
Gly Thr Asp Ser Ser Gln Pro Cys Arg Leu Ser Asn Phe Cys Arg Thr
            170                 175                 180 ctt atg acc aag gcc ggc tgc tca ggc tac agc ctc tcc cat cag ctg         631
Leu Met Thr Lys Ala Gly Cys Ser Gly Tyr Ser Leu Ser His Gln Leu
        185                 190                 195 ctc ttc ttc ctc tgg gcc aga atg caa ggg tgc acg gag gga ctg ttc         679
Leu Phe Phe Leu Trp Ala Arg Met Gln Gly Cys Thr Glu Gly Leu Phe
    200                 205                 210 ctc cag agc caa cac tac atg gac atc ttc tgt gcc aat atg atg gaa         727
Leu Gln Ser Gln His Tyr Met Asp Ile Phe Cys Ala Asn Met Met Glu
215                 220                 225 ctg aac cac aga gct gag gcc gtt gga tac gct tac ccc acc caa gac         775
Leu Asn His Arg Ala Glu Ala Val Gly Tyr Ala Tyr Pro Thr Gln Asp
230                 235                 240                 245 ctc ttc atg gaa aac att atg ttc tgt ggt atg gct ggc ttc tct gac         823
Leu Phe Met Glu Asn Ile Met Phe Cys Gly Met Ala Gly Phe Ser Asp
                250                 255                 260 ttc tac aag ctg cgc tgg ctg gag gcc att ctc agc tgg cag aac ccc         871
Phe Tyr Lys Leu Arg Trp Leu Glu Ala Ile Leu Ser Trp Gln Asn Pro
            265                 270                 275 cag gtg gga tgc ttc ggg agg cct gac aca aag ggt gaa cct tct gaa         919
Gln Val Gly Cys Phe Gly Arg Pro Asp Thr Lys Gly Glu Pro Ser Glu
        280                 285                 290 gtt cca cat cag cag ggc att ctg aga aga gtg cga agg cgg gaa aaa         967
Val Pro His Gln Gln Gly Ile Leu Arg Arg Val Arg Arg Arg Glu Lys
    295                 300                 305 ctg ttc gca gat ggc tgt tcg tgc cac aac aca gcc aca gca gtc gca        1015
Leu Phe Ala Asp Gly Cys Ser Cys His Asn Thr Ala Thr Ala Val Ala
310                 315                 320                 325 gcc ctg ggt ggc ttt ctc tac atc ctg gca gaa tac cac cca gac aat        1063
Ala Leu Gly Gly Phe Leu Tyr Ile Leu Ala Glu Tyr His Pro Asp Asn
                330                 335                 340 gga gat gca cat cca gaa tac tac cca aac cat gga gat cca tac tca        1111
Gly Asp Ala His Pro Glu Tyr Tyr Pro Asn His Gly Asp Pro Tyr Ser
            345                 350                 355 tcc tca cag tca cca gca agc aac tac caa gat ggt gct gcc ggc cct        1159
Ser Ser Gln Ser Pro Ala Ser Asn Tyr Gln Asp Gly Ala Ala Gly Pro
        360                 365                 370 gac gtc cag agg act ggc agg ccc ctt agt gtt tct taagtcctga            1205
Asp Val Gln Arg Thr Gly Arg Pro Leu Ser Val Ser
    375                 380                 385 gtcagaggtc acaggctgag gaggcaattg aggaaagtga ccagctatat ccccatcgcc    1265
acttctgggt gtttaaaagt cttgggagag cagggccagg gaaagcaggg ttggagagtg    1325
gggtggccca gatgtcagca gaatacataa agcacagtca attggagctg aaaaaaaaaa    1385
aaaaagggcg gccgc                                                      1400

<210> SEQ ID NO 30
<211> LENGTH: 385
<212> TYPE: PRT
<213> ORGANISM: Mus musculus

<400> SEQUENCE: 30

Met Ala Arg Leu Gly Leu Leu Leu Leu Leu Leu Ala Leu Pro Pro
 1               5                  10                  15

His Phe Ser Ser Val Ser Trp Pro Asp Thr Ala Gln Gly Thr Met Ala
                20                  25                  30

Asn Leu Ile Leu Thr Ala Leu Glu Lys Ala Thr Leu Phe Leu Glu Asp
```

```
                35                  40                  45
Arg Leu Pro Thr Ile Asn Leu Asp Gly Val Val Gly Phe Gln Val Leu
 50                  55                  60

Glu Val Gln Leu Arg Gly Val Gln Glu Lys Trp Ala His Lys Pro Leu
 65                  70                  75                  80

Leu Gln Pro Leu Ser Met Arg Ala Gly Gln Met Ala Asn Thr Leu Ser
                 85                  90                  95

Ala Leu Leu Gln Lys Ser Ile Phe Tyr Leu Lys Gln Ser Asp Pro Thr
            100                 105                 110

Tyr Leu Arg Glu Phe Gln Pro Ser Ile Gln Pro Gly Phe Trp Lys Leu
        115                 120                 125

Pro Asn Asp Trp Thr Arg Thr Asn Ala Ser Leu Val Tyr Pro Trp Leu
130                 135                 140

Glu Pro Leu Asp Ser Phe Ser Glu Glu Ser Ser Asp Val Cys Leu Val
145                 150                 155                 160

Gln Leu Leu Gly Thr Gly Thr Asp Ser Ser Gln Pro Cys Arg Leu Ser
                165                 170                 175

Asn Phe Cys Arg Thr Leu Met Thr Lys Ala Gly Cys Ser Gly Tyr Ser
            180                 185                 190

Leu Ser His Gln Leu Leu Phe Phe Leu Trp Ala Arg Met Gln Gly Cys
        195                 200                 205

Thr Glu Gly Leu Phe Leu Gln Ser Gln His Tyr Met Asp Ile Phe Cys
210                 215                 220

Ala Asn Met Met Glu Leu Asn His Arg Ala Glu Ala Val Gly Tyr Ala
225                 230                 235                 240

Tyr Pro Thr Gln Asp Leu Phe Met Glu Asn Ile Met Phe Cys Gly Met
                245                 250                 255

Ala Gly Phe Ser Asp Phe Tyr Lys Leu Arg Trp Leu Glu Ala Ile Leu
            260                 265                 270

Ser Trp Gln Asn Pro Gln Val Gly Cys Phe Gly Arg Pro Asp Thr Lys
        275                 280                 285

Gly Glu Pro Ser Glu Val Pro His Gln Gln Gly Ile Leu Arg Arg Val
290                 295                 300

Arg Arg Arg Glu Lys Leu Phe Ala Asp Gly Cys Ser Cys His Asn Thr
305                 310                 315                 320

Ala Thr Ala Val Ala Leu Gly Gly Phe Leu Tyr Ile Leu Ala Glu
                325                 330                 335

Tyr His Pro Asp Asn Gly Asp Ala His Pro Glu Tyr Tyr Pro Asn His
            340                 345                 350

Gly Asp Pro Tyr Ser Ser Gln Ser Pro Ala Ser Asn Tyr Gln Asp
        355                 360                 365

Gly Ala Ala Gly Pro Asp Val Gln Arg Thr Gly Arg Pro Leu Ser Val
370                 375                 380

Ser
385

<210> SEQ ID NO 31
<211> LENGTH: 1239
<212> TYPE: DNA
<213> ORGANISM: Homo sapiens

<400> SEQUENCE: 31
ctcacaggag gagttggcgg ggagccttgg gccctctgg cctcagccgg atttcccagc      60
caaacgcaga gagagatgcc ctggaccatc ttgctctttg cagctggctc cttggcgatc     120
```

-continued

```
ccagcaccat ccatccggct ggtgccccg tacccaagca gccaagagga ccccatccac    180
atcgcatgca tggcccctgg gaacttcccg ggggcgaatt tcacactgta tcgaggggg     240
caggtggtcc agctcctgca ggcccccacg gaccagcgcg ggtgacatt taacctgagc    300
ggcggcagca gcaaggctcc aggggaccc ttccactgcc agtatggagt gttaggtgag    360
ctcaaccagt cccagctgtc agacctcagc gagcccgtga acgtctcctt cccagtgccc    420
acttggatct tggtgctctc cctgagcctg gctggtgccc tcttcctcct tgctgggctg    480
gtggctgttg ccctggtggt cagaaaagtt aaactcagaa atttacagaa gaaaagagat    540
cgagaatcct gctgggccca gattaacttc gacagcacag acatgtcctt cgataactcc    600
ctgtttaccg tctccgcgaa aacgatgcca gaagaagacc cggccacctt ggatgatcac    660
tcaggcacca ctgccacccc cagcaactcc aggacccgga gaggcccac ttccacgtcc    720
tcctcgcctg agacccccga attcagcact ttccgggcct gccagtgagg ctgaggactg    780
ggggaccct ctgtctccag gcattcgggg gcctgaggtc cctccagcta cttctggggg    840
ggctctgtca gccactttct cagggaattg acagaggaa aggaagggga accctggcct    900
tgggatttc atcacagagg agtgggagag ggacacagg catgggcctg gcactataca    960
gacaacagga agttcccctc tcgaccttcg gctcctcagg accaccagag aaggagatgt   1020
caggacccct tcttgtcccc cagctgggcc ataagacgtc ccaggtctct gcacaccgt   1080
ggaattcctc ccttccccag tgggtttttg agcatagggt gcccttgggt gtgttgtgtg   1140
tctgcctgct ggcttgctta agttattaat tataacacgg gtcaaggtgt taaaaaaaaa   1200
aaaaaaaaa aaaaaaaaa aaaaaaaaa aaaaaaaa                              1239
```

<210> SEQ ID NO 32
<211> LENGTH: 230
<212> TYPE: PRT
<213> ORGANISM: Homo sapiens

<400> SEQUENCE: 32

```
Met Pro Trp Thr Ile Leu Leu Phe Ala Ala Gly Ser Leu Ala Ile Pro
 1               5                  10                  15

Ala Pro Ser Ile Arg Leu Val Pro Tyr Pro Ser Ser Gln Glu Asp
                20                  25                  30

Pro Ile His Ile Ala Cys Met Ala Pro Gly Asn Phe Pro Gly Ala Asn
            35                  40                  45

Phe Thr Leu Tyr Arg Gly Gly Gln Val Val Gln Leu Leu Gln Ala Pro
        50                  55                  60

Thr Asp Gln Arg Gly Val Thr Phe Asn Leu Ser Gly Gly Ser Ser Lys
65                  70                  75                  80

Ala Pro Gly Gly Pro Phe His Cys Gln Tyr Gly Val Leu Gly Glu Leu
                85                  90                  95

Asn Gln Ser Gln Leu Ser Asp Leu Ser Glu Pro Val Asn Val Ser Phe
            100                 105                 110

Pro Val Pro Thr Trp Ile Leu Val Leu Ser Leu Ser Leu Ala Gly Ala
        115                 120                 125

Leu Phe Leu Leu Ala Gly Leu Val Ala Val Ala Leu Val Val Arg Lys
    130                 135                 140

Val Lys Leu Arg Asn Leu Gln Lys Lys Arg Asp Arg Glu Ser Cys Trp
145                 150                 155                 160

Ala Gln Ile Asn Phe Asp Ser Thr Asp Met Ser Phe Asp Asn Ser Leu
                165                 170                 175

Phe Thr Val Ser Ala Lys Thr Met Pro Glu Glu Asp Pro Ala Thr Leu
```

```
               180                 185                 190
Asp Asp His Ser Gly Thr Thr Ala Thr Pro Ser Asn Ser Arg Thr Arg
        195                 200                 205

Lys Arg Pro Thr Ser Thr Ser Ser Ser Pro Glu Thr Pro Glu Phe Ser
        210                 215                 220

Thr Phe Arg Ala Cys Gln
225                 230

<210> SEQ ID NO 33
<211> LENGTH: 1778
<212> TYPE: DNA
<213> ORGANISM: Homo sapiens

<400> SEQUENCE: 33
cgactttcag tccccgacgc gccccgccca acccctacga tgaagagggc gtccgctgga      60
gggagccggc tgctggcatg ggtgctgtgg ctgcaggcct ggcaggtggc agccccatgc     120
ccaggtgcct gcgtatgcta caatgagccc aaggtgacga caagctgccc ccagcagggc     180
ctgcaggctg tgcccgtggg catccctgct gccagccagc gcatcttcct gcacggcaac     240
cgcatctcgc atgtgccagc tgccagcttc cgtgcctgcc gcaacctcac catcctgtgg     300
ctgcactcga atgtgctggc ccgaattgat gcggctgcct tcactggcct ggccctcctg     360
gagcagctgg acctcagcga taatgcacag ctccggtctg tggaccctgc acattccac      420 ggcctgggcc gcgtacacac gctgcacctg accgctgcg gcctgcagga gctgggcccg     480
gggctgttcc gcggcctggc tgccctgcag tacctctacc tgcaggacaa cgcgctgcag     540
gcactgcctg atgacacctt ccgcgacctg gcaacctca cacacctctt cctgcacggc      600
aaccgcatct ccagcgtgcc cgagcgcgcc ttccgtgggc tgcacagcct cgaccgtctc     660
ctactgcacc agaaccgcgt ggcccatgtg cacccgcatg ccttccgtga ccttggccgc     720
ctcatgacac tctatctgtt tgccaacaat ctatcagcgc tgcccactga ggccctggcc     780
cccctgcgtg ccctgcagta cctgaggctc aacgacaacc cctgggtgtg tgactgccgg     840
gcacgcccac tctgggcctg gctgcagaag ttccgcggct cctcctccga ggtgccctgc     900
agcctcccgc aacgcctggc tggccgtgac ctcaaacgcc tagctgccaa tgacctgcag     960
ggctgcgctg tggccaccgg cccttaccat cccatctgga ccggcagggc caccgatgag    1020
gagccgctgg ggcttcccaa gtgctgccag ccagatgccg ctgacaaggc ctcagtactg    1080
gagcctggaa gaccagcttc ggcaggcaat gcgctgaagg gacgcgtgcc gcccggtgac    1140
agcccgccgg gcaacggctc tggcccacgg cacatcaatg actcacccct tgggactctg    1200
cctggctctg ctgagccccc gctcactgca gtgcggcccg agggctccga gccaccaggg    1260
ttccccacct cgggccctcg ccggaggcca ggctgttcac gcaagaaccg cacccgcagc    1320
cactgccgtc tgggccaggc aggcagcggg ggtggcggga ctggtgactc agaaggctca    1380
ggtgccctac ccagcctcac ctgcagcctc accccctgg gcctggcgct ggtgctgtgg    1440
acagtgcttg ggccctgctg accccagcg gacacaagag cgtgctcagc agccaggtgt    1500
gtgtacatac ggggtctctc tccacgccgc caagccagcc gggcggccga cccgtgggc     1560 aggccaggcc aggtcctccc tgatggacgc ctgccgcccg ccaccccat ctccacccca     1620 tcatgtttac agggttcggc ggcagcgttt gttccagaac gccgcctccc acccagatcg    1680
cggtatatag agatatgcat tttattttac ttgtggaaaa atatcggacg acgtggaata    1740
aagagctctt ttcttaaaaa aaaaaaaaa aaaaaaaa                              1778
```

<210> SEQ ID NO 34
<211> LENGTH: 473
<212> TYPE: PRT
<213> ORGANISM: Homo sapiens

<400> SEQUENCE: 34

```
Met Lys Arg Ala Ser Ala Gly Gly Ser Arg Leu Leu Ala Trp Val Leu
 1               5                  10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Val His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
```

```
            385                 390                 395                 400
Glu Gly Ser Glu Pro Pro Gly Phe Pro Thr Ser Gly Pro Arg Arg
                405                 410                 415
Pro Gly Cys Ser Arg Lys Asn Arg Thr Arg Ser His Cys Arg Leu Gly
            420                 425                 430
Gln Ala Gly Ser Gly Gly Gly Thr Gly Asp Ser Glu Gly Ser Gly
            435                 440                 445
Ala Leu Pro Ser Leu Thr Cys Ser Leu Thr Pro Leu Gly Leu Ala Leu
        450                 455                 460
Val Leu Trp Thr Val Leu Gly Pro Cys
465                 470

<210> SEQ ID NO 35
<211> LENGTH: 1946
<212> TYPE: DNA
<213> ORGANISM: Homo sapiens

<400> SEQUENCE: 35
```

| | | | | | |
|---|---|---|---|---|---|
| cgcgctgcga | gcgccccgcc | agtccgcgcc | gccgccctca | ccctgtgcgc | ccgcagcccg | 60 |
| cgagcccagc | ccggcccggt | agagcggagc | gccggagcct | cgtcccgcgg | ccgggccggg | 120 |
| accgggccgg | agcagcggcg | cctggatgcg | gacccggccg | cgcgcagacg | ggcgcccgcc | 180 |
| ccgaagccgc | ttccagtgcc | cgacgcgccc | cgctcgaccc | cgaagatgaa | gagggcgtcc | 240 |
| tccggaggaa | gcaggctgct | ggcatggtg | ttatggctac | aggcctggag | ggtagcaaca | 300 |
| ccatgccctg | gtgcttgtgt | gtgctacaat | gagcccaagg | taacaacaag | ctgccccag | 360 |
| cagggtctgc | aggctgtgcc | cactggcatc | ccagcctcta | gccagcgaat | cttcctgcat | 420 |
| ggcaaccgaa | tctctcacgt | gccagctgcg | agcttccagt | catgccgaaa | tctcactatc | 480 |
| ctgtggctgc | actctaatgc | gctggctcgg | atcgatgctg | ctgccttcac | tggtctgacc | 540 |
| ctcctggagc | aactagatct | tagtgataat | gcacagcttc | atgtcgtgga | ccctaccacg | 600 |
| ttccacggcc | tgggccacct | gcacacactg | cacctagacc | gatgtggcct | gcgggagctg | 660 |
| ggtcccggcc | tattccgtgg | actagcagct | ctgcagtacc | tctacctaca | agacaacaat | 720 |
| ctgcaggcac | tccctgacaa | cacctttcga | gacctgggca | acctcacgca | tctctttctg | 780 |
| catggcaacc | gtatcccag | tgtgcctgag | cacgctttcc | gtggcctgca | cagtcttgac | 840 |
| cgcctcctct | tgcaccagaa | ccatgtggct | cgtgtgcacc | cacatgcctt | ccgggacctt | 900 |
| ggccgcctca | tgaccctcta | cctgtttgcc | aacaacctct | ccatgctgcc | tgcagaggtc | 960 |
| ctaatgcccc | tgaggtctct | gcagtacctg | cgactcaatg | acaacccctg | ggtgtgtgac | 1020 |
| tgccgggcac | gtccactctg | ggcctggctg | cagaagttcc | gaggttcctc | atcagaggtg | 1080 |
| ccctgcaacc | tgcccaacg | cctggcagac | cgtgatctta | agcgcctcgc | tgccagtgac | 1140 |
| ctagagggct | gtgctgtggc | ttcaggaccc | ttccgtccca | tccagaccag | tcagctcact | 1200 |
| gatgaggagc | tgctgagcct | ccccaagtgc | tgccagccag | atgctgcaga | caaagcctca | 1260 |
| gtactggaac | ccgggaggcc | agcttctgcc | ggaaacgccc | tcaagggacg | tgtgcctccc | 1320 |
| ggtgacactc | caccaggcaa | tggctcaggc | cctcggcaca | tcaatgactc | tccatttgga | 1380 |
| actttgccca | gctctgcaga | gcccccactg | actgccctgc | ggcctggggg | ttccgagcca | 1440 |
| ccaggacttc | ccaccactgg | tccccgcagg | aggccaggtt | gttcccggaa | gaatcgcacc | 1500 |
| cgcagccact | gccgtctggg | ccaggcggga | agtggggcca | gtggaacagg | ggacgcagag | 1560 |
| ggttcagggg | ctctgcctgc | tctggcctgc | agccttgctc | ctctgggcct | tgcactggta | 1620 |
| ctttggacag | tgcttgggcc | ctgctgacca | gccaccagcc | accaggtgtg | tgtacatatg | 1680 |

-continued

```
gggtctccct ccacgccgcc agccagagcc agggacaggc tctgaggggc aggccaggcc    1740
ctccctgaca gatgcctccc caccagccca ccccatctc cacccatca tgtttacagg     1800 gttccggggg tggcgtttgt tccagaacgc cacctcccac ccggatcgcg gtatatagag    1860
atatgaattt tattttactt gtgtaaaata tcggatgacg tggaataaag agctcttttc    1920
ttaaaaaaaa aaaaaaaaa aaaaaa                                          1946
```

<210> SEQ ID NO 36
<211> LENGTH: 473
<212> TYPE: PRT
<213> ORGANISM: Mus musculus

<400> SEQUENCE: 36

```
Met Lys Arg Ala Ser Ser Gly Gly Ser Arg Leu Leu Ala Trp Val Leu
 1               5                  10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser His Val Pro Ala Ala Ser Phe Gln Ser Cys
65                  70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Asn
        275                 280                 285

Leu Pro Gln Arg Leu Ala Asp Arg Asp Leu Lys Arg Leu Ala Ala Ser
    290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
```

```
                    325                 330                 335
Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
            355                 360                 365

Pro Pro Gly Asn Gly Ser Gly Pro Arg His Ile Asn Asp Ser Pro Phe
    370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
            435                 440                 445

Ala Leu Pro Ala Leu Ala Cys Ser Leu Ala Pro Leu Gly Leu Ala Leu
        450                 455                 460

Val Leu Trp Thr Val Leu Gly Pro Cys
465                 470
```

<210> SEQ ID NO 37
<211> LENGTH: 1348
<212> TYPE: DNA
<213> ORGANISM: Homo sapiens

<400> SEQUENCE: 37

```
gccaaagaga catatccaag gttgagatta gtttccattt tctttgtact attttctgga      60
taataagaca ttagacattt gaagagatgg agaatgaaga tgggtatatg acgctgagtt     120
tcaagaatcg ttgtaaatcg aagcagaaat ctaaagattt ctccctatat ccacaatatt     180
attgtcttct gctcatattt ggatgcattg tgatccttat attcattatg cagggattg      240
acctgaagtt ctggcataaa aaaatggatt tctcccagaa tgtaaacatc agcagtctat     300
caggacacaa ttacttgtgc ccaaatgact ggctgttgaa cgaagggaaa tgttactggt     360
tttcaacttc ttttaaaacg tggaaagaga gtcaacgtga ttgtacacag ctacaggcac     420
atttactggt gattcaaaat ttggatgagc tggagttcat acagaacagt ttaaaacctg     480
gacattttgg ttggattgga ctatatgtta cattccaagg gaacctatgg atgtggatag     540
atgaacactt tttagttcca gaattgtttt cagtgattgg accaactgat gacaggagct     600
gtgccgttat cacaggaaac tgggtgtatt ctgaagactg tagctccaca tttaagggca     660
tttgccagag agatgcgatc ttgacgcaca atggaaccag tggtgtgtaa atgtacaacc     720
aaatatagaa atactttgca tgttaaagca gagctagatt ttaaagactt aagattttta     780
gataaagttt ctaacagaaa gtttctgcta acagacatca tctaaatagg agaaaagtat     840
tttatcctga attgactata aagacaactt ctgaacagaa cttttactct atacttggat     900
ttctggtttg tcttttccat ggcattgaca agaaaagcta ataaaaaat tagtaattat      960
tttaatagtt atttaatagt ttgattttt tgcatttaaa atagcataga ataaaacaac     1020
tttaaaggaa tgttatttag ctatatgtgc tatgtggtag attggaagga agaagcagt     1080
atatgtacaa atataatatt tgaagcatgg aattctgaat ttttcatctg tgtattatag    1140
cctgaagtgt ttggtgggga gtgggtaatg agaaattacc tactgggtat aatgtacaat    1200
atttaggtga tggataaact aaaagctcag acttctccac tttgtgatat atccatgtaa    1260
caaaattatg cttgtacccct ttaaatgtat tcaaataaaa taaaataaag tcatgtggcc    1320
```

```
aaatattcaa acaaaaaaa aaaaaaaa                                        1348
```

<210> SEQ ID NO 38
<211> LENGTH: 207
<212> TYPE: PRT
<213> ORGANISM: Homo sapiens

<400> SEQUENCE: 38

```
Met Glu Asn Glu Asp Gly Tyr Met Thr Leu Ser Phe Lys Asn Arg Cys
  1               5                  10                  15

Lys Ser Lys Gln Lys Ser Lys Asp Phe Ser Leu Tyr Pro Gln Tyr Tyr
             20                  25                  30

Cys Leu Leu Leu Ile Phe Gly Cys Ile Val Ile Leu Ile Phe Ile Met
         35                  40                  45

Thr Gly Ile Asp Leu Lys Phe Trp His Lys Lys Met Asp Phe Ser Gln
     50                  55                  60

Asn Val Asn Ile Ser Ser Leu Ser Gly His Asn Tyr Leu Cys Pro Asn
 65                  70                  75                  80

Asp Trp Leu Leu Asn Glu Gly Lys Cys Tyr Trp Phe Ser Thr Ser Phe
                 85                  90                  95

Lys Thr Trp Lys Glu Ser Gln Arg Asp Cys Thr Gln Leu Gln Ala His
            100                 105                 110

Leu Leu Val Ile Gln Asn Leu Asp Glu Leu Glu Phe Ile Gln Asn Ser
        115                 120                 125

Leu Lys Pro Gly His Phe Gly Trp Ile Gly Leu Tyr Val Thr Phe Gln
    130                 135                 140

Gly Asn Leu Trp Met Trp Ile Asp Glu His Phe Leu Val Pro Glu Leu
145                 150                 155                 160

Phe Ser Val Ile Gly Pro Thr Asp Asp Arg Ser Cys Ala Val Ile Thr
                165                 170                 175

Gly Asn Trp Val Tyr Ser Glu Asp Cys Ser Ser Thr Phe Lys Gly Ile
            180                 185                 190

Cys Gln Arg Asp Ala Ile Leu Thr His Asn Gly Thr Ser Gly Val
        195                 200                 205
```

<210> SEQ ID NO 39
<211> LENGTH: 3345
<212> TYPE: DNA
<213> ORGANISM: Homo sapiens

<400> SEQUENCE: 39

```
gggggggcgca ggaccctcgc aacttcttcg caggactcca gcctggccgc cggcgcccgc        60
agccgtccga gagccctgcg cccgcgcctc cccttgcgca ccgtggcagc gcccggcggg       120
cggtcctgcc agccccgacg ggatgcccgc agccatgctc ccctacgctt gcgtcctggt       180
gcttttggga gcccacactg caccggcggc tgggaggcc ggggcagct gcctgcgctg        240 ggaaccccac tgccagcagc ccttgccaga tagagtgccc agcactgcga tcctgcctcc       300 acgcctaat ggaccttgga tctccacagg ccggctcttt cgagcccacc agttctacta        360
cgaggacccc ttctgcgggg aacctgccca ctcgctgctc gtcaagggca agtccgcct        420 gcgccgggcc tcctgggtca cccgggggagc accgaggcc gactaccacc tgcacaaggt       480
gggcatcgtc ttccacagcc gccgggccct ggtcgacgtc accgggcgcc tcaaccagac       540
ccgcgccggc cgggactgcg cgcggcggct gcctccggcc cgggcctggc tgcctggggc       600
gctgtacgag ctgcggagcg cccgggctca gggggactgc ctggaggcgc tgggcctcac       660
```

```
catgcacgag ctcagcctgg tccgcgtgca gcgccgcctg cagccgcagc cccgggcgtc    720
gccccggctg gtggaggagc tgtacctggg ggacatccac accgacccgg cggagaggcg    780
gcactaccgg cccacgggct accagcgccc gctgcagagc gcactgcacc acgtgcagcc    840
gtgcccagcc tgtggcctca ttgcccgctc cgatgtgcac caccegeccg tgctgccgcc    900
ccctctggcc ctgcccctgc acctgggcgg ctggtgggtc agctcggggt gcgaggtgcg    960
cccagcagtc ctgttcctca cccggctctt cactttccac gggcacagcc gctcctggga   1020
agggtattac caccacttct cagacccagc ctgccggcag cccaccttca ccgtgtatgc   1080
cgccggccgc tacaccaggg gcacgccatc caccagggtc cgcggcggca ccgagctggt   1140
gtttgaggtc acacgggccc atgtgacccc catggaccag gtcaccacgg ccatgctcaa   1200
cttctctgag ccaagcagct gtgggggtgc ggggcctgg tccatgggca ctgagcggga   1260
tgtcacagcc accaacggct gcctaccgct gggcatccgg ctcccgcatg tggagtacga   1320
gcttttcaag atggaacaag accccctcgg gcaaagcctg ctcttcatcg acaaaggcc    1380
caccgatggc tcaagtcccg atacccecaga gaaacgtccc acctcctacc aagcacccct   1440
ggtgctctgt catggggagg cccccgactt ctccaggcca ccgcagcaca ggccatcgct   1500
gcagaagcac cccagcacag ggggtcttca catagccccc ttcccacttc tgcccctagt   1560
tctagggctg gccttcctcc actggctatg acattggact tgacatcagg atggcggctc   1620
tggacaccca ttcaacccctt cagactccct cctggcagct gtagggaagg aaccattctc   1680
ctctgctctg tcatggatgg atgcacagcc ccactgcttc caaactctgc ctgtgtccca   1740
tgtggctcag gacatgagct taaccctgc aaagcctata ccacatccca cagcccgggt   1800
ccccagtcaa gcacttggat gcggcagtga tgttcatcgc tacgtgagtt tctaaagatc   1860
actcccaatt tttctacttt cctcatcctt ggcagctcgc caacaggtgc agtcaggggg   1920
ccacacggaa cacccccatc ccatgttccc cccagttctt cccatcctga cccttgggat   1980
tccaagatgg gagcaagagg agatcctgag gctctgccta gggacgaggc ctacagttct   2040
gccatgtctg taggttgttg tttaaagatt attaattcga atttagcaat acgatctcta   2100
agtggtgcca tgaattaaag atgccacttc gggctttcag tgcttctcag cttttgggca   2160
aagggcttgt gtcttcaggg gcagctcagc tttcctgagt cctgactgct ggcattcgtc   2220
tgcatttgcc tgtgcttctg cgagtcggac ctcaagctgc caacactgca tgtggataaa   2280
tccagttttc ccgggccagc atgcaaaatg aagaggactc catctaagct gagaagcatg   2340
gcctccccag agcagcctgc agcctccaag ccttcctggc ccaggcaaat gccagtgtgc   2400
accaggctgg ctgctggggg caggtctttg gagggagca gcatttccag ccttctgaac    2460
atagttaata gtaatgacag ccgtaacact aacgcgctct gcaattcgcc ctgcccagcc   2520
atcctcggtt gccaagattg cctgtgcctg cctgacaaag aagagaatc tccgaatgtg    2580
tatctttggg cccacccctag ggagaggtcg gggtcaccag gctacatggc gacatctagg   2640
cagctccgcc ttgcccagcc tccttgccat aatcctaata tattggtgtc ctctgctcag   2700
aggggactgt catcatggtg ggaacaggct gtgcctcccc agggactctg cccatgttcc   2760
cagggcctca tctgtacact gtgaaattaa ctggcatcct ggtgggccca agggttttca   2820
ggactggggg ccaatgactc acccetcct tcctcctcct gatccctatc tctagctctt   2880
atcacagatt ttgaacaatt gtctgtgagg ttaatgatgg tttcagaggg aagccctttt   2940
cctccctgag actgtgtggg gttcagtcag cctgctgaaa ttgcttccac ttattaccca   3000
tccttcctct taaaaaaaaa aaaaagccca ccaagttagt attctctgta gctctcagac   3060
```

-continued

```
agctacaagt gttcctggca tatttaccaa agtacaagaa atcattacat tatttacggt  3120
ctcagactac atcagggttg ggggagctcc tggtggggat ggcagtgggt gtcgatgata  3180
tgtccacggc tgagcaggtc ttgtatccga agcttgaagt aaccatgcca ccatttatca  3240
tcaaatttga accttttaat aaaattaaac agcctgaaaa aaaaaaaaaa aaaaaaaaaa  3300
aaaaaaaaaa aaaaaaaaaa aaaaaaaaaa aaaaaaaaaa aaaaa                 3345
```

<210> SEQ ID NO 40
<211> LENGTH: 482
<212> TYPE: PRT
<213> ORGANISM: Homo sapiens

<400> SEQUENCE: 40

```
Met Pro Ala Ala Met Leu Pro Tyr Ala Cys Val Leu Val Leu Leu Gly
 1               5                  10                  15

Ala His Thr Ala Pro Ala Ala Gly Glu Ala Gly Gly Ser Cys Leu Arg
                20                  25                  30

Trp Glu Pro His Cys Gln Gln Pro Leu Pro Asp Arg Val Pro Ser Thr
            35                  40                  45

Ala Ile Leu Pro Pro Arg Leu Asn Gly Pro Trp Ile Ser Thr Gly Arg
        50                  55                  60

Leu Phe Arg Ala His Gln Phe Tyr Glu Asp Pro Phe Cys Gly Glu
 65                 70                  75                  80

Pro Ala His Ser Leu Leu Val Lys Gly Lys Val Arg Leu Arg Arg Ala
                85                  90                  95

Ser Trp Val Thr Arg Gly Ala Thr Glu Ala Asp Tyr His Leu His Lys
            100                 105                 110

Val Gly Ile Val Phe His Ser Arg Arg Ala Leu Val Asp Val Thr Gly
        115                 120                 125

Arg Leu Asn Gln Thr Arg Ala Gly Arg Asp Cys Ala Arg Arg Leu Pro
    130                 135                 140

Pro Ala Arg Ala Trp Leu Pro Gly Ala Leu Tyr Glu Leu Arg Ser Ala
145                 150                 155                 160

Arg Ala Gln Gly Asp Cys Leu Glu Ala Leu Gly Leu Thr Met His Glu
                165                 170                 175

Leu Ser Leu Val Arg Val Gln Arg Arg Leu Gln Pro Gln Pro Arg Ala
            180                 185                 190

Ser Pro Arg Leu Val Glu Glu Leu Tyr Leu Gly Asp Ile His Thr Asp
        195                 200                 205

Pro Ala Glu Arg Arg His Tyr Arg Pro Thr Gly Tyr Gln Arg Pro Leu
    210                 215                 220

Gln Ser Ala Leu His His Val Gln Pro Cys Pro Ala Cys Gly Leu Ile
225                 230                 235                 240

Ala Arg Ser Asp Val His His Pro Pro Val Leu Pro Pro Pro Leu Ala
                245                 250                 255

Leu Pro Leu His Leu Gly Gly Trp Trp Val Ser Ser Gly Cys Glu Val
            260                 265                 270

Arg Pro Ala Val Leu Phe Leu Thr Arg Leu Phe Thr Phe His Gly His
        275                 280                 285

Ser Arg Ser Trp Glu Gly Tyr Tyr His His Phe Ser Asp Pro Ala Cys
    290                 295                 300

Arg Gln Pro Thr Phe Thr Val Tyr Ala Ala Gly Arg Tyr Thr Arg Gly
305                 310                 315                 320

Thr Pro Ser Thr Arg Val Arg Gly Gly Thr Glu Leu Val Phe Glu Val
                325                 330                 335
```

```
Thr Arg Ala His Val Thr Pro Met Asp Gln Val Thr Thr Ala Met Leu
            340                 345                 350

Asn Phe Ser Glu Pro Ser Ser Cys Gly Gly Ala Gly Ala Trp Ser Met
            355                 360                 365

Gly Thr Glu Arg Asp Val Thr Ala Thr Asn Gly Cys Leu Pro Leu Gly
370                 375                 380

Ile Arg Leu Pro His Val Glu Tyr Glu Leu Phe Lys Met Glu Gln Asp
385                 390                 395                 400

Pro Leu Gly Gln Ser Leu Leu Phe Ile Gly Gln Arg Pro Thr Asp Gly
            405                 410                 415

Ser Ser Pro Asp Thr Pro Glu Lys Arg Pro Thr Ser Tyr Gln Ala Pro
            420                 425                 430

Leu Val Leu Cys His Gly Glu Ala Pro Asp Phe Ser Arg Pro Pro Gln
            435                 440                 445

His Arg Pro Ser Leu Gln Lys His Pro Ser Thr Gly Gly Leu His Ile
450                 455                 460

Ala Pro Phe Pro Leu Leu Pro Leu Val Leu Gly Leu Ala Phe Leu His
465                 470                 475                 480

Trp Leu

<210> SEQ ID NO 41
<211> LENGTH: 3575
<212> TYPE: DNA
<213> ORGANISM: Homo sapiens

<400> SEQUENCE: 41
gcttcccgag gctccgcacc agccgcgctt ctgtccgcct gcagggcatt ccagaaagat      60
gaggatattt gctgtcttta tattcatgac ctactggcat ttgctgaacg catttactgt     120
cacggttccc aaggacctat atgtggtaga gtatggtagc aatatgacaa ttgaatgcaa     180
attcccagta gaaaaacaat tagacctggc tgcactaatt gtctattggg aaatggagga     240
taagaacatt attcaatttg tgcatggaga ggaagacctg aaggttcagc atagtagcta     300
cagacagagg gcccggctgt tgaaggacca gctctccctg ggaaatgctg cacttcagat     360
cacagatgtg aaattgcagg atgcaggggt gtaccgctgc atgatcagct atggtggtgc     420
cgactacaag cgaattactg tgaaagtcaa tgccccatac aacaaaatca accaaagaat     480
tttggttgtg gatccagtca cctctgaaca tgaactgaca tgtcaggctg agggctaccc     540
caaggccgaa gtcatctgga caagcagtga ccatcaagtc ctgagtggta agaccaccac     600
caccaattcc aagagagagg agaagctttt caatgtgacc agcacactga aatcaacac      660 aacaactaat gagattttct actgcacttt taggagatta gatcctgagg aaaaccatac     720
agctgaattg gtcatcccag aactacctct ggcacatcct ccaaatgaaa ggactcactt     780
ggtaattctg ggagccatct tattatgcct tggtgtagca ctgacattca tcttccgttt     840
aagaaagggg agaatgatgg atgtgaaaaa atgtggcatc aagatacaa actcaaagaa     900 gcaaagtgat acacatttgg aggagacgta atccagcatt ggaacttctg atcttcaagc     960
agggattctc aacctgtggt ttaggggttc atcggggctg agcgtgacaa gaggaaggaa    1020
tgggcccgtg ggatgcaggc aatgtgggac ttaaaaggcc caagcactga aaatggaacc    1080
tggcgaaagc agaggaggag aatgaagaaa gatggagtca acagggagc ctggagggag     1140 accttgatac tttcaaatgc ctgaggggct catcgacgcc tgtgacaggg agaaggata      1200 cttctgaaca aggagcctcc aagcaaatca tccattgctc atcctaggaa gacgggttga    1260
```

```
gaatccctaa tttgagggtc agttcctgca gaagtgccct ttgcctccac tcaatgcctc   1320
aatttgtttt ctgcatgact gagagtctca gtgttggaac gggacagtat ttatgtatga   1380
gttttcccta tttattttga gtctgtgagg tcttcttgtc atgtgagtgt ggttgtgaat   1440
gatttctttt gaagatatat tgtagtagat gttacaattt tgtcgccaaa ctaaacttgc   1500
tgcttaatga tttgctcaca tctagtaaaa catggagtat ttgtaaggtg cttggtctcc   1560
tctataacta caagtataca ttggaagcat aaagatcaaa ccgttggttg cataggatgt   1620
cacctttatt taacccatta atactctggt tgacctaatc ttattctcag acctcaagtg   1680
tctgtgcagt atctgttcca tttaaatatc agctttacaa ttatgtggta gcctacacac   1740
ataatctcat ttcatcgctg taaccaccct gttgtgataa ccactattat tttacccatc   1800
gtacagctga ggaagcaaac agattaagta acttgcccaa accagtaaat agcagacctc   1860
agactgccac ccactgtcct tttataatac aatttacagc tatattttac tttaagcaat   1920
tcttttattc aaaaaccatt tattaagtgc ccttgcaata tcaatcgctg tgccaggcat   1980
tgaatctaca gatgtgagca agacaaagta cctgtcctca aggagctcat agtataatga   2040
ggagattaac aagaaaatgt attattacaa tttagtccag tgtcatagca taaggatgat   2100
gcgaggggaa aacccgagca gtgttgccaa gaggaggaaa taggccaatg tggtctggga   2160
cggttggata tacttaaaca tcttaataat cagagtaatt ttcatttaca aagagaggtc   2220
ggtacttaaa ataaccctga aaaataacac tggaattcct tttctagcat tatatttatt   2280
cctgatttgc ctttgccata taatctaatg cttgtttata tagtgtctgg tattgtttaa   2340
cagttctgtc ttttctattt aaatgccact aaatttaaa ttcataccctt ccatgattc    2400 aaaattcaaa agatcccatg ggagatggtt ggaaaatctc cacttcatcc tccaagccat   2460
tcaagtttcc tttccagaag caactgctac tgcctttcat tcatatgttc ttctaaagat   2520
agtctacatt tggaaatgta tgttaaaagc acgtattttt aaatttttt tcctaaatag    2580 taacacattg tatgtctgct gtgtacttg ctattttat ttattttagt gtttcttata     2640
tagcagatgg aatgaatttg aagttcccag ggctgaggat ccatgccttc tttgtttcta   2700
agttatcttt cccatagctt ttcattatct ttcatatgat ccagtatatg ttaaatatgt   2760
cctacatata catttagaca accaccattt gttaagtatt tgctctagga cagagtttgg   2820
atttgtttat gtttgctcaa aaggagaccc atgggctctc cagggtgcac tgagtcaatc   2880
tagtcctaaa aagcaatctt attattaact ctgtatgaca gaatcatgtc tggaactttt   2940
gttttctgct ttctgtcaag tataaacttc actttgatgc tgtacttgca aaatcacatt   3000
ttctttctgg aaattccggc agtgtacctt gactgctagc taccctgtgc cagaaaagcc   3060
tcattcgttg tgcttgaacc cttgaatgcc accagctgtc atcactacac agccctccta   3120
agaggcttcc tggaggtttc gagattcaga tgccctggga gatcccagag tttccttttcc  3180 ctcttggcca tattctggtg tcaatgacaa ggagtacctt ggctttgcca catgtcaagg   3240
ctgaagaaac agtgtctcca acagagctcc ttgtgttatc tgtttgtaca tgtgcatttg   3300
tacagtaatt ggtgtgacag tgttctttgt gtgaattaca ggcaagaatt gtggctgagc   3360
aaggcacata gtctactcag tctattccta agtcctaact cctccttgtg gtgttggatt   3420
tgtaaggcac tttatccctt ttgtctcatg tttcatcgta aatggcatag gcagagatga   3480
tacctaattc tgcatttgat tgtcactttt tgtacctgca ttaatttaat aaaatattct   3540
tatttatttt gttacttggt aaaaaaaaaa aaaaa                              3575
```

<210> SEQ ID NO 42

<211> LENGTH: 290
<212> TYPE: PRT
<213> ORGANISM: Homo sapiens

<400> SEQUENCE: 42

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290
```

<210> SEQ ID NO 43
<211> LENGTH: 891
<212> TYPE: DNA
<213> ORGANISM: Mus musculus
<220> FEATURE:
<221> NAME/KEY: misc_feature
<222> LOCATION: 660, 661, 726
<223> OTHER INFORMATION: n = A,T,C or G

<400> SEQUENCE: 43

| | | |
|---|---|---|
| cgtccgcttg cacgtcgcgg gccagtctcc tcgcctgcag atagttccca aaacatgagg | 60 |
| atatttgctg gcattatatt cacagcctgc tgtcacttgc tacgggcgtt tactatcacg | 120 |
| gctccaaagg acttgtacgt ggtggagtat ggcagcaacg tcacgatgga gtgcagattc | 180 |

-continued

```
cctgtagaac gggagctgga cctgcttgcg ttagtggtgt actgggaaaa ggaagatgag      240
caagtgattc agtttgtggc aggagaggag gaccttaagc ctcagcacag caacttcagg      300
gggagagcct cgctgccaaa ggaccagctt ttgaagggaa atgctgccct tcagatcaca      360
gacgtcaagc tgcaggacgc aggcgtttac tgctgcataa tcagctacgg tggtgcggac      420
tacaagcgaa tcacgctgga agtcaatgcc ccataccgca aaatcaacca gagaattttcc     480 gtggatccag ccacttctga gcatgaacta atatgtcagg ccgagggtta tccagaagct      540
gaggtaatct ggacaaacag tgaccaccaa cccgtgagtg ggaagagaag tgtcaccact      600
tcccggacag aggggatgct tctcaatgtg accagcagtc tgaggtcaac gccacatgan      660
nagcgaatga tgtttctact gtacgtattg gagatcacag ccagggcaaa accacacagc      720
ggcganatca tcccagaact gcctgcaaca catcctccac agaacaggac tcactgggtg      780
cttctgggat ccatcctgtt gttcctcatt gtagtgtcca cggtcctcct cttcttgaga      840
aaacaagtga gaatgctaga gtgtggagaaa tgtggcgttg aagatacaag c              891
```

<210> SEQ ID NO 44
<211> LENGTH: 279
<212> TYPE: PRT
<213> ORGANISM: Mus musculus
<220> FEATURE:
<221> NAME/KEY: SITE
<222> LOCATION: 202, 203, 224
<223> OTHER INFORMATION: Xaa = Unknown Amino Acid

<400> SEQUENCE: 44

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
    65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Glu Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Ser Thr Pro His Xaa Xaa Arg Met Met Phe Leu
        195                 200                 205

Leu Tyr Val Leu Glu Ile Thr Ala Arg Ala Lys Pro His Ser Gly Xaa
    210                 215                 220

Ile Ile Pro Glu Leu Pro Ala Thr His Pro Pro Gln Asn Arg Thr His

```
                   225                 230                 235                 240

Trp Val Leu Leu Gly Ser Ile Leu Leu Phe Leu Ile Val Val Ser Thr
                    245                 250                 255

Val Leu Leu Phe Leu Arg Lys Gln Val Arg Met Leu Asp Val Glu Lys
                    260                 265                 270

Cys Gly Val Glu Asp Thr Ser
                    275

<210> SEQ ID NO 45
<211> LENGTH: 135
<212> TYPE: PRT
<213> ORGANISM: Oryctolagus cuniculus
<220> FEATURE:
<221> NAME/KEY: SITE
<222> LOCATION: 95, 119
<223> OTHER INFORMATION: Xaa = Unknown Amino Acid

<400> SEQUENCE: 45

Met Leu Gly Ser Pro Cys Leu Leu Trp Leu Leu Ala Val Thr Phe Leu
 1               5                  10                  15

Val Pro Arg Ala Gln Pro Leu Ala Ser Gln Asp Ser Glu Glu Glu Gly
                20                  25                  30

Asp Asp Gln Pro Ser Leu Pro Pro Ser Arg Ala Val Pro Cys Asp Tyr
            35                  40                  45

Asp Arg Cys Arg His Leu Gln Val Pro Cys Gln Glu Leu Gln Lys Ala
        50                  55                  60

Glu Pro Val Pro Cys Leu Cys Pro Gly Leu Ser Ser Pro Asp Gln Pro
 65                 70                  75                  80

Pro Glu Pro Pro Arg Leu Gly Glu Val His Val Val Ala Glu Xaa Gly
                85                  90                  95

Arg Ala Leu Val His Trp Cys Ala Pro Ser Ser Pro Val Leu Gln Tyr
               100                 105                 110

Trp Leu Leu Leu Trp Glu Xaa Asn Gly Asp Pro Trp Lys Gly Thr Asn
           115                 120                 125

Leu Asn Ala His Gly Pro Gln
       130                 135

<210> SEQ ID NO 46
<211> LENGTH: 52
<212> TYPE: PRT
<213> ORGANISM: Homo sapiens

<400> SEQUENCE: 46

Lys Thr Ala Leu Gly Glu Leu Leu Lys Pro Leu Asn Ser Glu Tyr Gly
 1               5                  10                  15

Lys Val Ala Pro Gly Trp Gly Thr Thr Pro Leu Met Gly Val Phe Met
                20                  25                  30

Ala Leu Phe Ala Val Phe Leu Leu Ile Ile Leu Glu Ile Tyr Asn Ser
            35                  40                  45

Ser Val Leu Leu
        50

<210> SEQ ID NO 47
<211> LENGTH: 273
<212> TYPE: PRT
<213> ORGANISM: Homo sapiens

<400> SEQUENCE: 47

Met Thr Phe Asp Asp Leu Lys Ile Gln Thr Val Lys Asp Gln Pro Asp
 1               5                  10                  15
```

```
Glu Lys Ser Asn Gly Lys Lys Ala Lys Gly Leu Gln Phe Leu Tyr Ser
            20                  25                  30

Pro Trp Trp Cys Leu Ala Ala Thr Leu Gly Val Leu Cys Leu Gly
        35                  40                  45

Leu Val Val Thr Ile Met Val Leu Gly Met Gln Leu Ser Gln Val Ser
 50                  55                  60

Asp Leu Leu Thr Gln Glu Gln Ala Asn Leu Thr His Gln Lys Lys
 65                  70                  75                  80

Leu Glu Gly Gln Ile Ser Ala Arg Gln Gln Ala Glu Ala Ser Gln
                85                  90                  95

Glu Ser Glu Asn Glu Leu Lys Glu Met Ile Glu Thr Leu Ala Arg Lys
                100                 105                 110

Leu Asn Glu Lys Ser Lys Glu Gln Met Glu Leu His His Gln Asn Leu
            115                 120                 125

Asn Leu Gln Glu Thr Leu Lys Arg Val Ala Asn Cys Ser Ala Pro Cys
130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
            195                 200                 205

Arg Asn Pro Ser Tyr Pro Trp Leu Trp Glu Asp Gly Ser Pro Leu Met
210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln
```

<210> SEQ ID NO 48
<211> LENGTH: 247
<212> TYPE: PRT
<213> ORGANISM: Mus musculus

<400> SEQUENCE: 48

```
Met Leu Leu Leu Pro Ile Leu Asn Leu Ser Leu Gln Leu His Pro
 1               5                  10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
            35                  40                  45

Cys Thr Glu Leu Glu Gly Ile Arg Ala Ser Leu Gln Lys Val Glu Asn
 50                  55                  60

Asp Thr Ser Leu Gln Ser Glu Arg Ala Thr Leu Leu Glu Glu Gln Leu
 65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
                100                 105                 110
```

```
Lys Tyr Leu Thr Val Lys Val Lys Ala Ser Tyr Met Arg Ile Asp Thr
        115                 120                 125
Arg Ile Leu Glu Val Pro Gly Thr Gly Glu Val Gln Leu Thr Cys Gln
    130                 135                 140
Ala Arg Gly Tyr Pro Leu Ala Glu Val Ser Trp Gln Asn Val Ser Val
145                 150                 155                 160
Pro Ala Asn Thr Ser His Ile Arg Thr Pro Glu Gly Leu Tyr Gln Val
                165                 170                 175
Thr Ser Val Leu Arg Leu Lys Pro Gln Pro Ser Arg Asn Phe Ser Cys
            180                 185                 190
Met Phe Trp Asn Ala His Met Lys Glu Leu Thr Ser Ala Ile Ile Asp
        195                 200                 205
Pro Leu Ser Arg Met Glu Pro Lys Val Pro Arg Thr Trp Pro Leu His
    210                 215                 220
Val Phe Ile Pro Ala Cys Thr Ile Ala Leu Ile Phe Leu Ala Ile Val
225                 230                 235                 240
Ile Ile Gln Arg Lys Arg Ile
                245
```

<210> SEQ ID NO 49
<211> LENGTH: 702
<212> TYPE: DNA
<213> ORGANISM: Mus musculus
<220> FEATURE:
<221> NAME/KEY: misc_feature
<222> LOCATION: 299, 488, 699
<223> OTHER INFORMATION: n = A,T,C or G

<400> SEQUENCE: 49

```
gcaacaagcg gcccaccttc ctgaagatcg agaagccact gtcgtaccgc aagcccatgg    60
acacggacct ggtgtacatg gagaagtcgc ccaactactg cgaggaggac ccggtcaccg   120
gcagtgtggg cacccagggc cgcgcctgca caagacggc tccccaggcc agcggctgtg    180
acctcatgtg ctgtgggcgt ggctacaaca cccaccagtc cgcccgcgtg tggcagtgca   240
actgtaagtt ccactggtgc tgctatgtca agtgcaacac gtgcagcgag cgcacggang   300
atgtacacgt gcaagtgagc cccgtgtgca caccaccctc ccgctgcaag tcagattgct   360
gggaggactg gaccgtttcc aagctgcggg ctccctggca ggatgctgcg cttgtctttt   420
ctgctgagga gggtactttt cctgggtttc ctgcaggcat ccgtggggga aaaaaaatct   480
ctcagagncc tcaactattc tgttccacac ccaatgctga tccacccctcc cccagacaca   540
gcccaggtcc ctccgcggct ggagcgaagc cttctgcagc aggaactctg gacccctggg   600
cctcatcaca gcaatattta acaatttatt cctgataaaa ataatattaa tttatttaat   660
taaaagaat tcttccaaaa aaaaaaaaaa aaaaaaacnt cg                       702
```

<210> SEQ ID NO 50
<211> LENGTH: 15
<212> TYPE: PRT
<213> ORGANISM: Mus musculus

<400> SEQUENCE: 50

```
Ser Glu Arg Ser Asp Arg Val Leu Glu Gly Phe Ile Lys Gly Arg
1               5                   10                  15
```

<210> SEQ ID NO 51
<211> LENGTH: 182
<212> TYPE: PRT
<213> ORGANISM: Unknown
<220> FEATURE:

<223> OTHER INFORMATION: MAM consensus sequence

<400> SEQUENCE: 51

Asp Gly Cys Asp Phe Glu Asp Gly Asn Gln Lys Thr Val Cys Gly Tyr
1               5                   10                  15

Ile Gln Asp Leu Ser Asp Ala Glu Trp Glu Arg Leu Asn Ser Ser
            20                  25                  30

Thr Pro Pro Ser Thr Gly Pro Thr Gln Asp His Thr Leu Val Gly
        35                  40                  45

Gln Cys Lys Asp Ser Gly Phe Phe Met Leu Val Asn Thr Ser Glu Gly
    50                  55                      60

Ala Glu Gly Glu Arg Ala Arg Leu Leu Ser Pro Val Leu Lys Pro Lys
65                  70              75                  80

Arg Asp Gln His Cys Leu Asp Phe Trp Tyr Tyr Met Ser Gly Lys Ser
                85                  90                  95

Asn Val Gly Pro Leu Ser Ile Asn Val Arg Val Asp Val Asn Glu Gly
                100                 105                 110

Lys Val Pro Leu Leu Asn Thr Ile Trp Thr Val Ser Gly Asn Pro Gly
            115                 120                 125

Arg Asn Trp Lys Arg Ala Glu Val Thr Leu Asn Thr Phe Glu Thr Lys
        130                 135                 140

Glu Tyr Gln Val Ile Phe Glu Gly Thr Lys Gly Asp Pro Gly Gly Ser
145                 150                 155                 160

Ser Gly Gly Ile Ala Ile Asp Asp Ile Lys Leu Thr Glu Thr Pro Ser
                165                 170                 175

Pro Ser Gln Cys Pro Ala
            180

<210> SEQ ID NO 52
<211> LENGTH: 132
<212> TYPE: PRT
<213> ORGANISM: Unknown
<220> FEATURE:
<223> OTHER INFORMATION: Consensus sequence
<220> FEATURE:
<221> NAME/KEY: SITE
<222> LOCATION: (14)...(14)
<223> OTHER INFORMATION: Xaa = Thr or absent
<220> FEATURE:
<221> NAME/KEY: SITE
<222> LOCATION: (23)...(23)
<223> OTHER INFORMATION: Xaa = Pro, Phe or Ile
<220> FEATURE:
<221> NAME/KEY: SITE
<222> LOCATION: (26)...(26)
<223> OTHER INFORMATION: Xaa = Pro, Ser or Leu
<220> FEATURE:
<221> NAME/KEY: SITE
<222> LOCATION: (29)...(29)
<223> OTHER INFORMATION: Xaa = Phe, Ser or Tyr
<220> FEATURE:
<221> NAME/KEY: SITE
<222> LOCATION: (36)...(36)
<223> OTHER INFORMATION: Xaa = Glu, Asp or absent
<220> FEATURE:
<221> NAME/KEY: SITE
<222> LOCATION: (37)...(37)
<223> OTHER INFORMATION: Xaa = Thr, Val or absent
<220> FEATURE:
<221> NAME/KEY: SITE
<222> LOCATION: (38)...(38)
<223> OTHER INFORMATION: Xaa = Glu, Gln or Thr
<220> FEATURE:
<221> NAME/KEY: SITE
<222> LOCATION: (39)...(39)
<223> OTHER INFORMATION: Xaa = Thr, Pro, or Val
<220> FEATURE:

```
<221> NAME/KEY: SITE
<222> LOCATION: (41)...(41)
<223> OTHER INFORMATION: Xaa = Trp, Leu or Thr
<220> FEATURE:
<221> NAME/KEY: SITE
<222> LOCATION: (45)...(45)
<223> OTHER INFORMATION: Xaa = Pro, Arg or absent
<220> FEATURE:
<221> NAME/KEY: SITE
<222> LOCATION: (48)...(48)
<223> OTHER INFORMATION: Xaa = Pro, Tyr or Arg
<220> FEATURE:
<221> NAME/KEY: SITE
<222> LOCATION: (93)...(93)
<223> OTHER INFORMATION: Xaa = Ser, His or Ala
<220> FEATURE:
<221> NAME/KEY: SITE
<222> LOCATION: (94)...(94)
<223> OTHER INFORMATION: Xaa - Ile, Val or Asn
<220> FEATURE:
<221> NAME/KEY: SITE
<222> LOCATION: (98)...(98)
<223> OTHER INFORMATION: Xaa = any amino acid
<220> FEATURE:
<221> NAME/KEY: SITE
<222> LOCATION: (102)...(102)
<223> OTHER INFORMATION: Xaa = Val or Leu
<220> FEATURE:
<221> NAME/KEY: SITE
<222> LOCATION: (109)...(109)
<223> OTHER INFORMATION: Xaa = Phe or Ser
<220> FEATURE:
<221> NAME/KEY: SITE
<222> LOCATION: (114)...(114)
<223> OTHER INFORMATION: Xaa = His or Gln
<220> FEATURE:
<221> NAME/KEY: SITE
<222> LOCATION: (121)...(121)
<223> OTHER INFORMATION: Xaa = Asp or Glu
<220> FEATURE:
<221> NAME/KEY: SITE
<222> LOCATION: (122)...(122)
<223> OTHER INFORMATION: Xaa = Gly or absent
<220> FEATURE:
<221> NAME/KEY: SITE
<222> LOCATION: (123)...(123)
<223> OTHER INFORMATION: Xaa = Any amino acid
<220> FEATURE:
<221> NAME/KEY: SITE
<222> LOCATION: (124)...(124)
<223> OTHER INFORMATION: Xaa = Arg or Asn
<220> FEATURE:
<221> NAME/KEY: SITE
<222> LOCATION: (126)...(126)
<223> OTHER INFORMATION: Xaa = Leu or Asp
<220> FEATURE:
<221> NAME/KEY: SITE
<222> LOCATION: (127)...(127)
<223> OTHER INFORMATION: Xaa = Arg or Pro
<220> FEATURE:
<221> NAME/KEY: SITE
<222> LOCATION: (128)...(128)
<223> OTHER INFORMATION: Xaa = Arg or Trp
<220> FEATURE:
<221> NAME/KEY: SITE
<222> LOCATION: (129)...(129)
<223> OTHER INFORMATION: Xaa = Arg or Lys
<220> FEATURE:
<221> NAME/KEY: SITE
<222> LOCATION: (131)...(131)
<223> OTHER INFORMATION: Xaa = Pro or Thr
<220> FEATURE:
<221> NAME/KEY: SITE
<222> LOCATION: (132)...(132)
<223> OTHER INFORMATION: Xaa = Arg or Asn

<400> SEQUENCE: 52

Met Leu Gly Ser Pro Cys Leu Leu Trp Leu Leu Ala Met Xaa Thr Phe
 1               5                  10                  15
```

-continued

Leu Val Pro Arg Ala Gln Xaa Leu Ala Xaa Gln Asp Xaa Glu Glu Glu
              20                  25                  30

Glu Glu Asp Xaa Xaa Xaa Ala Xaa Pro Pro Leu Xaa Ala Val Xaa
          35                  40                  45

Cys Asp Tyr Asp Arg Cys Arg His Leu Gln Val Pro Cys Gln Glu Leu
    50                  55                  60

Gln Lys Ala Gly Pro Val Ala Cys Leu Cys Pro Gly Leu Ser Ser Pro
65                  70                  75                  80

Asp Gln Gln Pro Glu Pro Pro Arg Leu Gly Glu Val Xaa Xaa Val Ala
                85                  90                  95

Glu Xaa Gly Arg Ala Xaa Val His Trp Cys Ala Pro Xaa Ser Pro Val
            100                 105                 110

Leu Xaa Tyr Trp Leu Leu Leu Trp Xaa Xaa Xaa Gly Xaa Xaa Xaa
        115                 120                 125

Xaa Gly Xaa Xaa
    130

<210> SEQ ID NO 53
<211> LENGTH: 78
<212> TYPE: PRT
<213> ORGANISM: Unknown
<220> FEATURE:
<223> OTHER INFORMATION: Consensus immunoglobulin domain

<400> SEQUENCE: 53

Gly Glu Ser Val Thr Leu Thr Cys Ser Val Ser Gly Phe Gly Pro Pro
 1               5                  10                  15

Gly Val Ser Val Thr Trp Tyr Phe Lys Asn Gly Lys Leu Gly Pro Ser
            20                  25                  30

Leu Leu Gly Tyr Ser Tyr Ser Arg Leu Glu Ser Gly Glu Lys Ala Asn
        35                  40                  45

Leu Ser Glu Gly Arg Phe Ser Ile Ser Ser Leu Thr Leu Thr Ile Ser
    50                  55                  60

Ser Val Glu Lys Glu Asp Ser Gly Thr Tyr Thr Cys Val Val
65                  70                  75

<210> SEQ ID NO 54
<211> LENGTH: 819
<212> TYPE: DNA
<213> ORGANISM: Homo sapiens

<400> SEQUENCE: 54
atgactttgt gatgacctaaa gatccagact gtgaaggacc agcctgatga aagtcaaat      60 ggaaaaaaag ctaaaggtct tcagtttctt tactctccat ggtggtgcct ggctgctgcg     120
actctagggg tcctttgcct gggattagta gtgaccatta tggtgctggg catgcaatta     180
tcccaggtgt ctgacctcct aacacaagag caagcaaacc taactcacca gaaaagaaa      240 ctggagggac agatctcagc ccggcaacaa gcagaagaag cttcacagga gtcagaaaac     300
gaactcaagg aaatgataga aacccttgct cggaagctga tgagaaatc aaagagcaa      360 atggaacttc accaccagaa tctgaatctc aagaaacac tgaagagagt agcaaattgt     420
tcagctcctt gtccgcaaga ctggatctgg catggagaaa actgttacct atttcctcg     480 ggctcattta actgggaaaa gagccaagag aagtgcttgt ctttggatgc aagttgctg     540 aaaattaata gcacagctga tctggacttc atccagcaag caatttccta ttccagtttt     600
ccattctgga tggggctgtc tcggaggaac cccagctacc catggctctg ggaggacggt     660

```
tctcctttga tgccccactt atttagagtc cgaggcgctg tctcccagac ataccttca     720 ggtacctgtg catatataca acgaggagct gtttatgcgg aaaactgcat tttagctgcc    780
ttcagtatat gtcagaagaa ggcaaaccta agagcacag                            819
```

```
<210> SEQ ID NO 55
<211> LENGTH: 42
<212> TYPE: PRT
<213> ORGANISM: Unknown
<220> FEATURE:
<221> NAME/KEY: SITE
<222> LOCATION: 5, 18
<223> OTHER INFORMATION: amino acid with basic side chain
<220> FEATURE:
<221> NAME/KEY: SITE
<222> LOCATION: 12, 35, 38
<223> OTHER INFORMATION: amino acid with uncharged polar or nonpolar
      side chain
<220> FEATURE:
<221> NAME/KEY: SITE
<222> LOCATION: 14
<223> OTHER INFORMATION: amino acid with basic or uncharged polar side
      chain
<220> FEATURE:
<221> NAME/KEY: SITE
<222> LOCATION: 19, 22, 23, 41
<223> OTHER INFORMATION: amino acid with nonpolar side chain
<220> FEATURE:
<221> NAME/KEY: SITE
<222> LOCATION: 20
<223> OTHER INFORMATION: amino acid with acidic or uncharged polar side
      chain
<220> FEATURE:
<221> NAME/KEY: SITE
<222> LOCATION: 31
<223> OTHER INFORMATION: amino acid with basic or uncharged polar side
      chain
<220> FEATURE:
<221> NAME/KEY: SITE
<222> LOCATION: (32)...(33)
<223> OTHER INFORMATION: amino acid with acidic or nonpolar side chain
<220> FEATURE:
<221> NAME/KEY: SITE
<222> LOCATION: (37)...(37)
<223> OTHER INFORMATION: amino acid with acidic side chain

<400> SEQUENCE: 55

Cys Asp Tyr Asp Xaa Cys Arg His Leu Gln Val Xaa Cys Xaa Glu Leu
1               5                   10                  15

Gln Xaa Xaa Xaa Pro Xaa Xaa Cys Leu Cys Pro Gly Leu Ser Xaa Xaa
            20                  25                  30

Xaa Gln Xaa Pro Xaa Xaa Pro Arg Xaa Gly
        35                  40
```

What is claimed is:

1. An in vitro method for identifying a compound which binds to a polypeptide selected from the group consisting of:
   a) a polypeptide comprising the amino acid sequence of SEQ ID NO:42;
   b) a polypeptide comprising amino acids 19 to 290 of SEQ ID NO:42;
   c) a polypeptide which is encoded by a nucleic acid molecule comprising the nucleotide sequence of SEQ ID NO:41; and
   d) a polypeptide which is encoded by the nucleotide sequence of the cDNA insert of the plasmid deposited as ATCC® Accession number PTA-438;
   the method comprising:
   i) contacting a sample comprising the polypeptide with a test compound under conditions suitable for binding; and
   ii) detecting binding of the test compound to the polypeptide;
   thereby identifying a compound which binds to the polypeptide.

2. The method of claim 1, wherein the polypeptide further comprises heterologous sequences.

3. The method of claim 1, wherein the sample is an isolated polypeptide, a membrane-bound form of an isolated polypeptide or cells comprising the polypeptide.

4. The method of claim 3, wherein the cells are mammalian cells.

5. The method of claim 1, wherein the binding of the test compound to the polypeptide is detected by a method selected from the group consisting of:
   a) direct detecting of test compound/polypeptide binding;
   b) an immunoassay; and
   c) a two-hybrid assay.

* * * * *